(12) United States Patent
Harel et al.

(10) Patent No.: US 8,666,495 B2
(45) Date of Patent: Mar. 4, 2014

(54) GASTROINTESTINAL METHODS AND APPARATUS FOR USE IN TREATING DISORDERS AND CONTROLLING BLOOD SUGAR

(75) Inventors: Tami Harel, Haifa (IL); Yuval Mika, Shmurat Zichron (IL)

(73) Assignee: Metacure Limited, Hamilton (BM)

( * ) Notice: Subject to any disclaimer, the term of this patent is extended or adjusted under 35 U.S.C. 154(b) by 1085 days.

(21) Appl. No.: 10/599,015

(22) PCT Filed: Mar. 18, 2005

(86) PCT No.: PCT/IL2005/000316
§ 371 (c)(1),
(2), (4) Date: Nov. 19, 2008

(87) PCT Pub. No.: WO2005/087310
PCT Pub. Date: Sep. 22, 2005

(65) Prior Publication Data
US 2009/0088816 A1    Apr. 2, 2009

Related U.S. Application Data

(63) Continuation-in-part of application No. 10/804,560, filed on Mar. 18, 2004, and a continuation-in-part of application No. PCT/IL2004/000797, filed on Sep. 5, 2004, and a continuation-in-part of application No. PCT/IL2004/000551, filed on Jun. 20, 2004, and a
(Continued)

(51) Int. Cl.
*A61N 1/36*    (2006.01)

(52) U.S. Cl.
USPC ............................................ 607/40

(58) Field of Classification Search
USPC ............................................ 607/40
See application file for complete search history.

(56) References Cited

U.S. PATENT DOCUMENTS 1,918,386 A    7/1933    Esau
2,593,067 A    4/1952    Spencer
(Continued)

FOREIGN PATENT DOCUMENTS

EP    0057048    8/1982
EP    0129483    12/1984
(Continued)

OTHER PUBLICATIONS http://medical-dictionary.thefreedictionary.com/pyloric+antrum) within the Free Dictionary.com.*
(Continued)

*Primary Examiner* — Carl H Layno
*Assistant Examiner* — Paula J Stice
(74) *Attorney, Agent, or Firm* — William H. Dippert; Eckert Seamans Cherin & Mellott, LLC

(57) ABSTRACT

A method of glucose level control comprising providing at least one electrode adapted to apply an electric field to a pancreas; and applying an electric field to the pancreas using said at least one electrode such that blood glucose levels are significantly reduced and blood insulin levels are not significantly increased compared to a regular insulin response in a same person.

63 Claims, 75 Drawing Sheets

Related U.S. Application Data continuation-in-part of application No. PCT/IL2004/000550, filed on Jun. 20, 2004, and a continuation-in-part of application No. PCT/IL03/00736, filed on Sep. 4, 2003, which is a continuation-in-part of application No. 10/237,263, filed on Sep. 5, 2002, now Pat. No. 8,019,421, which is a continuation-in-part of application No. PCT/IL00/00566, filed on Sep. 13, 2000, and a continuation-in-part of application No. 09/914,889, filed as application No. PCT/IL00/00132 on Mar. 5, 2000, now Pat. No. 7,006,871, and a continuation-in-part of application No. PCT/IL02/00856, filed on Oct. 24, 2002, and a continuation-in-part of application No. PCT/IL01/00501, filed on May 30, 2001.

(60) Provisional application No. 60/488,964, filed on Jul. 21, 2003, provisional application No. 60/480,208, filed on Jun. 20, 2003, provisional application No. 60/480,205, filed on Jun. 20, 2003, provisional application No. 60/123,532, filed on Mar. 5, 1999, provisional application No. 60/208,157, filed on May 31, 2000.

(56) References Cited

U.S. PATENT DOCUMENTS

| | | |
|---|---|---|
| 3,211,154 A | 10/1965 | Becker et al. |
| 3,411,507 A | 11/1968 | Wingrove |
| 3,516,412 A | 6/1970 | Ackerman |
| 3,541,390 A | 11/1970 | Jahnke |
| 3,572,345 A | 3/1971 | Auphan |
| 3,587,567 A | 6/1971 | Schiff |
| 3,650,277 A | 3/1972 | Sjostrand et al. |
| 3,651,805 A | 3/1972 | Brelling |
| 3,651,806 A | 3/1972 | Hirshberg |
| 3,658,051 A | 4/1972 | MacLean |
| 3,737,579 A | 6/1973 | Bolduc |
| 3,796,221 A | 3/1974 | Hagfors |
| 3,911,930 A | 10/1975 | Hagfors et al. |
| 3,924,641 A | 12/1975 | Weiss |
| 3,933,147 A | 1/1976 | Du Vall et al. |
| 3,942,536 A | 3/1976 | Mirowski et al. |
| 3,944,740 A | 3/1976 | Murase et al. |
| 3,952,750 A | 4/1976 | Mirowski et al. |
| 4,000,745 A | 1/1977 | Goldberg et al. |
| 4,010,758 A | 3/1977 | Rockland et al. |
| 4,030,509 A | 6/1977 | Heilman et al. |
| 4,055,190 A | 10/1977 | Tany |
| 4,106,494 A | 8/1978 | McEachern |
| 4,133,315 A | 1/1979 | Berman et al. |
| 4,164,216 A | 8/1979 | Person |
| 4,165,454 A | 8/1979 | Carlsson et al. |
| 4,168,711 A | 9/1979 | Cannon, III et al. |
| 4,177,818 A | 12/1979 | De Pedro |
| 4,184,493 A | 1/1980 | Langer et al. |
| 4,202,340 A | 5/1980 | Langer et al. |
| 4,223,678 A | 9/1980 | Langer et al. |
| 4,235,246 A | 11/1980 | Weiss |
| 4,237,895 A | 12/1980 | Johnson |
| 4,273,114 A | 6/1981 | Barkalow et al. |
| 4,280,503 A | 7/1981 | Ackerman |
| 4,293,734 A | 10/1981 | Pepper, Jr. |
| 4,312,354 A | 1/1982 | Walters |
| 4,313,448 A | 2/1982 | Stokes |
| 4,315,503 A | 2/1982 | Ryaby et al. |
| 4,316,472 A | 2/1982 | Mirowski et al. |
| 4,337,776 A | 7/1982 | Daly et al. |
| 4,342,896 A | 8/1982 | Teich |
| 4,354,153 A | 10/1982 | Lentz |
| 4,357,946 A | 11/1982 | Dutcher et al. |
| 4,369,791 A | 1/1983 | Friedman |
| 4,377,733 A | 3/1983 | Yamaguchi et al. |
| 4,378,023 A | 3/1983 | Trabucco |
| 4,384,585 A | 5/1983 | Zipes |
| 4,387,717 A | 6/1983 | Brownlee et al. |
| 4,403,614 A | 9/1983 | Engle et al. |
| 4,406,288 A | 9/1983 | Horwinski et al. |
| 4,407,288 A | 10/1983 | Langer et al. |
| 4,411,268 A | 10/1983 | Cox |
| 4,416,267 A | 11/1983 | Garren et al. |
| 4,428,366 A | 1/1984 | Findl et al. |
| 4,431,888 A | 2/1984 | Simpson |
| 4,440,172 A | 4/1984 | Langer |
| 4,447,693 A | 5/1984 | Buck |
| 4,452,254 A | 6/1984 | Goldberg et al. |
| 4,475,024 A | 10/1984 | Tateda |
| 4,485,805 A | 12/1984 | Foster, Jr. |
| 4,506,680 A | 3/1985 | Stokes |
| 4,537,195 A | 8/1985 | McDonnell |
| 4,537,203 A | 8/1985 | Machida |
| 4,543,738 A | 10/1985 | Mower |
| 4,543,956 A | 10/1985 | Herscovici |
| 4,550,221 A | 10/1985 | Mabusth |
| 4,552,150 A | 11/1985 | Zacouto |
| 4,554,922 A | 11/1985 | Prystowsky et al. |
| 4,554,992 A | 11/1985 | Kassai |
| 4,559,946 A | 12/1985 | Mower |
| 4,559,947 A | 12/1985 | Renger et al. |
| 4,566,456 A | 1/1986 | Koning et al. |
| 4,572,191 A | 2/1986 | Mirowski et al. |
| 4,592,339 A | 6/1986 | Kuzmak |
| 4,596,915 A | 6/1986 | Simpson |
| 4,628,934 A | 12/1986 | Pohndorf et al. |
| 4,637,397 A | 1/1987 | Jones et al. |
| 4,639,720 A | 1/1987 | Rympalski et al. |
| 4,651,716 A | 3/1987 | Forester et al. |
| 4,674,508 A | 6/1987 | DeCote |
| 4,679,572 A | 7/1987 | Baker, Jr. |
| 4,686,332 A | 8/1987 | Greanias et al. |
| 4,690,155 A | 9/1987 | Hess |
| 4,693,253 A | 9/1987 | Adams |
| 4,696,288 A | 9/1987 | Kuzmak et al. |
| 4,708,145 A | 11/1987 | Tacker et al. |
| 4,717,581 A | 1/1988 | Robblee |
| 4,726,279 A | 2/1988 | Kepler et al. |
| 4,726,379 A | 2/1988 | Altman et al. |
| 4,765,341 A | 8/1988 | Mower et al. |
| 4,807,632 A | 2/1989 | Liess et al. |
| 4,823,808 A | 4/1989 | Clegg et al. |
| 4,830,006 A | 5/1989 | Haluska et al. |
| 4,834,100 A | 5/1989 | Charms |
| 4,850,959 A | 7/1989 | Findl |
| 4,870,974 A | 10/1989 | Wang |
| 4,873,986 A | 10/1989 | Wallace |
| 4,878,553 A | 11/1989 | Yamanami et al. |
| 4,884,576 A | 12/1989 | Alt |
| 4,914,624 A | 4/1990 | Dunthorn et al. |
| 4,928,688 A | 5/1990 | Mower |
| 4,967,749 A | 11/1990 | Cohen |
| 4,971,058 A | 11/1990 | Pless et al. |
| 4,975,682 A | 12/1990 | Kerr et al. |
| 4,979,507 A | 12/1990 | Heinz et al. |
| 4,988,837 A | 1/1991 | Murakami et al. |
| 4,996,984 A | 3/1991 | Sweeney |
| 4,998,531 A | 3/1991 | Bocchi et al. |
| 4,998,532 A | 3/1991 | Griffith |
| 5,002,052 A | 3/1991 | Haluska et al. |
| 5,003,976 A | 4/1991 | Alt |
| 5,018,522 A | 5/1991 | Mehra |
| 5,020,544 A | 6/1991 | Dahl et al. |
| 5,022,396 A | 6/1991 | Watanabe |
| 5,025,787 A | 6/1991 | Sutherland et al. |
| 5,026,397 A | 6/1991 | Aoki et al. |
| 5,031,617 A | 7/1991 | Klettner |
| 5,041,107 A | 8/1991 | Heil, Jr. |
| 5,044,375 A | 9/1991 | Bach, Jr. et al. |
| 5,048,522 A | 9/1991 | Petrofsky |
| 5,050,612 A | 9/1991 | Matsumura |
| 5,063,929 A | 11/1991 | Bartelt et al. |
| 5,074,868 A | 12/1991 | Kuzmak |

(56) References Cited

U.S. PATENT DOCUMENTS

| | | |
|---|---|---|
| 5,083,564 A | 1/1992 | Scherlag |
| 5,083,565 A | 1/1992 | Parins |
| 5,085,218 A | 2/1992 | Heil et al. |
| 5,087,243 A | 2/1992 | Avitall |
| 5,097,832 A | 3/1992 | Buchanan |
| 5,097,833 A | 3/1992 | Campos |
| 5,097,843 A | 3/1992 | Soukup et al. |
| 5,101,814 A | 4/1992 | Palti |
| 5,103,804 A | 4/1992 | Abele |
| 5,105,812 A | 4/1992 | Corman |
| 5,107,834 A | 4/1992 | Ideker et al. |
| 5,111,814 A | 5/1992 | Goldfarb |
| 5,111,815 A | 5/1992 | Mower |
| 5,129,394 A | 7/1992 | Mehra |
| 5,133,354 A | 7/1992 | Kallok |
| 5,137,021 A | 8/1992 | Wayne et al. |
| 5,144,554 A | 9/1992 | Zhang et al. |
| 5,154,501 A | 10/1992 | Svenson et al. |
| 5,156,147 A | 10/1992 | Warren et al. |
| 5,156,149 A | 10/1992 | Hudrlik |
| 5,161,527 A | 11/1992 | Nappholz et al. |
| 5,163,427 A | 11/1992 | Keimel |
| 5,163,428 A | 11/1992 | Pless |
| 5,172,690 A | 12/1992 | Nappholz et al. |
| 5,172,699 A | 12/1992 | Svenson et al. |
| 5,174,286 A | 12/1992 | Chirife |
| 5,184,616 A | 2/1993 | Weiss |
| 5,184,620 A | 2/1993 | Cudahy et al. |
| 5,185,620 A | 2/1993 | Cooper |
| 5,188,104 A | 2/1993 | Wernicke et al. |
| 5,188,106 A | 2/1993 | Nappholz et al. |
| 5,190,036 A | 3/1993 | Linder |
| 5,190,041 A | 3/1993 | Palti |
| 5,190,141 A | 3/1993 | Boldrini et al. |
| 5,197,491 A | 3/1993 | Anderson et al. |
| 5,199,428 A | 4/1993 | Obel et al. |
| 5,202,095 A | 4/1993 | Houchin et al. |
| 5,205,284 A | 4/1993 | Freeman |
| 5,213,098 A | 5/1993 | Bennett et al. |
| 5,226,429 A | 7/1993 | Kuzmak |
| 5,231,381 A | 7/1993 | Duwaer |
| 5,231,988 A | 8/1993 | Wernicke et al. |
| 5,233,985 A | 8/1993 | Hudrlik |
| 5,234,454 A | 8/1993 | Bangs |
| 5,236,413 A | 8/1993 | Feiring |
| 5,243,980 A | 9/1993 | Mehra et al. |
| 5,247,938 A | 9/1993 | Silverstein et al. |
| 5,263,480 A | 11/1993 | Wernicke et al. |
| 5,267,560 A | 12/1993 | Cohen |
| 5,281,219 A | 1/1994 | Kallok |
| 5,282,785 A | 2/1994 | Shapland et al. |
| 5,284,491 A | 2/1994 | Sutton et al. |
| 5,286,254 A | 2/1994 | Shapland et al. |
| 5,292,344 A | 3/1994 | Douglas |
| 5,305,745 A | 4/1994 | Zacouto |
| 5,314,463 A | 5/1994 | Camps et al. |
| 5,318,591 A | 6/1994 | Causey, III et al. |
| 5,320,543 A | 6/1994 | Barton et al. |
| 5,320,642 A | 6/1994 | Scherlag |
| 5,320,643 A | 6/1994 | Roline et al. |
| 5,324,327 A | 6/1994 | Cohen |
| 5,325,856 A | 7/1994 | Nitzsche et al. |
| 5,327,887 A | 7/1994 | Nowakowski |
| 5,346,506 A | 9/1994 | Mower et al. |
| 5,350,403 A | 9/1994 | Stroetmann et al. |
| 5,353,800 A | 10/1994 | Pohndorf et al. |
| 5,365,461 A | 11/1994 | Stein et al. |
| 5,366,485 A | 11/1994 | Kroll et al. |
| 5,366,486 A | 11/1994 | Zipes et al. |
| 5,368,028 A | 11/1994 | Palti |
| 5,368,040 A | 11/1994 | Carney |
| 5,370,665 A | 12/1994 | Hudrlik |
| 5,374,787 A | 12/1994 | Miller et al. |
| 5,381,160 A | 1/1995 | Landmeier |
| 5,386,835 A | 2/1995 | Elphick et al. |
| 5,386,837 A | 2/1995 | Sterzer |
| 5,387,419 A | 2/1995 | Levy et al. |
| 5,391,192 A | 2/1995 | Lu et al. |
| 5,391,199 A | 2/1995 | Ben-Haim |
| 5,397,344 A | 3/1995 | Garfield et al. |
| 5,398,683 A | 3/1995 | Edwards et al. |
| 5,402,151 A | 3/1995 | Duwaer |
| 5,411,531 A | 5/1995 | Hill et al. |
| 5,415,629 A | 5/1995 | Henley |
| 5,417,717 A | 5/1995 | Salo et al. |
| 5,419,763 A | 5/1995 | Hildebrand |
| 5,423,872 A | 6/1995 | Cigaina |
| 5,425,363 A | 6/1995 | Wang |
| 5,431,682 A | 7/1995 | Hedberg |
| 5,431,688 A | 7/1995 | Freeman |
| 5,431,693 A | 7/1995 | Schroeppel |
| 5,433,730 A | 7/1995 | Alt |
| 5,443,485 A | 8/1995 | Housworth et al. |
| 5,443,489 A | 8/1995 | Ben-Haim |
| 5,445,609 A | 8/1995 | Lattin et al. |
| 5,447,520 A | 9/1995 | Spano et al. |
| 5,447,525 A | 9/1995 | Powell et al. |
| 5,447,526 A | 9/1995 | Karsdon |
| 5,449,368 A | 9/1995 | Kuzmak |
| 5,451,751 A | 9/1995 | Takimoto et al. |
| 5,458,568 A | 10/1995 | Racchini et al. |
| 5,464,020 A | 11/1995 | Lerner |
| 5,464,429 A | 11/1995 | Hedberg et al. |
| 5,468,254 A | 11/1995 | Hahn et al. |
| 5,472,453 A | 12/1995 | Alt |
| 5,476,484 A | 12/1995 | Hedberg |
| 5,476,485 A | 12/1995 | Weinberg et al. |
| 5,476,487 A | 12/1995 | Sholder |
| 5,476,497 A | 12/1995 | Mower et al. |
| 5,480,422 A | 1/1996 | Ben-Haim |
| 5,482,052 A | 1/1996 | Lerner |
| 5,489,293 A | 2/1996 | Pless et al. |
| 5,495,077 A | 2/1996 | Miller et al. |
| 5,499,971 A | 3/1996 | Shapland et al. |
| 5,501,662 A | 3/1996 | Hofmann |
| 5,505,700 A | 4/1996 | Leone et al. |
| 5,510,813 A | 4/1996 | Makinwa et al. |
| 5,514,162 A | 5/1996 | Bornzin et al. |
| 5,514,175 A | 5/1996 | Kim et al. |
| 5,520,642 A | 5/1996 | Bigagli et al. |
| 5,522,853 A | 6/1996 | Kroll |
| 5,527,345 A | 6/1996 | Infinger |
| 5,528,002 A | 6/1996 | Katabami |
| 5,531,764 A | 7/1996 | Adams et al. |
| 5,534,015 A | 7/1996 | Kroll et al. |
| 5,540,722 A | 7/1996 | Clare et al. |
| 5,540,730 A | 7/1996 | Terry et al. |
| 5,540,734 A | 7/1996 | Zabara |
| 5,543,589 A | 8/1996 | Buchana et al. |
| 5,546,951 A | 8/1996 | Ben-Haim |
| 5,549,646 A | 8/1996 | Katz et al. |
| 5,551,425 A | 9/1996 | Essen |
| 5,552,150 A | 9/1996 | Horrobin et al. |
| 5,556,421 A | 9/1996 | Prutchi et al. |
| 5,556,425 A | 9/1996 | Hewson et al. |
| 5,556,760 A | 9/1996 | Nakamura et al. |
| 5,558,640 A | 9/1996 | Pfeiler et al. |
| 5,561,165 A | 10/1996 | Lautt et al. |
| 5,562,708 A | 10/1996 | Combs et al. |
| 5,562,720 A | 10/1996 | Stern et al. |
| 5,565,632 A | 10/1996 | Ogawa |
| 5,568,809 A | 10/1996 | Ben-Haim |
| 5,571,143 A | 11/1996 | Hoegnelid et al. |
| 5,571,997 A | 11/1996 | Gray et al. |
| 5,578,061 A | 11/1996 | Stroetmann et al. |
| 5,584,803 A | 12/1996 | Stevens et al. |
| 5,584,804 A | 12/1996 | Klatz et al. |
| 5,584,868 A | 12/1996 | Salo et al. |
| 5,587,200 A | 12/1996 | Lorenz et al. |
| 5,589,856 A | 12/1996 | Stein et al. |
| 5,601,604 A | 2/1997 | Vincent |
| 5,601,609 A | 2/1997 | Duncan |
| 5,601,611 A | 2/1997 | Fayram et al. |
| 5,616,268 A | 4/1997 | Carr |

(56) References Cited

U.S. PATENT DOCUMENTS

| | | |
|---|---|---|
| 5,620,468 A | 4/1997 | Mongeon et al. |
| 5,622,687 A | 4/1997 | Krishnan et al. |
| 5,626,622 A | 5/1997 | Cooper |
| 5,632,267 A | 5/1997 | Hoegnelid et al. |
| 5,634,895 A | 6/1997 | Igo et al. |
| 5,634,899 A | 6/1997 | Shapland et al. |
| 5,649,966 A | 7/1997 | Noren et al. |
| 5,651,378 A | 7/1997 | Matheny et al. |
| 5,654,030 A | 8/1997 | Munshi et al. |
| 5,662,687 A | 9/1997 | Hedberg et al. |
| 5,670,755 A | 9/1997 | Kwon |
| 5,674,251 A | 10/1997 | Combs et al. |
| 5,674,259 A | 10/1997 | Gray |
| 5,683,429 A | 11/1997 | Mehra |
| 5,683,431 A | 11/1997 | Wang |
| 5,687,734 A | 11/1997 | Dempsey et al. |
| 5,690,691 A | 11/1997 | Chen et al. |
| 5,694,945 A | 12/1997 | Ben-Haim |
| 5,697,953 A | 12/1997 | Kroll et al. |
| 5,704,368 A | 1/1998 | Asano et al. |
| 5,713,924 A | 2/1998 | Min et al. |
| 5,713,929 A | 2/1998 | Hess et al. |
| 5,713,935 A | 2/1998 | Prutchi et al. |
| 5,716,385 A | 2/1998 | Mittal et al. |
| 5,720,768 A | 2/1998 | Verboven-Nelissen |
| 5,727,558 A | 3/1998 | Hakki et al. |
| 5,735,876 A | 4/1998 | Kroll et al. |
| 5,738,096 A | 4/1998 | Ben-Haim |
| 5,738,105 A | 4/1998 | Kroll |
| 5,741,211 A | 4/1998 | Renirie et al. |
| 5,741,791 A | 4/1998 | Olsen |
| 5,749,906 A | 5/1998 | Kieval et al. |
| 5,755,740 A | 5/1998 | Nappholz |
| 5,777,607 A | 7/1998 | Koolen |
| 5,779,661 A | 7/1998 | Stephen et al. |
| 5,782,876 A | 7/1998 | Flammang |
| 5,782,881 A | 7/1998 | Lu et al. |
| 5,783,951 A | 7/1998 | Inoue et al. |
| 5,790,106 A | 8/1998 | Hirano et al. |
| 5,790,107 A | 8/1998 | Kasser et al. |
| 5,792,189 A | 8/1998 | Gray et al. |
| 5,792,198 A | 8/1998 | Nappholz |
| 5,792,208 A | 8/1998 | Gray |
| 5,792,210 A | 8/1998 | Wamubu et al. |
| 5,795,304 A | 8/1998 | Sun et al. |
| 5,797,967 A | 8/1998 | KenKnight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,824,016 A | 10/1998 | Ekwall |
| 5,825,352 A | 10/1998 | Bisset et al. |
| 5,836,994 A | 11/1998 | Bourgeois |
| 5,837,006 A | 11/1998 | Ocel et al. |
| 5,841,078 A | 11/1998 | Miller et al. |
| 5,854,881 A | 12/1998 | Yoshida et al. |
| 5,861,014 A | 1/1999 | Familoni |
| 5,865,787 A | 2/1999 | Shapland et al. |
| 5,868,141 A | 2/1999 | Ellias |
| 5,871,506 A | 2/1999 | Mower |
| 5,891,185 A | 4/1999 | Freed et al. |
| 5,906,607 A | 5/1999 | Taylor et al. |
| 5,911,223 A | 6/1999 | Weaver et al. |
| 5,913,876 A | 6/1999 | Taylor et al. |
| 5,914,465 A | 6/1999 | Allen et al. |
| 5,919,216 A | 7/1999 | Houben et al. |
| 5,920,309 A | 7/1999 | Bisset et al. |
| 5,925,070 A | 7/1999 | King et al. |
| 5,927,284 A | 7/1999 | Borst et al. |
| 5,938,669 A | 8/1999 | Klaiber et al. |
| 5,954,761 A | 9/1999 | Machek et al. |
| 5,956,020 A | 9/1999 | D'Amico et al. |
| 5,961,871 A | 10/1999 | Bible et al. |
| 5,962,246 A | 10/1999 | Ladner et al. |
| 5,979,449 A | 11/1999 | Steer |
| 5,991,649 A | 11/1999 | Garfield et al. |
| 5,995,872 A | 11/1999 | Bourgeois |
| 6,002,594 A | 12/1999 | Ledin et al. |
| 6,006,134 A | 12/1999 | Hill et al. |
| 6,023,640 A | 2/2000 | Ross |
| 6,026,326 A | 2/2000 | Bardy |
| 6,026,626 A | 2/2000 | Fisher |
| 6,032,074 A | 2/2000 | Collins |
| 6,032,672 A | 3/2000 | Taylor |
| 6,037,882 A | 3/2000 | Levy |
| 6,041,252 A | 3/2000 | Walker et al. |
| 6,041,258 A | 3/2000 | Cigaina et al. |
| 6,057,374 A | 5/2000 | Huntington et al. |
| 6,066,163 A | 5/2000 | John |
| 6,067,470 A | 5/2000 | Mower |
| 6,067,991 A | 5/2000 | Forsell |
| 6,071,305 A | 6/2000 | Brown et al. |
| 6,075,520 A | 6/2000 | Inoue et al. |
| 6,083,249 A | 7/2000 | Familoni |
| 6,086,582 A | 7/2000 | Altman et al. |
| 6,091,992 A | 7/2000 | Bourgeois |
| 6,092,528 A | 7/2000 | Edwards |
| 6,093,167 A | 7/2000 | Houben et al. |
| 6,096,361 A | 8/2000 | Yamane et al. |
| 6,104,955 A | 8/2000 | Bourgeois |
| 6,115,635 A | 9/2000 | Bourgeois |
| 6,122,536 A | 9/2000 | Sun et al. |
| 6,128,007 A | 10/2000 | Seybold et al. |
| 6,129,685 A | 10/2000 | Howard |
| 6,132,372 A | 10/2000 | Essen |
| 6,133,906 A | 10/2000 | Geaghan |
| 6,135,978 A | 10/2000 | Houben et al. |
| 6,135,987 A | 10/2000 | Tsai et al. |
| 6,136,019 A | 10/2000 | Mower |
| 6,141,586 A | 10/2000 | Mower |
| 6,141,587 A | 10/2000 | Mower |
| 6,151,586 A | 11/2000 | Brown |
| 6,178,351 B1 | 1/2001 | Mower |
| 6,185,452 B1 | 2/2001 | Schulman et al. |
| 6,216,039 B1 | 4/2001 | Bourgeois |
| 6,216,045 B1 | 4/2001 | Black et al. |
| 6,233,484 B1 | 5/2001 | Ben-Haim et al. |
| 6,233,487 B1 | 5/2001 | Mika et al. |
| 6,236,887 B1 | 5/2001 | Ben-Haim et al. |
| 6,239,389 B1 | 5/2001 | Allen et al. |
| 6,243,607 B1 | 6/2001 | Mintchev |
| 6,249,697 B1 | 6/2001 | Asano et al. |
| 6,261,280 B1 | 7/2001 | Houben et al. |
| 6,278,443 B1 | 8/2001 | Amro et al. |
| 6,285,906 B1 | 9/2001 | Ben-Haim et al. |
| 6,292,693 B1 | 9/2001 | Darvish et al. |
| 6,292,704 B1 | 9/2001 | Malonek et al. |
| 6,295,470 B1 | 9/2001 | Mower |
| 6,296,693 B1 | 10/2001 | McCarthy |
| 6,298,254 B2 | 10/2001 | Tamada |
| 6,298,268 B1 | 10/2001 | Ben-Haim et al. |
| 6,317,631 B1 | 11/2001 | Ben-Haim et al. |
| 6,330,476 B1 | 12/2001 | Ben-Haim |
| 6,334,073 B1 | 12/2001 | Levine |
| 6,337,995 B1 | 1/2002 | Mower |
| 6,341,235 B1 | 1/2002 | Mower |
| 6,343,232 B1 | 1/2002 | Mower |
| 6,363,279 B1 | 3/2002 | Ben-Haim et al. |
| 6,363,937 B1 | 4/2002 | Hovda et al. |
| 6,381,495 B1 | 4/2002 | Jenkins |
| 6,392,636 B1 | 5/2002 | Ferrari et al. |
| 6,405,732 B1 | 6/2002 | Edwards |
| 6,411,842 B1 | 6/2002 | Cigaina et al. |
| 6,411,847 B1 | 6/2002 | Mower |
| 6,415,178 B1 | 7/2002 | Ben-Haim et al. |
| 6,417,846 B1 | 7/2002 | Lee |
| 6,424,864 B1 | 7/2002 | Matsuura |
| 6,427,089 B1 | 7/2002 | Knowlton |
| 6,433,069 B1 | 8/2002 | Oeltjen et al. |
| 6,449,511 B1 | 9/2002 | Mintchev |
| 6,452,514 B1 | 9/2002 | Philipp |
| 6,453,199 B1 | 9/2002 | Kobozev |
| 6,454,699 B1 | 9/2002 | Forsell |
| 6,463,323 B1 | 10/2002 | Conrad-Vlasak et al. |

(56) References Cited

U.S. PATENT DOCUMENTS

| | | |
|---|---|---|
| 6,463,324 B1 | 10/2002 | Ben-Haim et al. |
| 6,473,069 B1 | 10/2002 | Gerpheide |
| 6,476,766 B1 | 11/2002 | Cohen |
| 6,498,944 B1 | 12/2002 | Ben-Haim et al. |
| 6,504,530 B1 | 1/2003 | Wilson et al. |
| 6,505,745 B1 | 1/2003 | Anderson |
| 6,507,093 B2 | 1/2003 | Kaneda et al. |
| 6,535,764 B2 | 3/2003 | Imran et al. |
| RE38,119 E | 5/2003 | Mower |
| 6,558,345 B1 | 5/2003 | Houben et al. |
| 6,567,700 B1 | 5/2003 | Turcott et al. |
| 6,570,557 B1 | 5/2003 | Westerman et al. |
| 6,571,127 B1 | 5/2003 | Ben-Haim et al. |
| 6,572,542 B1 | 6/2003 | Houben et al. |
| 6,583,676 B2 | 6/2003 | Krah et al. |
| 6,584,348 B2 | 6/2003 | Glukhovsky |
| 6,587,093 B1 | 7/2003 | Shaw et al. |
| 6,587,721 B1 | 7/2003 | Prutchi et al. |
| 6,591,137 B1 | 7/2003 | Fischell et al. |
| 6,594,515 B2 | 7/2003 | Watson |
| 6,600,953 B2 | 7/2003 | Flesler et al. |
| 6,605,039 B2 | 8/2003 | Houben et al. |
| 6,606,523 B1 | 8/2003 | Jenkins |
| 6,609,025 B2 | 8/2003 | Barrett et al. |
| 6,611,258 B1 | 8/2003 | Tanaka et al. |
| 6,612,983 B1 | 9/2003 | Marchal |
| 6,630,123 B1 | 10/2003 | Woltering et al. |
| 6,633,280 B1 | 10/2003 | Matsumoto et al. |
| 6,634,895 B2 | 10/2003 | Agro |
| 6,652,444 B1 | 11/2003 | Ross |
| 6,658,297 B2 | 12/2003 | Loeb |
| 6,667,740 B2 | 12/2003 | Ely et al. |
| 6,684,104 B2 | 1/2004 | Gordon et al. |
| 6,690,156 B1 | 2/2004 | Weiner et al. |
| 6,690,963 B2 | 2/2004 | Ben-Haim et al. |
| 6,735,477 B2 | 5/2004 | Levine |
| 6,745,079 B2 | 6/2004 | King |
| 6,754,536 B2 | 6/2004 | Swoyer et al. |
| 6,762,752 B2 | 7/2004 | Perski et al. |
| 6,781,577 B2 | 8/2004 | Shigetaka |
| 6,810,286 B2 | 10/2004 | Donovan et al. |
| 6,826,428 B1 | 11/2004 | Chen et al. |
| 6,832,114 B1 | 12/2004 | Whitehurst et al. |
| 6,852,110 B2 | 2/2005 | Roy et al. |
| 6,853,862 B1 | 2/2005 | Marchal et al. |
| 6,869,431 B2 | 3/2005 | Maguire et al. |
| 6,876,885 B2 | 4/2005 | Swoyer et al. |
| 6,895,279 B2 | 5/2005 | Loeb et al. |
| 6,918,906 B2 | 7/2005 | Long |
| 6,919,205 B2 | 7/2005 | Brighton |
| 6,939,349 B2 | 9/2005 | Fleischman et al. |
| 6,947,792 B2 | 9/2005 | Ben-Haim et al. |
| 6,949,081 B1 | 9/2005 | Chance |
| 6,952,613 B2 | 10/2005 | Swoyer et al. |
| 6,993,391 B2 | 1/2006 | Flesler et al. |
| 7,006,871 B1 | 2/2006 | Darvish et al. |
| 7,027,863 B1 | 4/2006 | Prutchi et al. |
| 7,043,295 B2 | 5/2006 | Starkebaum |
| 7,054,690 B2 | 5/2006 | Imran |
| 7,062,318 B2 | 6/2006 | Ben-Haim et al. |
| 7,076,305 B2 | 7/2006 | Imran et al. |
| 7,076,306 B2 | 7/2006 | Marchal et al. |
| 7,092,753 B2 | 8/2006 | Darvish et al. |
| 7,120,497 B2 | 10/2006 | Ben-Haim et al. |
| 7,167,748 B2 | 1/2007 | Ben-Haim et al. |
| 7,171,263 B2 | 1/2007 | Darvish et al. |
| 7,190,997 B1 | 3/2007 | Darvish et al. |
| 7,218,963 B2 | 5/2007 | Ben-Haim et al. |
| 7,221,978 B2 | 5/2007 | Ben-Haim et al. |
| 7,440,806 B1 | 10/2008 | Whitehurst et al. |
| 7,460,907 B1 | 12/2008 | Darvish et al. |
| 7,840,262 B2 | 11/2010 | Mika et al. |
| 7,966,071 B2 | 6/2011 | Ben-Haim et al. |
| 2001/0011543 A1 | 8/2001 | Forsell |
| 2002/0026141 A1 | 2/2002 | Houben |
| 2002/0032444 A1 | 3/2002 | Mische |
| 2002/0052632 A1 | 5/2002 | Ben-Haim et al. |
| 2002/0065455 A1 | 5/2002 | Ben-Haim et al. |
| 2002/0081732 A1 | 6/2002 | Bowlin et al. |
| 2002/0103424 A1 | 8/2002 | Swoyer et al. |
| 2002/0123771 A1 | 9/2002 | Ideker et al. |
| 2002/0161414 A1 | 10/2002 | Flesler et al. |
| 2002/0162836 A1 | 11/2002 | Taino et al. |
| 2002/0165589 A1 | 11/2002 | Imran et al. |
| 2002/0183682 A1 | 12/2002 | Darvish et al. |
| 2002/0183686 A1 | 12/2002 | Darvish et al. |
| 2003/0018367 A1 | 1/2003 | DiLorenzo |
| 2003/0028221 A1 | 2/2003 | Zhu et al. |
| 2003/0040777 A1 | 2/2003 | Shemer et al. |
| 2003/0045919 A1 | 3/2003 | Swoyer et al. |
| 2003/0055464 A1 | 3/2003 | Darvish |
| 2003/0055465 A1* | 3/2003 | Ben-Haim et al. ............... 607/40 |
| 2003/0055466 A1 | 3/2003 | Ben-Haim et al. |
| 2003/0055467 A1 | 3/2003 | Ben-Haim et al. |
| 2003/0066536 A1 | 4/2003 | Forsell |
| 2003/0144708 A1 | 7/2003 | Starkebaum |
| 2003/0167476 A1 | 9/2003 | Conklin |
| 2003/0181958 A1 | 9/2003 | Dobak, III |
| 2003/0188899 A1 | 10/2003 | Chao et al. |
| 2003/0195600 A1 | 10/2003 | Tronnes et al. |
| 2003/0208212 A1 | 11/2003 | Cigaina |
| 2003/0208242 A1 | 11/2003 | Harel et al. |
| 2003/0211475 A1 | 11/2003 | Roberts |
| 2003/0220678 A1 | 11/2003 | Tronnes et al. |
| 2004/0044376 A1 | 3/2004 | Flesler et al. |
| 2004/0059393 A1 | 3/2004 | Policker et al. |
| 2004/0088023 A1 | 5/2004 | Imran et al. |
| 2004/0095333 A1 | 5/2004 | Morag et al. |
| 2004/0105040 A1 | 6/2004 | Oh et al. |
| 2004/0106954 A1 | 6/2004 | Whitehurst et al. |
| 2004/0107004 A1 | 6/2004 | Levine et al. |
| 2004/0134904 A1 | 7/2004 | Clemen |
| 2004/0138710 A1 | 7/2004 | Shemer et al. |
| 2004/0147816 A1 | 7/2004 | Policker et al. |
| 2004/0155871 A1 | 8/2004 | Perski et al. |
| 2004/0158138 A1 | 8/2004 | Kilcoyne et al. |
| 2004/0158289 A1 | 8/2004 | Girouard et al. |
| 2004/0162469 A1 | 8/2004 | Imran |
| 2004/0162595 A1 | 8/2004 | Foley |
| 2004/0167583 A1 | 8/2004 | Knudson et al. |
| 2004/0193184 A1 | 9/2004 | Laufer et al. |
| 2004/0193229 A1 | 9/2004 | Starkebaum et al. |
| 2004/0230273 A1 | 11/2004 | Cates et al. |
| 2004/0232140 A1 | 11/2004 | Kanzaki et al. |
| 2004/0236316 A1 | 11/2004 | Danitz |
| 2004/0243190 A1 | 12/2004 | Ben-Haim et al. |
| 2004/0243211 A1 | 12/2004 | Colliou et al. |
| 2004/0249421 A1 | 12/2004 | Harel et al. |
| 2005/0020965 A1 | 1/2005 | Rioux et al. |
| 2005/0021101 A1 | 1/2005 | Chen et al. |
| 2005/0033396 A1 | 2/2005 | Ospyka |
| 2005/0055038 A1 | 3/2005 | Kelleher et al. |
| 2005/0065505 A1 | 3/2005 | Ryan |
| 2005/0065553 A1 | 3/2005 | Ben Ezra et al. |
| 2005/0075654 A1 | 4/2005 | Kelleher |
| 2005/0090873 A1 | 4/2005 | Imran |
| 2005/0095227 A1 | 5/2005 | Rosenzweig et al. |
| 2005/0096514 A1 | 5/2005 | Starkebaum |
| 2005/0107829 A1 | 5/2005 | Edwards et al. |
| 2005/0143784 A1 | 6/2005 | Imran |
| 2005/0149142 A1 | 7/2005 | Starkebaum |
| 2005/0164925 A1 | 7/2005 | Jakubowski et al. |
| 2005/0183732 A1 | 8/2005 | Edwards |
| 2005/0192542 A1 | 9/2005 | Dev et al. |
| 2005/0192615 A1 | 9/2005 | Torre et al. |
| 2005/0203500 A1 | 9/2005 | Saadat et al. |
| 2005/0209653 A1 | 9/2005 | Herbert et al. |
| 2005/0222638 A1 | 10/2005 | Foley et al. |
| 2006/0036126 A1 | 2/2006 | Ross et al. |
| 2006/0064037 A1 | 3/2006 | Shalon et al. |
| 2006/0074459 A1 | 4/2006 | Flesler et al. |
| 2006/0079475 A1 | 4/2006 | Zhang et al. |
| 2006/0085045 A1 | 4/2006 | Harel et al. |
| 2006/0097991 A1 | 5/2006 | Hotelling et al. |

(56) References Cited

U.S. PATENT DOCUMENTS

| | | |
|---|---|---|
| 2006/0142803 A1 | 6/2006 | Mintchev |
| 2006/0173238 A1 | 8/2006 | Starkebaum |
| 2006/0184207 A1 | 8/2006 | Darvish et al. |
| 2006/0247718 A1 | 11/2006 | Starkebaum |
| 2006/0264699 A1 | 11/2006 | Gertner |
| 2007/0016262 A1 | 1/2007 | Gross et al. |
| 2007/0027487 A1 | 2/2007 | Mika et al. |
| 2007/0027490 A1 | 2/2007 | Ben-Haim et al. |
| 2007/0027493 A1 | 2/2007 | Ben-Haim et al. |
| 2007/0051848 A1 | 3/2007 | Watts et al. |
| 2007/0051849 A1 | 3/2007 | Watts et al. |
| 2007/0060812 A1 | 3/2007 | Harel et al. |
| 2007/0060971 A1 | 3/2007 | Glasberg et al. |
| 2007/0088393 A1 | 4/2007 | Ben-Haim et al. |
| 2007/0092446 A1 | 4/2007 | Haddad et al. |
| 2007/0156177 A1 | 7/2007 | Harel et al. |
| 2007/0161851 A1 | 7/2007 | Takizawa et al. |
| 2007/0162079 A1 | 7/2007 | Shemer et al. |
| 2007/0171211 A1 | 7/2007 | Perski et al. |
| 2007/0179556 A1 | 8/2007 | Ben Haim et al. |
| 2007/0185540 A1 | 8/2007 | Ben-Haim et al. |
| 2007/0239216 A9 | 10/2007 | Shemer et al. |
| 2007/0293901 A1 | 12/2007 | Rousso et al. |
| 2007/0299320 A1 | 12/2007 | Policker et al. |
| 2008/0046062 A1 | 2/2008 | Camps et al. |
| 2008/0051849 A1 | 2/2008 | Ben-Haim et al. |
| 2008/0058879 A1 | 3/2008 | Ben-Haim et al. |
| 2008/0058889 A1 | 3/2008 | Ben-Haim et al. |
| 2008/0058891 A1 | 3/2008 | Ben-Haim et al. |
| 2008/0065159 A1 | 3/2008 | Ben-Haim et al. |
| 2008/0065163 A1 | 3/2008 | Ben-Haim et al. |
| 2008/0065164 A1 | 3/2008 | Ben-Haim et al. |
| 2008/0065168 A1 | 3/2008 | Bitton et al. |
| 2008/0077174 A1 | 3/2008 | Mische |
| 2008/0140142 A1 | 6/2008 | Darvish et al. |
| 2008/0178684 A1 | 7/2008 | Spehr |
| 2008/0188837 A1 | 8/2008 | Belsky et al. |
| 2009/0062893 A1 | 3/2009 | Spehr et al. |
| 2009/0088816 A1 | 4/2009 | Harel et al. |
| 2009/0118797 A1 | 5/2009 | Kliger et al. |
| 2009/0131993 A1 | 5/2009 | Rousso et al. |
| 2009/0204063 A1 | 8/2009 | Policker et al. |
| 2009/0281449 A1 | 11/2009 | Thrower et al. |
| 2009/0292324 A1 | 11/2009 | Rousso et al. |
| 2010/0016923 A1 | 1/2010 | Rousso et al. |
| 2010/0228105 A1 | 9/2010 | Policker et al. |
| 2010/0305468 A1 | 12/2010 | Policker et al. |
| 2010/0324644 A1 | 12/2010 | Levi et al. |

FOREIGN PATENT DOCUMENTS

| | | |
|---|---|---|
| EP | 0129483 A1 | 12/1984 |
| EP | 144705 | 6/1985 |
| EP | 0148687 | 7/1985 |
| EP | 0156593 | 10/1985 |
| EP | 0250931 | 1/1988 |
| EP | 0268379 | 5/1988 |
| EP | 0314078 | 5/1989 |
| EP | 0421780 | 4/1991 |
| EP | 0481684 | 4/1992 |
| EP | 0503839 | 9/1992 |
| EP | 0528751 | 2/1993 |
| EP | 0220916 | 4/1994 |
| EP | 0727241 | 8/1996 |
| EP | 0996482 | 5/2000 |
| EP | 1036545 | 9/2000 |
| EP | 1263498 | 12/2002 |
| EP | 1 447 052 | 8/2004 |
| EP | 1447632 | 8/2004 |
| EP | 0910429 | 3/2005 |
| EP | 1515102 | 3/2005 |
| GB | 1394171 | 5/1975 |
| GB | 2033587 | 5/1980 |
| GB | 2280377 | 2/1995 |
| JP | 62-112530 | 5/1987 |
| JP | 62-275471 | 11/1987 |
| JP | 04-117967 | 4/1992 |
| JP | 04-282168 | 10/1992 |
| JP | 04-365493 | 12/1992 |
| JP | 06-169998 | 6/1994 |
| JP | 06-193884 | 7/1994 |
| JP | 06-506619 | 7/1994 |
| JP | 06-310268 | 11/1994 |
| JP | 07-503865 | 4/1995 |
| JP | 07-126600 | 5/1995 |
| JP | 07-144024 | 6/1995 |
| JP | 07-508662 | 9/1995 |
| JP | 08-064359 | 3/1996 |
| JP | 08-243176 | 9/1996 |
| JP | 09-229372 | 9/1997 |
| JP | 2001-086967 | 4/2001 |
| JP | 2003/319945 | 11/2003 |
| JP | 2003319945 | 11/2003 |
| RU | 386634 | 6/1973 |
| RU | 553977 | 5/1977 |
| RU | 0553977 | 5/1977 |
| RU | 0709078 | 1/1980 |
| RU | 0831131 | 5/1981 |
| RU | 831131 | 5/1981 |
| RU | 1039506 | 9/1983 |
| RU | 1147408 | 3/1985 |
| RU | 2014844 | 6/1994 |
| RU | 1827793 | 5/1995 |
| RU | 2055606 | 3/1996 |
| RU | 2075980 | 3/1997 |
| RU | 2077273 | 4/1997 |
| RU | 2078547 | 5/1997 |
| RU | 2260451 | 10/2001 |
| WO | WO 91/19534 | 12/1991 |
| WO | WO 92/00716 | 1/1992 |
| WO | WO 92/13592 | 8/1992 |
| WO | WO 93/02743 | 2/1993 |
| WO | WO 93/02745 | 2/1993 |
| WO | WO 93/08874 | 5/1993 |
| WO | WO 93/18820 | 9/1993 |
| WO | WO 94/01172 | 1/1994 |
| WO | WO 94/17855 | 8/1994 |
| WO | WO 95/02995 | 2/1995 |
| WO | WO 95/08316 | 3/1995 |
| WO | WO 96/05768 | 2/1996 |
| WO | WO 96/10358 | 4/1996 |
| WO | WO 96/16696 | 6/1996 |
| WO | WO 97/15227 | 1/1997 |
| WO | WO 97/06849 | 2/1997 |
| WO | WO 97/24981 | 7/1997 |
| WO | WO 97/24983 | 7/1997 |
| WO | WO 97/25098 | 7/1997 |
| WO | WO 97/25101 | 7/1997 |
| WO | WO 97/26042 | 7/1997 |
| WO | WO 97/27900 | 7/1997 |
| WO | WO 97/29679 | 8/1997 |
| WO | WO 97/29682 | 8/1997 |
| WO | WO 97/29684 | 8/1997 |
| WO | WO 97/29700 | 8/1997 |
| WO | WO 97/29701 | 8/1997 |
| WO | WO 97/29709 | 8/1997 |
| WO | WO 97/41921 | 11/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 98/11840 | 3/1998 |
| WO | WO 98/15317 | 4/1998 |
| WO | WO 98/19719 | 5/1998 |
| WO | WO 98/56378 | 12/1998 |
| WO | WO 98/57701 | 12/1998 |
| WO | WO 99/03533 | 1/1999 |
| WO | WO 99/06105 | 2/1999 |
| WO | WO 99/09971 | 3/1999 |
| WO | WO 99/55360 | 4/1999 |
| WO | WO 99/24110 | 5/1999 |
| WO | WO 99/29307 | 6/1999 |

(56) References Cited

FOREIGN PATENT DOCUMENTS

| | | |
|---|---|---|
| WO | WO 99/59548 | 11/1999 |
| WO | WO 00/01443 | 1/2000 |
| WO | WO 00/04947 | 2/2000 |
| WO | WO 00/16741 | 3/2000 |
| WO | WO 00/27475 | 5/2000 |
| WO | WO 00/42914 | 7/2000 |
| WO | WO 00/12525 | 9/2000 |
| WO | WO 00/53257 | 9/2000 |
| WO | WO 00/61223 | 10/2000 |
| WO | WO 00/74773 | 12/2000 |
| WO | WO 01/10375 | 2/2001 |
| WO | WO 01/24871 | 4/2001 |
| WO | WO 01/41671 | 6/2001 |
| WO | WO 01/49367 | 7/2001 |
| WO | WO 01/52931 | 7/2001 |
| WO | WO 01/66183 | 9/2001 |
| WO | WO 01/83019 | 11/2001 |
| WO | WO 01/91854 | 12/2001 |
| WO | WO 01/93950 | 12/2001 |
| WO | WO 01/93951 | 12/2001 |
| WO | WO 02/10791 | 2/2002 |
| WO | WO 02/23953 | 3/2002 |
| WO | WO 02/053093 | 7/2002 |
| WO | WO 02/082968 | 10/2002 |
| WO | WO 02/089655 | 11/2002 |
| WO | WO 03/020365 | 3/2003 |
| WO | WO 02/089655 | 4/2003 |
| WO | WO 03/045493 | 6/2003 |
| WO | WO 2004/021858 | 3/2004 |
| WO | WO2004/021858 | 3/2004 |
| WO | WO 2004/043280 | 5/2004 |
| WO | WO 2004/059393 | 7/2004 |
| WO | WO 2004/066903 | 8/2004 |
| WO | WO 2004/070396 | 8/2004 |
| WO | WO 2004/080533 | 9/2004 |
| WO | WO 2004/091361 | 10/2004 |
| WO | WO 2004/096337 | 11/2004 |
| WO | WO 2004/069330 | 12/2004 |
| WO | WO 2004/112563 | 12/2004 |
| WO | WO 2004/112883 | 12/2004 |
| WO | WO 2005/007232 | 1/2005 |
| WO | WO 2005/007237 | 1/2005 |
| WO | WO 2005/009288 | 2/2005 |
| WO | WO 2005/023081 | 3/2005 |
| WO | WO 2005/037152 | 4/2005 |
| WO | WO 2005/041749 | 5/2005 |
| WO | WO 2005/087310 | 9/2005 |
| WO | WO 2005/106333 | 11/2005 |
| WO | WO 2005/114369 | 12/2005 |
| WO | WO 2005/016181 | 2/2006 |
| WO | WO 2006/018851 | 2/2006 |
| WO | WO 2006/035446 | 4/2006 |
| WO | WO2006045075 | 4/2006 |
| WO | WO 2006/073671 | 7/2006 |
| WO | WO 2006/087712 | 8/2006 |
| WO | WO 2006/087717 | 8/2006 |
| WO | WO 2006/097934 | 9/2006 |
| WO | WO 2006/097935 | 9/2006 |
| WO | WO 2006/102626 | 9/2006 |
| WO | WO 2006/119467 | 9/2006 |
| WO | WO 2006/129321 | 9/2006 |
| WO | WO 2006/118790 | 11/2006 |
| WO | WO 2006/119467 | 11/2006 |
| WO | WO 2007/080595 | 7/2007 |
| WO | WO 2007/091255 | 8/2007 |
| WO | WO 2007/096877 | 8/2007 |
| WO | WO 2007/096878 | 8/2007 |
| WO | WO 2008/007368 | 1/2008 |
| WO | WO 2008/117296 | 10/2008 |
| WO | WO 2008/139463 | 11/2008 |
| WO | WO 2011/092710 | 8/2011 |
| ZA | 97/06341 | 2/1998 |

OTHER PUBLICATIONS

An Office Action dated Nov. 15, 2010, which issued during the prosecution of Applicant's U.S. Appl. No. 11/336,099.

Jaremko, et al., "Advances toward the implantable artificial pancreas for treatment of diabetes", Diabetes Care, 21(3), Mar. 1998.

Lamb F.S. et al., "Cyclosporine augments reactivity of isolated blood vessels", Life Sciences, 40, pp. 2571-2578, Jun. 1987.

Johansson B. et al., "Static and dynamic components in the vascular myogenic response to passive changes in length as revealed by electrical and mechanical recordings from the rat portal vein", Circulation Research, 36, pp. 76-83, Jan. 1975.

Zelcer E. et al., "Spontaneous electrical activity in pressurized small mesenteric arteries" Blood Vessels, 19, pp. 301-310, Nov. 1982.

Schobel H.P. et al., "Preeclampsia—a state of sympathetic overactivity", New England Journal of Medicine, 335, pp. 148-1485, Nov. 1996.

Rosenpire A.J. et al., "Pulsed DC Electric Fields Couple to Natural NAD(P)H Oscillations in HT-1080 Fibrosarcoma Cells", Journal of Cell Science, 114(Pt. 8), pp. 1515-1520, Apr. 2001.

Gomis A. et al., "Oscillatory patterns of electrical activity in mouse pancreatic islets of Langerhans recorded in vivo", Pflugers Archiv European Journal of Physiology, Abstract vol. 432(3), pp. 510-515, Jul. 1996.

Soria B. et al., "Cytosolic calcium oscillations and insulin release in pancreatic islets of Langerhans", Diabetes Metab., 24(1), pp. 37-40, Feb. 1998.

Magnus G. et al., "Model of Beta-cell mitochondrial calcium handling and electrical activity, II. Mitochondrial variables", American Journal of Physiology, 274(4 Pt 1): C1174-1184, Apr. 1998.

Yamada, "Effects of drugs on electromechanical activities of the stomach and duodenum of conscious dogs", Nippon Heikatsukin Gakkai Zasshi. Feb. 1983;19(1):25-35. (abstract only).

Nadal A. et al., "Homologous and heterologous asynchronicity between identified alpha-, beta-, and delta-cells within intact islets of Langerhans in the mouse", Journal of Physiology, 517(Pt. 1), pp. 85-93, May 1999.

M D Robertson, et al, "The influence of the colon on postprandial glucagons-like peptide 1 (7-36) amide concentration in man", Journal of Endocrinology (1999) 161, 25-31, Apr. 1999.

J Schirra, et al, "Mechanisms of the antidiabetic action of subcutaneous glucagons-like peptide-1 (7-36) amide in non-insulin dependent diabetes mellitus", Journal of Endocrinology (1998) 156, 177-186, Jan. 1998.

T Vilsboll and Associates, Research design and methods, Diabetes, vol. 50, Mar. 2001, pp. 610-613.

Jeannie F. Todd, et al, "Subcutaneous glucagons-like peptide-1 improves postprandial glycaemic control over 3-week period in patients with early type 2 diabetes", Clinical Science (1998) 95, 325-329, Dec. 1998.

Daniel J. Drucker, "Development of glucagon-like peptide-1-based pharmaceuticals as therapeutic agents for the treatment of diabetes", Current Pharmaceutical Design, 2001, 7, 1399-1412, Sep. 2001.

Shemerovskii KA, "Effect of feeding on the activity of duodenal smooth muscle in dogs", Biull Ekap Biol Med. Oct. 1978; 86(10):394-7. (Abstract only).

U.S. Appl. No. 10/237,263.

An International Search Report and a Written Opinion, both date Oct. 28, 2008, which issued during the prosecution of Applicant's PCT/IL08/00646.

A Supplementary Partial European Search Report dated Feb. 20, 2009, which issued during the prosecution of Applicant's European Patent Application No. EP 02 72 7012.

Europe—European Patent Appln. No. EP 06 74 8690—European Exam. Report dated Apr. 7, 2009.

China—Chinese Patent Appln. No. 2004-80027283.3—Chinese Office Action dated Jul. 13, 2009.

Birmingham, A., "The arrangement of the muscular fibres of the stomach," Transactions of the Royal Academy of Medicine in Ireland, Springer London (1898).

Bilgutay, AM et al., "Gastro-intestinal Pacing: A New Concept in the Treatment of Ileus," Ann Surg. Sep. 1963; 158(3): 338-347.

International Search Report and the Written Opinion Dated Sep. 2, 2011 From the International Searching Authority Re. Application No. PCT/IL 11/00116.

(56) References Cited

OTHER PUBLICATIONS

Japanese Patent Office—Office Action dated Feb. 1, 3011 for Japanese Patent Appln. No. 2006-520981.
An Office Action dated Nov. 30, 2011, which issued during the prosecution of U.S. Appl. No. 11/336,099.
An Office Action dated Jul. 28, 2008, which issued during the prosecution of U.S. Appl. No. 11/336,099.
An Office Action dated Nov. 4, 2008, which issued during the prosecution of U.S. Appl. No. 11/336,099.
An Office Action dated Aug. 6, 2009, which issued during the prosecution of U.S. Appl. No. 11/336,099.
An Office Action dated May 20, 2011, which issued during the prosecution of U.S. Appl. No. 11/336,099.
Communication Pursuant to Article 94(3) EPC Dated Mar. 11, 2008 From the European Patent Office Re.: Application No. 06127216.7.
Communication Under Rule 71(3) EPC Dated Oct. 7, 2008 From the European Patent Office Re.: Application No. 06127216.7.
Notice of Allowance Dated Aug. 9, 2010 From the US Patent and Trademark Office Re.: U.S. Appl. No. 11/736,183.
Notice of Allowance Dated Feb. 15, 2011 From the US Patent and Trademark Office Re.: U.S. Appl. No. 11/932,963.
Notice of Allowance Dated Apr. 19, 2010 From the US Patent and Trademark Office Re.: U.S. Appl. No. 11/932,812.
Notice of Allowance Dated Mar. 29, 2012 From the US Patent and Trademark Office Re.: U.S. Appl. No. 11/736,183.
Notice of Reason for Rejection Dated Jun. 12, 2007 From the Japanese Patent Office Re.: Application No. 2000-502823.
Notice of Reasons for Rejection Dated Oct. 3, 2006 From the Japanese Patent Office Re.: Application No. 2000-502823.
Office Action Dated Nov. 29, 2004 From the Israeli Patent Office Re.: Application No. 133902.
Official Action Dated Mar. 8, 2010 From the US Patent and Trademark Office Re.: U.S. Appl. No. 11/736,183.
Official Action Dated Dec. 11, 2009 From the US Patent and Trademark Office Re.: U.S. Appl. No. 11/932,881.
Official Action Dated Sep. 15, 2009 From the US Patent and Trademark Office Re.: U.S. Appl. No. 11/736,183.
Official Action Dated Apr. 16, 2010 From the US Patent and Trademark Office Re.: U.S. Appl. No. 11/566,775.
Official Action Dated Jun. 22, 2010 From the US Patent and Trademark Office Re.: U.S. Appl. No. 11/736,183.
Official Action Dated Feb. 23, 2010 From the US Patent and Trademark Office Re.: U.S. Appl. No. 11/932,963.
Official Action Dated Jun. 26, 2009 From the US Patent and Trademark Office Re.: U.S. Appl. No. 11/932,812.
Official Action Dated Jun. 28, 2010 From the US Patent and Trademark Office Re.: U.S. Appl. No. 11/932,963.
Official Action Dated Aug. 31, 2011 From the US Patent and Trademark Office Re.: U.S. Appl. No. 11/736,183.
Requisition by the Examiner Dated Sep. 5, 2008 From the Canadian Intellectual Property Office Re.: Application No. 2,296,632.
Requisition by the Examiner Dated Jul. 14, 2004 From the Canadian Intellectual Property Office Re.: Application No. 2,296,632.
Requisition by the Examiner Dated Nov. 23, 2006 From the Canadian Intellectual Property Office Re.: Application No. 2,296,632.
Antoni et al. "Polarization Effects of Sinusoidal 50-Cycle Alternating Current on Membrane Potential of Mammalian Cardiac Fibres", Pfl?gers Archiv European Journal of Physiology, 314(4): 274-291, 1970. Abstract.
Devedeux et al. "Uterine Electromyography: A Critical Review", American Journal of Obstetric Gynecology, 169: 1636-1653, 1993.
Holst et al. "Nervous Contril of Pancreatic Endocrine Secretion in Pigs. I. Insulin and Glucagon Responses to Electrical Stimulation of the Vagus Nerves", Acta Physiologica Scandinavica, 111(1): 1-7, Jan. 1981. Abstract.
Holst et al. "Nervous Control of Pancreatic Endocrine Secretion in Pigs. II. The Effect of Pharmacological Blocking Agents on the Response to Vagal Stimulation", Acta Physiologica Scandinavica, 111(1): 9-14, Jan. 1981. Abstract.

Park et al. "Significant Cholinergic Role in Secretin-Stimulated Exocrine Secretion in Isolated Rat Pancreas", American Journal of Physiology, AJP—Gastrointestinal and Liver Physiology, 274(2): G413-G418, Feb. 1998.
Shmit et al. Physiology of Man, 1: 78, 1996.
Shuba et al. Physiology of Vessel Smooth Muscles, p. 11-15, 142, 1988.
Singh et al. "Effects of Islet Hormones on Nerve-Mediated and Acetylcholine-Evoked Secretory Responses in the Isolated Pancreas of Normal and Diabetic Rats", International Journal of Molecular Medicine, 1(3): 627-634, Mar. 1998. Abstract.
Van Riper et al. "Electrical Field Stimulation—Mediated Relaxation of a Rabbit Middle Cerebral Artery. Evidence of a Cholinergic Endothelium-Dependent Component", Circulation Research, 70: 1104-1112, 1992.
Zhou et al. "Prevention of Action Potentials During Extracellular Electrical Stimulation of Long Duration", Journal of Cardiovascular & Electrophysiology, 8(7): 779-789, 1997. Abstract.
Communication Pursuant to Article 94(3) EPC Dated Jun. 18, 2013 From the European Patent Office Re.: Application No. 04745004.4.
Official Action Dated Jun. 14, 2013 From the US Patent and Trademark Office Re. U.S. Appl. No. 10/526,708.
U.S. Appl. No. 90/008,688, filed Jun. 15, 2007, Ben Haim.
U.S. Appl. No. 90/008,689, Ben Haim.
U.S. Appl. No. 90/008,707, filed Jun. 7, 2007, Ben Haim.
U.S. Appl. No. 95/000,032, Ben Haim.
Advisory Action Before the Filing of an Appeal Brief Dated Mar. 22, 2012 From the US Patent and Trademark Office Re. U.S. Appl. No. 11/886,154.
Amended Request for Ex Parte Reexamination of US Patent No. 6,317,631 Dated Aug. 20, 2007 From the US Patent and Trademark Office Re.: U.S. Appl. No. 90/008,689.
Communication Pursuant to Article 94(3) EPC Dated Mar. 2, 2009 From the European Patent Office Re.: Application No. 05853465.2.
Communication Pursuant to Article 94(3) EPC Dated Aug. 11, 2010 From the European Patent Office Re. Application No. 99931435.4.
Communication Pursuant to Article 94(3) EPC Dated Aug. 26, 2011 From the European Patent Office Re. Application No. 06759102.4.
Communication Pursuant to Article 94(3) EPC Dated Aug. 26, 2011 From the European Patent Office Re.: Application No. 05853465.2.
Communication Pursuant to Article 94(3) EPC Dated Jan. 29, 2009 From the European Patent Office Re.: Application No. 04106247.2.
Communication Pursuant to Article 96(2) EPC Dated Mar. 2, 2007 From the European Patent Office Re.: Application No. 97929478.2.
Communication to Pursuant to Article 94(3) EPC Dated Mar. 4, 2009 From the European Search Report Re.: Application No. 06759102.4.
Corrected Notice of Allowability Dated Jul. 13, 2012 From the US Patent and Trademark Office Re. U.S. Appl. No. 11/933,168.
Corrected Notice of Allowability Dated Aug. 17, 2012 From the US Patent and Trademark Office Re. U.S. Appl. No. 11/931,724.
Inter Partes Reexamination Communication of Patent US 6,330,476 Dated Sep. 4, 2007 From the US Patent and Trademark Office Re.: U.S. Appl. No. 95/000,032.
International Preliminary Report on Patentability Dated Nov. 15, 2007 From the International Bureau of WIPO Re.: Application No. PCT/US2006/017281.
International Preliminary Report on Patentability Dated Jun. 21, 2007 From the International Bureau of WIPO Re.: Application No. Jun. 21, 2007.
International Preliminary Report on Patentability Dated Sep. 27, 2007 From the International Bureau of WIPO Re.: Application No. PCT/TL2006/000345.
International Search Report and the Written Opinion Dated May 12, 2006 From the International Searching Authority Re.: Application No. PCT/US05/44557.
International Search Report and the Written Opinion Dated Oct. 16, 2006 From the International Searching Authority Re.: Application No. PCT/US06/17281.
Invitation Pursuant to Rule 62a(1) EPC and Rule 63(1) EPC Dated May 5, 2010 From the European Patent Office Re.: Application No. 04719312.3.
Notice of Allowability Dated Jul. 13, 2012 From the US Patent and Trademark Office Re. U.S. Appl. No. 11/933,168.

(56) References Cited

OTHER PUBLICATIONS

Notice of Allowance Dated Jul. 11, 2012 From the US Patent and Trademark Office Re. U.S. Appl. No. 11/550,560.
Notice of Allowance Dated Jan. 14, 2011 From the US Patent and Trademark Office Re.: U.S. Appl. No. 11/550,560.
Notice of Allowance Dated May 15, 2012 From the US Patent and Trademark Office Re.: U.S. Appl. No. 11/932,149.
Notice of Allowance Dated Jul. 16, 2012 From the US Patent and Trademark Office Re. U.S. Appl. No. 11/931,889.
Notice of Allowance Dated May 16, 2012 From the US Patent and Trademark Office Re. U.S. Appl. No. 11/886,154.
Notice of Allowance Dated Jul. 18, 2012 From the US Patent and Trademark Office Re.: U.S. Appl. No. 11/931,724.
Notice of Allowance Dated Jun. 20, 2012 From the US Patent and Trademark Office Re. U.S. Appl. No. 11/933,168.
Notice of Allowance Dated Jun. 27, 2012 From the US Patent and Trademark Office Re.: U.S. Appl. No. 11/932,064.
Notice of Allowance Dated May 27, 2010 From the US Patent and Trademark Office Re.: U.S. Appl. No. 10/549,216.
Notice of Allowance Dated Dec. 28, 2010 From the US Patent and Trademark Office Re.: U.S. Appl. No. 11/932,064.
Notice of Allowance Dated Aug. 31, 2012 From the US Patent and Trademark Office Re. U.S. Appl. No. 12/910,943.
Notice of Non-Compliant Amendment Dated Jun. 1, 2011 From the US Patent and Trademark Office Re. U.S. Appl. No. 11/886,154.
Notice of Non-Compliant Amendment Dated Dec. 12, 2011 From the US Patent and Trademark Office Re. U.S. Appl. No. 11/792,811.
Notice of Non-Compliant Amendment Dated Jul. 15, 2011 From the US Patent and Trademark Office Re. U.S. Appl. No. 11/886,154.
Office Action Dated Jan. 8, 2010 From the State Intellectual Property Office (SIPO) of the People's Republic of China Re.: Application No. 200480012687.5 and Its Translation Into English.
Office Action Dated Oct. 12, 2004 From the Israeli Patent Office Re.: Application No. 128955.
Office Action Dated Dec. 15, 2008 From the State Intellectual Property Office (SIPO) of the People's Republic of China Re.: Application No. 200480012687.5 and Its Translation Into English.
Office Action Dated Jan. 18, 2012 From the State Intellectual Property Office (SIPO) of the People's Republic of China Re.: Application No. 200480012687.5 and Its Translation Into English.
Office Action Dated Nov. 25, 2010 From the State Intellectual Property Office (SIPO) of the People's Republic of China Re.: Application No. 200480012687.5 and its Translation into English.
Official Action Dated Aug. 1, 2007 From the US Patent and Trademark Office Re.: U.S. Appl. No. 90/008,312.
Official Action Dated Jun. 1, 2009 From the US Patent and Trademark Office Re.: U.S. Appl. No. 10/039,845.
Official Action Dated Dec. 2, 2009 From the US Patent and Trademark Office Re.: U.S. Appl. No. 11/932,149.
Official Action Dated Jan. 3, 2011 From the US Patent and Trademark Office Re.: U.S. Appl. No. 11/932,149.
Official Action Dated Jul. 3, 2012 From the US Patent and Trademark Office Re. U.S. Appl. No. 12/910,943.
Official Action Dated Nov. 3, 2009 From the US Patent and Trademark Office Re.: U.S. Appl. No. 11/931,724.
Official Action Dated Feb. 4, 2010 From the US Patent and Trademark Office Re.: U.S. Appl. No. 10/039,845.
Official Action Dated Jan. 4, 2012 From the US Patent and Trademark Office Re. U.S. Appl. No. 11/673,812.
Official Action Dated Dec. 5, 2008 From the US Patent and Trademark Office Re.: U.S. Appl. No. 11/550,560.
Official Action Dated Jan. 5, 2010 From the US Patent and Trademark Office Re.: U.S. Appl. No. 11/802,685.
Official Action Dated Nov. 5, 2009 From the US Patent and Trademark Office Re.: U.S. Appl. No. 10/549,216.
Official Action Dated Oct. 5, 2010 From the US Patent and Trademark Office Re.: U.S. Appl. No. 10/039,845.
Official Action Dated Jan. 6, 2010 From the US Patent and Trademark Office Re. U.S. Appl. No. 11/933,168.
Official Action Dated Jan. 6, 2011 From the US Patent and Trademark Office Re.: U.S. Appl. No. 11/931,724.
Official Action Dated Jan. 6, 2012 From the US Patent and Trademark Office Re. U.S. Appl. No. 11/933,168.
Official Action Dated Mar. 6, 2009 From the US Patent and Trademark Office Re.: U.S. Appl. No. 11/931,889.
Official Action Dated Mar. 6, 2009 From the US Patent and Trademark Office Re.: U.S. Appl. No. 11/932,064.
Official Action Dated Oct. 6, 2009 From the US Patent and Trademark Office Re.: U.S. Appl. No. 11/550,560.
Official Action Dated Nov. 8, 2011 From the US Patent and Trademark Office Re.: U.S. Appl. No. 11/931,889.
Official Action Dated Oct. 8, 2009 From the US Patent and Trademark Office Re.: U.S. Appl. No. 10/116,201.
Official Action Dated Aug. 9, 2011 From the US Patent and Trademark Office Re.: U.S. Appl. No. 11/932,149.
Official Action Dated May 10, 2012 From the US Patent and Trademark Office Re. U.S. Appl. No. 10/599,015.
Official Action Dated Oct. 10, 2008 From the US Patent and Trademark Office Re. U.S. Appl. No. 09/980,748.
Official Action Dated Jun. 11, 2010 From the US Patent and Trademark Office Re.: U.S. Appl. No. 11/550,560.
Official Action Dated Jun. 11, 2010 From the US Patent and Trademark Office Re.: U.S. Appl. No. 11/932,064.
Official Action Dated Oct. 11, 2011 From the US Patent and Trademark Office Re.: U.S. Appl. No. 11/919,491.
Official Action Dated Sep. 11, 2009 From the US Patent and Trademark Office Re. U.S. Appl. No. 09/980,748.
Official Action Dated Jun. 12, 2012 From the US Patent and Trademark Office Re. U.S. Appl. No. 11/573,722.
Official Action Dated May 12, 2011 From the US Patent and Trademark Office Re.: U.S. Appl. No. 10/039,845.
Official Action Dated Sep. 12, 2008 From the US Patent and Trademark Office Re.: U.S. Appl. No. 10/039,845.
Official Action Dated Jan. 13, 2011 From the US Patent and Trademark Office Re.: U.S. Appl. No. 11/931,889.
Official Action Dated May 13, 2011 From the US Patent and Trademark Office Re. U.S. Appl. No. 11/933,168.
Official Action Dated Oct. 13, 2010 From the US Patent and Trademark Office Re.: U.S. Appl. No. 11/919,491.
Official Action Dated Apr. 14, 2011 From the US Patent and Trademark Office Re.: U.S. Appl. No. 11/932,149.
Official Action Dated Sep. 14, 2009 From the US Patent and Trademark Office Re.: U.S. Appl. No. 11/931,889.
Official Action Dated Sep. 14, 2011 From the US Patent and Trademark Office Re. U.S. Appl. No. 11/886,154.
Official Action Dated Dec. 15, 2011 From the US Patent and Trademark Office Re. U.S. Appl. No. 12/910,943.
Official Action Dated Feb. 15, 2012 From the US Patent and Trademark Office Re. U.S. Appl. No. 11/802,685.
Official Action Dated Jul. 15, 2008 From the US Patent and Trademark Office Re.: U.S. Appl. No. 10/116,201.
Official Action Dated Feb. 17, 2012 From the US Patent and Trademark Office Re.: U.S. Appl. No. 11/932,149.
Official Action Dated Jun. 17, 2010 From the US Patent and Trademark Office Re.: U.S. Appl. No. 10/549,216.
Official Action Dated Jan. 18, 2012 From the US Patent and Trademark Office Re.: U.S. Appl. No. 11/886,154.
Official Action Dated Jul. 18, 2007 From the US Patent and Trademark Office Re.: U.S. Appl. No. 10/039,845.
Official Action Dated Dec. 20, 2011 From the US Patent and Trademark Office Re.: U.S. Appl. No. 10/039,845.
Official Action Dated Feb. 21, 2012 From the US Patent and Trademark Office Re. U.S. Appl. No. 10/116,201.
Official Action Dated Jul. 21, 2010 From the US Patent and Trademark Office Re.: U.S. Appl. No. 11/802,685.
Official Action Dated May 21, 2007 From the US Patent and Trademark Office Re. U.S. Appl. No. 09/980,748.
Official Action Dated May 21, 2010 From the US Patent and Trademark Office Re.: U.S. Appl. No. 10/116,201.
Official Action Dated Mar. 22, 2011 From the US Patent and Trademark Office Re.: U.S. Appl. No. 11/886,154.

(56) References Cited

OTHER PUBLICATIONS

Official Action Dated Dec. 23, 2010 From the US Patent and Trademark Office Re. U.S. Appl. No. 09/980,748.
Official Action Dated Jun. 23, 2009 From the US Patent and Trademark Office Re.: U.S. Appl. No. 10/549,216.
Official Action Dated Jan. 24, 2011 From the US Patent and Trademark Office Re.: U.S. Appl. No. 11/919,491.
Official Action Dated Jun. 26, 2008 From the US Patent and Trademark Office Re.: U.S. Appl. No. 11/536,794.
Official Action Dated Aug. 27, 2012 From the US Patent and Trademark Office Re.: U.S. Appl. No. 11/919,491.
Official Action Dated Apr. 28, 2011 From the US Patent and Trademark Office Re. U.S. Appl. No. 11/931,889.
Official Action Dated Apr. 28, 2011 From the US Patent and Trademark Office Re.: U.S. Appl. No. 11/931,889.
Official Action Dated Aug. 28, 2009 From the US Patent and Trademark Office Re.: U.S. Appl. No. 11/802,685.
Official Action Dated Aug. 28, 2009 From the US Patent and Trademark Office Re.: U.S. Appl. No. 11/932,064.
Official Action Dated Feb. 28, 2008 From the US Patent and Trademark Office Re. U.S. Appl. No. 09/980,748.
Official Action Dated Jun. 28, 2010 From the US Patent and Trademark Office Re.: U.S. Appl. No. 11/931,889.
Official Action Dated Apr. 29, 2009 From the US Patent and Trademark Office Re. U.S. Appl. No. 09/980,748.
Official Action Dated Sep. 29, 2010 From the US Patent and Trademark Office Re. U.S. Appl. No. 11/933,168.
Official Action Dated Apr. 30, 2010 From the US Patent and Trademark Office Re.: U.S. Appl. No. 11/931,724.
Official Action Dated Apr. 30, 2010 From the US Patent and Trademark Office Re.: U.S. Appl. No. 11/932,149.
Official Action Dated Aug. 30, 2006 From the US Patent and Trademark Office Re. U.S. Appl. No. 09/980,748.
Official Action Dated Aug. 30, 2012 From the US Patent and Trademark Office Re. U.S. Appl. No. 12/160,616.
Official Action Dated Aug. 31, 2007 From the US Patent and Trademark Office Re.: U.S. Appl. No. 11/536,794.
Official Action Dated Aug. 31, 2010 From the US Patent and Trademark Office Re.: U.S. Appl. No. 11/550,560.
Official Action Dated Mar. 31, 2011 From the US Patent and Trademark Office Re. U.S. Appl. No. 11/673,812.
Pre-Appeal Brief Request for Review Dated Aug. 9, 2011 From the US Patent and Trademark Office Re. U.S. Appl. No. 11/933,168.
Request for Ex Parte Reexamination of Patent No. 6,363,279—IDS Submitted Dec. 31, 2007 From the US Patent and Trademark Office Re.: U.S. Appl. No. 90/008,688.
Request for Ex Parte Reexamination of Patent No. 6,363,279—Notice of Intent to Issue Reexamination Certificate Dated Mar. 18, 2009 From the US Patent and Trademark Office Re.: U.S. Appl. No. 90/008,688.
Request for Ex Parte Reexamination of Patent No. 6,363,279—Official Action Dated Jun. 20, 2008 From the US Patent and Trademark Office Re.: U.S. Appl. No. 90/008,688.
Request for Ex Parte Reexamination of Patent No. 6,363,279—Order Granting Request Dated Nov. 5, 2007 From the US Patent and Trademark Office Re.: U.S. Appl. No. 90/008,688.
Request for Ex Parte Reexamination of Patent No. 6,363,279 Dated Jun. 8, 2007 From the US Patent and Trademark Office Re.: U.S. Appl. No. 90/008,688.
Request for Ex Parte Reexamination of Patent No. 6,363,279, Response to Official Action Dated Jun. 20, 2008 Submitted Aug. 20, 2008 From the US Patent and Trademark Office Re.: U.S. Appl. No. 90/008,688.
Request for Ex Parte Reexamination of US Patent No. 6,236,887—IDS Submitted Oct. 17, 2007 From the US Patent and Trademark Office Re.: U.S. Appl. No. 90/008,707.
Request for Ex Parte Reexamination of US Patent No. 6,236,887—IDS Submitted Sep. 29, 2008 From the US Patent and Trademark Office Re.: U.S. Appl. No. 90/008,707.
Request for Ex Parte Reexamination of US Patent No. 6,236,887—Notice of Intent to issue Ex Parte Examination Certificate Dated Mar. 19, 2009 From the US Patent and Trademark Office Re.: U.S. Appl. No. 90/008,707.
Request for Ex Parte Reexamination of US Patent No. 6,236,887—Official Action and IDS Considered Dated Jun. 20, 2008 From the US Patent and Trademark Office Re.: U.S. Appl. No. 90/008,707.
Request for Ex Parte Reexamination of US Patent No. 6,236,887—Official Action Granting Request for Ex Parte Examination Dated Aug. 17, 2007 From the US Patent and Trademark Office Re.: U.S. Appl. No. 90/008,707.
Request for Ex Parte Reexamination of US Patent No. 6,236,887 Dated Jun. 13, 2007 From the US Patent and Trademark Office Re.: U.S. Appl. No. 90/008,707.
Request for Ex Parte Reexamination of US Patent No. 6,298,268—Certificate of Reexamination Issued Mar. 7, 2006, U.S. Appl. No. 90/006,788.
Request for Ex Parte Reexamination of US Patent No. 6,298,268—IDS Considered Feb. 22, 2005, U.S. Appl. No. 90/006,788.
Request for Ex Parte Reexamination of US Patent No. 6,298,268—Notice of Intent to Issue Certificate of Reexamination Dated Mar. 29, 2005, U.S. Appl. No. 90/006,788.
Request for Ex Parte Reexamination of US Patent No. 6,298,268 Dated Oct. 10, 2003, U.S. Appl. No. 90/006,788.
Request for Ex Parte Reexamination of US Patent No. 6,298,268 Order Granting Request for Ex Parte Reexamination Dated Dec. 19, 2003, U.S. Appl. No. 90/006,788.
Request for Ex Parte Reexamination of US Patent No. 6,317,631—Amendment in Response to Official Action Dated Jun. 20, 2008, Filed Aug. 20, 2008 From the US Patent and Trademark Office Re.: U.S. Appl. No. 90/008,689.
Request for Ex Parte Reexamination of US Patent No. 6,317,631—IDS Dated Sep. 26, 2008 From the US Patent and Trademark Office Re.: U.S. Appl. No. 90/008,689.
Request for Ex Parte Reexamination of US Patent No. 6,317,631—IDS Dated Dec. 31, 2007 From the US Patent and Trademark Office Re.: U.S. Appl. No. 90/008,689.
Request for Ex Parte Reexamination of US Patent No. 6,317,631—Notice of intent to Issue Certificate of Reexamination Dated Mar. 18, 2009 From the US Patent and Trademark Office Re.: U.S. Appl. No. 90/008,689.
Request for Ex Parte Reexamination of US Patent No. 6,317,631—Official Action Dated Jun. 20, 2008, U.S. Appl. No. 90/008,689.
Request for Ex Parte Reexamination of US Patent No. 6,317,631—Order Granting Reexamination Dated Nov. 5, 2007, U.S. Appl. No. 90/008,689.
Request for Ex Parte Reexamination of US Patent No. 6,317,631—IDS Dated Jun. 8, 2007, U.S. Appl. No. 90/008,689.
Request for Ex Parte Reexamination of US Patent No. 6,330,476—IDS Dated May 31, 2006.
Request for Ex Parte Reexamination of US Patent No. 6,330,476—Comments by 3rd Party Requestor, Response Thereto and Official Action Issued Jul. 16, 2008, U.S. Appl. No. 95/000,032.
Request for Ex Parte Reexamination of US Patent No. 6,330,476—Communication of Right to Appeal dated Jul. 16, 2008, U.S. Appl. No. 95/000,032.
Request for Ex Parte Reexamination of US Patent No. 6,330,476—IDS Filed May 4, 2007, U.S. Appl. No. 95/000,032.
Request for Ex Parte Reexamination of US Patent No. 6,330,476—Official Action by USPTO issued Mar. 23, 2004, U.S. Appl. No. 95/000,032.
Request for Ex Parte Reexamination of US Patent No. 6,330,476—Order Granting Request for Reexamination Dated Mar. 23, 2004 From the US Patent and Trademark Office Re.: U.S. Appl. No. 95/000,032.
Request for Ex Parte Reexamination of US Patent No. 6,330,476 Dated Dec. 31, 2003 From the US Patent and Trademark Office Re.: U.S. Appl. No. 95/000,032.
Request for Ex Parte Reexamination of US Patent No. 6,463,324—Amendment in Response to Official Action Dated Aug. 1, 2007 Filed Oct. 1, 2007 From the US Patent and Trademark Office Re.: U.S. Appl. No. 90/008,312.

(56) References Cited

OTHER PUBLICATIONS

Request for Ex Parte Reexamination of US Patent No. 6,463,324—Certificate of Reexamination Dated Apr. 29, 2008 From the US Patent and Trademark Office Re.: U.S. Appl. No. 90/008,312.
Request for Ex Parte Reexamination of US Patent No. 6,463,324—Official Action—Notice of Intent to Reexamine Dated Jan. 24, 2008 From the US Patent and Trademark Office Re.: U.S. Appl. No. 90/008,312.
Request for Ex Parte Reexamination of US Patent No. 6,463,324—Official Action Dated Aug. 1, 2007 From the US Patent and Trademark Office Re.: U.S. Appl. No. 90/008,312.
Request for Ex Parte Reexamination of US Patent No. 6,463,324—Official Action, Interview Summary and References Considered Dated Nov. 6, 2007 From the US Patent and Trademark Office Re.: U.S. Appl. No. 90/008,312.
Request for Ex Parte Reexamination of US Patent No. 6,463,324 Dated Nov. 1, 2006 From the US Patent and Trademark Office Re.: U.S. Appl. No. 90/008,312.
Summons to Attend Oral Proceedings Pursuant to Rule 115(1) Epc Dated Dec. 22, 2008 From the European Patent Office Re.: Application No. 97929480.8.
Supplemental Response Dated Apr. 18, 2011 to Response of Apr. 10, 2011 to Official Action of Jan. 6, 2011 From the US Patent and Trademark Office Re.: U.S. Appl. No. 11/931,724.
Supplementary European Search Report and the European Search Opinion Dated Nov. 28, 2008 From the European Patent Office Re.: Application No. 006759102.4.
Supplementary European Search Report and the European Search Opinion Dated Nov. 28, 2008 From the European Patent Office Re.: Application No. 05853465.2.
Supplementary Partial European Search Report Dated Nov. 4, 2010 From the European Patent Office Re. Application No. 04719312.3.
Translation of Notice of Reasons for Rejection Dated Jul. 18, 2006 From the Japanese Patent Office Re.: Application No. 09-529637.
Translation of Notice of Reasons for Rejection Dated Apr. 27, 2010 From the Japanese Patent Office Re.: Application No. 2007-206282.
Translation of Office Action Dated Aug. 3, 2011 From the State Intellectual Property Office (SIPO) of the People's Republic of China Re.: Application No. 200480012687.5.
Translation of Office Action Dated Apr. 20, 2011 From the State Intellectual Property Office (SIPO) of the People's Republic of China Re.: Application No. 200480012687.5.
USPTO Public Print Out of Interference File Content of Interference Dated Apr. 4, 2011 From the US Patent and Trademark Office Re. Interference No. 105,765.
USPTO Public Print Out of Interference File Content of Interference Dated Apr. 4, 2011 From the US Patent and Trademark Office Re. Interference No. 105,768.
Adeghate et al. "Effect of Electrical Field Stimulation on Insulin and Glucagon Secretion From the Pancreas of Normal and Diabetic Rats", Hormone and Metabolic Research, 33(5): 281-289, May 2001. Abstract.
Bergsten et al. "Synchronous Oscillations of Cytoplasmic Ca2+ and Insulin Release in Glucose-Stimulated Pancreatic Islets", The Journal of Biological Chemistry, 269(12): 8749-8753, Mar. 25, 1994.
Blank et al. "Initial Interactions in Electromagnetic Field-Induced Biosynthesis", Journal of Cellular Physiology, 199: 359-363, 2004.
Burfeind et al "The Effects of Mechanical Cardiac Stabilization on Left Ventricular Performance", European Journal of Cardio-Thoracic Surgery, 14: 285-289, 1998.
Devedeux et al. "Uterine Electromyography: A Critical Review", American Journal of Obstetric Gynecology, 169(6): 1636-1653, 1993.
Erol-Yilmaz et al. "Reversed Remodelling of Dilated Left Sided Cardiomyopathy After Upgrading from VVIR to VVIR Biventricular Pacing", Europace, 4: 445-449, 2002.
Fromer et al. "Ultrarapid Subthreshold Stimulation for Termination of Atriventricular Node Reentrant Tachycardia", Journal of the American College Cardiology, 20: 879-883, 1992.

Gardner "Natriuretic Peptides: Markers or Modulators of Cardiac Hypertrophy?", Trends in Endocrinology and Metabolism, 14(9): 411-416, Nov. 2003.
Gilmour Jr. et al. "Dynamics of Circus Movement Re-Entry Across Canine Purkinje Fibre-Muscle Junctions", The Journal of Physiology, 476(3): 473-485, 1994.
Gilmour Jr. et al. "Overdrive Suppression of Conduction at the Canine Purkinje-Muscle Junction", Circulation, 76(6): 1388-1396, 1987.
Gold et al. "Evidence That Glucose 'Marks' Beta Cells Resulting in Preferential Release of Newly Synthesized Insulin", Science, 218(4567): 56-58, Oct. 1, 1982. Abstract.
Gussoni et al. "Dystrophin Expression in the MDX Mouse Restored by Stem Cell Transplantation", Nature, 401(6751): 390-394, 1999.
Hammond et al. "Motor Innervation of the Cricopharyngeus Muscle by the Recurrent Lanryngeal Nerve", Journal of Applied Physiology, JAP, 83: 89-94, 1997.
Highfill et al. "Large-Scale Production of Murine Bone Marrow Cells in an Airlift Packed Bed Bioreactor", Biotechnology and Bioengineering, 50(5): 514-520, 1996.
Hinke et al. "Dipeptidyl Peptidase IV (DPIV/CD26) Degradation of Glucagon. Characterization of Glucagon Degradation Products and DPIV-Resistant Analogs", The Journal of Biological Chemistry, 275(6): 3827-3834, Feb. 11, 2000.
Holst et al. "Nervous Control of Pancreatic Endocrine Secretion in Pigs. I. Insulin and Glucagon Responses to Electrical Stimulation of the Vagus Nerves", Acta Physiologica Scandinavica, 111(1): 1-7, Jan. 1981. Abstract.
Holst et al. "Nervous Control of Pancreatic Endocrine Secretion in Pigs. II. The Effect of Pharmacological Blocking Agents on the Response to Vagal Stimulation", Acta Physiologica Scandinavica, 111(1): 9-14, 1981. Abstract.
Horner et al. "Electrode for Recording Direction of Activation, Conduction Velocity and Monophasic Action Potential of Myocardium", American Journal of Physiology, 272(4): H1917-H1927, 1997. Abstract.
Kurose et al. "Glucagon, Insulin and Somatostatin Secretion in Response to Sympathetic Neural Activation in Streptozotocin-Induced Diabetic Rats. A Study With the Isolated Perfused Rat Pancreas In Vitro", Diabetologia, 35(11): 1035-1041, Nov. 1992. Abstract.
Luiken et al. "Contraction-Induced Fatty Acid Translocase/CD36 Translocation in Rat Cardiac Myocytes Is Mediated Through AMP-Activated Protein Kinase Signaling", Diabetes, 52: 1627-1634, 2003.
Meurer et al. "Properties of Native and in Vitro Glycosylated Forms of the Glucogan-Like Peptide-1 Receptor Antagonist Exendin(9-39)", Metabolism: Clinical and Experimental, 48(6): 716-724, Jun. 1999. Abstract.
Misler et al. "Electrophysiology of Stimulus-Secretion Coupling in Human Beta-Cells", Diabetes, 41(10): 1221-1228, Oct. 1992. Abstract.
Ohinata et al. "Proadrenomedullin N-Terminal 20 Peptide (PAMP) Elevates Blood Glucose Levels Via Bombesin Receptor in Mice", FEBS Letters, 473(2): 207-211, May 2000. Abstract.
Palti et al. "Islets of Langerhans Generate Wavelike Electric Activity Modulated by Glucose Concentration", Diabetes, 45(5): 595-601, May 1996. Abstract.
Patterson et al. "Therapeutic Angiogenesis: The New Electrophysiology?", Circulation, 99(20): 2614-2616, 1999.
Porksen et al. "Section 6: Pulsatile and Phasic Insulin Release in Normal and Diabetic Man. Pulsatile Insulin Secretion: Detection, Regulation, and Role in Diabetes", Diabetes, 51(Suppl. 1): S245-S254, Feb. 2002.
Rivera et al. "Regulation of Protein Secretion Through Controlled Aggregation in the Endoplasmic Reticulum", Science, 287(5454): 826-830, Feb. 4, 2000. Abstract.
Sakuma et al. "A Model Analysis of Aftereffects of High-Intensity DC Stimulation on Action Potential of Ventricular Muscle", IEEE Transactions on Biomedical Engineering, 45(2): 258-267, 1998.
San Mauro et al. "Nerves of the Heart: A Comprehensive Review With a Clinical Point of View", Neuroanatomy, 8: 28-31, 2009.

(56) References Cited

OTHER PUBLICATIONS

Schirra et al. "Exendin(9-39) Amide is an Antagonist of Glucagon-Like Peptide-1(7-36) Amide in Humans", Journal of Clinical Investigation, 101(7): 1421-1430, Apr. 1998.
Serre et al. "Exendin-(9-39) is an Inverse Agonist of the Murine Glucagon-Like Peptide-1 Receptor: Implications for Basal Intracellular Cyclic Adenosine 3',5'- Monophosphate Levels and ?-Cells Glucose Competence", Endocrinology, 139(11): 4448-4454, 1998.
Shah et al. "Impact of Lack of Suppression of Glucagon on Glucose Tolerance in Humans", American Journal of Physiology, AJP—Endocrinology and Metabolism, 277(2 Pt. 1): E283-E290, 1999.
Shmit et al. "Physiology of Man", Moscow Medicine, Mir, 1: 78, 1996.
Shuba et al. "Physiology of Vessel Smooth Muscles", Kiev Naukova Dumka, 142: 11-15, 142, 1988.
Sukhorukov et al. "The Effect of Electrical Deformation Forces on the Electropermeabilization of Erythrocyte Membranes in Low-and High-Conductivity Media", The Journal of Membrane Biology, 163(3): 235-245, 1998. Abstract.
Sutton et al. "The Foundation of Cardiac Pacing, Part I: An Illustrated Practical Guide to Basic Pacing", The Bakken Research Center Series, Chap.4: 50-59, 1991.
Sutton et al. "What is a Pacemaker?", The Foundations of Cardiac Pacing, Part I: An Illustrated Practical Guide to Basic Pacing, Chap. 4.5: 73-74, 1991.
Swerdlow et al. "Cardiovascular Collapse Caused by Electrocardiographically Silent 60-Hz Intracardiac Leakage Current: Implications for Electrical Safety", Circulation, 99: 2559-2564, 1999.
Valdeolmillos et al. "In Vivo Synchronous Membrane Potential Oscillations in Mouse Pancreatic Beta-Cells: Lack of Co-Ordination Between Islets", Journal of Physiology, 493(1): 9-18, 1996.
Van Riper et al. "Electrical Field Stimulation-Mediated Relaxation of a Rabbit Middle Cerebral Artery. Evidence of a Cholinergic Endothelium-Dependent Component", Circulation Research, 70(6): 1104-1112, Jun. 1992.
Wang et al. "Islet Amyloid Polypeptide Tonally Inhibits Beta-, Alpha-, and Delta-Cell Secretion in Isolated Rat Pancreatic Islets", American Journal of Physiology, AJP—Endocrinology and Metabolism, 276(1 Pt.1): E19-E24, 1999.
Webster "Electrodes, Leads, and Biocompatibility", Design of Cardiac Pacemakers, IEEE Press, p. 141-144, 1995.
Wright et al. "Structure of Fab hGR-2 F6, A Competitive Antagonist of the Glucagon Receptor", Acta Crystallographica, Section D, Biological Crystallography, 56(Pt.5): 573-580, May 2000. Abstract.
Xue et al. "Neural-Network-Based Adaptive Matched Filtering for QRS Detection", IEEE Transactions on Biomedical Engineering, 39(4): 317-329, 1992. Abstract.
Yonemura et al. "Amelioration of Diabetes Mellitus in Partially Depancreatized Rats by Poly(ADP-Ribose) Synthetase Inhibitors. Evidence of Islet B-Cell Regeneration", Diabetes, 33(4): 401-404, Apr. 1984. Abstract.
Official Action Dated Oct. 30, 2012 From the US Patent and Trademark Office Re. U.S. Appl. No. 12/160,616.
Official Action Dated Jul. 2, 2013 From the US Patent and Trademark Office Re.: U.S. Appl. No. 10/570,576.
Communication Pursuant to Article 94(3) EPC Dated Oct. 10, 2011 From the European Patent Office Re. Application No. 07110023.4.
Communication Pursuant to Article 94(3) EPC Dated Jan. 27, 2010 From the European Patent Office Re. Application No. 07110023.4.
Communication Pursuant to Article 94(3) EPC Dated Jan. 28, 2009 From the European Patent Office Re.: Application No. 03794043.4.
Communication Pursuant to Article 94(3) EPC Dated Aug. 30, 2012 From the European Patent Office Re. Application No. 07110023.4.
European Search Report and the European Search Opinion Dated Jul. 27, 2007 From the European Patent Office Re. Application No. 07110023.4.
Examination Report Dated Mar. 13, 2012 From the Government of India, Patent Office, Intellectual Property Building Re. Application No. 2988/CHENP/2007.
Examination Report Dated May 18, 2011 From the Government of India, Patent Office, Intellectual Property Building Re. Application No. 2988/CHENP/2007.
Examination Report Dated Jun. 26, 2009 From the Government of India, Patent Office Re.: Application No. 1161/CHENP/2006.
Examination Report Dated Nov. 30, 2010 From the Government of India, Patent Office Re. Application No. 212/MUMNP/2006.
International Preliminary Report on Patentability Dated Dec. 1, 2004 From the International Preliminary Examining Authority Re.: Application No. PCT/IL03/00736.
International Preliminary Report on Patentability Dated Aug. 30, 2007 From the International Bureau of WIPO Re.: Application No. PCT/IL2006/000204.
International Search Report and the Written Opinion Dated Sep. 29, 2006 From the International Searching Authority Re.: Application No. PCT/IL06/00204.
International Search Report Dated Sep. 13, 2004 From the International Searching Authority Re.: Application No. PCT/IL03/00736.
Notice of Allowance Dated Sep. 7, 2006 From the US Patent and Trademark Office Re.: U.S. Appl. No. 10/804,560.
Notice of Allowance Dated May 11, 2011 From the US Patent and Trademark Office Re.: U.S. Appl. No. 10/237,263.
Notice of Allowance Dated Nov. 29, 2010 From the US Patent and Trademark Office Re. U.S. Appl. No. 10/237,263.
Notice of Allowance Dated Aug. 31, 2012 From the US Patent and Trademark Office Re. U.S. Appl. No. 11/318,845.
Notification of Reasons of Rejection Dated Sep. 29, 2008 From the Japanese Patent Office Re.: Application No. 2004-534013 and Its Translation Into English.
Office Action Dated Dec. 4, 2009 From the State Intellectual Property Office of the People's Republic of China Re.: Application No. 03824661.9 and Its Translation Into English.
Office Action Dated Nov. 7, 2008 From the State Intellectual Property Office of the People's Republic of China Re.: Application No. 03824661.9 and Its Translation Into English.
Office Action Dated May 8, 2009 From the State Intellectual Property Office of the People's Republic of China Re.: Application No. 03824661.9 and Its Translation Into English.
Office Action Dated Apr. 13, 2010 From the State Intellectual Property Office of the People's Republic of China Re. Application No. 200480027293.3 and Its Translation Into English.
Official Action Dated Nov. 1, 2011 From the US Patent and Trademark Office Re.: U.S. Appl. No. 10/804,560.
Official Action Dated Oct. 1, 2009 From the US Patent and Trademark Office Re.: U.S. Appl. No. 10/237,263.
Official Action Dated Dec. 3, 2009 From the US Patent and Trademark Office Re.: U.S. Appl. No. 11/318,845.
Official Action Dated Sep. 3, 2009 From the US Patent and Trademark Office Re.: U.S. Appl. No. 10/804,560.
Official Action Dated Dec. 4, 2009 From the US Patent and Trademark Office Re.: U.S. Appl. No. 11/884,389.
Official Action Dated Jan. 4, 2011 From the US Patent and Trademark Office Re.: U.S. Appl. No. 11/318,845.
Official Action Dated May 5, 2010 From the US Patent and Trademark Office Re.: U.S. Appl. No. 11/884,389.
Official Action Dated Dec. 6, 2011 From the US Patent and Trademark Office Re.: U.S. Appl. No. 11/318,845.
Official Action Dated Aug. 8, 2007 From the US Patent and Trademark Office Re.: U.S. Appl. No. 10/804,560.
Official Action Dated Dec. 8, 2008 From the US Patent and Trademark Office Re.: U.S. Appl. No. 10/804,560.
Official Action Dated Jun. 8, 2011 From the US Patent and Trademark Office Re. U.S. Appl. No. 11/566,775.
Official Action Dated Oct. 8, 2009 From the US Patent and Trademark Office Re. U.S. Appl. No. 11/566,775.
Official Action Dated Dec. 9, 2010 From the US Patent and Trademark Office Re. U.S. Appl. No. 11/566,775.
Official Action Dated Jul. 9, 2007 From the US Patent and Trademark Office Re.: U.S. Appl. No. 10/237,263.
Official Action Dated Mar. 10, 2011 From the US Patent and Trademark Office Re.: U.S. Appl. No. 11/884,389.
Official Action Dated May 11, 2011 From the US Patent and Trademark Office Re.: U.S. Appl. No. 10/804,560.

(56) References Cited

OTHER PUBLICATIONS

Official Action Dated Sep. 11, 2008 From the US Patent and Trademark Office Re.: U.S. Appl. No. 10/237,263.
Official Action Dated Oct. 13, 2010 From the US Patent and Trademark Office Re.: U.S. Appl. No. 10/237,263.
Official Action Dated Sep. 13, 2007 From the US Patent and Trademark Office Re.: U.S. Appl. No. 10/237,263.
Official Action Dated Dec. 14, 2010 From the US Patent and Trademark Office Re.: U.S. Appl. No. 11/884,389.
Official Action Dated Jul. 14, 2008 From the US Patent and Trademark Office Re.: U.S. Appl. No. 10/526,708.
Official Action Dated Dec. 15, 2010 From the US Patent and Trademark Office Re.: U.S. Appl. No. 10/804,560.
Official Action Dated Apr. 16, 2010 From the US Patent and Trademark Office Re. U.S. Appl. No. 11/566,775.
Official Action Dated Apr. 18, 2007 From the US Patent and Trademark Office Re.: U.S. Appl. No. 10/804,560.
Official Action Dated Aug. 18, 2009 From the US Patent and Trademark Office Re.: U.S. Appl. No. 10/570,576.
Official Action Dated Jul. 19, 2007 From the US Patent and Trademark Office Re.: U.S. Appl. No. 10/526,708.
Official Action Dated Jun. 19, 2008 From the US Patent and Trademark Office Re.: U.S. Appl. No. 10/237,263.
Official Action Dated Jan. 21, 2009 From the US Patent and Trademark Office Re.: U.S. Appl. No. 10/570,576.
Official Action Dated Dec. 24, 2008 From the US Patent and Trademark Office Re.: U.S. Appl. No. 10/237,263.
Official Action Dated Feb. 24, 2009 From the US Patent and Trademark Office Re.: U.S. Appl. No. 11/318,845.
Official Action Dated Mar. 25, 2010 From the US Patent and Trademark Office Re.: U.S. Appl. No. 10/804,560.
Official Action Dated Sep. 25, 2009 From the US Patent and Trademark Office Re.: U.S. Appl. No. 10/526,708.
Official Action Dated May 26, 2010 From the US Patent and Trademark Office Re.: U.S. Appl. No. 11/318,845.
Official Action Dated Apr. 27, 2010 From the US Patent and Trademark Office Re.: U.S. Appl. No. 10/570,576.
Official Action Dated Mar. 27, 2008 From the US Patent and Trademark Office Re.: U.S. Appl. No. 10/804,560.
Official Action Dated Sep. 27, 2010 From the US Patent and Trademark Office Re.: U.S. Appl. No. 10/804,560.
Official Action Dated Jul. 31, 2008 From the US Patent and Trademark Office Re.: U.S. Appl. No. 11/318,845.
Official Action Dated Mar. 31, 2010 From the US Patent and Trademark Office Re.: U.S. Appl. No. 10/237,263.
Response Dated Aug. 1, 2010 to Notification of Reasons of Rejection of Apr. 12, 2010 From the Japanese Patent Office Re.: Application No. 2006-525265.
Response Dated Aug. 2, 2010 to Official Action of Mar. 31, 2010 From the US Patent and Trademark Office Re.: U.S. Appl. No. 10/237,263.
Response Dated Mar. 3, 2010 to Official Action of Sep. 3, 2009 From the US Patent and Trademark Office Re.: U.S. Appl. No. 10/804,560.
Response Dated May 3, 2010 to Official Action of Dec. 3, 2009 From the US Patent and Trademark Office Re.: U.S. Appl. No. 11/318,845.
Response Dated Feb. 4, 2010 to Official Action of Dec. 4, 2009 From the US Patent and Trademark Office Re.: U.S. Appl. No. 11/884,389.
Response Dated Jan. 5, 2010 to Official Action of Oct. 8, 2009 From the US Patent and Trademark Office Re. U.S. Appl. No. 11/566,775.
Response Dated Oct. 5, 2010 to Official Action of May 5, 2010 From the US Patent and Trademark Office Re.: U.S. Appl. No. 11/884,389.
Response Dated Jun. 6, 2011 to Official Action of Jan. 4, 2011 From the US Patent and Trademark Office Re.: U.S. Appl. No. 11/318,845.
Response Dated May 7, 2007 to Examination Report of Mar. 2, 2007 From the Government of India, Patent Office Re.: Application No. 533/CHENP/2005.
Response Dated Feb. 8, 2010 to Official Action Dated Oct. 1, 2009 From the US Patent and Trademark Office Re.: U.S. Appl. No. 10/237,263.

Response Dated Oct. 10, 2011 to Official Action Dated May 11, 2011 From the US Patent and Trademark Office Re.: U.S. Appl. No. 10/804,560.
Response Dated Dec. 12, 2011 to Communication Pursuant to Article 94(3) EPC of Oct. 10, 2011 From the European Patent Office Re. Application No. 07110023.4.
Response Dated May 16, 2011 to Official Action of Dec. 14, 2010 From the US Patent and Trademark Office Re.: U.S. Appl. No. 11/884,389.
Response Dated Feb. 18, 2010 to Official Action of Aug. 18, 2009 From the US Patent and Trademark Office Re.: U.S. Appl. No. 10/570,576.
Response Dated Aug. 24, 2010 to the Supplementary European Search Report of Jun. 7, 2010 From the European Patent Office Re. Application No. 04770468.9.
Response Dated Feb. 24, 2011 to Notice of Allowance of Nov. 29, 2010 From the US Patent and Trademark Office Re. U.S. Appl. No. 10/237,263.
Response Dated Jan. 25, 2007 to Examination Report of Jul. 7, 2006 From the Government of India, Patent Office Re.: Application No. 533/CHENP/2005.
Response Dated Mar. 25, 2010 to Official Action of Sep. 25, 2009 From the US Patent and Trademark Office Re.: U.S. Appl. No. 10/526,708.
Response Dated Aug. 26, 2010 to Official Action of May 26, 2010 From the US Patent and Trademark Office Re.: U.S. Appl. No. 11/318,845.
Response Dated Aug. 26, 2011 to the Summons to Oral Proceedings of Jul. 4, 2011 From the European Patent Office Re.: Application No. 03794043.4.
Response Dated Jul. 26, 2010 to Official Action of Mar. 25, 2010 From the US Patent and Trademark Office Re.: U.S. Appl. No. 10/804,560.
Response Dated Jan. 27, 2011 to Official Action of Sep. 27, 2010 From the US Patent and Trademark Office Re.: U.S. Appl. No. 10/804,560.
Response Dated Jul. 27, 2010 to Communication Pursuant to Article 94(3) EPC of Jan. 27, 2010 From the European Patent Office Re. Application No. 07110023.4.
Response Dated Sep. 27, 2010 to Official Action of Apr. 27, 2010 From the US Patent and Trademark Office Re.: U.S. Appl. No. 10/570,576.
Response Dated Aug. 28, 2011 to Summons to Attend Oral Proceedings Pursuant to Rule 115(1) EPC of Jul. 4, 2011 From the European Patent Office Re.: Application No. 03794043.4.
Summons to Attend Oral Proceedings Pursuant to Rule 115(1) EPC Dated Jul. 4, 2011 From the European Patent Office Re.: Application No. 03794043.4.
Supplemental Response Dated Mar. 28, 2010 After an Interview of Mar. 4, 2010 From the US Patent and Trademark Office Re. U.S. Appl. No. 10/237,263.
Supplementary European Search Report and the European Search Opinion Dated Sep. 25, 2012 From the European Patent Office Re.: Application No. 06711186.4.
Supplementary European Search Report Dated Jun. 7, 2010 From the European Patent Office Re. Application No. 04770468.9.
Supplementary European Search Report Dated Jan. 12, 2011 From the European Patent Office Re. Application No. 05718889.8.
Supplementary Notice of Allowability Dated Nov. 22, 2006 From the US Patent and Trademark Office Re.: U.S. Appl. No. 10/804,560.
Translation of Decision of Rejection Dated Apr. 22, 2009 From the Japanese Patent Office Re.: Application No. 2004-534013.
Translation of Notification of Reasons of Rejection Dated Apr. 12, 2010 From the Japanese Patent Office Re.: Application No. 2006-525265.
Translation of Office Action Dated Sep. 12, 2008 From the State Intellectual Property Office of the People's Republic of China Re.: Application No. 200480032636.9.
Antman et al. "Treatment of 150 Cases of Life-Threatening Digitalis Intoxication With Digoxin-Specific Fab Antibody Fragments", Circulation, 81(6): 1744-1752, 1990.

(56) References Cited

OTHER PUBLICATIONS

Antoni et al. "Polarization Effects of Sinusoidal 50-Cycle Alternating Current on Membrane Potential of Mammalian Cardiac Fibres", Pflueger's Archiv European Journal of Physiology, 314(4): 274-291, 1970. Abstract.
Bakker et al. "Beneficial Effects of Biventricular Pacing of Congestive Heart Failure", Pace, 17(Part II): 318, 1994.
Bargheer et al. "Prolongation of Monophasic Action Potential Duration and the Refractory Period in the Human Heart by Tedisamil, A New Potassium-Blocking Agent", Journal European Heart, 15(10): 1409-1414, 1994, Abstract.
Bers "Excitation Contraction Coupling and Cardiac Contractile Force", Internal Medicine, 237(2): 17, 1991, Abstract.
Borst et al. "Coronary Artery Bypass Grafting Without Cardiopulomonary Bypass and Without Interuption of Native Coronary Flow Using a Novel Anastomosis Site Restraining Device (Octupus)", Journal of the American College of Cardiology, 27(6): 1356-1364, 1996. Abstract only.
Bouaziz et al. "Direct Electrical Stimulation of Insulin Secretion by Intact Murine Islets of Langerhans Through the Culture Support", Electromagnetic Biology and Medicine, 17(2): 171-184, 1998. Abstract.
Bronzino "Biomedical Engineering Handbook", IEEE Press/CRC Press, Chap. 82.5: 1288, 1995.
Cano et al. "Dose-Dependent Reversal of Dixogin-Inhibited Activity of an In-Vitro Na+K+ATPase Model by Digoxin-Specific Antibody", Toxicology Letters, 85(2): 107-1011, 1996.
Cazeau et al. "Multisite Pacing for End-Stage Heart Failure: Early Experience", Pacing and Clinical Electrophysiology, 19(11/Pt.2): 1748-1757, 1996. Abstract.
Cheng et al. "Calcium Sparks: Elementary Events Underlying Excitation-Contraction Coupling in Heart Muscle", Science, 262(5134): 740-744, 1993. Abstract.
Cooper "Postextrasystolic Potention. Do We Really Know What It Means and How to Use It?", Circulation, 88: 2962-2971, 1993.
Coulton et al. "Magnetic Fields and Intracellular Calcium; Effects on Lymphocytes Exposed to Conditions for 'Cyclotron Resonance'", Phys. Med. Biol., 38: 347-360, 1993, Abstract.
Dillion "Optial Recordings in the Rabbit Heart Show That Defibrillation Shocks Prolong the Duration of Depolarization and the Refractory Period", Circulation Research, 69: 842-856, 1991.
Dillon "Synchronized Repolarization After Defibrillation Shocks. A Possible Component of the Defibrillation Process Demonstration by Optical Recordings in Rabbit Heart", Circulation, 85(5): 1865-1878, 1992.
Fain et al. "Improved Internal Defibrillation Efficacy With a Biphasic Waveform", American Heart Journal, 117(2): 358-364, 1989, Abstract.
Fleg et al. "Impact of Age on the Cardiovasvular Response to Dynamic Upright Exercise in Healthy Men and Women", Journal of Applied Physiologyl, 78: 890-900, 1995, Abstract.
Fleischhauer et al. "Electrical Resistances of Interstitial and Microvascular Space as Determinants of the Extracellular Electrical Field and Velocity of Propagation in Ventricular Myocardium", Circulation, 92: 587-594, 1995.
Foster et al. "Acute Hemodynamic Effects of Atrio—Biventricular Padng in Humans", The Society of Thoracic Surgeons, 59: 294-300, 1995, Abstract.
Franz "Bridging the Gap Between Basic Clinical Electrophysiology: What Can Be Learned From Monophasic Action Potential Recordings?", Journal Cardiovasc Electrophysiology, 5(8): 699-710, 1994, Abstract.
Franz "Method and Theory of Monophasic Action Potential Recording", Progress in Cardiovascular Diseases, 33(6): 347-368, 1991. Abstract.
Fu et al. "System Identification of Electrically Coupled Smooth Music Cells: The Passive Electrically Coupled Smooth Muscle Cells: The Passive Electrical Properties", IEEE Transactions on Biomedical Engineering, 38(11): 1130-1140, 1991.

Gill et al. "Refractory Period Extension During Ventricular Pacing at Fibrillatory Pacing Rates", Pacing and Clinical Elctrophysiology, 20(3): 647-653, 1997, Abstract.
Ham et al. "Classification of Cardiac Arrhythmias Using Fuzzy Artmap", IEEE Transactions on Biomedical Engineering, 43(4): 425-429, 1996, Abstract.
Hoffman et al. "Effects of Postextrasystolic Potentiation on Normal and Failing Hearts", Bulletin of the New York Academy of Medicine, 41(5): 498-534, 1965.
Josephson "Clinical Cardiac Electrophysiology: Techniques and Interpertations", Lea & Febiger, 2nd Ed., 2 P., 1991.
King et al. "The Inotropic Action of Paired Pulse Stimulation in the Normal and Failing Heart: An Experimental Study", Cardiovascular Research, 2: 122-129, 1968.
Knisley et al. "Effect of Field Stimulation on Cellular Repolarization in Rabbit Myocardium. Implications for Reentry Induction", Circulation Research, 70(4): 707-715, Apr. 1992.
Knisley et al. "Prolongation and Shortening of Action Potentials by Electrical Shocks in Frog Ventricular Muscle", American Journal of Physiology, 266(6): H2348-H2358, 1994, Abstract.
Koller et al. "Relation Between Repolarization and Refractoriness During Programmed Electrical Stimulation in the Human Right Ventricle", Circulation, 91(9): 2378-2384, 1995, Abstract.
Langberg et al. "Identification of Ventricular Tachycardia With Use of the Morphology of the Endocardial Electrogram", Circulation, 77(6): 1363-1369, 1988.
Lindstroem et al. "Intracellular Calcium Oscillations in A T-Cell Line After Exposure to Extremely-Low-Frequency Magnetic Fields With Variable Frequencies and Flux Densities", Bioelectromagnetics, 16(1): 41-47, 1995. Abstract.
Loginov et al. "Effects of an Impulse Electromagnetic Field on Calcium Ion Accumulation in the Sarcoplasmic . . . ", Kosm. Biol. Aviakosm. Med., 15: 51-53, 1991.
Lubart et al. "Effect of Light on Calcium Transport in Bull Sperm Cells", Journal of Photochemistry and Photobiology B, Biology, 15(4): 337-341, Sep. 15, 1992. Abstract.
Matheny et al. "Vagus Nerve Stimulation as a Method to Temporarily Slow or Arrest the Heart", Annals of Thoracic Surgery, 63(6): S28-29, 1997, Abstract.
McVeigh et al. "Noninvasive Measurement of Transmural Gradients in Myocardial Strain With MR Imaging", Radiology, 180(3): 677, 679-684, 1991.
Mercando et al. "Automated Detection of Tachycardias by Antitachycardia Devices", Cardiac Electrophysiology: From Cell to Bedside, Chap.100: 943-948, 2004.
Moran et al. "Digoxin-Specific Fab Fragments Impair Renal Function in the Rat", Journal of Pharmacy and Pharmacology, 46(10): 854-856, 1994, Abstract.
Morse et al. "A Guide to Cardiac Pacemakers, Defibrillators and Related Products", Drocgc Computing Services, Inc., vol. I, Nov. 19, 1996.
Nannini et al. "Muscle Recruitment With Intrafascicular Electrodes", IEEE Transactions on Biomedical Engineering, 38: 769-776, 1991, Abstract.
Paul et al. "Automatic Recognition of Ventricular Arrhythmias Using Temporal Electrogram Analysis", PACE, 14: 1265-1273, 1991.
Pumir et al. "Control of Rotating Waves in Cardiac Muscle: Analysis of the Effect of Electric Fields", Proceedings of the Royal Society B: Biological Sciences, 257(1349): 129-134, 1994. Abstract.
Ranjan et al. "Electrical Stimulation of Cardiac Myocytes", Annals of Biomedical Engineering, 23(6): 812-821, 1995, Abstract.
Saksena et al. "Prevention of Recurrent Atrial Fibrillation With Chronic Dual-Site Right Atrial Pacing", Journal of the American College of Cardiology, 28(3): 687-694, 1996, Abstract.
Saveliev et al. "Guidebook on Clinical Endoscopy", Moscow Medicine, p. 21, 35, Extract, 1985.
Schwartz et al. "Exposure of Frog Hearts to CW or Amplitude-Modified VHF Fields: Selective Efflux of Calcium Ions at 16 Hz", Bioelectromagnetics, 11(4): 349-358, 1990, Abstract.
Shumaik et al. "Oleander Poisoning: Treatment With Digoxin-Specific Fab Antibody Fragments", Annals of Emergency Medicine, 17(7): 732-735, 1988.

(56) References Cited

OTHER PUBLICATIONS

SkaLe et al. "Inhibition of Premature Ventricular Extrastimuli by Subthreshold Conditioning Stimuli", Journal of the American College of Cardiology, 6: 133-140, 1985. Abstract.
Solomonow et al. "Control of Muscle Contractile Force Through Indirect High-Frequency Stimulation", American Journal of Physical Medicine, 62(2): 71-82, Apr. 1983. Abstract.
Stevenson et al. "Electrophysiologic Characteristics of Ventricular Tachycardia or Fibrillation in Relation to Age of Myocardial Infarction", The American Journal of Cardiology, 57(6): 387-391, Feb. 15, 1986. Abstract.
Sweeny et al. "Countershock Strength-Duration Relationship for Myocardial Refractory Period Extension", Academic Emergency Medicine, 2(1): 57-62, 1995, Abstract.
Sweeny et al. "Refractory Interval After Transcardiac Shocks During Ventricular Fibrillation", Circulation, 94(11): 2947-2952, 1996.
Sweeny et al. "Ventricular Refractory Period Extension Caused by Defibrillation Shocks", Circulation, 82(3): 965-972, 1990.
Talit et al. "The Effect of External Cardiac Pacing on Stroke Volume", Pace, 13(5): 598-602, 1990. Abstract.
Taniguchi et al. "Inhomogeneity of Cellular Activation Time and Vmax in Normal Myocardial Tissue Under Electrical Field Stimulation", Am. J. Physiol., 267: H694-H705, 1994, Abstract.
Thakor et al. "Effect of Varying Pacing Waveform Shapes on Propagation and Hemodynamics in the Rabbit Heart", The Americal Journal of Cardiology, 79(6A): 36-43, 1997, Abstract.
Tsong "Electroporation of Cell Membranes", Biophysical Journal, 60: 297-306, 1991.
Verrier et al. "Electrophysiologic Basis for T Wave Alternans as an Index of Vulnerability to Ventricular Fibrillation", Journal of Cardiovascular Electrophysiology, 5(5): 445-461, 1994. Abstract.
Webster "Design of Cardiac Pacemakers", IEEE Press, p. xi-xiii, 1995.
Wessale et al. "Stroke Volume and the Three Phase Cardiac Output Rate Relationship With Ventricular Pacing", PACE, 13: 673-680, 1990.
Windle et al. "Subthreshold Conditioning Stimuli Prolong Human Ventricular Refractoriness", American Journal of Cardiology, 57(6): 381-386, 1986. Abstract.
Wirtzfeld et al. "Physiological Pacing: Present Status and Future Developments", Pace, 10(Part I): 41-57, 1987. Abstract.
Yokoyama "The Phase of Supernormal Excitation in Relation to the Strength of Subthreshold Stimuli", Japanese Heart Journal, 17(3): 315-325, May 1976.
Zipes et al. "Cardiac Electrophysiology—From Cell to Bedside", Saunders Co., 4th Ed., 1990.
Communication Pursuant to Rules 70(2) and 70a(2) EPC Dated Oct. 12, 2012 From the European Patent Office Re.: Application No. 06711186.4.
Official Action Dated Oct. 26, 2012 From the US Patent and Trademark Office Re. U.S. Appl. No. 11/336,099.
Official Action Dated Sep. 12, 2013 From the US Patent and Trademark Office Re. U.S. Appl. No. 10/804,560.

* cited by examiner

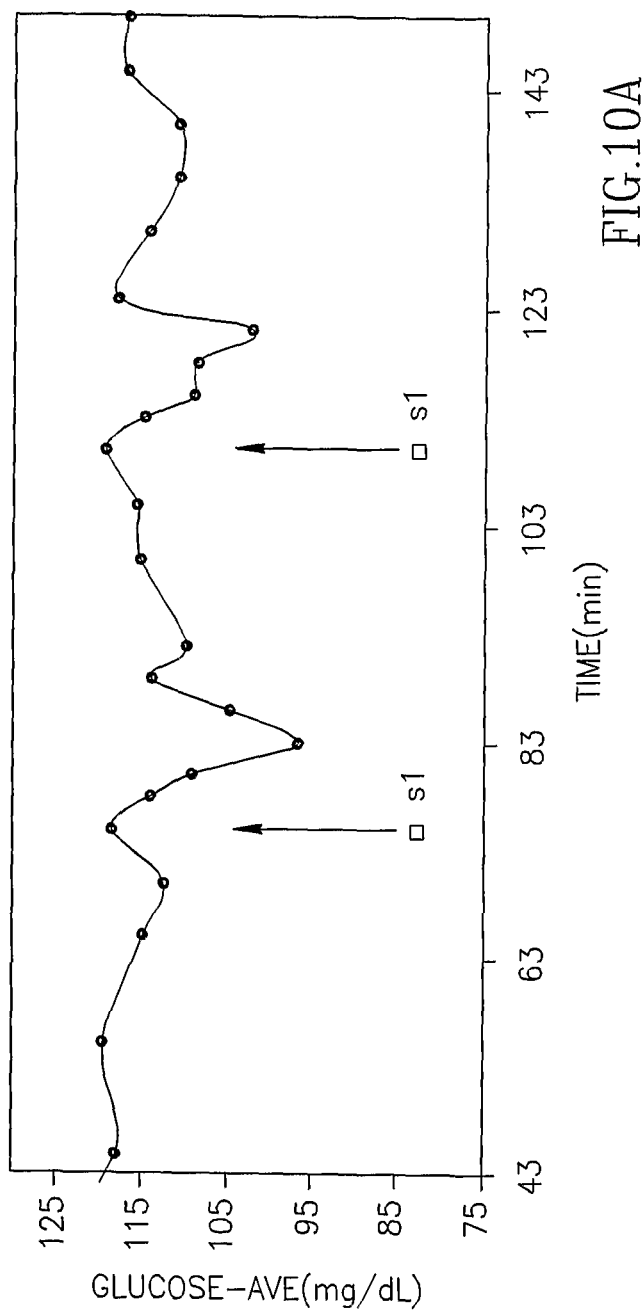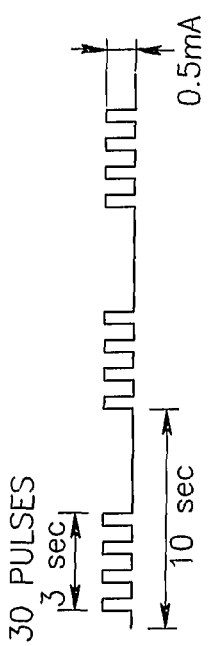

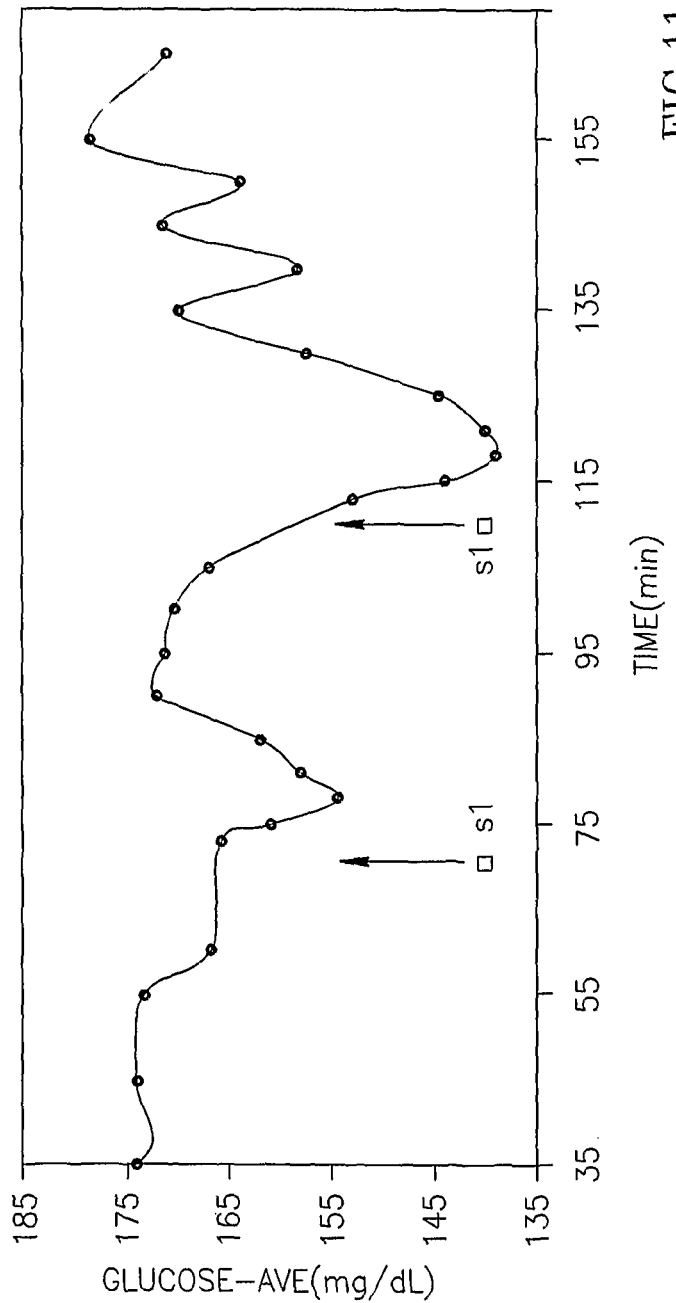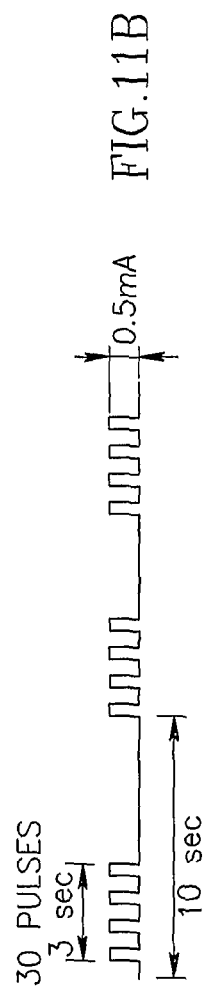

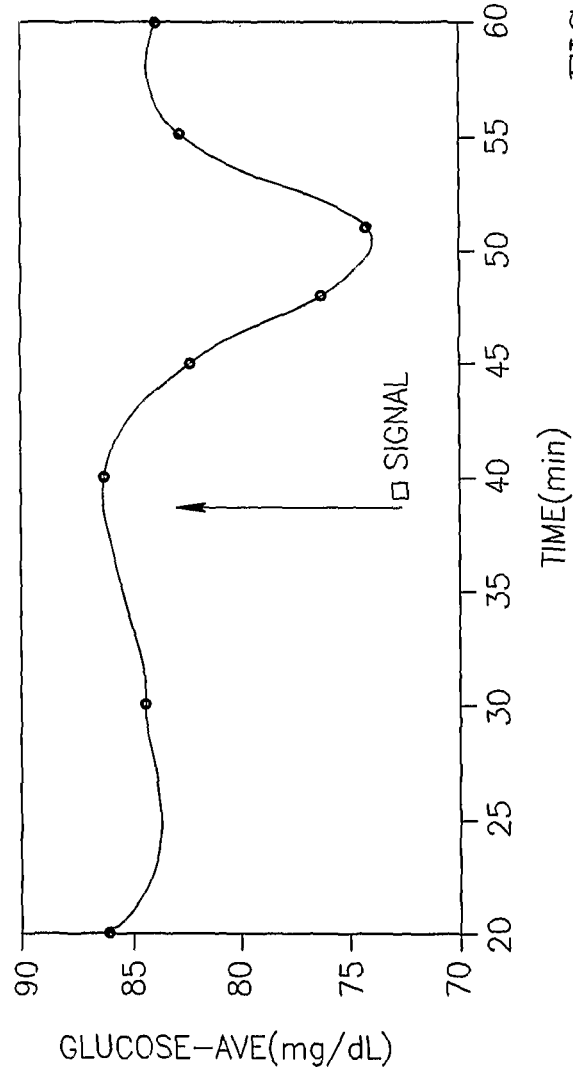
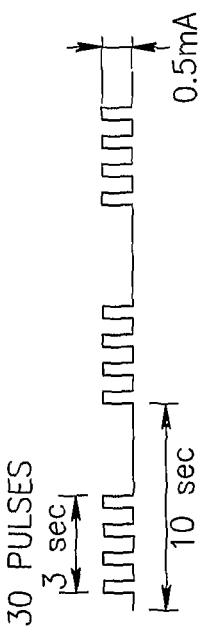
FIG.13A
FIG.13B

GASTROINTESTINAL METHODS AND APPARATUS FOR USE IN TREATING DISORDERS AND CONTROLLING BLOOD SUGAR

CROSS-REFERENCES TO RELATED APPLICATIONS

The present patent application claims the priority of and is a continuation in part of:

(a) U.S. patent application Ser. No. 10/804,560, filed Mar. 18, 2004, which claims the benefit under 35 U.S.C. §119(e) of U.S. Provisional Application No. 60/488,964, filed on Jul. 21, 2003, (b) PCT/IL2004/000797, filed Sep. 5, 2004, (c) PCT/IL2004/000551 to Glasberg et al., filed Jun. 20, 2004, which claims priority from (i) U.S. Provisional Patent Application 60/480,208, filed Jun. 20, 2003, entitled, "Hepatic device for treatment, eating detection, and glucose level detection," and (ii) U.S. Provisional Patent Application 60/488,964, filed Jul. 21, 2003, entitled, "Gastrointestinal methods and apparatus for use in treating disorders and controlling blood sugar,"

(d) PCT/IL2004/000664 to Ben Haim et al., filed Jul. 21, 2004, which also claims priority from U.S. 60/488,964, and (e) PCT/IL2004/000550, filed Jun. 20, 2004, which claims priority from U.S. Provisional Patent Application 60/480,205, filed Jun. 20, 2003, entitled, "Gastrointestinal methods and apparatus for use in treating disorders," and U.S. Provisional Patent Application 60/480,208, filed Jun. 20, 2003, entitled, "Hepatic device for treatment, eating detection, and glucose level detection;" and this application is a continuation in part of:

(a) a US national phase application of PCT Application No. PCT/IL03/00736, which was filed on Sep. 4, 2003 and which is a continuation-in-part of U.S. application Ser. No. 10/237,263, filed on Sep. 5, 2002, which is a continuation-in-part of PCT Application PCT/IL00/00566, filed on Sep. 13, 2000, now published as WO 01/66183, which designates the US, (b) U.S. application Ser. No. 09/914,889, filed on Jan. 24, 2002, which is the US national phase application of PCT Application PCT/IL00/00132, filed on Mar. 5, 2000, which designates the US and which claims the benefit under 35 U.S.C. §119(e) of U.S. Provisional Application 60/123,532, filed on Mar. 5, 1999, and (c) a US national phase application of PCT Application PCT/IL02/00856, which (i) claims priority from U.S. Provisional Patent Application No. 60/334,017, filed Nov. 29, 2001, entitled, "In situ sensing of pancreatic electrical activity," and (ii) is a continuation-in-part of PCT Patent Application PCT/IL01/00501, filed May 30, 2001, entitled, "Electropancreatography," which claims priority from U.S. Provisional Patent Application 60/208,157, filed May 31, 2000, entitled, "Electrical activity sensor for the whole pancreas;" and this application claims the benefit of (a) a US provisional patent application to Ben-Haim et al., filed Feb. 17, 2005, entitled, "Charger with data transfer capabilities," and (b) a US provisional patent application to Kliger et al., filed Aug. 18, 2004, entitled, "Monitoring, analysis, and regulation of eating habits."

This application is also related to PCT Publication WO 99/03533.

Each of the above-referenced applications is incorporated herein by reference.

FIELD OF THE INVENTION

The present invention is related to controlling physiology of a subject, for example, using electricity. The physiology may be controlled, for example, in order to regulate blood serum glucose levels and/or to treat obesity.

BACKGROUND OF THE INVENTION

Control of insulin secretion is important, as there are many living diabetes patients whose pancreas is not operating correctly. In some types of diabetes, the total level of insulin is reduced below that required to maintain normal blood glucose levels. In others, the required insulin is generated, but only at an unacceptable delay after the increase in blood glucose levels. In others, the body is, for some reason, resistant to the effects of insulin.

Although continuous control (e.g., avoiding dangerous spikes and dips) of blood glucose level is desirable, it cannot currently be achieved in some patients.

The insulin secretion process operates as follows: glucose levels in the blood are coupled to depolarization rates of beta islet cells in the Pancreas. It is postulated that when there is a higher glucose level, a higher ratio of ATP/ADP is available in the beta cell and this closes potassium channels, causing a depolarization of the beta cell. When a beta cell depolarizes, the level of calcium in the cell goes up and this elevated calcium level causes the conversion of pro-insulin to insulin and causes secretion of insulin from the cell.

The beta cells are arranged in islets, within a reasonable range of blood glucose levels, an action potential is propagated in the islet. Generally, the electrical activity of a beta cell in an islet is in the form of bursts, each burst comprises a large number of small action potentials.

PCT Patent Publication WO 99/03533 to Ben-Haim et al., entitled, "Smooth muscle controller," and U.S. patent application Ser. No. 09/481,253 in the national phase thereof, both of which are incorporated herein by reference, describe apparatus and methods for applying signals to smooth muscle so as to modify the behavior thereof. In particular, apparatus for controlling the stomach is described in which a controller applies an electrical field to electrodes on the stomach wall so as to modify the reaction of muscle tissue therein to an activation signal, while not generating a propagating action potential in the tissue. In the context of the present patent application and in the claims, the use of such a non-excitatory signal to modify the response of one or more cells to electrical activation thereof, without inducing action potentials in the cells, is referred to as Excitable-Tissue Control (ETC). In PCT Publication WO 99/03533, the disclosure of which is incorporated herein by reference, it was suggested to reduce the output of a pancreas using a non-excitatory electric field.

US Patent Application Publication 2005/0033375, which is incorporated herein by reference, describes a gastroelectric stimulator that includes a neurostimulator for producing a stimulation signal, at least one electrical lead, and at least two electrical contacts. The electrical lead has a proximal end and a distal end, the proximal end being connected to the neurostimulator and the distal end positionable in a lead position within the patient's abdomen. The electrodes are carried near the electrical lead distal end. The electrodes are electrically connected through the electrical lead to the neurostimulator to receive the stimulation signal and convey this signal to an electrode position within the patient's digestive system. The stimulation signal is described as being adapted to influence pancreatic secretions.

PCT publication WO 98/57701 to Medtronic, the disclosure of which is incorporated herein by reference, suggests providing a stimulating electric pulse to an islet, causing an early initiation of a burst and thus, increasing the frequency of the bursts and increasing insulin secretion.

The above PCT publication to Medtronic suggests providing a stimulating (e.g., above stimulation threshold) pulse during a burst, thereby stopping the burst and reducing insulin secretion. This publication also suggests stimulating different parts of the pancreas in sequence, thereby allowing unstimulated parts to rest.

However, one limitation of the methods described in the Medtronic PCT publication is that increasing the burst rate may increase the level of intra-cellular calcium in the beta cells over a long period of time, without the level being allowed to go down, during intra-burst intervals. This increase may cause various cell death mechanisms to be activated and/or otherwise upset the normal balance of the beta cell, eventually killing the cell. In addition, such high calcium levels may cause hyper-polarization of beta cells, thereby reducing insulin secretion and preventing propagation of action potentials. To date, no working electrical pancreatic control device is known.

Diabetologia (1992) 35:1035-1041, for example, the disclosures of which are incorporated herein by reference, describe the interaction of the various hormones generated by the pancreas. Insulin enhances glucose utilization, thereby reducing blood glucose levels. Insulin also stimulates the secretion of glucagon, which causes the liver to secrete glucose, increasing the blood glucose level. Somatostatin reduces the secretion of both insulin and glucagon. This publication also describes an experiment in which sympathetic nervous stimulation caused an increase in Somatostatin secretion. It is suggested in this paper that normal glucose levels in a healthy human may be maintained with the aid of glucagon secretion.

SUMMARY OF THE INVENTION

An aspect of some embodiments of the invention relates to reducing glucose levels while not appreciably increasing insulin levels, at least not for more than small amounts and/or short periods of time and/or compared to a regular response in a same person. In an exemplary embodiment of the invention, an electric field is applied to a pancreas in a manner which reduces blood glucose levels and does not significantly raise insulin levels or even reduces such insulin levels. In an exemplary embodiment of the invention, reducing glucose levels prevents insulin levels from rising. This may have a beneficial effect on the pancreas by preventing exhaustion. In an exemplary embodiment of the invention, insulin is not raised by more than 20%, 15%, 10%, 5% or less, or even reduced, by 5%, 10% or more. A duration of insulin raise may be, for example, limited to less than 10 minutes, less than 5 minutes or less than 1 minute.

In an exemplary embodiment of the invention, while a significant insulin increase is seen, this increase is caused by increased glucose levels and is considerably less than an increase which would have otherwise been expected for a same glucose ingestion event. For example, the accumulated insulin secretion in a stimulated case over a glucose event may be 20%, 40% 60% or more reduced as compared to a control case.

In an exemplary embodiment of the invention, glucose reduction and, in some embodiments, insulin reduction is achieved by applying an electrical field to the pancreas. In some embodiments of the invention, the electrical field reduces glucagon secretion, directly or indirectly. Alternatively or additionally, the electric field causes the release of other non-insulin factors which reduce blood glucose levels in the blood and/or glucose uptake. In some embodiments of the invention, an electric field or other control means is used to delay gastric emptying, thereby reducing availability of glucose.

In some embodiments of the invention, glucose levels are also reduced by the application of a stimulation to the same or a different part of the pancreas, which stimulation causes a reduction in glucose levels via insulin secretion.

An aspect of some embodiments of the invention relates to electrically stimulating or otherwise applying a field to a pancreas, with electrodes located away from the pancreas. In an exemplary embodiment of the invention, the electrodes are placed near the pancreas such that an electric field applied by the electrodes has a significant value at or about the pancreas. Optionally, the electric field is applied using electrodes on opposite sides of the stomach, so that a main conductive pathway between the electrode, which cannot pass through the hollow of the stomach, circumvents the stomach and passes through a portion of the pancreas. Optionally, the electric field has little or no effect on other organs, such as the stomach. Optionally, the electric field has a beneficial effect (e.g., glucose reduction) on one or more nearby organs. A potential advantage of placing electrodes on the stomach is that the stomach is relatively stable and relatively immune to injury. In particular, the problem of pancreatic perforation or infection may be avoided.

An aspect of some embodiments of the invention relates to timing a glucose control therapy to prevent or reduce an initial raise in blood glucose levels when eating. In an exemplary embodiment of the invention, the therapy, for example the application of an electric field to the pancreas, is timed to reduce glucagon levels quickly so that digesting food will not cause a large glucose peak. Alternatively or additionally, the pancreas is controlled to give a fast bolus of insulin. Alternatively or additionally, delaying of gastric emptying, for example by electrical or pharmaceutical control, reduces and/or delays a glucose peak. It is believed that for some patient suitable reduction or delay of such a peak will reduce peak insulin output and possibly prevent overshooting by the pancreas. Eating may be detected, for example, automatically, for example by a gastric activity sensor. Optionally, a pharmaceutical pump provides pharmaceuticals, for example to slow gastric emptying. Alternatively, eating can be manually indicated, for example, using a magnetic programming "wand".

In an exemplary embodiment of the invention, a glucose peak due to eating is delayed by at least 5, 10, 15 or 20 minutes. Alternatively or additionally, such a peak has its amplitude reduced (relative to a baseline value) by at least 10%, 20%, 30%, 50%, 60% or more. Alternatively or additionally, such a peak has its duration shortened (duration where its value is more than 40% over the baseline) by at least 10%, 20%, 30%, 50%, 60% or more. Alternatively or additionally, an integral over the increased glucose levels due to eating is reduced by at least 10%, 20%, 30%, 50%, 60% or more.

In an exemplary embodiment of the invention, an insulin peak due to eating is delayed by at least 5, 10, 15 or 20 minutes. Alternatively or additionally, such a peak has its amplitude reduced (relative to a baseline value) by at least 10%, 20%, 30%, 50%, 60% or more. Alternatively or additionally, such a peak has its duration shortened (duration where its value is more than 40% over the baseline) by at least 10%, 20%, 30%, 50%, 60% or more. Alternatively or additionally, an integral over the increased insulin levels due to eating is reduced by at least 10%, 20%, 30%, 50%, 60% or more.

In an exemplary embodiment of the invention, these differences are measured over a time period corresponding to the body response to an event of ingesting glucose, for example, about 60 minutes. In an exemplary embodiment of the invention, these reductions or lack of significant increase is relative to an expected increase if no control were exerted (e.g., after eating). In some embodiments and/or cases, the lack of increase is relative to a base-line condition.

Alternatively or additionally, blood insulin values are maintained at a relatively low value, for example, under 30, 20, 15 or 10 micro-units per ml.

An aspect of some embodiments of the invention relates to a method of glucose control by electrically stimulating a pancreas with a built-in safety effect. In an exemplary embodiment of the invention, the applied field does not substantially reduce glucose levels once baseline glucose levels are achieved. Alternatively or additionally, application of the field for significant periods of time, such as several days or weeks does not cause significant interference with exocrine pancreas functions and/or with pancreas viability. In an exemplary embodiment of the invention, glucose level reduction below baseline is less than 30%, 20%, 10% or less. In an exemplary embodiment of the invention, the glucose levels at which further substantial reduction is not provided is less than 40%, 30%, 20% or less over a baseline glucose level.

An aspect of some embodiments of the invention relates to selective and/or integrative control of the various hormones generated by the pancreas and which affect blood glucose level, to provide a control of blood glucose levels. The control may be achieved using pure electrical stimulation, or possibly using one or more pharmaceuticals and/or other molecules to interact with the electrical stimulation in a desired manner. The pharmaceuticals may prevent the pancreatic cells from producing and/or secreting a hormone. Alternatively, the pharmaceuticals may prevent the action of the hormone, for example by blocking the receptors or disabling the hormone. Alternatively or additionally, hormones, such as insulin, Somatostatin or glucagon may be provided from outside the body or using an insulin pump. In some embodiments of the invention, the control is non-excitatory (defined below). In other embodiments of the invention, the control is excitatory or a combination of excitatory and non-excitatory control.

In some exemplary embodiments of the invention, the control is not merely of the blood glucose levels but also of the hormone levels required to provide a satisfactory physiological effect, rather than merely prevention of symptomatic effects of incorrect blood glucose levels. Such control may be effected, for example to achieved desirable short term effects alternatively or additionally to achieving desirable long term effects. This type of positive control of two parameters should be distinguished from merely controlling blood glucose by varying the insulin level. Such mere controlling may not allow both desired blood glucose levels and insulin levels to be achieved, possibly leading to over-exertion of the pancreas.

It is hypothesized that one possible reason for lack of success of some prior art nervous or direct stimulation of the pancreas for glucose control is the simultaneous and non-selective effect of the stimulation on the secretion of several different hormones, reducing the effectiveness of the hormones secreted and/or overworking the pancreas.

In an exemplary embodiment of the invention, the secretion of a counteracting type of hormone (e.g., glucagon or insulin) is suppressed, to prevent feedback interactions whereby the secretion of a target hormone (e.g., insulin or glucagon) increases the secretion of the counteracting hormone.

Alternatively or additionally, the stimulation of secretion of the target hormone is maintained at low enough levels that do not cause a significant secretion of the counteracting hormone. The secretion time may be extended, so that the total amount of hormone is sufficient for a desired result.

Alternatively or additionally, the stimulation of secretion of the target of hormone is controlled to be in bursts that are not long enough to stimulate a significant secretion of the counteracting hormone. Alternatively, the secretion may be sustained, to purposely cause secretion and/or production of the counteracting hormone to a desired degree.

Alternatively or additionally, the secretion of the target hormone is maintained at a high enough level to overcome the counteracting effects.

Alternatively or additionally, the stimulation of secretion of the target hormone is maintained at a high enough level to cause the generation of significant amounts of a secretion limiting hormone (e.g., Somatostatin), which secretion prevents the secretion of the counteracting hormone, but is not sufficient to prevent the stimulation from releasing of the target hormone.

Alternatively or additionally, the secretion of several of pancreatic hormones is suppressed by hyper-polarizing the pancreas. Such hyper-polarization can be electrical in nature or chemical. For example, Diazoxide causes hyper-polarization and reduces activity in the pancreas.

Alternatively or additionally, beta cell response (e.g., insulin secretion) to high blood glucose levels is dampened, rather than blocked, so as to prevent hypoglycemia. Alternatively or additionally, glucagon secretion is provided to prevent hyperglycemia, when high insulin levels persist in spite of reduced glucose intake. In some cases, damping of insulin response and/or provision of glucagon are used to prevent overshoots caused, for example, by a delayed response to the artificial control of the pancreas. In some cases, the insulin (or other hormone) increasing or decreasing pulse is applied and/or removed gradually (e.g., with regard to effect or temporal frequency), to prevent such an overshoot. Alternatively or additionally, an active measure, such as providing an antagonistic hormone, is used.

In an exemplary embodiment of the invention, when a stimulation is used to effect a large insulin secretion, glucose levels are also increased to prevent hypoglycemia. In one example, this is provided by a glucose pump. In another, this is provided by directly stimulating the release of glucagon. In another example, the insulin secretion is large or fast enough so it directly or indirectly causes glucagon secretion. In one example, insulin is secreted faster than it can be cleared away by blood flow (e.g., natural or artificially reduced), causing a local (to the pancreas) very high level of insulin, which may stimulate glucagon production. Alternatively or additionally, the insulin level is made high enough (and/or increase fast enough) in the body in general, to stimulate glucagon production. In an alternative embodiment of the invention, the insulin increase is kept slow, to prevent secretion of glucose and/or various hormones by the body, for example, by promoting habitation of the relevant physiological mechanism and/or preventing the triggering of rate-sensitive mechanisms.

An aspect of some embodiments of the invention relates to effecting control of insulin and/or glucose blood levels by controlling glucagon secretion. In an exemplary embodiment of the invention, such increased glucagon secretion is used to increase blood glucose levels, instead of insulin secretion reduction or additional to it. Optionally, the secretion of glucagon is limited so as not to cause a complete depletion of glucose sources in the liver. Alternatively or additionally, insulin secretion is stimulated by an increase in glucagon secretion. In an exemplary embodiment of the invention, both a desired glucose level and a desired insulin level can be achieved simultaneously, by suitably controlling glucagon secretion. Alternatively or additionally, the need for abnormally high levels of insulin are prevented by not stimulating glucagon secretion. In some cases, insulin secretion is provided to prompt the creating of glucose stores in the liver or glucagon is provided to deplete such stores.

In some exemplary embodiments of the invention, controlling both glucose levels and insulin levels allows control over effects of insulin other than blood glucose level, for example effects on lipid metabolism, gluconeogenesis in liver, ketogenesis, fat storage, glycogen formation.

Alternatively or additionally, the liver may be overwhelmed with glucose and/or insulin, without associated hyperglycemia, so as to force complete filling of glycogen reserves and/or prevent hepatic absorption of glucose at a later time.

Alternatively or additionally, insulin levels may be reduced so that less glycogen is stored in the liver. This may be useful in von Gierke's over-storage disorder and/or in other over-storage disorders.

An aspect of some embodiments of the invention relates to mapping the response and/or feedback behavior of a pancreas. Such mapping may be used for, for example, a particular patient and/or for a type of patient and/or pancreatic disorder.

In an exemplary embodiment of the invention, one or more of the following properties of a pancreas is determined:

(a) the interaction between two or more hormones, including one or more of the amplification gain (positive or negative), the effect of short vs. long sustained changes in one hormone level on another, delay times for effect of one hormone on another, and/or natural sequences of hormone activation;

(b) response of hormone secretion and/or production to various stimulatory and inhibitory effects, such as electrical fields, pharmaceuticals and/or nervous stimulation;

(c) the effect of glucose levels, previous stimulation of the pancreas and/or pharmaceutical levels on the hormone interactions and responses to stimulation and to levels of other pancreatic hormones and/or other physiological parameters, for example levels of digestive enzymes;

(d) burst ability vs. hormone creating ability, including, for example, intra-cellular hormone and pre-hormone storage capacity and/or time constants;

(e) different behavior of different parts of the pancreas; and (f) electrical activity of all or some of the pancreas.

In some embodiments, the mapping also determines the effect of non-pancreatic hormones, for example pituitary, thyroid and adrenal hormones. Some of these hormones may increase or reduce blood glucose level by direct effect on the liver.

In an exemplary embodiment of the invention, a direct measurement of absolute or relative hormone levels and/or a measurement of glucose levels and/or other physiological parameters, is/are used to determine the effect of various stimulation. Such measurements may be on-line or off-line. In an exemplary embodiment of the invention, a fiber-optic chemical sensor is used to assay hormone levels. Alternatively or additionally, an anti-body based test is used. In an exemplary embodiment of the invention, the controller includes a port or a guide wire to the pancreatic and/or portal circulatory system. Possibly, the port or guide wire exits the body, reach until just under the skin and/or open into a body lumen, for easy access. Such a port or guide wire may be adapted for guiding a catheter, for removing hormone laden blood from the pancreas. The catheter and/or guide wire may be removed once a mapping stage is over. Alternatively or additionally, the port is used to guide an endoscope, for implantation and/or repositioning of sensors and/or electrodes.

Alternatively or additionally to measuring intra-pancreatic interactions, the adaptation of the pancreas to various physiological states and/or the adaptation of the body to various pancreatic states and/or blood hormone levels, is also measured. Such measuring may be performed in a laboratory. Alternatively or additionally, an ambulatory or implanted device is provided to a patent, to measure the above pancreatic behaviors over time.

In an exemplary embodiment of the invention, the above measured behaviors are used as parameters for a predictive model of the behavior of the pancreas. Alternatively or additionally, a new model, for example a neural network type model is created from the measurements. Such a model is possibly sued to predict the effect of a therapy and/or to choose between alternative therapies. In an exemplary embodiment of the invention, such a model is used to select a therapy for glucose level reduction which increases insulin secretion but does not increase glucagon secretion.

An aspect of some exemplary embodiments of the invention relates to controlling pancreatic behavior indirectly by controlling the flow of blood to the pancreas, for affecting hormone generation and secretion and/or by controlling blood flow from the pancreas, to effect hormone dissemination and/or local levels of hormone in the pancreas. In an exemplary embodiment of the invention, the blood flow is controlled using non-excitatory electrical fields that selectively contract or relax arteries and/or veins to, from or inside some or all of the pancreas.

An aspect of one exemplary embodiment of the invention relates to a method of increasing insulin secretion, while avoiding unacceptable calcium level profiles. In an exemplary embodiment of the invention, insulin output is increased by extending a burst duration, while maintaining a suitably lengthy interval between bursts, thus allowing calcium levels to decay during the interval. Alternatively or additionally, insulin output is increased by increasing the effectiveness of calcium inflow during a burst, possibly without changing the burst frequency and/or duty cycle. Alternatively, in both methods, the burst frequency may be reduced and/or the interval increased, while allowing higher insulin output levels or maintaining same output levels.

In an exemplary embodiment of the invention, the effects on insulin secretion are provided by applying a non-excitatory pulse to at least part of the pancreas. As used herein the term non-excitatory is used to describe a pulse that does not generate a new action potential, but may modify an existing or future potential. This behavior may be a result of the pulse, amplitude, frequency or pulse envelope, and generally also depends on the timing of the pulse application. It is noted that a single pulse may have excitatory and non-excitatory parts. For example a 100 ms pacing pulse, may cease to have a pacing effect after 20 ms and have real non-excitatory effects after 40 ms.

In an exemplary embodiment of the invention, when a pulse is applied in accordance with an exemplary embodiment of the invention, it increases burst amplitude, with the effect possibly continuing for some duration. Optionally, the pulse does not stopping the burst. Possibly, the burst is also lengthened. It is believed that increasing burst amplitude may increase insulin generation and/or secretion.

The pulse may be synchronized to the local electrical activity, for example, to bursts or to individual action potentials. Alternatively or additionally, the pulse may be synchronized to the cycle of changes in insulin level in the blood (typically a 12 minute cycle in healthy humans). Alternatively, the pulse may be unsynchronized to local or global pancreatic electrical activity. Alternatively, the applied pulse may cause synchronization of a plurality of islets in the pancreas, for example by initiating a burst. A two part pulse may be provided, one part to synchronize and one part to provide the non-excitatory activity of the pulse. Although the term "pulse" is used, it is noted that the applied electric field may have a duration longer than an action potential or even longer than a burst.

An aspect of some exemplary embodiments of the invention relates to reducing calcium levels in beta islet cells. In an exemplary embodiment of the invention, the levels are reduced by providing an oral drug. Alternatively, the levels are reduced by increasing the interval between bursts. The intervals may be increased, for example, by suppressing bursts of action potentials, for example using excitatory or non-excitatory pulses. Alternatively, an electro-physiological drug is provided for that purpose. For example, Procainamide HCL and Quinidine sulfate are Na channel antagonists, Minoxidil and Pinacidil are K channel activators, and Amiloride HCL is an Na channel and epithelial antagonist. Other suitable pharmaceuticals are known in the art, for example as described in the RBI Handbook of Receptor Classification, and available from RBI Inc. This reduction in calcium levels may be performed to reduce the responsiveness of the pancreas to glucose levels in the blood. Alternatively or additionally, this reduction is used to offset negative side effects of drugs or other treatment methods and/or to enforce a rest of at least a part of the pancreas. Alternatively or additionally, this reduction may be offset by increasing the effectiveness of insulin secretion.

An aspect of some exemplary embodiments of the invention relates to pacing at least a portion of the pancreas and, at a delay after the pacing, applying a non-excitatory pulse. The non-excitatory pulse may be provided to enhance or suppress insulin secretion or for other reasons. In an exemplary embodiment of the invention, the pacing pulse provides a synchronization so that the non-excitatory pulse reaches a plurality of cells at substantially a same phase of their action potentials. A further pulse, stimulating or non-excitatory may then be provided based on the expected effect of the non-excitatory pulse on the action potential.

In an exemplary embodiment of the invention, the stimulation pulse that is used to affect the insulin production is also used to cause pacing. In one example, the pulse resets the electrical activity in the pancreas, possibly in a manner similar to that of a defibrillation pulse applied to the heart. Alternatively or additionally, the stimulation pulse may cause an immediate burst to occur, causing later pulses to be automatically delayed relative to that pulse. Independent of the actual reason for such synchronization, in an exemplary embodiment of the invention, a stimulation pulse is used which causes a short delay of a few seconds after the pulse before a new, (at least nominally) normal length burst is generated.

An aspect of some exemplary embodiments of the invention relates to simultaneously providing pharmaceuticals and electrical control of a pancreas. In an exemplary embodiment of the invention, the electrical control counteracts negative effects of the pharmaceuticals. Alternatively or additionally, the pharmaceutical counteracts negative effects of the electrical control. Alternatively or additionally, the electrical control and the pharmaceutical complement each other, for example, the pharmaceutical affecting the insulin production mechanisms and the electrical control affecting the insulin secretion mechanism. The electrical control and/or the pharmaceutical control may be used to control various facets of the endocrinic pancreatic activity, including one or more of: glucose level sensing, insulin production, insulin secretion, cellular regeneration, healing and training mechanisms and/or action potential propagation. In an exemplary embodiment of the invention, electrical and/or pharmaceutical mechanisms are used to replace or support pancreatic mechanisms that do not work well, for example, to replace feedback mechanisms that turn off insulin production when a desired blood glucose level is achieved. The pharmaceuticals that interact with the pancreatic controller may be provided for affecting the pancreas. Alternatively, they may be for other parts of the body, for example for the nervous system or the cardiovascular system.

An aspect of some exemplary embodiments of the invention relates to activating pancreatic cells in various activation profiles, for example to achieve training, regeneration, healing and/or optimal utilization. In an exemplary embodiment of the invention, such activating can include one or more of excitatory pulses, non-excitatory pulses and application of pharmaceuticals and/or glucose. It is expected that diseased cells cannot cope with normal loads and will degenerate if such loads are applied. However, by providing sub-normal loads, these cells can continue working and possibly heal after a while using self healing mechanisms. In particular, it is expected that certain diseased cells, when stimulated at least a minimal activation level, will heal, rather than degenerate. Alternatively or additionally, it is expected that by stressing cells by a certain amount, compensation mechanisms, such as increase in cell size, response speed and profile to glucose levels cell effectiveness and/or cell numbers, will operate, thereby causing an increase in insulin production capability, insulin response time and/or other desirable pancreatic parameters. The appropriate activation profiles may need to be determined on a patient by patient basis. Possibly, different activation profiles are tested on one part of the pancreas, and if they work as desired, are applied to other parts of the pancreas. These other parts of the pancreas may be suppressed during the testing, to prevent over stressing thereof. Alternatively, they may be maintained at what is deemed to be a "safe" level of activity, for example by electrical control or by pharmaceutical or insulin control.

An aspect of some exemplary embodiments of the invention relates to electrically affecting and preferably controlling insulin generation, alternatively or additionally to affecting insulin secretion. In an exemplary embodiment of the invention, insulin production is enhanced by "milking" insulin out of beta cells so that their supplies of insulin are always under par. Alternatively or additionally, by under-milking such cells (e.g., prevention of secretion), insulin production is decreased. In some patients opposite effects may occur; over-milking will cause a reduction in insulin production and/or under-milking will increase insulin production. Alternatively, insulin production is suppressed by preventing a cell from secreting insulin (e.g., by preventing depolarization), thereby causing large amount of insulin to stay in the cell, and possibly, prevent further production of insulin. Such mechanisms for stopping the production of insulin have been detected in pancreatic cells.

In an exemplary embodiment of the invention, by causing a cell to store a large amount of insulin, a faster response time can be achieved, when large amounts of insulin are required, for example to combat hyperglycemia. The cells can then be systemically depolarized to yield their stores of insulin. Possibly, a plurality of pancreatic cells (the same or different ones at different times) are periodically set aside to serve as insulin burst providers.

Alternatively or additionally, suppression of insulin output is used during medical procedures, to prevent hypoglycemia. Alternatively or additionally, suppression or enhancement of insulin output is used to overwork pancreatic tumor cells, so they die from over-production or from over-storage of insulin. In some cases, the overworking of cells caused by cycling demand may be used as a form of stress to weaken cells, and in combination with another stress source, kill the cells. Alternatively or additionally, suppression of insulin output is used to reduce the activity of an implanted pancreas or pancreatic portion, to assist in its getting over the shock of transplantation.

An aspect of some exemplary embodiments of the invention relates to controlling the propagation of action potentials and/or other parameters of action potentials in islet cells, alternatively or additionally to controlling parameters of burst activity. In an exemplary embodiment of the invention, a pulse, optionally synchronized to individual action potentials in an islet, is used to control the action potential, for example to increase or decrease its plateau duration. Alternatively or additionally, a reduction in action potential frequency towards the end of a burst is counteracted, for example by pacing the cells to have a desired frequency or to be more excitable.

In an exemplary embodiment of the invention, action potential propagation is controlled, for example enhanced or blocked, by selectively sensitizing or desensitizing the beta cells in an islet, using chemical and/or electrical therapy. Enhancement of action potential may be useful for increasing insulin production rates, especially if the glucose sending mechanism in some cells are damaged. Suppression of action potential propagation is useful for preventing insulin production and/or enforcing rest.

An aspect of some exemplary embodiments of the invention relates to indirectly affecting the pancreatic activity by changing pancreatic response parameters, such as response time to increases in glucose level and response gain to increases in glucose level. Thus, for example, a non-responsive pancreas can be sensitized, so that even small changes in glucose level will cause an outflow of insulin. Alternatively, a weak or over-responsive pancreas can be desensitized, so that it isn't required to generate (large amounts of) insulin for every small fluctuation in blood glucose level. It is noted that the two treatments can be simultaneously applied to different parts of a single pancreas.

An aspect of some exemplary embodiments of the invention relates to synchronizing the activities of different parts of the pancreas. Such synchronization may take the form of all the different parts being activated together. Alternatively, the synchronization comprises activating one part (or allowing it be become active) while suppressing other parts of the pancreas (or allowing them to remain inactive). In an exemplary embodiment of the invention, the synchronization is applied to enforce rest on different parts of the pancreas. Alternatively or additionally, the synchronization is provided to selectively activate fast-responding parts of the pancreas or slow responding parts of the pancreas.

In an exemplary embodiment of the invention, synchronization between islets or within islets is enhanced by providing pharmaceuticals, for example Connexin, to reduce gap resistance. Such pharmaceuticals may be administered, for example, orally, systemically via the blood locally or locally, for example via the bile duct. In an exemplary embodiment of the invention, such pharmaceuticals are provided by genetically altering the cells in the pancreas, for example using genetic engineering methods.

An aspect of some exemplary embodiments of the invention relates to implanting electrodes (and/or sensors) in the pancreas. In an exemplary embodiment of the invention, the electrodes are provided via the bile duct. Possibly, a controller, attached to the electrode is also provided via the bile duct. In an exemplary embodiment of the invention, the implantation procedure does not require general anesthesia and is applied using an endoscope. Alternatively, the electrodes are provided through the intestines. Possibly, also the device which controls the electrification of the electrodes is provided through the intestines. In an exemplary embodiment of the invention, the device remains in the intestines, possibly in a folded out portion of the intestines, while the electrodes poke out through the intestines and into the vicinity or the body of the pancreas. Alternatively, the electrodes may be provided through blood vessels, for example the portal vein. In an exemplary embodiment of the invention, the electrodes are elongated electrodes with a plurality of dependent or independent contact points along the electrodes. The electrodes may be straight or curved. In an exemplary embodiment of the invention, the electrodes are poked into the pancreas in a curved manner, for example being guided by the endoscope, so that the electrodes cover a desired surface or volume of the pancreas. The exact coverage may be determined by imaging, or by the detection of the electric field emitted by the electrodes, during a post implantation calibration step.

An aspect of some exemplary embodiments of the invention relates to a pancreatic controller adapted to perform one or more of the above methods. In an exemplary embodiment of the invention, the controller is implanted inside the body. An exemplary controller includes one or more electrodes, a power source for electrifying the electrodes and control circuitry for controlling the electrification. Optionally, a glucose or other sensor is provided for feedback control.

There is therefore provided, in accordance with an embodiment of the present invention, apparatus, including:

a set of electrodes, adapted to be implanted at an implantation site in a patient; and a control unit, adapted to drive a first subset of the set of electrodes to apply a signal to the site configured to reduce a blood glucose level of the patient, and to drive a second subset of the set of electrodes to apply a signal to the site configured to treat obesity of the patient.

In an embodiment, the control unit is adapted to configure the signal applied by the first subset to include an ETC signal.

In an embodiment, the control unit is adapted to configure the signal applied by the second subset to include an ETC signal.

In an embodiment, the first subset and the second subset include at least one electrode in common.

In an embodiment, first subset and the second subset are identical.

In an embodiment, the first subset and the second subset have no electrodes in common.

In an embodiment, the implantation site includes a stomach of the patient, and wherein the set of electrodes are adapted to be fixed to the stomach.

In an embodiment, the implantation site includes an antrum of a stomach of the patient, and wherein the set of electrodes are adapted to be fixed to the antrum.

In an embodiment, the implantation site includes a non-gastric site of the patient, and wherein the set of electrodes are adapted to be fixed to the non-gastric site.

In an embodiment, the implantation site includes an intestinal site of the patient, and wherein the set of electrodes are adapted to be fixed to the intestinal site.

In an embodiment, the control unit is adapted to drive the first subset even in the absence of a detection of eating by the patient, and to drive the second subset responsive to a detection of eating by the patient.

In an embodiment, the control unit is adapted to drive the first subset responsive to a detection of eating by the patient.

In an embodiment, the implantation site includes an antrum of a stomach of the patient, and wherein the set of electrodes includes at least two pairs of electrodes, adapted to be fixed to the antrum.

In an embodiment, the set of electrodes includes at least four pairs of electrodes, adapted to be fixed to the antrum.

In an embodiment, one of the pairs is adapted to be fixed to a posterior portion of the antrum, and wherein another one of the pairs is adapted to be fixed to an anterior portion of the antrum.

In an embodiment, the at least two pairs of electrodes are adapted to be fixed to the antrum in a longitudinal orientation with respect to an axis of the stomach.

In an embodiment, the at least two pairs of electrodes are adapted to be fixed to the antrum in a perpendicular orientation with respect to an axis of the stomach.

In an embodiment, the at least two pairs of electrodes are adapted to be fixed to the antrum in a mixed orientation with respect to an axis of the stomach.

In an embodiment, the at least two pairs of electrodes include a first pair and a second pair of electrodes, adapted to be fixed to the antrum at different respective orientations with respect to an axis of the stomach, wherein the first pair of electrodes is in the first subset of the set of electrodes, and wherein the second pair of electrodes is in the second subset of the set of electrodes.

In an embodiment, the first pair of electrodes is adapted to be fixed to the antrum in a longitudinal orientation with respect to the axis of the stomach.

In an embodiment, the second pair of electrodes is adapted to be fixed to the antrum in a perpendicular orientation with respect to the axis of the stomach.

In an embodiment, the control unit is adapted to drive the first subset with a signal having a first frequency component, and to drive the second subset with a signal having a second frequency component, the first frequency component being smaller than the second frequency component.

In an embodiment, the control unit is adapted to drive the second subset to apply the signal having the second frequency component without driving the second subset to apply a pacing pulse prior to applying the signal.

In an embodiment, the signal having the first frequency component is non-excitatory.

In an embodiment, the signal having the second frequency component is non-excitatory.

In an embodiment, the control unit is adapted to drive the first subset to alternate application of (a) a pacing pulse and (b) the signal having the first frequency component.

In an embodiment, the control unit is adapted to initiate applying the signal having the first frequency component during a refractory period of the implantation site induced by the pacing pulse.

In an embodiment, the control unit is adapted to initiate applying the signal having the first frequency component within 500 ms following the pacing pulse.

In an embodiment, the first frequency component is less than 10 Hz, and wherein the second frequency component is greater than 10 Hz.

In an embodiment, the second frequency component is between 60 Hz and 100 Hz.

In an embodiment, the first frequency component is less than half of the second frequency component.

In an embodiment, the first frequency component is less than one fifth of the second frequency component.

There is further provided, in accordance with an embodiment of the present invention, a method, including:

fixing at least two pairs of electrodes to a stomach site of a patient, in a longitudinal orientation with respect to an axis of the stomach; and driving the electrodes to apply a signal to the site configured to treat a pathology of the patient.

There is yet further provided, in accordance with an embodiment of the present invention, method, including:

fixing at least two pairs of electrodes to a stomach site of a patient, in a perpendicular orientation with respect to an axis of the stomach; and driving the electrodes to apply a signal to the site configured to treat a pathology of the patient.

There is still further provided, in accordance with an embodiment of the present invention, a method, including:

fixing at least two pairs of electrodes to a stomach site of a patient, in a mixed orientation with respect to an axis of the stomach; and driving the electrodes to apply a signal to the site configured to treat a pathology of the patient.

In an embodiment, the pathology includes diabetes.

In an embodiment, the pathology includes obesity.

In an embodiment, driving the electrodes includes driving the electrodes even in the absence of a detection of eating by the patient.

In an embodiment, driving the electrodes includes driving the electrodes responsive to a detection of eating by the patient.

In an embodiment, fixing the at least two pairs of electrodes includes fixing the at least two pairs of electrodes to an antrum of the stomach of the patient.

In an embodiment, fixing the at least two pairs of electrodes includes fixing at least four pairs of electrodes to the antrum.

In an embodiment, fixing the at least two pairs of electrodes includes fixing one of the pairs to a posterior portion of the antrum and fixing another one of the pairs to an anterior portion of the antrum.

In an embodiment, driving the electrodes to apply the signal includes driving the electrodes to apply an ETC signal having a frequency component.

In an embodiment, the method includes driving the electrodes to apply the ETC signal includes driving the electrodes to apply the ETC signal without driving the electrodes to apply a pacing pulse prior to applying the ETC signal.

In an embodiment, the method includes driving the electrodes to alternate application of (a) a pacing pulse and (b) the ETC signal.

In an embodiment, the method includes initiating applying the ETC signal during a refractory period of the stomach site induced by the pacing pulse.

In an embodiment, the method includes initiating applying the ETC signal within 500 ms following the pacing pulse.

In an embodiment, driving the electrodes includes setting the frequency component to be less than 10 Hz.

In an embodiment, driving the electrodes includes setting the frequency component to be greater than 10 Hz.

There is also provided in accordance with an exemplary embodiment of the invention, a pancreatic controller, comprising:

a glucose sensor, for sensing a level of glucose or insulin in a body serum;

at least one electrode, for electrifying an insulin producing cell or group of cells;

a power source for electrifying said at least one electrode with a pulse that does not initiate an action potential in said cell and has an effect of increasing insulin secretion; and a controller which receives the sensed level and controls said power source to electrify said at least one electrode to have a desired effect on said level. Optionally, said insulin producing cell is contiguous with a pancreas and wherein said electrode is adapted for being placed adjacent said pancreas. Alternatively or additionally, said controller comprises a casing suitable for long term implantation inside the body. Alternatively or additionally, said electrode is adapted for long term contact with bile fluids. Alternatively or additionally, the apparatus comprises an electrical activity sensor for sensing electrical activity of said cell and wherein said power source electrifies said electrode at a frequency higher than a sensed depolarization frequency of said cell, thereby causing said cell to depolarize at the higher frequency.

In an exemplary embodiment of the invention, said pulse is designed to extend a plateau duration of an action potential of said cell, thereby allowing more calcium inflow into the cell. Optionally, said pulse is deigned to reduce an action potential frequency of said cell, while not reducing insulin secretion from said cell.

In an exemplary embodiment of the invention, said pulse is designed to extend a duration of a burst activity of said cell.

In an exemplary embodiment of the invention, said pulse has an amplitude sufficient to recruit non-participating insulin secreting cells of said group of cells.

In an exemplary embodiment of the invention, the apparatus comprises at least a second electrode adjacent for electrifying a second cell of group of insulin secreting cells, wherein said controller electrifies said second electrode with a second pulse different from said first electrode. Optionally, said second pulse is designed to suppress insulin secretion. Optionally, said controller is programmed to electrify said second electrode at a later time to forcefully secrete said insulin whose secretion is suppressed earlier. Alternatively, said second pulse is designed to hyper-polarize said second cells.

In an exemplary embodiment of the invention, said controller electrifies said at least one electrode with a pacing pulse having a sufficient amplitude to force a significant portion of said cells to depolarize, thus aligning the cells' action potentials with respect to the non-excitatory pulse electrification.

In an exemplary embodiment of the invention, said controller synchronizes the electrification of said electrode to a burst activity of said cell.

In an exemplary embodiment of the invention, said controller synchronizes the electrification of said electrode to an individual action potential of said cell.

In an exemplary embodiment of the invention, said controller does not synchronize the electrification of said electrode to electrical activity of said cell.

In an exemplary embodiment of the invention, said controller does not apply said pulse at every action potential of said cell.

In an exemplary embodiment of the invention, said controller does not apply said pulse at every burst activity of said cell.

In an exemplary embodiment of the invention, said pulse has a duration of less than a single action potential of said cell. Optionally, said pulse has a duration of less than a plateau duration of said cell.

In an exemplary embodiment of the invention, said pulse has a duration of longer than a single action potential of said cell.

In an exemplary embodiment of the invention, said pulse has a duration of longer than a burst activity duration of said cell.

In an exemplary embodiment of the invention, said controller determines said electrification in response to a pharmaceutical treatment applied to the cell. Optionally, said pharmaceutical treatment comprises a pancreatic treatment. Alternatively or additionally, said controller applies said pulse to counteract adverse effects of said pharmaceutical treatment.

In an exemplary embodiment of the invention, said controller applies said pulse to synergistically interact with said pharmaceutical treatment. Alternatively, said controller applies said pulse to counteract adverse effects of pacing stimulation of said cell.

In an exemplary embodiment of the invention, said apparatus comprises an alert generator. Optionally, said controller activates said alert generator if said glucose level is below a threshold. Alternatively or additionally, said controller activates said alert generator if said glucose level is above a threshold.

There is also provided in accordance with an exemplary embodiment of the invention, a method of controlling insulin secretion, comprising:

providing an electrode to at least a part of a pancreas;

applying a non-excitatory pulse to the at least part of a pancreas, which pulse increases secretion of insulin. Optionally, the method comprises applying an excitatory pulse in association with said non-excitatory pulse. Alternatively or additionally, the method comprises applying a secretion reducing non-excitatory in association with said non-excitatory pulse.

In an exemplary embodiment of the invention, the method comprises applying a plurality of pulses in a sequence designed to achieve a desired effect on said at least a part of a pancreas.

There is thus provided in accordance with an exemplary embodiment of the invention, a pancreatic controller, comprising:

at least one electrode adapted for electrifying at least a portion of a pancreas; and a controller programmed to electrify said electrode so as to positively control at least the effect of at least two members of a group consisting of blood glucose level, blood insulin level and blood level of another pancreatic hormone. Optionally, controlling comprises modifying said at least two members simultaneously. Alternatively or additionally, controlling comprises selectively modifying only one of said at least two members, while at least reducing a causative interaction between said two members. Alternatively or additionally, controlling comprises maintaining at least one of said members within a desired physiologic range. Alternatively or additionally, said at least two members comprise glucose level and insulin level. Optionally, controlling comprises modulating an effect of said insulin not related to carbohydrate metabolism.

In an exemplary embodiment of the invention, at least one of said two members comprise glucagon. Optionally, controlling comprises increasing glucagon secretion, to contract an effect of insulin. Alternatively or additionally, controlling comprises increasing glucagon secretion, to achieve higher blood glucose levels. Alternatively or additionally, controlling comprises reducing the secretion of glucagon, when insulin secretion is increased.

In an exemplary embodiment of the invention, at least one of said two members comprise Somatostatin. Alternatively or additionally, at least one of said members comprises glucose level. Optionally, said controller selects between alternative control therapies, a therapy that has a least disrupting effect on said glucose levels.

In an exemplary embodiment of the invention, said controller uses solely electrical fields to control said members.

In an exemplary embodiment of the invention, said controller takes molecules provided in the body, into account, for said control. Optionally, said molecules are provided without a control of said controller. Alternatively, said molecules are provided under a control of said controller.

In an exemplary embodiment of the invention, said molecules suppress the secretion of at least one pancreatic hormone. Alternatively or additionally, wherein said molecules suppress the effect of at least one pancreatic hormone. Alternatively or additionally, said molecules enhance the secretion of at least one pancreatic hormone. Alternatively or additionally, said molecules enhance the effect of at least one pancreatic hormone.

In an exemplary embodiment of the invention, controlling a member hormone comprises suppressing a secretion of an antagonistic hormone. Alternatively or additionally, controlling a member hormone comprises enhancing a secretion of an antagonistic hormone.

In an exemplary embodiment of the invention, said controller comprises a learning memory module for storing therein feedback interaction of said pancreas. Optionally, said feedback interactions comprises interactions between hormone levels. Alternatively or additionally, said feedback interactions comprises interactions between hormone levels. Alternatively or additionally, said feedback interactions are dependent on blood glucose levels. Alternatively or additionally, said feedback interactions are determined by said controller, by tracking a behavior of said pancreas. Optionally, said controller actively modifies at least one of a glucose level and a pancreatic hormone level, to collect feedback interaction information.

In an exemplary embodiment of the invention, the controller comprises a sensor for sensing a level of said controlled member. Alternatively or additionally, the controller comprises an estimator for estimating a level of said controlled member. Alternatively or additionally, said electrode applies a non-excitatory pulse to effect said control. Alternatively or additionally, said electrode applies an excitatory pulse to effect said control.

In an exemplary embodiment of the invention, said electrode modifies blood flow associated with said pancreas to effect said control. Optionally, said modified blood flow comprises blood flow to hormone generating cells of said pancreas. Alternatively, said modified blood flow comprises blood flow from said pancreas.

In an exemplary embodiment of the invention, said modified blood flow comprises blood flow from hormone generating cells of said pancreas.

In an exemplary embodiment of the invention, said at least one electrode comprises at least two electrodes that selectively electrify different parts of said pancreas, to achieve a desired control of said at least two members.

In an exemplary embodiment of the invention, controlling comprises controlling secretion.

In an exemplary embodiment of the invention, controlling comprises controlling production. Alternatively or additionally, controlling comprises controlling physiological activity.

There is also provided in accordance with an exemplary embodiment of the invention, a method of mapping pancreatic behavior of a pancreas, comprising:

determining a behavior of a pancreas at a first set of conditions;

determining a behavior of a pancreas at a second set of conditions; and analyzing the behavior of the pancreas and the sets of conditions, to determine a behavior pattern of the pancreas. Optionally, said behavior pattern comprises an interrelationship between two hormones of said pancreas. Alternatively or additionally, said sets of conditions are naturally occurring. Alternatively, said sets of conditions are at least partially artificially induced.

In an exemplary embodiment of the invention, the method comprises controlling said pancreas responsive to said determined behavior. Optionally, controlling comprises controlling using pharmaceuticals. Alternatively or additionally, controlling comprises controlling using electrical fields.

There is also provided in accordance with an exemplary embodiment of the invention, a method of controlling burst activity of a pancreas, comprising:

applying an electrical field to at least part of a pancreas such that burst activity is initiated a few seconds after said application; and repeating said application a plurality of times such that substantially all burst activity of said part of a pancreas during a time period spanning said applications is synchronized to said application and repeated application. Optionally, the method comprises varying a repetition rate of said application to control a burst rate of said at least part of a pancreas.

There is also provided in accordance with an exemplary embodiment of the invention, a method of controlling activity of a pancreas, comprising:

providing a source of electrical fields; and electrifying said source to apply an electric field to at least part of a pancreas, such that said applied field increases an amplitude of at least one burst following said application. Optionally, said applied field does not induce a new burst. Alternatively or additionally, said applied field does not substantially change a burst rate of said pancreas. Alternatively or additionally, said increased amplitude burst provides an increased level of insulin relative to a normal amplitude burst. Alternatively or additionally, the method comprises synchronizing said electrification to a natural burst sequence of said at least part of a pancreas.

There is also provided in accordance with an exemplary embodiment of the invention, a method of glucose level control, comprising:

providing at least one electrode adapted to apply an electric field to a pancreas, and applying an electric field to the pancreas using said at least one electrode such that blood glucose levels are significantly reduced and blood insulin levels are not significantly increased compared to a regular insulin response in a same person. Optionally, the method comprises subsequently applying a second electric field to said pancreas, which second field increases insulin levels.

Optionally, said electric field is operative to reduce glucagon secretion.

Optionally, said electric field is operative to reduce glucose secretion by a liver physiologically coupled to said pancreas.

Optionally, said electric field is operative to increase glucose uptake by cells in a body containing said pancreas.

Optionally, said electric field is operative to affect nervous tissue in said pancreas.

Optionally, said electric field is non-excitatory in that it does not substantially induce new bursts of islet activity in said pancreas.

Optionally, said electric field is applied as a bi-phasic and charge balanced time varying field. Optionally, said electric field is applied for a short duration every period of time. Optionally, said period of time gives an application frequency of between 1 Hz and 15 Hz. Alternatively or additionally, said period of time gives an application frequency of about 5 Hz. Alternatively or additionally, said duration is less than 30 ms. Alternatively or additionally, said duration is about 10 ms.

Optionally, said electric field is repeated for a period of less than 30 minutes.

Optionally, said electric field is repeated for a period of between 30 and 180 minutes.

Optionally, said electric field is applied for substantially all of a duration of a glucose absorption event.

Optionally, said electric field is applied prior to an expected glucose ingestion event.

Optionally, the method comprises triggering said electric field by a glucose ingestion event.

Optionally, said electric field is applied irrespectively of an ingestion event.

Optionally, said electric field is applied at least part of the time irrespective of a blood glucose level.

Optionally, said electric field is applied continuously for at least 24 hours.

Optionally, said electric field is applied for a period of at least 15 minutes without sensing of its effect.

Optionally, said electric field is of a magnitude and temporal extent so that it does not significantly change blood insulin and glucose levels in the absence of an ingestion event.

Optionally, said electric field reduces blood glucose levels by at least 20% of an elevation of the glucose level above a fasting baseline glucose level.

Optionally, said electric field does not increase blood insulin levels, as measured by an average over five minutes, by more than 20%.

Optionally, said electric field reduces blood insulin levels, as measured by an accumulated amount for a glucose ingestion event and in comparison to a regular response of said person, by more than 20%.

Optionally, the method comprises delaying a gastric emptying by applying a treatment to the stomach.

Optionally, said electric field is operative to delay a glucose peak at least by a duration of its application.

Optionally, said electric field is operative to delay a glucose peak at least by 10 minutes.

Optionally, said electric field is operative to delay an insulin peak at least by 10 minutes.

Optionally, said electric field is operative to truncate an insulin peak.

Optionally, said electric field is operative to truncate a glucose peak.

Optionally, said electrode is not attached to a pancreas.

Optionally, said electrode is attached to a pancreas.

There is also provided in accordance with an exemplary embodiment of the invention, a method of glucose level control, comprising:

providing at least one electrode adapted to apply an electric field to a pancreas; and applying an electric field to the pancreas operative to reduce blood glucose levels if elevated and not significantly reduce such levels in an acute manner if not substantially elevated. Optionally, said electric field reduces elevated glucose levels by at least 10%. Optionally, said electric field does not acutely reduce unelevated glucose levels by more than 10%. Optionally, said electric field does not impair exocrine functions of said pancreas.

There is also provided in accordance with an exemplary embodiment of the invention, apparatus for blood glucose control, comprising:

at least one electrode adapted to apply an electric field to a pancreas; and circuitry adapted to electrify said at least one electrode and configured to electrify said electrode with a non-excitatory field in a manner which compensates for a loss of acute response by said pancreas. Optionally, said circuitry compensates by causing the secretion of an insulin bolus.

Optionally, said circuitry compensates by reducing glucose levels in a non-insulin manner. Optionally, said circuitry compensates by reducing glucagon secretion.

Optionally, said circuitry reduces or prevents a substantial increase in insulin secretion during said compensation.

Optionally, for at least 20% of ingestion events said circuitry applies only an acute control of insulin levels. Optionally, said apparatus is programmed with a knowledge of a slow acting chemical-based insulin therapy provided to said pancreas.

Optionally, the apparatus comprises an automatic ingestion sensor for automatically detecting an ingestion event.

Optionally, the apparatus comprises an automatic glucose sensor for automatically detecting a situation requiring an acute response.

Optionally, the apparatus comprises an automatic glucose sensor for automatically detecting a situation requiring an acute insulin response.

Optionally, said response is an acute insulin response.

Optionally, said electrode is adapted for attachment to a pancreas.

Optionally, said electrode is adapted for attachment to a muscular organ.

There is also provided in accordance with an exemplary embodiment of the invention, apparatus for blood glucose control, comprising:

at least one electrode adapted to apply an electric field to a pancreas; and circuitry adapted to electrify said at least one electrode and configured to electrify said electrode in a manner which significantly reduces elevated blood glucose levels, said circuitry configured to apply said field also when glucose levels are not elevated. Optionally, said circuitry is a closed loop system including sensing of the effect of the electrification and wherein said circuitry is configured to over stimulate in cases of doubt.

Optionally, said circuitry is a semi-open loop system where a relatively long stimulation series is applied without feedback.

Optionally, said circuitry is an open loop system where a stimulation series is applied responsive to a trigger and without feedback.

There is also provided in accordance with an exemplary embodiment of the invention, apparatus for blood glucose control, comprising:

at least one electrode adapted to apply an electric field to pancreatic tissue; and circuitry adapted to electrify said at least one electrode and configured to electrify said electrode in a manner which reduces glucose levels and does not substantially elevate insulin levels above a baseline value, when glucose levels are elevated. Optionally, said circuitry is a closed loop system including sensing of the effect of the electrification and wherein said circuitry is configured to over stimulate in cases of doubt.

Optionally, said circuitry is a semi-open loop system where a relatively long stimulation series is applied without feedback.

Optionally, said circuitry is an open loop system where a stimulation series is applied responsive to a trigger and without feedback.

Optionally, said circuitry applies a constant voltage field.

Optionally, said circuitry applies a constant current field.

Optionally, said pancreatic tissue comprises an in-vivo pancreas.

Optionally, said pancreatic tissue comprises a pancreatic tissue implant.

Optionally, said baseline is a baseline insulin response of a person for which the apparatus is used.

There is also provided in accordance with an exemplary embodiment of the invention, a method of insulin level control, comprising:

providing at least one electrode adapted to apply an electric field to a pancreas; and applying an electric field to the pancreas using said at least one electrode such that blood glucose levels are not significantly increased and blood insulin levels are significantly reduced.

There is also provided in accordance with an exemplary embodiment of the invention, a method of applying an electric field to a pancreas or functionally and positionally associated tissue, comprising:

attaching at least one electrode to a tissue other than said pancreas; and electrifying said electrode such that a significant field is applied to said pancreas or associated tissue to control at least one of a level of a pancreas secretion and a blood glucose level. Optionally, the method comprises using said at least one electrode to also control eating habits.

There is also provided in accordance with an exemplary embodiment of the invention apparatus for applying an electric field to a pancreas or functionally and positionally associated tissue, comprising:

at least one electrode adapted to be attached to a tissue other than said pancreas; and means for electrifying said electrode such that a significant field is applied to said pancreas or associated tissue to control at least one of a level of a pancreas secretion and a blood glucose level.

There is yet further provided, in accordance with an embodiment of the present invention, a method for treating a subject, including:

applying an electrical signal to a colon or a distal small intestine of the subject; and configuring the signal to stimulate cells to increase secretion of glucagon-like-peptide-1 (GLP-1), in order to treat the subject.

In an embodiment, the method includes detecting eating by the subject, and applying the electrical signal includes applying the signal responsive to detecting the eating.

There is also provided, in accordance with an embodiment of the present invention, a method for treating a subject, including:

applying an electrical signal to a stomach of the subject; and configuring the electrical signal to reduce a blood glucose level of the subject, in order to treat the subject.

In an embodiment, the method includes detecting eating by the subject, wherein applying the electrical signal includes applying the electrical signal responsive to detecting the eating.

Alternatively or additionally, applying the electrical signal includes applying an Excitable-Tissue Control (ETC) signal.

There is additionally provided, in accordance with an embodiment of the present invention, a method for treating a subject, including:

applying an electrical signal to a small intestine of the subject; and configuring the electrical signal to reduce a blood glucose level of the subject, in order to treat the subject.

There is yet additionally provided, in accordance with an embodiment of the present invention, a method for treating a subject, including:

applying an Excitable-Tissue Control (ETC) signal to a smooth muscle of the subject; and configuring the ETC signal to reduce a blood glucose level of the subject, in order to treat the subject.

For some applications, applying the ETC signal includes applying the ETC signal to a site of a gastrointestinal tract of the subject. In an embodiment, applying the ETC signal includes applying the ETC signal to a duodenal site of the subject. Alternatively or additionally, applying the ETC signal includes applying the ETC signal to a site of a colon of the subject.

There is still additionally provided, in accordance with an embodiment of the present invention, a method for treating a subject, including:

applying an Excitable-Tissue Control (ETC) signal to cardiac muscle tissue of the subject; and configuring the ETC signal to reduce a blood glucose level of the subject, in order to treat the subject.

There is further provided, in accordance with an embodiment of the present invention, a method for treating a subject, including:

applying an electrical signal to at least one stomach site of the subject; and configuring the electrical signal to reduce a rise in a blood glucose level of the subject, in order to treat the subject.

In an embodiment, applying the electrical signal includes applying an Excitable-Tissue Control (ETC) signal.

There is still further provided, in accordance with an embodiment of the present invention, a method for treating a subject, including:

applying an electrical signal to at least one small intestine site of the subject; and configuring the electrical signal to reduce a rise in a blood glucose level of the subject, in order to treat the subject.

There is yet further provided, in accordance with an embodiment of the present invention, a method for treating a subject, including:

applying an Excitable-Tissue Control (ETC) electrical signal to at least one smooth muscle site of the subject; and configuring the ETC electrical signal to reduce a rise in a blood glucose level of the subject, in order to treat the subject.

In an embodiment, the smooth muscle site includes a gastrointestinal tract site of the subject, and applying the ETC electrical signal includes applying the ETC electrical signal to the gastrointestinal tract site.

In an embodiment, the gastrointestinal tract site includes a duodenal site of the subject, and applying the ETC electrical signal includes applying the ETC electrical signal to the duodenal site.

In an embodiment, the gastrointestinal tract site includes a colon site of the subject, and applying the ETC electrical signal includes applying the ETC electrical signal to the colon site.

In an embodiment, the at least one site includes a gastric corpus site and a gastric antrum site, and applying the signal includes applying the signal between the gastric corpus site and the gastric antrum site.

In an embodiment, the gastric corpus site includes a posterior gastric corpus site, and applying the signal includes applying the signal between the posterior gastric corpus site and the gastric antrum site.

In an embodiment, the gastric antrum site includes a posterior gastric antrum site, and applying the signal includes applying the signal between the posterior gastric corpus site and the posterior gastric antrum site.

In an embodiment, the gastric antrum site includes an anterior gastric antrum site, and applying the signal includes applying the signal between the posterior gastric corpus site and the anterior gastric antrum site.

In an embodiment, the gastric corpus site includes an anterior gastric corpus site, and applying the signal includes applying the signal between the anterior gastric corpus site and the gastric antrum site.

In an embodiment, the gastric antrum site includes a posterior gastric antrum site, and applying the signal includes applying the signal between the anterior gastric corpus site and the posterior gastric antrum site.

In an embodiment, the gastric antrum site includes an anterior gastric antrum site, and applying the signal includes applying the signal between the anterior gastric corpus site and the anterior gastric antrum site.

In an embodiment, the at least one site includes a first gastric corpus site and a second gastric corpus site, and applying the signal includes applying the signal between the first gastric corpus site and the second gastric corpus site.

In an embodiment, the first gastric corpus site includes a posterior first gastric corpus site, and applying the signal includes applying the signal between the posterior first gastric corpus site and the second gastric corpus site.

In an embodiment, the second gastric corpus site includes a posterior second gastric corpus site and applying the signal includes applying the signal between the posterior first gastric corpus site and the posterior second gastric corpus site.

In an embodiment, the second gastric corpus site includes an anterior second gastric corpus site, and applying the signal includes applying the signal between the posterior first gastric corpus site and the anterior second gastric corpus site.

In an embodiment, the first gastric corpus site includes an anterior first gastric corpus site, and applying the signal includes applying the signal between the anterior first gastric corpus site and the second gastric corpus site.

In an embodiment, the second gastric corpus site includes a posterior second gastric corpus site, and applying the signal includes applying the signal between the anterior first gastric corpus site and the posterior second gastric corpus site.

In an embodiment, the second gastric corpus site includes an anterior second gastric corpus site, and applying the signal includes applying the signal between the anterior first gastric corpus site and the anterior second gastric corpus site.

In an embodiment, the at least one site includes a first gastric antrum site and a second gastric antrum site, and applying the signal includes applying the signal between the first gastric antrum site and the second gastric antrum site.

In an embodiment, the first gastric antrum site includes a posterior first gastric antrum site, and applying the signal includes applying the signal between the posterior first gastric antrum site and the second gastric antrum site.

In an embodiment, the second gastric antrum site includes a posterior second gastric antrum site, and applying the signal includes applying the signal between the posterior first gastric antrum site and the posterior second gastric antrum site.

In an embodiment, the second gastric antrum site includes an anterior second gastric antrum site, and applying the signal includes applying the signal between the posterior first gastric antrum site and the anterior second gastric antrum site.

In an embodiment, the first gastric antrum site includes an anterior first gastric antrum site, and applying the signal includes applying the signal between the anterior first gastric antrum site and the second gastric antrum site.

In an embodiment, the second gastric antrum site includes a posterior second gastric antrum site, and applying the signal includes applying the signal between the anterior first gastric antrum site and the posterior second gastric antrum site.

In an embodiment, the second gastric antrum site includes an anterior second gastric antrum site, and applying the signal includes applying the signal between the anterior first gastric antrum site and the anterior second gastric antrum site.

There is also provided, in accordance with an embodiment of the present invention, a method for treating a subject, including:

applying an Excitable-Tissue Control (ETC) electrical signal to at least one cardiac muscle tissue site of the subject; and configuring the ETC electrical signal to reduce a rise in a blood glucose level of the subject, in order to treat the subject.

In an embodiment, configuring the electrical signal includes configuring the electrical signal to reduce a rise in a blood insulin level of the subject.

In an embodiment, applying the electrical signal includes applying five or more pulses to the site during each of a plurality of slow wave cycles of the subject.

In an embodiment, applying the electrical signal includes applying 1 to 5 pulses to the site during each of a plurality of slow wave cycles of the subject. In an embodiment, applying 1 to 5 pulses includes applying one pulse to the site during each of the plurality of slow wave cycles.

In an embodiment, applying the electrical signal includes configuring a frequency of the electrical signal to be between 1 and 30 Hz. In an embodiment, configuring the frequency includes configuring the frequency to be between 10 and 30 Hz. In an embodiment, configuring the frequency includes configuring the frequency to be between 1 and 10 Hz. In an embodiment, configuring the frequency includes configuring the frequency to be between 2.5 and 7.5 Hz.

In an embodiment, applying the electrical signal includes configuring a frequency of the electrical signal to be between 30 and 200 Hz. In an embodiment, configuring the frequency includes configuring the frequency to be between 100 and 200 Hz. In an embodiment, configuring the frequency includes configuring the frequency to be between 30 and 100 Hz. In an embodiment, configuring the frequency includes configuring the frequency to be between 60 and 100 Hz.

In an embodiment, applying the electrical signal includes applying pulses and configuring a pulse amplitude of the pulses to be between 2 and 15 mA. In an embodiment, configuring the pulse amplitude includes configuring the pulse amplitude to be between 2.5 and 7.5 mA.

In an embodiment, applying the electrical signal includes applying pulses in a pulse train and configuring a length of the pulse train to be between 1 and 6 seconds. In an embodiment, configuring the length of the pulse train includes configuring the length of the pulse train to be between 3 and 6 seconds.

In an embodiment, applying the electrical signal includes applying a train of biphasic pulses. In an embodiment, applying the train of biphasic pulses includes setting a duration of each phase of the biphasic pulses to be between 1 and 10 ms. In an embodiment, setting the duration includes setting the duration of each phase of the biphasic pulses to be between 4 and 6 ms.

In an embodiment, applying the electrical signal includes sensing a physiological attribute of the subject and applying the electrical signal responsive thereto. In an embodiment, sensing the physiological attribute of the subject includes sensing that the subject is eating. In an embodiment, sensing the physiological attribute includes sensing a gastrointestinal tract attribute. In an embodiment, sensing the gastrointestinal tract attribute includes sensing a slow wave.

In an embodiment, applying the electrical signal includes:
applying an initiating pulse; and
applying a burst of pulses at least 100 ms following a termination of the initiating pulse.

In an embodiment, applying the initiating pulse includes applying the initiating pulse not responsively to any physiological attribute of the subject sensed within one minute prior to the applying of the initiating pulse.

In an embodiment, applying the initiating pulse includes applying the initiating pulse not responsively to any sensing of a slow wave within one minute prior to the applying of the initiating pulse.

In an embodiment, applying the burst of pulse includes configuring a frequency of the burst of pulses to be between 1 and 10 Hz.

In an embodiment, applying the burst of pulse includes configuring a frequency of the burst of pulses to be between 10 and 100 Hz.

In an embodiment, applying the initiating pulse includes sensing a physiological attribute of the subject and applying the initiating pulse responsive thereto. In an embodiment, sensing the physiological attribute includes sensing a gastrointestinal tract attribute of the subject. In an embodiment, sensing the gastrointestinal tract attribute includes sensing an indication of a slow wave. In an embodiment, sensing the gastrointestinal tract attribute includes sensing an indication of eating by the subject.

In an embodiment, applying the burst of pulses at least 100 ms following the termination of the initiating pulse includes initiating applying the burst of pulses less than 4 seconds following the termination of the initiating pulse. In an embodiment, applying the burst of pulse includes initiating applying the burst of pulses between 100 and 500 ms following the termination of the initiating pulse. In an embodiment, applying the initiating pulse includes configuring a duration of the initiating pulse to be between 50 and 500 ms. In an embodiment, configuring the duration includes configuring the duration to be between 50 and 150 ms.

BRIEF DESCRIPTION OF THE DRAWINGS

Particular embodiments of the invention will be described with reference to the following description of exemplary embodiments in conjunction with the figures, wherein identical structures, elements or parts which appear in more than one figure are optionally labeled with a same or similar number in all the figures in which they appear, in which:

FIGS. 10A-10B are a chart and a pulse diagram, respectively, of an experiment showing reduction in glucose levels as a result of applying an electrical pulse in accordance with an exemplary embodiment of the invention;

FIGS. 11A-11B are a chart and a pulse diagram, respectively, of an experiment showing reduction in glucose levels as a result of applying an electrical pulse in accordance with an exemplary embodiment of the invention;

FIGS. 13A-13B are a chart and a pulse diagram, respectively, of an experiment showing reduction in glucose levels as a result of applying an electrical pulse in accordance with an exemplary embodiment of the invention;

DETAILED DESCRIPTION OF EXEMPLARY EMBODIMENTS

Overview

Figure 1:
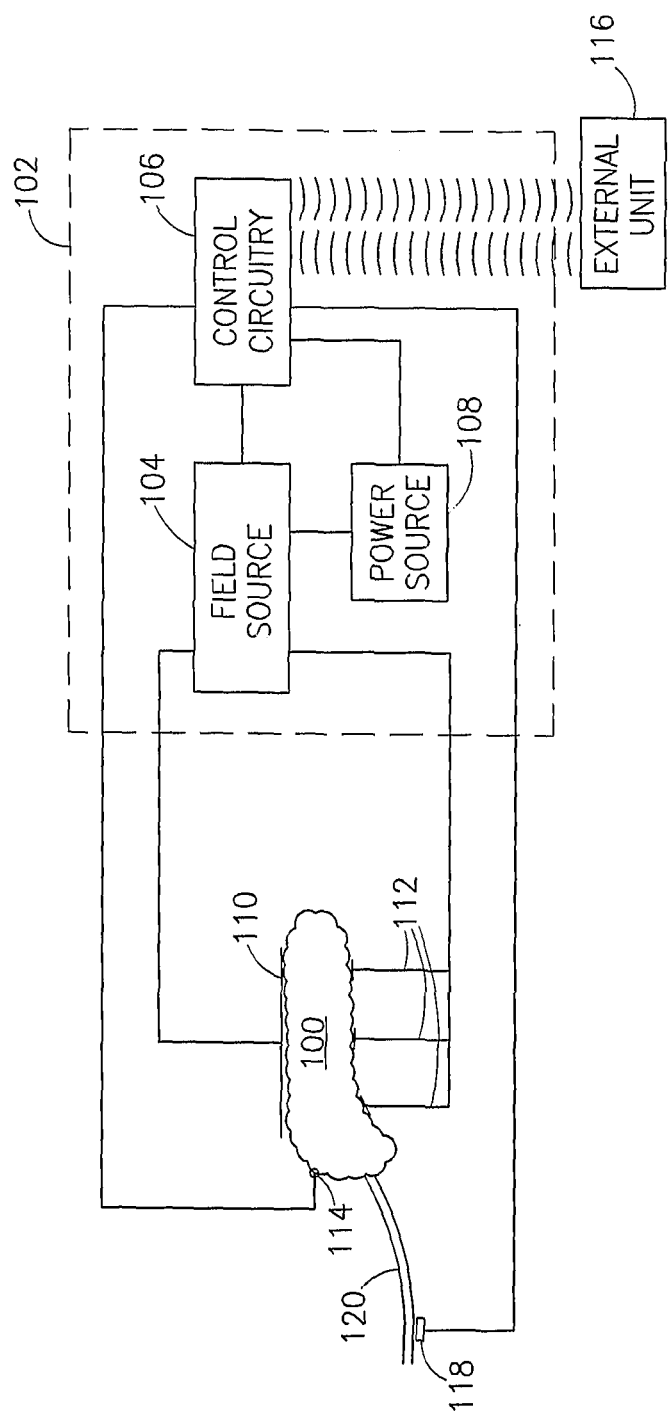
FIG. 1 is a block diagram of a pancreatic controller, in accordance with an exemplary embodiment of the invention.

FIG. 1 is a block diagram of a pancreatic controller 102, in accordance with an exemplary embodiment of the invention. In an exemplary embodiment of the invention, device 102 is used to provide controlling pulses of electricity to a pancreas 100. Such controlling pulses may include excitatory stimulating pulses and non-excitatory pulses. In particular, such pulses can include pacing pulses and action potential modifying pulses.

In an exemplary embodiment of the invention, the controlling pulses are used to control the glucose and insulin level of a patient. Further, a particular desired profile of glucose and/or insulin may be achieved. Alternatively or additionally, the secretion and/or generation of other pancreatic hormones may be controlled. Other uses of controller 102 will be evident from the description below and can include, for example, training, healing and preventing damage of pancreatic cells.

Exemplary and non-limiting examples of metabolic and/or hormonal disorders that may be treated by suitable application of the methods described below, include non-insulin dependent diabetes mellitus, insulin dependent diabetes mellitus and hyperinsulinemia.

The following description includes many different pulses that may be applied to achieve a desired effect; it should be clear that the scope of the description also covers apparatus, such as controller 102 that is programmed to apply the pulses and/or process feedback, as required. It should also be noted that a desired effect may be achieved by applying various combinations of the pulses described below, for two different sequences. The particular combinations of pulses that is appropriate for a particular patient may need to be determined on a patient by patient basis and may also change over time. Exemplary pulses and sequences, however, are described below.

Exemplary Device

Pancreatic controller 102, includes generally a field source 104 for generating electric fields across pancreas 100 or portions thereof, which field source is controlled by control circuitry 106. A power source 108 optionally powers field source 104 and control circuitry 106. The electrification is applied using a plurality of electrodes for example a common electrode 110 and a plurality of individual electrodes 112. Alternatively other electrode schemes are used, for example a plurality of electrode pairs.

Electrical and other sensors may be provided as well, for input into controller 106. Although the electrodes may also serve as electrical sensors, in an exemplary embodiment of the invention, separate sensors, such as a pancreatic sensor 114 or a glucose blood sensor 118 on a blood vessel 120, are provided. Extra-cellular sensors, for measuring inter-cellular glucose levels, may also be provided. Controller 102 may also include an external unit 116, for example for transmitting power or programming to control circuitry 106 and/or power source 108. Alternatively or additionally, the external unit may be used to provide indications from a patient and/or sensor information. Alternatively or additionally, the external unit may be used to provide alerts to the patient, for example if the glucose level is not properly under control. Alternatively or additionally, such alerts may be provided from inside the body, for example using low frequency sounds or by electrical stimulation of a nerve, a muscle or the intestines.

Additional details of this and other exemplary implementations will be provided below. However, the general structure of controller 102 may utilize elements and design principles used for other electro-physiological controllers, for example as described in PCT publications WO97/25098, WO98/10831, WO98/10832 and U.S. patent application Ser. No. 09/260,769, issued as U.S. Pat. No. 6,292,693 the disclosures of which are incorporated herein by reference. It is noted, however, that the frequencies, power levels and duration of pulses in the pancreas may be different from those used, for example, in the heart. In particular, the power levels may be lower. Additionally, the immediate effects of an error in applying a pulse to the pancreas are not expected to be as life threatening as a similar error in the heart would be, excepting the possibility of tissue damage, which could cause an increase in severity of disease of the patient.

Tissue to which the Controller is Applied

The present invention is described mainly with reference to pancreatic tissues. Such tissue may be in the pancreas or be part of an implant, possibly elsewhere in the body, or even in the controller envelope itself, the implant comprising, for example, homologous, autologous or heterologous tissue. Alternatively or additionally, the implant may be genetically modified to produce insulin. It should be noted that different parts of the pancreas may have different secretion-related behavior and/or response to electric fields.

Electrical Activity in the Pancreas

Figure 2:
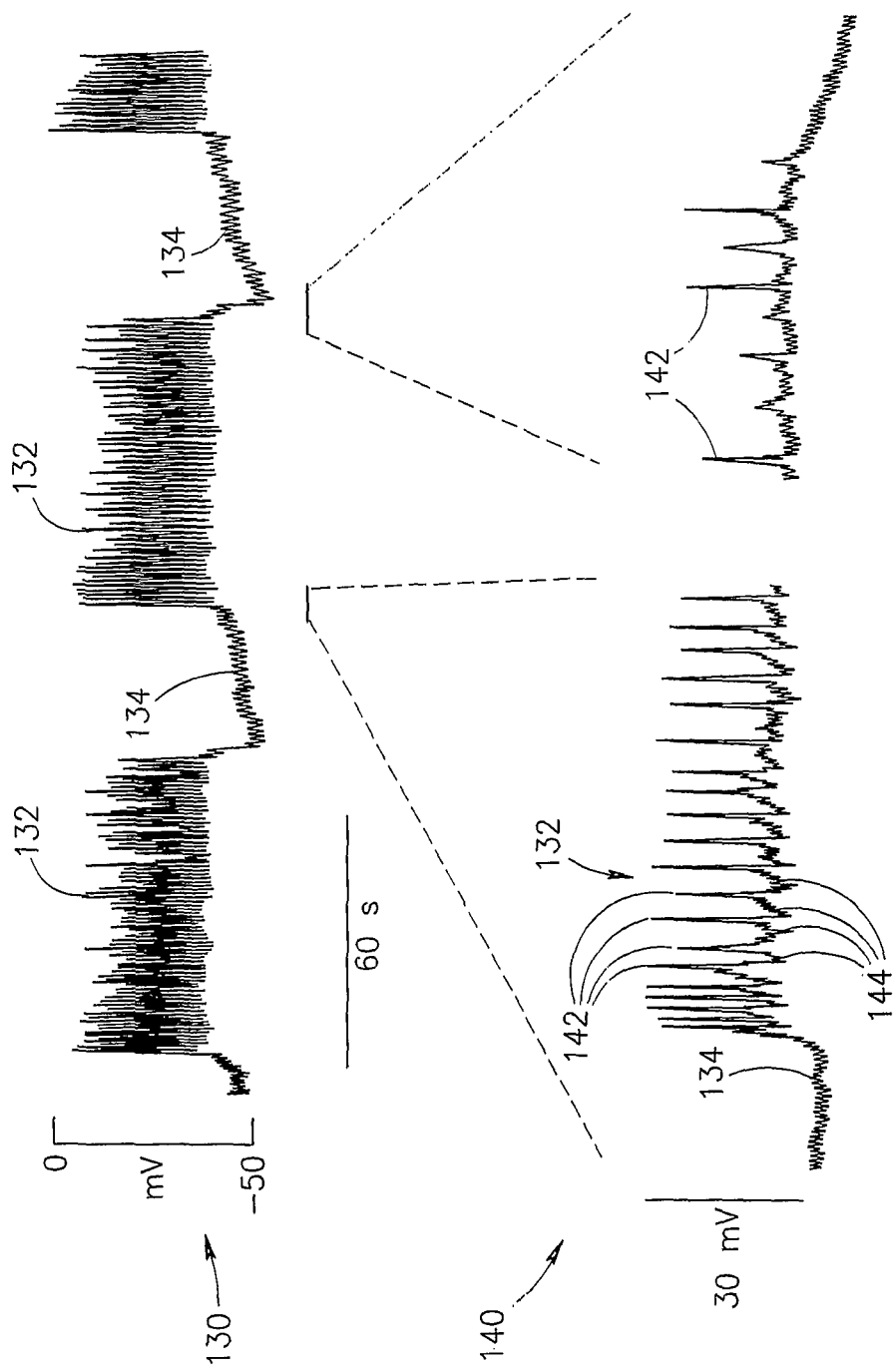
FIG. 2 is a diagram of an exemplary electrical activity of a single beta cell, operating at slightly elevated glucose levels.

FIG. 2 is a diagram of an exemplary electrical activity of a single beta cell, operating at slightly elevated glucose levels. In a large scale graph 130, the activity of a single cell is shown as comprising a plurality of burst periods 132 comprising a plurality of individual action potentials and separated by a plurality of interval periods 134, in which periods there are substantially no action potentials. As shown in a blow-up graph 140, each burst comprises a plurality of depolarization events 142, each followed by a repolarization period 144. The level of intra cellular calcium increases during the burst 132 and decreases during interval 134.

The beta cells of a pancreas are arranged in islets, each such islet acts as a single activation domain, in which, when the glucose levels are high enough, a propagating action potential is to be found. Thus, the aggregate electrical activity of an islet is that of a repeating average action potential, at a frequency of, for example, 1 Hz, which generally depends on the propagation time of an action potential through the islet. During intervals 134, if enough of the beta cells share the interval, the entire islet may be generally silent or contain only sporadic depolarization events. Individual cells may operate at higher frequencies, for example, 5-20 Hz. Alternatively or additionally, a slow wave may provide an envelope of about 3-5 cycles/min. It should be noted that the synchronization and/or correlation between cells in an islet may depend on gap junctions between beta and other cells. The resistance or such gap junctions may depend on the glucose and/or hormone levels, and as such, may also be determined and controlled, in accordance with some embodiments of the invention. Alternatively or additionally, the level of synchronization in an islet and/or between islets may be used as an indicator for glucose and/or hormone levels. Recent studies suggest that synchronization of different parts of the pancreas is mediated by nervous pathways. In an exemplary embodiment of the invention, such nervous pathways are stimulated and/or blocked by the application of electric fields and/or pharmaceuticals, in order to achieve desired results. An example such study is described in "Pulsatile insulin secretion: detection, regulation, and role in diabetes", Diabetes. 2002 February; 51 Suppl 1:S245-54, by Porksen N, Hollingdal M, Juhl C, Butler P, Veldhuis J D, Schmitz O, of the Department of Endocrinology and Metabolism M, Aarhus University Hospital, Aarhus, Denmark, the disclosure of which is incorporated herein by reference.

Insulin Secretion Increase

The secretion of insulin, as differentiated from the production of insulin, may be increased in several ways, in accordance with exemplary embodiments of the invention. The following methods may be applied together or separately. Also, these methods may be applied locally, to selected parts of the pancreas, or globally, to the pancreas as a whole.

In a first method, the duration of a burst 132 is increased, thus allowing more calcium to enter the beta cells. It is believed that the level of calcium in the cell is directly related to the amount of insulin released by the cell. One type of pulse which may be applied is a pacing pulse, which forces the cells in the islet to depolarize. Such a pulse is optionally applied at the same frequency as individual action potentials, e.g., 10 Hz. However, it may not be necessary to pace every action potential, a periodic pacing signal may be sufficient to force continuous depolarization events. As well known in the art of cardiac pacing, many techniques can be applied to increase the capture probability of the pacing signal, for example, double pacing, pulse shape and duration. These methods may also be applied, with suitable modifications, to the pacing of the pancreas. An alternative method of increasing burst length is by increasing the sensitivity of the beta cells to depolarization, for example, by sub-threshold pulses. Another method of sensitizing the cells and/or increasing their action potential duration is by hyperpolarizing the cells prior to a forced or normal depolarization. Possibly, by preventing the normal reduction in depolarization frequency towards the end of a burst, a higher insulin output can be achieved for a same length burst.

In another method, insulin secretion is increasing by increasing the calcium inflow efficiency of the individual action potentials. In an exemplary embodiment of the invention, this is achieved by increasing the length of the plateau durations 144, for example by applying an electric pulse during the repolarization period associated with each of depolarization events 142. If such a pulse is applied early enough in the repolarization phase of an action potential, period, prior to closing of the calcium channels that provide the calcium inflow, these channels may stay open longer and will provide more calcium inflow. It is noted that the frequency of firing of the beta cells may be reduced.

In some cells, the calcium inflow may be more efficient during the depolarization period. In these cells, depolarization period 142 is optionally extended, for example by applying an additional depolarizing pulse during the depolarization or very shortly after. Alternatively or additionally, a pharmaceutical that enhances repolarization may be provided, so that the repolarization time is shorter and more of the duration of a burst 132 can be spent in depolarization events. Alternatively or additionally, a plateau duration can be shortened by applying a suitable pulse during the plateau. In one example, applying a pulse after the calcium channels close, is expected to shorten the repolarization time. Alternatively or additionally, the individual action potentials are paced, at a rate higher than normal for the glucose level. This pacing can override the end of repolarization and force more frequent depolarization events. It is noted that a considerably higher pacing rate can be achieved by pacing than would naturally occur for same physiological conditions. Possibly, the pacing rate is higher than physiologically normal for an islet at any glucose level.

In another method, the insulin secretion is enhanced by pacing the islets to have a higher frequency of bursts (as opposed to a higher frequency of action potentials, described above). The resulting shortening in intervals 134 may have undesirable effects, for example by maintaining high calcium levels in a cell for too long a period of time. In an exemplary embodiment of the invention, this potential shortcoming is overcome by increasing the interval durations, for example, by applying a hyper-polarizing pulse during the interval, thus allowing calcium to leak out of the beta cells. It is noted however, that in some cases, sustained elevated calcium levels may be desirable, in which case, the intervals may be artificially shortened. In compensation, the effectiveness of the burst in causing the secretion of insulin may be reduced.

A potential advantage of pacing is that the pacing signal will cause depolarization and associated recruitment of beta cells that would not otherwise take part in the activity of the pancreas. It is expected that as intra-cellular calcium levels rise (or some other control mechanism), some cells will cease to participate in electrical activity. By applying a pacing pulse, such cells are expected to be forced to participate and, thus, continue to secret insulin.

Another potential advantage of pacing is related to the synchronization problem. As can be appreciated, some types of controlling pulses need to be applied at a certain phase in the cellular action potential. In a propagating action potential situation, it may be difficult to provide a single pulse with timing that matches all the cells, especially as the depolarization frequency increases. However, by forcing simultaneous depolarization of an entire islet, the phases are synchronized, making a desirable pulse timing easier to achieve. It is noted, however, that even if there is no pacing, some pulses, such as for extending a plateau of an action potentials, can be applied at a time that is effective for a large fraction of the cells in the islet.

In some exemplary methods of insulin secretion increase, the amplitude of the islets depolarization is apparently increased. This may be, for example, by recruitment of otherwise non-participating cells, or be a result of synchronization of cells so that the electrical signals are additive.

Alternatively or additionally to calcium mediated vesicle transport, in an exemplary embodiment of the invention, the electrical field also directly releases insulin from the REP of the cell and/or from other organelles in the cell.

Insulin Secretion Suppression

In some cases, for example if the glucose level is too low, suppression of insulin secretion may be desirable. Again, the following methods may be applied together or separately. Also, as noted above, different methods may be applied to different parts of the pancreas, for example, by differently electrifying electrodes 112 of FIG. 1, thus for example, increasing secretion from one part of the pancreas while decreasing secretion from a different part at the same time. Another case where insulin repression may be desirable is to prevent a runaway feedback loop in which insulin secretion causes glucagon secretion which then releases more glucose from the liver.

In a first method of insulin secretion reduction, the beta cells are hyper-polarized, for example by applying a DC pulse. Thus, the cells will not respond to elevated glucose levels by depolarization and insulin secretion. It is noted that the applied pulse does not need to be synchronized to the electrical activity. It is expected that the hyper polarization will last a short while after the pulse is terminated. Possibly, only the length of the interval is increased, instead of completely stopping the burst activity.

In a second method, the insulin stores of the pancreas are dumped, so that at later times, the cells will not have significant amounts of insulin available for secretion. Such dumping may be performed for example, with simultaneous provision of glucose or an insulin antagonist, to prevent adverse effects. The insulin antagonist, glucose or other pharmaceuticals described herein may be provided in many ways. However, in an exemplary embodiment of the invention, they are provided by external unit 116 or by an internal pump (not shoe) in controller 102.

In a third method, the plateau durations 144 are shortened, for example by over-pacing the islet cells, so that there is less available time for calcium inflow. Alternatively, the intra-depolarization periods may be extended, by hyper-polarizing the cells during repolarization and after the calcium channels close (or forcing them closed by the hyper polarization). This hyper polarization will delay the onset of the next depolarization and thus, reduce the total inflow of calcium over a period of time.

Alternatively or additionally, a hyper-polarizing pulse may be applied during a burst, to shorten the burst.

Affecting Insulin Production

Various feedback mechanisms are believed to link the electrical activity of the beta cells and the production of insulin. In an exemplary embodiment of the invention, these feedback mechanisms are manipulated to increase or decrease insulin production, alternatively or additionally to directly controlling insulin secretion.

In an exemplary embodiment of the invention, beta cells are prevented from secreting insulin, for example, by applying a hyper-polarizing pulse. Thus, the intra-cellular stores remain full and less insulin is manufactured (and thus less insulin can reach the blood stream).

In an exemplary embodiment of the invention, the beta cells are stimulated to release insulin. Depending on the cell, it is expected that if a cell is over stimulated, it becomes tired out and requires a significant amount of time to recover, during which time it does not produce insulin. If a cell is under stimulated, it is expected that it will, over time produce less insulin, as it adapts to its new conditions. If a cell is stimulated enough, it will continuously produce insulin at a maximal rate.

Pancreatic Response Control

In an exemplary embodiment of the invention, rather than directly control insulin secretion levels, the response parameters of the pancreas are modified, to respond differently to glucose levels. One parameter that may be varied is the response time. Another parameter is the gain (amplitude) of the response. In some situations, these two parameters cannot be separated. However, it is noted that by providing complete control of the pancreas, many different response profiles can be provided by controller 102 directly.

In an exemplary embodiment of the invention, the response time of the pancreas is increased or reduced by blocking or priming the fast-responding portions of the pancreas, in patients that have both fast and slow responding portions. Blocking may be achieved, for example, by partial or complete hyper-polarization. Priming may be achieved, for example, by applying a sub-threshold pulse, for example, just before depolarization. A potential advantage of such a sub-threshold pulse is that it may use less power than other pulses.

The gain of the response may be controlled, for example, by blocking or by priming parts of the pancreas, to control the total amount of pancreatic tissue talking part in the response. It is noted that priming "slow response" cells causes them to act as fast response cells, thereby increasing the gain of the fast response. In some cases, the priming and/or blocking may need to be repeated periodically, to maintain the sensitivity profile of the pancreas as described.

Alternatively or additionally, the sensitivity of the pancreas may be enhanced (or decreased) by supporting (or preventing) the propagation of action potentials, for example by providing a suitable pharmaceutical. Octonal and Heptonal are examples of pharmaceuticals that decouple gap junctions.

In an alternative embodiment of the invention, the secretion and/or production ability of part or all of the pancreas is modified, by controlling the blood flow to and/or from the pancreas.

It is hypothesized that reducing the blood flow to the pancreas will reduce the production and/or secretion rate of various pancreatic hormones.

Alternatively or additionally, by preventing hormone laden blood from leaving the pancreas, the local concentration of the various hormones increases and exhibits a stronger secretion enhancing or inhibiting effect (as the case may be) for other hormones.

It should be noted that in type II diabetes, the pancreas responds to increased glucose levels by providing increased insulin levels. However, this response is delayed and therefore increased in magnitude. As a result, or due to a different mechanism, the response of the body to insulin is reduced and/or delayed, forcing an even greater output of insulin. In an exemplary embodiment of the invention, the control of pancreatic response is used to prevent this feedback loop from occurring. In one embodiment of the invention, the pancreas is prevented from secreting increased amounts of insulin. Alternatively or additionally, glucagon secretion is reduced when or before glucose levels increase (e.g., at a user indication prior to eating), which prevents (or reduces) a fast glucose peak from occurring due to eating. Alternatively or additionally, gastric emptying is delayed, for example electrically or using pharmaceutical control.

In an exemplary embodiment of the invention, when an abnormal response of the pancreas is sensed or expected, one or both of the following acts may be performed: (a) suppress pancreatic response; and (b) increase pancreatic response (e.g., insulin secretion and/or glucagon reduction) to be faster and/or greater than usual, to quickly reverse the physiological situation to which an abnormal response is expected. Further, in accordance with some embodiments of the invention, selective control of hormones allows a patient to be provided with selective hormone ratios, for example providing a higher (or lower) glucagon to an insulin output ratio than would be without the electrical stimulation. It should be appreciated that in some case independent control of hormones and/or glucose levels is not possible due to a biological coupling. However, using methods described herein, relative control, by reducing the coupling is possible.

In some cases it is expected that reducing over-reaction by the pancreas may allow the pancreas to heal and reduce or obviate the need for other or continued treatment. Optionally, controller 102 tests this possibility periodically, by not applying its control or by reducing a degree of the control and determining if the pancreatic response is normal.

Non-Insulin Control

Alternatively or additionally to controlling the secretion of production of insulin, the secretion and/or production of other pancreatic hormones may be controlled. Exemplary such hormones include glucagon, Somatostatin and pancreatic polypeptide (PP). The levels and/or profile of level of these hormones may be controlled while also controlling insulin levels or while allowing insulin levels to change without direct control. Thus, in some embodiments of the invention, the hormones may be controlled partially independently of insulin.

It should be noted that in some cases control of factors other than insulin will indirectly control insulin levels. For example, reducing glucose levels will generally cause a reduction in insulin levels. Similarly, some of the pancreatic hormones interact via biological feedback mechanisms, for example, an increase in glucagon also increases insulin. These interactions may be represented using a set of equations. In other embodiments, a neural network may be used. In an exemplary embodiment of the invention, use is made of the fact that the feedback equations are not linear. Instead, the equations typically include a time delay and different gains for different relative hormonal levels. Further, the physiological mechanism may depend on glucose levels, on nervous simulation, on previous activity of the pancreas and/or on various digestive hormone. The particular equations and/or equation parameter for a particular patient may need to determined for that patient, for example by controlled experimentation (e.g., modifying one hormonal level and tracking the effect on others) or by observation.

Once the equations are known, substantially independent (or less interdependent) control of one hormone relative to other hormones may be possible. For example, instead of providing a large increase in insulin, which will increase glucagon levels, a smaller increase, over a longer period of time, may have a similar effect on blood sugar, without prompting glucagon secretion (which would confound the glucose lowering effect of the insulin). Alternatively or additionally, the increase in glucagon (or, conversely, insulin or other pancreatic hormones) is made as a series of short bursts, with rest periods between bursts. Thus, even though the secreted hormone performs its activity, it does not build up in the blood and/or in the pancreatic cells, to levels which will cause significant secretion of the antagonistic hormone. As examples of various levels of less interdependency, a ratio between hormone secretion levels at a given physiological state (e.g., glucose level) may be changed by at least 10%, 20%, 30%, 40% or more, upwards or downwards, with the originally higher level as the denominator.

Alternatively or additionally, pharmaceuticals may be used to reduce the sensitivity of one cell type relative to other cell types (or to increase the sensitivity), thus modifying the feedback equations and allowing, some leeway in selective control of the hormones. Alternatively, the responses of the cells may be regularized by the pharmaceuticals, so all cell types respond in a more uniform manner. Exemplary pharmaceuticals that selectively affect pancreatic behavior, include streptozotocin and alloxan, which reduce insulin output from beta-cells and various drugs used for treatment of diabetes.

Alternatively or additionally, the pharmaceuticals that are provided block the receptors for the hormone to be selectively disabled. Alternatively or additionally, the pharmaceuticals, for example anti-bodies, disable the hormone in the blood stream.

Exemplary pharmaceuticals are described, for example, in J Biol Chem 2000 Feb. 11; 275(6):3827-37, Acta Crystallogr D Biol Crystallogr 2000 May; 56 (Pt 5):573-80, Metabolism 1999 June; 48(6); 716-24, Am J Physiol 1999 January; 276(1 Pt 1):E19-24, Endocrinology 1998 November; 139(11):4448-54, FEBS Lett 2000 May 12; 473(2):207-11, Am J Physiol 1999 August; 277(2 Pt 1):E283-90, Cur Pharm Des 1999 April; 5(4):255-63 and J Clin Invest 1998 Apr. 1; 101(7):1421-30, the disclosures of which are incorporated herein by reference.

Alternatively or additionally, as different parts of the pancreas have different ratios of cell types, differential modification of one hormone over other hormones may be achieved by selectively stimulating only certain pancreas portions and/or selectively blocking the activity of pancreas portions.

Alternatively or additionally, the response of different cell types to a same electrical field stimulation may be different, thus allowing differential control of different hormones.

A distinction should be noted between controlling hormonal levels and controlling glucose levels by causing the secretion of hormones. Glucose level control at least prevents the damage to the body cause by high or low glucose levels, however, it does not guarantee the availability of glucose to the body cells. Maintaining desirable hormone levels, on the other hand, can not only maintain glucose within a desired range, it can also guarantee that a sufficient level of insulin is available so the body cells can assimilate the glucose. Additionally, various desirable bodily effects caused by the hormones, such as control of fat and protein metabolism or prevention of insulin tolerance, can be achieved.

It should be noted, that in some cases what is desirable is a hormone ratio or a temporal hormone profile, rather than a simple hormonal value. These effects can be achieved, for example, by temporally varying the control of the hormones.

In an exemplary embodiment of the invention, a reduction of glucose levels is achieved by indirectly activating non-insulin dependent glucose transporters. This effect may result from direct local stimulation of neural afferent pathways in the (or near) the pancreas or by the pancreas enhanced activity (resulting from the stimulation) that is sensed by these local afferents. The neural signal that is induced can enhance activation of non-insulin dependent GLUT in remote tissue of the body thereby increasing glucose uptake and reducing blood glucose independently of Insulin or in parallel with low, temporary or local increase in Insulin secretion at the pancreas. Hormonal pathways are also possible. A recent article, shows that stimulating cells in the heart can cause an increase in glucose uptake by the cells. The existence of neural pathways that stimulate cells (e.g., such as the heart) are also well known. The article is "Contraction-Induced Fatty Acid Translocase/CD36 Translocation in Rat Cardiac Myocytes Is Mediated Through AMP-Activated Protein Kinase Signaling", in Diabetes 2003 July; 52(7):1627-34, by Luiken J J, Coort S L, Willems J, Coumans W A, Bonen A, Van Der Vusse G J, Glatz J F, of the Department of Physiology, Cardiovascular Research Institute Maastricht, Maastricht University, Maastricht, the Netherlands and the Department of Kinesiology, University of Waterloo, Waterloo, Canada, the disclosure of which is incorporated herein by reference.

Indirect Insulin Control

In an exemplary embodiment of the invention, insulin levels are indirectly controlled by reducing glucose levels. In an exemplary embodiment of the invention, glucose levels are reduced using electrical stimulation as described below. As a result, insulin levels are reduced and/or do not significantly increase. In an exemplary embodiment of the invention, the electrical stimulation reduces glucagon levels. Alternatively, some other pathway is used and when insulin levels drop, so do glucagon levels. In an exemplary embodiment of the invention, insulin levels are increased and/or glucagon levels are reduced prior to eating so that eating will not cause a fast sudden spike in glucose levels.

Exemplary Control Logic

Figure 3A:
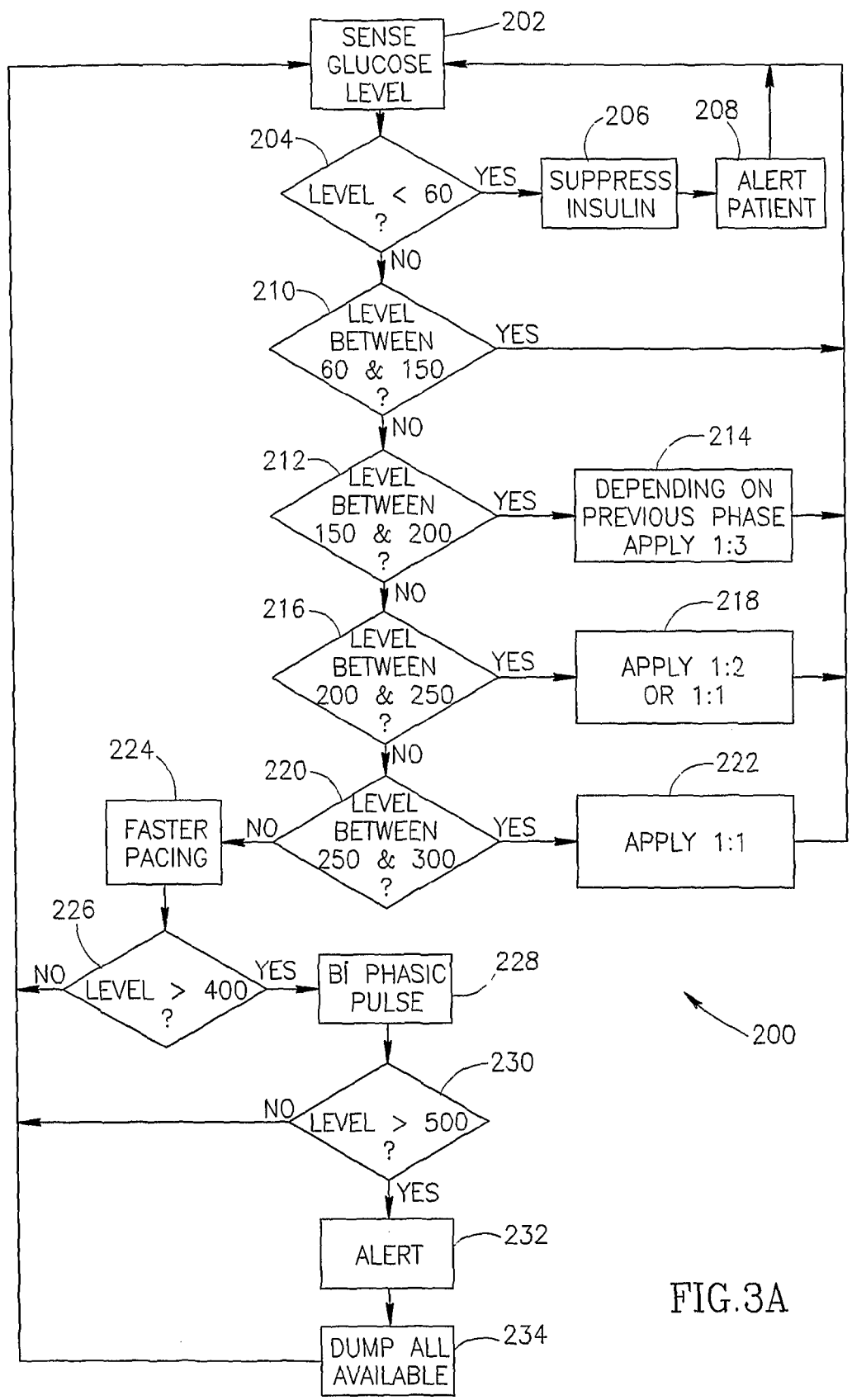
FIG. 3A is a flowchart of an exemplary control logic scheme, in accordance with an exemplary embodiment of the invention.

FIG. 3A is a flowchart of an exemplary control logic scheme 200, in accordance with an exemplary embodiment of the invention. In this scheme, the intensity of pancreatic activity (and associated dangers) is increased with the increase in glucose level. The various methods of increasing and decreasing pancreatic activity are described in more detail above or below. Alerts are optionally provided to the patient at extreme glucose levels. In addition, the method possibly prefers to error on the side of causing hyperglycemia, whose adverse effects are less critical than those of hypoglycemia, whose adverse effects are immediate. It is noted than automated control logic for controlling glucose levels have been developed previously for insulin pumps and may also be applied for controller 102. An added ability of controller 102 is to suppress the body's own production of insulin. An added limitation which controller 102 optionally takes into account is the avoidance of damaging the pancreas by over stimulation.

In a step 202, the glucose level is determined. Many methods may be used to determine glucose level. In an exemplary embodiment of the invention, in cases of hyperglycemia, the measurement is repeated several times before starting treatment. In cases of hypoglycemia, the measurements may be repeated few times or not at all, before starting treatment. The cycle of treatment is optionally repeated every two to five minutes. Alternatively, in critical situations such as hypoglycemia, the cycle is repeated even more frequently.

If the glucose level is under 60 (mg/dl) (step 204), further insulin production is optionally suppressed (206) and, optionally, the patient is alerted (208).

If the glucose level is between 60 and 150 (210), no action is taken, as these are normal glucose levels.

If the glucose level is between 150 and 200 (212), the action taken depends on the previous action taken and the previous measured glucose level. If, for example the previous level was higher, the insulin secretion activity may be maintained or reduced. If, on the other hand the glucose level was lower, the insulin secretion level may be increased. For example, a pulse application ratio of 1:3 between burst that are modified and bursts that are not modified may be provided (214) if the glucose level is now reduced from its previous measurement. It should be appreciated, of course that the exact glucose levels and pulse parameters used for a particular patent will depend only on the patient's medical history, but also on that patient's particular response to the pulse parameters used. Some patients may not respond as well as other patients and a more powerful pancreatic activity modification schedule used.

If the glucose level is between 200 and 250 (216), the action taken (218) can depend on the previous action taken for example providing a pulse application ratio between 1:1 and 1:2. Alternatively or additionally, the action taken can depend on the degree of change, direction of change and/or rate of change of glucose levels. Optionally, a model of insulin secretion, digestion and/or effect on blood glucose level are used to assess the significance of changes in glucose level.

If the glucose level is between 250 and 300 (220), an even higher pulse application rate, such as 1:1, can be applied (222).

Glucose levels higher than 300 can be quite dangerous. Thus, if such high rates are determined, a faster pacing rate, to the burst or to the individual action potentials (224), may be applied. Alternatively or additionally, a non-excitatory pulse to enhance secretion is also applied to at least some of the pacing pulses.

If the level is over 400 (226), a bi-phasic pacing pulse for the individual action potentials (225) may be provided. Such a pulse is expected at its first phase to induce depolarization and at its second phase to extend a plateau duration such that calcium inflow is increased. Alternatively or additionally, if not previous applied, control of multiple pancreatic regions may be provided, to increase the total portion of the pancreas being used to secret insulin at a higher rate.

If the glucose level is over 500 (230) emergency measures may be required, for example alerting the patient or his physician (232) and dumping all available insulin in the pancreas (234). A store of available insulin may be maintained in the pancreas or in device 102 (or an associated insulin pump) for just these cases.

It should be noted the above method is only exemplary. For example, the exact action at each may be modified, as can be the mixture of actions, the pulse parameters and the delays before changing action.

This control method utilizes delayed closed loop control circuits. Alternatively, open-loop circuits, which are similar to conventional glucose level management, may be provided. In such a loop, the amount of insulin output from a particular pulse application is known and is applied responsive to an infrequent measurement of the glucose level, for example using a blood test. Periodic glucose level testing may be applied to detect failed control. Intermediate control loops, control circuits having a smaller delay and combined control loops (having both open loop and closed loop) may be used in other exemplary embodiments of the invention.

Long Term and Short Term Considerations

When applying electrification pulses in accordance with exemplary embodiments of the invention, both short term and long term effects are optionally taken into consideration. Short term effects, include, for example effects on of insulin secretion and production. Long term effects include, for example, effects on tissue viability and capability and electrode polarization.

As will be described below, long terms effects may be negative, such as cell death, or positive, such as training or promoting healing.

Polarization and encrustation of the electrodes are optionally avoided by using ionic electrodes and applying balanced pulses (with substantially equal positive and negative charges). Alternatively, special coated electrodes, such as those coated with Iridium oxide or titanium nitride, may be used. Alternatively or additionally, relatively large electrodes may be used. The balancing may be on a per pulse basis or may be spread over several pulses.

In an exemplary embodiment of the invention, controller 102 stores in a memory associated therewith (not shown) a recording of the glucose levels, the applied electrical and/or pharmaceutical control, food intake and/or the effect of the applied control on electrical activity of the pancreas and/or effects on the blood glucose level.

It should also be noted that as the disease progresses over time, certain types of cells, for example beta cells may die out, so different stimulation methods and/or protocols may be suitable for different stages of the disease. For example, insulin secretion enhancement at the start of the disease and glucagon secretion reduction at the later stages of the disease. Other treatment protocols may be less affected by disease progress, for example, activation of non-insulin dependent GLUT.

Cellular Training

In an exemplary embodiment of the invention, the applied electrification and/or pharmaceutical profiles are used to modify the behavior of islet cells, in essence, training the cells to adapt to certain conditions. It is expected that slightly stressing a beta cell will cause the cell to compensate, for example by enlarging or by causing new beta cells to be produced. Such regeneration mechanism are known to exist, for example as described in "Amelioration of Diabetes Mellitus in partially Depancreatized Rats by poly(ADP-ribose) synthetase inhibitors. Evidence of Islet B-cell Regeneration", by Y Yonemura et. al, in *Diabetes;* 33(4):401-404, April 1984, the disclosure of which is incorporated herein by reference. Over stressing can kill the cell. Thus, the level of stress that enhances the cells' operation may need to be determined by trail and error for each patient. In an exemplary embodiment of the invention, the trial and errors are performed on different parts of the pancreas, optionally with a bias to under-stressing rather than for over stressing. In an exemplary embodiment of the invention, over stressing is determined by a marked reduction in insulin output or by reduced or abnormal electrical response.

Alternatively or additionally, a pancreatic cell insensitive to medium glucose levels may be trained to be sensitive to lower glucose level, by exciting it more frequently and/or exciting it at times of slightly elevated glucose levels.

In an exemplary embodiment of the invention, such training pulses are applied in combination with pharmaceuticals aimed to cause regeneration or healing.

It is noted that training and activation profile matching can also be used to maintain a cell in shape in a patient temporarily taking insulin, or to support a cell that is recuperating, for example from a toxic material or from the onset of diabetes.

Possibly, electrical stimulation increases intra-cellular calcium levels and as a result increases genomic activity in the cell. This may increase repair. Too much of an increase, however, may cause cell death by various mechanisms. Thus, in some embodiments of the invention, a relaxation time is provided for pancreatic cells, to allow such levels to go down. In other embodiments and/or cases, no such relaxation is provided.

Additional Exemplary Logic

Figure 3B:
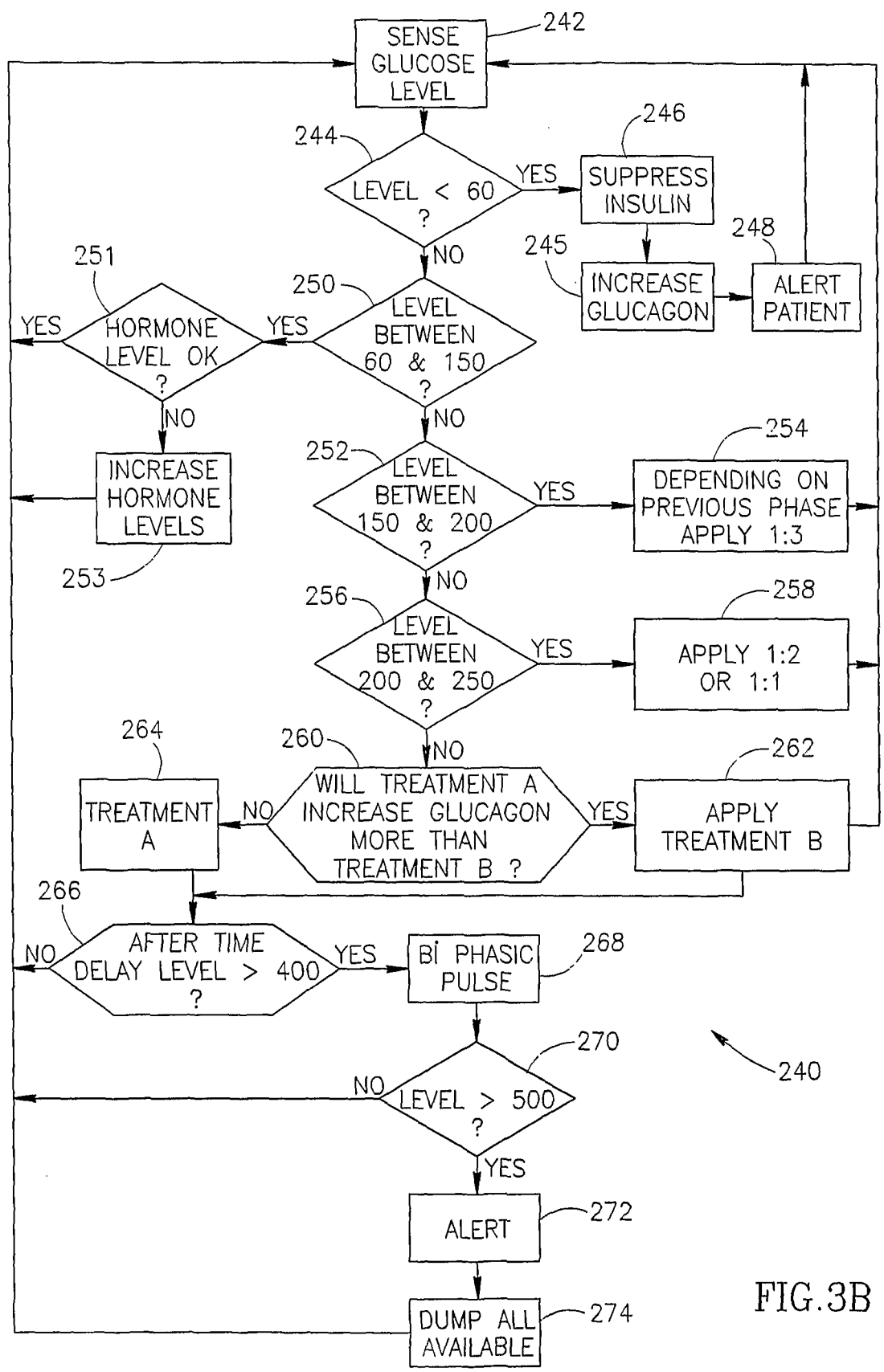
FIG. 3B is a flowchart of another exemplary control logic scheme, in accordance with an exemplary embodiment of the invention.

FIG. 3B is a flowchart of another exemplary control logic scheme 240, in accordance with an exemplary embodiment of the invention. FIG. 3B is similar to FIG. 3A, however, a lower degree of discrimination between glucose levels is shown in FIG. 3B, for clarity presentation. The reference numbers in FIG. 3B are 40 more than for corresponding elements in FIG. 3A.

FIG. 3B illustrates controlling hormonal levels, increasing glucagon secretion and selecting a treatment protocol or parameter based on the effect on pancreatic hormones other than insulin.

In response to a glucose level sensing (242), if the level is low, presenting hypoglycemia, insulin secretion is optionally suppressed (246). Alternatively or additionally, glucagon secretion is increased (245).

If the glucose levels are normal (250), an additional test is optionally performed, as to whether the hormonal levels are normal (251). In an exemplary embodiment of the invention, the hormone levels (e.g., insulin and/or glucagon) are directly measured using suitable sensors, for example fiber optic sensors or limited use chemical assay sensors. Alternatively or additionally, the levels are estimated based on the variation in blood glucose levels and/or electrical activity of the pancreas. If hormone levels are too low, they are increased (253). Possibly, if the hormone levels are too high, stimulation is stopped and/or even suppressed (not shown). Possibly, a control logic similar to that of FIGS. 3A and 3B is prompted by a sensing of hormone levels.

Skipping elements 252 through 258, which are the same as In FIG. 3A, if the glucose level is high and a fast response is desired, a test is made as to which one of a plurality of available treatments and/or treatment parameters is preferred (260). One issue is which treatment will cause the secretion of glucagon, which secretion will confound the desired glucose reducing effect.

In any case, if after a suitable time delay the glucose levels have not gone down (266) more drastic treatment is applied.

Artificial Gain Logic

FIGS. 3A and 3B show, inter alia, a progressive logic in which, as the glucose level goes higher, more drastic treatment is used. For some disease conditions, the pancreas may be capable of responding correctly, however, the pancreas is not sensitive enough in detection so that its response is delayed and/or is smaller than it should be to changes in blood glucose levels and/or digestion events. In other disease conditions, the pancreas is capable of a second, slower response (e.g., elevating insulin levels sufficiently after several tens of minutes) but not of an initial response (e.g., a fast bolus of insulin within a small number of minutes). In an exemplary embodiment of the invention, controller 102 is used to ensure that the pancreas responds (as indicated below) with a sufficient amplitude and/or minimal delay.

In an exemplary embodiment of the invention, controller 102 senses gastric activity, identifies it as digestive behavior or as release of food from the stomach and accordingly stimulates the pancreas to secrete a bolus of insulin and/or reduce glucose in another way. Alternatively or additionally, the stimulation lowers the sensitivity threshold of the pancreas so that it responds properly to the natural stimuli, i.e., it does not over-respond. Alternatively or additionally, the stimulation causes the pancreas to increase its response to raised glucose levels, when its natural response is too low.

It is hypothesized that a large initial bolus of insulin, may have a non-linear effect on the body, for example, causing a fast shut-down of glucose secretion by the liver, or shutdown of glucagon release by the pancreas. The non-linear effect may depend, for example on the total amount of insulin and/or on its rapid appearance. Further, the total effect of such a bolus may be to reduce the amount of insulin actually secreted by the pancreas. Optionally, such a bolus is applied before ingestion (e.g., 5, 10 or 20 minutes before), for example, to preemptively shut down glucose secretion by the liver.

It should be noted that a normal pancreas is expected to exhibit an acute response to an ingestion event by providing an initial bolus of Glucose and to cause the shutting down of glucose secretion by the liver (albeit, at a time delay).

One disadvantage of some pharmaceutical treatments is that peaks in insulin and glucose during the day are possible. In an exemplary embodiment of the invention, a significant number of such peaks are prevented and/or reduced using controller 102. For example, at least 20%, 40%, 60%, 80% or more of the peaks may be reduced by 50%, 70% or more relative to baseline values.

Open Loop Logic

For at least some stimulation pulses in accordance with an exemplary embodiment of the invention, over stimulation has fewer and/or less dangerous side effects than under stimulation. In some embodiments of the invention, this reduction in side effects is used to design control schemes which err on the side of over stimulation, i.e., open loop and partial open loop control, with a bias towards over rather than under stimulation. By partial open loop is meant that the decision if to apply a pulse series is made periodically (e.g., after ten minutes, half an hour, an hour or more) based on various events. Whoever, once such a decision is made, detailed measurements are not used to provide feedback on the effect of the pulse with an aim to modifying it. Once the series is completed, a decision if to apply a new stimulation series may be made. By open loop is meant that the pulse series is applied using a fixed protocol without checking its effect at all. In particular, some of the pulse series described below do not require synchronization to pancreatic activity and no measurement of pancreatic electrical activity is necessary, at least not during application of the pulse series.

In one example of a relatively safe pulse series, as shown below, some types of electrical stimulation reduce high glucose levels but do not substantially reduce normal glucose levels. In another example, general suppression of the pancreas when glucose levels are near normal (or even on the rise in some cases) may prevent secretion of insulin and/or glucagon which might upset the balance.

In an exemplary embodiment of the invention, open loop stimulation is used to reduce glucose levels prior to digestion and/or during digestion of a meal. In another example, open loop stimulation is used to periodically or semi-continuously reduce glucose levels. In these exemplary embodiments, a pulse series as shown below, which does not substantially affect normal glucose levels, is used.

In an exemplary embodiment of the invention, a user has an external controller, for example a magnetic or RF control wand which communicates the fact of eating with controller 102. Optionally, a signal (for example to decrease glucagon secretion) is sent prior to eating, as stopping glucose secretion by the liver (e.g., as a result of glucagon increase or other mechanism) may take tens of minutes.

Another safety feature of a stimulation in accordance with some embodiments of the invention is that prolonged stimulation appears to have no significant side effects on any of pancreatic viability, pancreatic endocrine function and pancreatic exocrine function.

Pulse Shapes and Parameters

The range of pulse forms that may be applied usefully is very wide. It must be noted that the response of the cells in different patients or of different cells in a same patient, even to same pulses, is expected to differ considerably, for example due to genetics and disease state. Also, the conduction of electrical signals in the vicinity of the pancreas is affected by the irregular geometrical form of the pancreas and the layers of fat surrounding it. These isolating layers may require the application of higher than expected amplitudes.

It is also noted that, at least for some embodiments, the application of the pulse is for affecting a certain portion of the pancreas and not the entire pancreas.

The lack of significant propagation of action potentials from one islet of the pancreas to another may require a relatively uniform field in the part of the pancreas to be affected. However, completely uniform fields are not required as any edge effects are contained only to the islets with the intermediate electric field strengths and/or because it is expected that the cell behavior does not vary sharply with the applied amplitude, except perhaps at certain threshold levels.

Further, the beta cells' behavior may be dependent on glucose level, on cellular insulin storage level and/or on previous activity of the cells. Unlike cardiac cells, which operate continuously and typically at a limit of their ability and/or oxygen usage, normal pancreatic cells are provided with long rests and are operated at sub-maximal levels.

A first parameter of the pulse is whether it is AC or DC. As the pulse may be applied periodically, the term DC pulse is used for a pulse that does not alternate in amplitude considerably during a single application, while an AC pulse does, for example having an intrinsic frequency an order of magnitude greater that 1/pulse duration. In an exemplary embodiment of the invention, DC pulses or pulses having a small number of cycles per application, are used. In this usage, a pulse that is synchronized to a burst is considered AC if it alternates in amplitude, for example ten times over the burst duration, even though this frequency is actually lower than the action potential frequency. If, conversely, the pulse is a square pulse synchronized to the individual action potentials, it will be considered a DC pulse, for this discussion, although its actual frequency is higher than the AC pulse.

Exemplary frequencies for AC pulses applied to bursts are between 1 and 1000 Hz and for AC pulses applied to action potentials, between 20 and 2000 Hz. Optionally, the AC frequencies are between 50 and 150 Hz.

Various pulse durations may be used. An advantage of a DC long duration pulse is the lack of transients that might inadvertently affect other tissue. Such a pulse is expected to be useful for hyper-polarization of cells and, thus, may last for several seconds or even minutes or hours. Optionally however, very long duration pulses are interrupted and possibly, their polarity switched to prevent adverse effects such as tissue polarization near the electrodes or over-polarization of the target tissue.

A pulse for affecting a burst may last, for example, between 1 ms and 100 seconds. Exemplary durations are 10 ms, 100 ms and 0.5 seconds. Long pulses may be, for example 2 or 20 seconds long. A pulse for affecting a single action potential will generally be considerably shorter, for example being between 10 and 500 ms long. Exemplary durations are 20, 50 and 100 ms. However, longer pulses, such as 600 or 6000 ms long may also be applied.

In AC pulses, various duty cycles can be used for example 10%, 50%, 90% and 100%. The percentages may reflect the on/off time of the pulse or they may reflect the relative charge densities during the on and off times. For example, a 50% duty cycle may be providing, on the average, 50% of the maximum charge flow of the pulse.

A pulse may be unipolar or bipolar. In an exemplary embodiment of the invention, balanced pulses, having a total of zero charge transfer, are used. Alternatively, however, the balancing may also be achieved over a train of pulses or over a longer period. It is expected that at least for some pulse effects, the islets will act independently of the polarity of the applied pulse. However, changes in polarity may still have desirable effects, for example by creating ionic currents.

Different pulse envelopes are known to interact with cell membranes in different ways. The pulse envelope may be, for example, sinusoid, triangular, square, exponential decaying, bi-phasic or sigmoid. The pulse may be symmetric or asymmetric. Optionally, the pulse envelope is selected to take into account variations in tissue impedance during the pulse application and/or efficiency and/or simplicity of the power electronics.

In an exemplary embodiment of the invention, the pulse current is controlled, for example to remain within a range. Alternatively or additionally, the pulse voltage is controlled, for example to remain within a range. Alternatively or additionally, both current and voltage are at least partly controlled, for example maintained in certain ranges. Possibly, a pulse is defined by its total charge.

Different types of pulses will generally, but not necessarily, have different amplitudes. The different effects of the pulse may also be a function of the cell activity phase and especially the sensitivity of the cell to electric fields at the time of application. Exemplary pulse amplitude types are sub-threshold pulses that affect the depolarization state of the cell and channel affecting pulses. These pulses are non-limiting examples of non-excitatory pulses, which do not cause a propagating action potential in the islet, either because of absolute low amplitude or due to relative low amplitude (relative to cell sensitivity). An islet current of 5 pA is suggested in the Medtronic PCT publication, for stimulating pulses.

Pacing pulses definitely cause a propagating action potential, unless the pacing pulse captures all the cells in the islet, in which case there may be nowhere for the action potential to propagate to.

"Defibrillation" pulses are stronger than pacing pulses and cause a rest in the electrical state of the affected cells.

Pore forming pulses, for example high voltage pulses, create pores in the membrane of the affected cells, allowing calcium to leak in or out and/or allowing insulin to leak out.

The above pulse types were listed in order of increasing typical amplitude. Exemplary amplitudes depend on many factors, as noted above. However, an exemplary pacing pulse is between 1 and 20 mA. An exemplary non-excitatory pulse is between 1 and 7 mA. A sub-threshold pulse may be, for example, between 0.1 and 0.5 mA. It is noted that the lack of excitation may be due to the timing of application of the pulse.

Simple pulse forms can be combined to form complex pulse shapes and especially to form pulse trains. One example of a pulse train is a double pacing pulse (two pulses separated by a 20 ms delay) to ensure capture of a pacing signal.

Another example of a pulse train is a pacing pulse followed, at a short delay, by a plateau extending pulse and/or other action potential control pulses. Thus, not only is pacing forced, possibly at a higher than normal rate, but also the effectiveness of each action potential is increased. The delay between the pacing pulse and the action potential control pulse can depend, for example, in the shape of the action potential and especially on the timing of opening and closing of the different ionic channels and pumps. Exemplary delays are 10, 50, 200 and 400 ms.

In some embodiments of the invention a graded pulse is applied. A first part of the pulse blocks first cells from responding to a second part of the pulse. Such a pulse may be used, for example, to differentiate between different cell tapes, between cells having different stimulation levels and/or between cells having a fast response and cells having a slow response. The exact behavior of such a pulse and/or suitable parameters may be determined during a training stage, described with reference to FIG. 7, below.

With the caveat that different experiments were performed on different animals species, in different stages of life, the experimental, it appears that as a general rule pulses of 20 HZ and 100 Hz, wider some parameter settings, induce new bursts (and increase insulin secretion). Pulses of 5 Hz, at least in-situ do not appear to induce new burst and are therefore non-excitatory. A particular 5 Hz pulse which is shown to reduce glucose without substantially increasing or even decreasing insulin is a bi-phasic pulse, with each phase being 5 ms long and 190 ms between individual pulses, i.e., a 5 Hz carrier. This pulse is applied without synchronization to pancreatic electrical activity.

While the pulse series can be applied continuously for several minutes, some pulses are applied for short times, such as one second every minute and appear to have an enhancing effect on the pancreas, for example, causing the pancreas to respond more strongly to existing heightened glucose levels.

In an exemplary embodiment of the invention, a pulse which consists of a short duty cycle repeated at a low frequency, can be viewed as a low frequency wave (e.g., 5 Hz) overlaid with a higher frequency wave (bi-phasic pulse of 10 ms duration). In an exemplary embodiment of the invention, the low frequency is used carry the effects of the electrical field into the pancreas. The higher frequency is used to carry the effects of the wave into individual cells, by creating a voltage drop on their cell walls. In an exemplary embodiment of the invention, the pulse low-frequency components are selected to have periodicity similar to that of (normal) pancreatic cells, of the type targeted. Alternatively or additionally, pulse width (e.g., the high-frequency components) are selected to specifically target certain cell types, for example, beta cells, alpha cells and nervous cells. For example, it appears, but is not certain, that lower frequencies (e.g., the 5 Hz component) affects islet activity and higher frequencies affect neural pathways. In addition, lower frequency pulses (e.g., even DC) are used for hyper polarization of cells. Various optimization and search techniques as known in the art may be used, especially to find optimal pulses for a particular patient.

Pulse Timings

Not only are various pulse forms contemplated, also different variations in their periodicity are contemplated.

A first consideration is whether to synchronize an excitatory and/or a non-excitatory pulse to the pancreatic activity or not. If the pulse is synchronized, it can be synchronized to the activity of particular cells or islets being measured. As noted above, a pacing pulse to the pancreas can force synchronization. The pulse may be synchronized to individual action potentials and/or to burst activity. Within an action potential, the pulse can be synchronized to different features of the action potential, for example the depolarization, plateau, repolarization and quiescent period before depolarization. Not all action potentials will exhibit exactly these features.

Within a burst, a pulse may be synchronized to the start or end of the burst or to changes in the burst envelope, for example, significant reductions in the action potential frequency or amplitude.

As used herein, synchronization to an event includes being applied at a delay relative to the event occurring or at a delay to when the event is expected to occur (positive or negative delay). Such a delay can be constant or can vary, for example being dependent on the action potential or the burst activity.

The pulse may be applied at every event to which it is synchronized for example every action potential or every burst. Alternatively, pulses are applied to fewer than all events, for example at a ratio of 1:2, 1:3, 1:10 or 1:20. An exemplary reason for reducing the pulse application ratio is to prevent overstressing the beta cells and causing cellular degeneration, or to provide finer control over secretion rate.

In some pulses, a significant parameter is the frequency of application of the pulse (as differentiated from the frequency of amplitude variations in a single pulse). Exemplary frequencies range from 0.1 HZ to 100 Hz, depending on the type of pulse.

In an exemplary embodiment of the invention, the pulse parameters depend on the islet or cellular electrical and/or physiological state. Such a state may be determined, for example using suitable sensors or may be estimated from a global state of the glucose level.

In an exemplary embodiment of the invention, the pulses are applied in a manner which provides an oscillatory insulin secretion. These oscillations optionally mimic natural oscillations, with the controller being used to provide natural oscillations and/or changes in oscillations as typical of a healthy pancreas. Alternatively, the oscillations are exaggerated, for example in amplitude or frequency or subdued, for example in amplitude or frequency. The oscillations may be provided, for example, by periodically increasing insulin secretion and/or by periodically decreasing insulin secretion.

Alternatively or additionally, the oscillations are provided by pacing which synchronizes the pancreas. Optionally, the treatment provided by device 102 is designed to increase natural oscillation behavior of the pancreas, for example by learning which stimulation sequences increase such behavior, under one or more conditions.

Sensors

Many types of sensors may be usefully applied towards providing feedback for controller 102, including, for example:

(a) Glucose sensors, for example for determining the actual glucose level and providing feedback on the effects of the pancreatic treatment. Thus, for example, in a patient with weakened pancreatic response, the pancreas will be stimulated to secrete more insulin when the glucose levels are too high. Many types of glucose sensors are known in the art and may be used for the purposes of the present invention, including, for example optical, chemical, ultrasonic, heart rate, biologic (e.g., encapsulated beta cells) and electric (tracking beta cell and/or islet electrical behavior). These sensors may be inside the body or outside of it, connected to controller 102 by wired or wireless means, be in contact with the blood or outside of blood vessels.

(b) Digestion sensors, for example for detecting the ingestion—or upcoming intake—of meals, and, for example, prompting the production of insulin or increase in cell sensitivity. Many suitable sensors are known in the art, for example impedance sensors that measure the stomach impedance, acceleration sensors that measure stomach or intestines movements and electrical sensors that measure electrical activity. Digestion sensing cells are inherently problematic in some embodiments of the invention if they do not provide a measure of glucose actually ingested. Optionally, they are used in combination with other sensors and/or only if the digestion system is activated in a profile matching eating, for example a long duration activation or activation that advances along the digestive system. In an exemplary embodiment of the invention, stimulation during the digestion may be stopped, to at least some parts of the pancreas (e.g., ones comprising fewer islets), to avoid interfering with other cell types in the pancreas, for example those that produce digestive juices. Alternatively or additionally, the application of stimulation in general may be optimized to reduce interaction with non-beta cells, for example alpha cells. As alpha cells generate glucagon, their stimulation may be determined by tracking serum glucagon levels. As noted elsewhere in this application, in some cases, glucagon reduction is a desirable effect and in some embodiments no interference with exocrine function is expected.

(c) Pancreatic activity sensors, for example electrodes coupled to the entire pancreas, small parts of it, individual islet(s) or individual cell(s) in an islet. Such sensors are useful not only for providing feedback on the activity of the pancreas and whether the applied pulses had a desired electrical (as opposed to glucose-) effect, but also for synchronizing to the pancreatic electrical activity. Exemplary sensors are described for example in PCT publication WO 03/045493, the disclosure of which is incorporated herein by reference.

(d) Calcium sensors, both for intracellular spaces and for extra-cellular spaces. As can be appreciated, measuring calcium inside a cell may affect the behavior of the cell. In an exemplary embodiment of the invention, only one or a few cells are used as a sample for the state of the other cells. An exemplary method of intracellular calcium measurement is to stain the cell with a calcium sensitive dye and track its optical characteristics. It is noted that both intra- and extra-cellular calcium levels may affect the electrical and secretary activity of beta cells.

(e) Insulin sensors, of any type known in the art may be used to measure the response of a single islet, the pancreas as a whole and/or to determine blood levels of insulin.

(f) Sensors for other pancreatic hormones, for example, for glucagon and/or Somatostatin. As will be mentioned below, in some cases the levels various pancreatic hormones may be estimated based on changes in blood glucose levels, which changes correspond to previously observed changes during which the hormone levels were measured.

The measurements of the above sensors are optionally used to modify the pulse parameters or pulse application regime. Alternatively or additionally, the sensors are used to track the response to the regime and/or lack of application of pulses, or for calibration.

Different sensing regiments may be use, including continuous sensing, and periodic sensing. Some sensors may provide a frequent measurement, for example every few seconds or minutes. Other sensors may be considerably slower, for example taking a measurement every ten minutes or hour. If only a periodic measurement is required, the measurement may be an average over the time between measurements or it may be an average over a shorter time or an instantaneous value. In some cases a long term integrative sensing, for example of total insulin production, is desirable. A one-time chemical sensor may be suitable for such integrative sensing.

Various sensing methods and sensors are described, for example in U.S. Pat. No. 6,600,953, PCT publication WO 01/91854, U.S. provisional patent application 60/259,925, U.S. provisional patent application 60/284,497, U.S. provisional patent application 60/334,017, PCT application PCT/IL02/00007, filed Jan. 3, 2002, PCT publication WO 02/082968, the above mentioned PCT publication WO 03/045493 and U.S. patent application Ser. No. 10/296,668, the disclosures of all of which are incorporated herein by reference. It should be noted that some of the sensing methods described in these applications allows estimating, for example an total glucose load, a rate of glucose increase and/or a delay until glucose starts increasing. This information may be used for suitably configuring the glucose control treatment to have a desired effect, for example, by setting stimulation duration and part of pancreas affected.

Types of Electrodes

The electrodes used may be single functionality electrodes, for example only for pacing or only for non-excitatory pulses. Also, different types of non-excitatory pulses, such as hyperpolarization and plateau extension pulses, may use different types of electrode geometries. Alternatively, a combination electrode, comprising both a pacing portion and a pulse application portion, may be provided. The different types of electrodes may have different shapes, for example due to the pacing electrode being designed for efficiency and the pulse electrode being designed for field uniformity. The two electrode functions may share a same lead or them may use different leads. Alternatively, a single electrode form is used for both pacing and non-excitatory pulse application.

FIGS. 4A-4D illustrate different types of electrodes that may be suitable for pancreatic electrification, in accordance with exemplary embodiments of the invention.

Figure 4A:
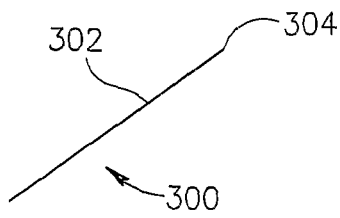
FIGS. 4A-4D illustrate different types of electrodes that may be suitable for pancreatic electrification, in accordance with exemplary embodiments of the invention.

FIG. 4A illustrates a point electrode 300 having a single electrical contact area at a tip 304 of a lead 302 thereof.

Figure 4B:
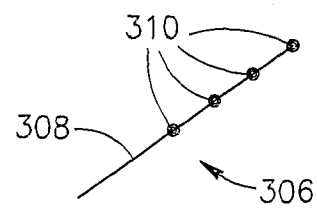

FIG. 4B illustrates a line electrode 306 having a plurality of electric contacts 310 along a length of a lead 308 thereof. An advantage of wire and point electrode is an expected ease in implantation using endoscopic and/or other minimally invasive techniques. In an exemplary embodiment of the invention, multiple wire electrodes are implanted.

Figure 4C:
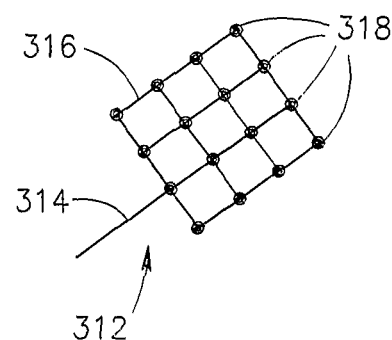

FIG. 4C illustrates a mesh electrode 312, including a lead 314 and having a plurality of contact points 318 at meeting points of mesh wires 316. Alternatively or additionally, some of the wire segments between meeting points provide elongate electrical contacts.

Each of the contact points can be made small, for example slightly larger than an islet. Alternatively, larger contact areas are used. In line electrodes, exemplary contact areas are 0.2, 0.5, 1, 2 or 5 mm long. In some embodiments of the invention, smaller contact areas than used for cardiac pacemakers may be suitable, as smaller fields may be sufficient.

Figure 4D:
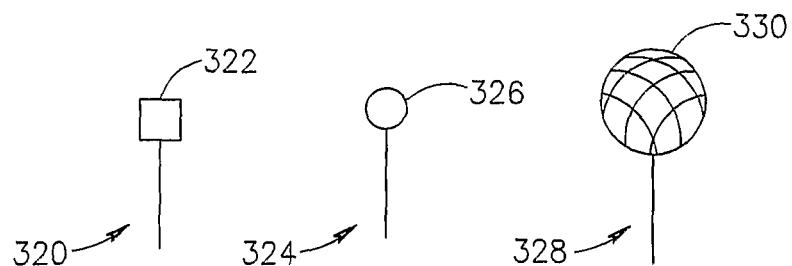

In some embodiments, volume excitation of the pancreas is desired. FIG. 4D illustrates various volume excitation electrodes. A plate electrode 320 includes a plate 322 that can simultaneously excite a large area. A ball electrode 324 includes a ball shaped contact area 326, with a radius of, for example, 2 or 4 mm, for exciting tissue surrounding ball 326. A hollow volume electrode 328, for example, includes an open volume contact area 330, for example a mesh ball or a goblet, which cane be used to excite tissue in contact with any part of ball 330, including its interior. Another possibility is a coil electrode. Optionally, the coils have a significant radius, such as 2 or 5 mm, so they enclose significant pancreatic tissue. It is noted that volume (and other electrodes as well) electrodes may encompass a small or large part of the pancreas or even be situated to electrify substantially all the insulin producing parts of the pancreas.

Any of the above electrodes can be unipolar or bipolar. In bipolar embodiments, a single contact area may be spilt or the bi-polar activity may be exhibited between adjacent contact points.

In addition, the above multi-contact point electrodes may have all the contact points shorted together. Alternatively, at least some of the contact points can be electrified separately and, optionally, independently, of other contact points in a same electrode.

Electrical contact between an electrode an the pancreas can be enhanced in many ways, for example using porous electrode, steroids (especially by using steroid eluting electrodes) and/or other techniques known in the art. The type of electrode may be any of those known in the art and especially those designed for long term electrical stimulation.

Figure 4E:
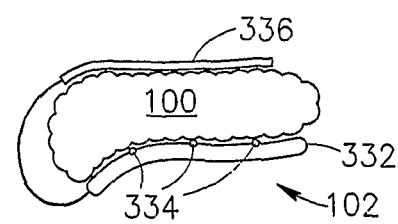
FIG. 4E illustrates an electrode, in which the body of the controller of FIG. 1 serves as at least one electrode, in accordance with an exemplary embodiment of the invention.

FIG. 4E illustrates a different type of electrode, in which a casing 332 of controller 102 serves as one or multiple electrodes. Casing 332 may be concave, convex or have a more complex geometry. Possibly, no external electrodes outside of casing 332 are used. Optionally, casing 332 is then made concave, to receive the pancreas. Alternatively, at least a common electrode 336 outside of controller 102 is provided. Alternatively or additionally, casing 332 of controller 102 serves as a common electrode. In an exemplary embodiment of the invention, a plurality of electrodes 334 are formed in casing 332. The electrode types can be any of those described above, for example. Optionally, but not necessarily, electrodes 334 stick out of casing 332. In an exemplary embodiment of the invention, controller 102 is placed in contact with pancreas 100, as an electrically insulating layer of fat usually encapsulates the pancreas. Optionally, the geometry of casing 332 is made to conform to the shape of the pancreas, thus assuring contact with the pancreas and minimal trauma to the pancreas by the implantation. Optionally, a flexible or multi-part hinged casing is provided, to better conform the casing to the pancreas.

The electrodes can be fixed to the pancreas in many means, including, for example, using one or more sutures or clips, providing coils or roughness in the electrode body, using adhesive or by impaling the pancreas or nearby tissue. An electrode may include a loop, a hole or other structure in it for fixing the suture or clip thereto. It is noted that the pancreas does not move around as much as the heart, so less resilient electrode and lead materials and attachment methods may be used.

Various combinations of the above electrodes may be used in a single device, for example a combination of a mesh electrode underneath the pancreas and a ground needle electrode above the pancreas. Such a ground electrode may also be inserted in nearby structures, such as the abdominal muscles.

As described below, the pancreas may be controlled as plurality of controlled regions. A single electrode may be shared between several regions. Alternatively or additionally, a plurality of different electrodes may be provided for the different regions or even for a single region.

Optionally, the electrodes, or tips thereof are coated with a cortisone or other anti-inflammatory, to prevent an inflammatory response by the organ with which the electrode is in contact with.

Pancreatic Control Regions

Figure 5:
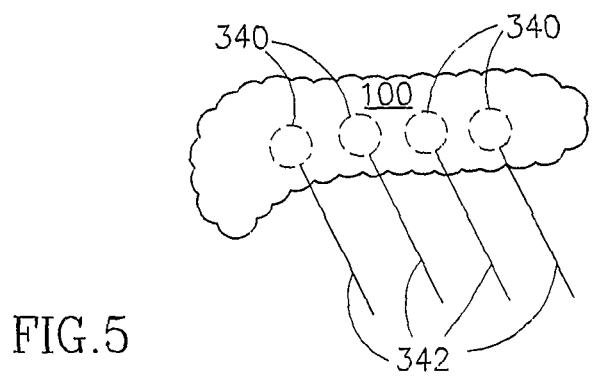
FIG. 5 illustrates a pancreas subdivided into a plurality of control regions, each region being electrified by a different electrode, in accordance with an exemplary embodiment of the invention.

FIG. 5 illustrates a pancreas subdivided into a plurality of control regions 340, each region being electrified by a different electrode 342. Control regions 340 may overlap (as shown) or they may be none-overlapping. Possibly, the entire pancreas is also a control region, for example for insulin secretion suppression. Although a significant percentage of the pancreas is optionally controlled, for example 10%, 20%, 40% or 60%, part of the pancreas may remain uncontrolled, for example as a control region or as a safety measure. The number of control regions can vary, being for example, two, three, four, six or even ten or more. In many of the experiments described below, it is estimated that between about 10% and 30% of the pancreas was activated.

One possible of different control regions is to allow one part of the pancreas to rest while another part is being stimulated to exert itself. Another possible use is for testing different treatment protocols on different regions. Another possible use is to provide different control logic for parts of the pancreas with different capabilities, to better utilize those regions or to prevent damage to those reasons. For example, different pulses may be applied to fast responding or slow responding portions. In addition, some parts of the pancreas may be more diseased than other parts.

Optionally, the density and/or size of the electrodes placement on the pancreas (and independently controllable parts of the electrodes) varies and is dependent, for example, on the distribution and density of islet cells in the pancreas. For example, a more densely populated section of the pancreas may be provided with finer electrical control. It is noted that the distribution may be the original distribution or may be the distribution after the pancreas is diseased and some of the cells died or were damaged.

As noted above, different parts of the pancreas may produce different types and/or relative amounts of various hormones. Thus, selective spatial control may be utilized to achieve a desired hormone level and/or mix.

Implantation Method

The implantation of controller 102 can include implantation of electrodes and implantation of the controller itself.

Optionally, the two implantations are performed as a single procedure. However, it is noted that each implantation has its own characteristics. Implanting a small casing into the stomach is a well-known technique and may be performed, for example using a laparoscope, using open surgery or using keyhole surgery.

Implantation of electrodes in the pancreas is not a standard procedure. Optionally, elongate, uncoiling or unfolding electrodes are used so that electrode implantation is simplified.

In an exemplary embodiment of the invention, the electrodes are implanted using a laparoscopic or endoscopic procedure. Optionally, also controller 102 is inserted using a laparoscope or endoscope. In an exemplary embodiment of the invention, the geometry of controller 102 is that of a cylinder, so it better passes through an endoscope (flexible, relatively narrow diameter tube) or a laparoscope (rigid, relatively large diameter tube). Alternatively, controller 102 is implanted separately from the electrodes. In one example, the electrodes are implanted faith a connection part (e.g., Wire ends) of the electrodes easily available. A second entry wound is made and the controller is attached to the connection parts. Possibly, the electrodes are implanted connection part first. Alternatively, after the electrodes are implanted, the endoscope is retracted, leaving the connection part in the body.

Figure 6A:
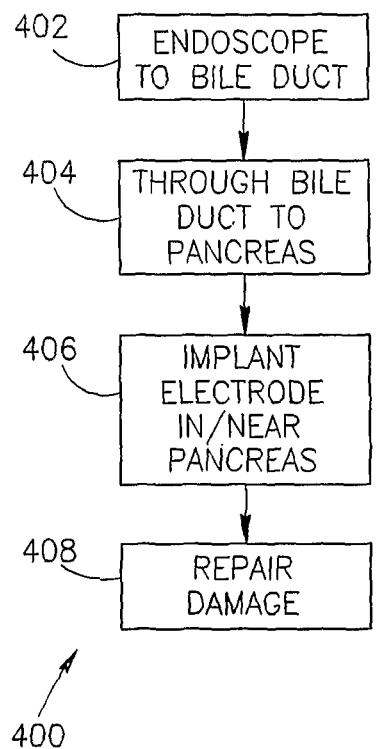
FIGS. 6A and 6B are flowcharts of implantation methods, in accordance with exemplary embodiments of the invention.
Figure 6B:
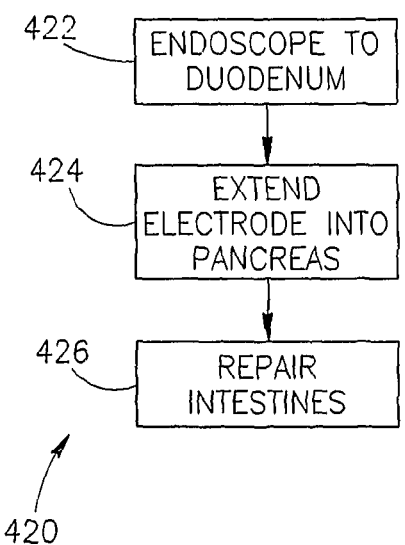

FIGS. 6A and 6B are flowcharts of implantation methods, in accordance with exemplary embodiments of the invention.

FIG. 6A is a flowchart 400 of a bile duct approach. First, an endoscope is brought to a bile duct, for example through the stomach (402). The endoscope then enters the bile duct (404) for example using methods known in the art. As shown, the endoscope may travel though the bile ducts along the pancreas. Alternatively, the electrodes may be provided by a catheterization of the splenic artery or vein. Alternatively, the portal vein may be catheterized, for example via a laparoscopic opening in the abdomen. The electrodes are implanted in, or alongside, the pancreas, for example in the blood vessels or the bile ducts, the pancreas being an elongated gland (406). In an exemplary embodiment of the invention, the endoscope (or an extension thereof) is first advanced to the far end of the pancreas, the electrodes are attached to the pancreas and then the endoscope is retracted, leaving the electrodes behind. Alternatively, the electrodes may be advanced out of the pancreas, by themselves or using a relative rigid and/or navigable jacket. Optionally, but not necessarily, imaging techniques, such as light, ultrasound or x-ray imaging, are used to track the electrode and/or the endoscope. The imaging may be from outside the body or from inside the body, for example from the tip of the endoscope.

Any damage to body structures is optionally repaired during endoscope/catheter retraction (408). Alternatively, other arterial and/or venous techniques may be used. In some techniques, controller 102 is implanted and then the electrodes are guided along or inside a blood vessel or other body structure to the pancreas.

In bile duct implantation, a special coating may be provided on the electrode or leads, to protect against the bile fluids. The contact part of the electrode may be embedded in tissue to prevent bile fluid damage thereto.

FIG. 6B is a flowchart 420 of an alternative implantation method. An endoscope is advanced to the duodenum or other part of the intestines adjacent the pancreas (422). Electrodes are extended from the intestines into the pancreas (424), while controller 102 remains in the intestines. The electrodes may also extend part way along the inside of the intestines. Electrodes on the far side of the pancreas may be implanted from a different part of the intestines or they pass through the pancreas. Alternatively, also the controller is pushed out through a hole formed in the side of the intestines. Alternatively, the controller is enclosed in a pocket of the intestines, the pocket optionally formed by suturing or clipping together part of the intestines. Alternatively, the controller is attached to the intestines, for example using clips or using sutures. Any damage to the intestines may then be repaired (426).

As noted above with reference to FIG. 1, controller 102 may be a wireless device, with the control circuitry separate from the electrodes. The electrodes can have individual power sources or they may be powered (or recharged) using beamed power.

In an alternative embodiment, controller 102 is a multi part device, for example comprising a plurality of mini-controllers, each mini controller controlling a different part of the pancreas. The activities of the mini-controllers may be synchronized by communication between the controllers or by a master controller, for example in the separate, possibly external unit 116. Unit 116 may directly synchronize the mini controllers and/or may provide programming to cause them to act in a synchronized manner. An exemplary geometry for a mini-controller is that of two balls connected by a wire. Each ball is an electrode, one ball contains a power source and the other ball contains control circuitry. Communication between the mini controllers may be, for example using radio waves, optionally low frequency, or using ultrasound. Suitable transmitter and/or receiver elements (not shown) are optionally provided in the mini-controllers.

Alternatively to an implanted controller, the controller may be external to the body with the electrodes being inserted percutaneously to the pancreas, or even remaining on the out side of the body. Alternatively, the controller and the electrodes may be completely enclosed by the intestines. These "implantation" methods are sometimes preferred for temporary use of the device.

In some cases, proper implantation of sensors may be problematic, for example sensors that impale single beta cells or islets. In an optional procedure, part of the pancreas is removed, sensors and/or electrodes are attached thereto and then the removed part is inserted back into the body.

In the above embodiments, it was suggested to impale the pancreas using electrodes or electrode guides. In an exemplary embodiment of the invention, when impaling, care is taken to avoid major nerves and blood vessels. In an exemplary embodiment of the invention, the implantation of electrodes takes into account other nearby excitable tissue and avoids inadvertent stimulation of such tissue.

As will be described below, some experiments have shown that applying an electric field to the stomach, using parameters as described above, can cause reduction in glucose levels. Without limiting the actual application, it is hypothesized that what is occurring is that electric field applied by the electrodes extends to a significant part of the pancreas (or other organ on which the field has the desired effect) and/or to nerve tissue in or near the pancreas. In humans, as well as pigs, the pancreas is located near the stomach. Optionally, electrodes for electrifying the pancreas are attached to the stomach. One potential benefit is that there is less danger of perforating the pancreas and/or causing inflammation or infection of the pancreas. Another potential benefit is that the stomach is a muscular organ and suturing or other attachment methods are generally more easily applied to it, than to the pancreas. This may also allow a greater number of electrodes and/or specificity to be used. Optionally, the controller itself is attached to the stomach. Another potential benefit of the stomach is that the same electrodes used for electrifying the pancreas may also be used for obesity control, for example as described in U.S. Pat. Nos. 6,571,127, 6,630,123 and 6,600, 953, U.S. application Ser. Nos. 09/734,358 and 10/250,714 and PCT publication WO02/082968, the disclosures of which are incorporated herein by reference. Another potential benefit of the stomach is that as the bulk of the stomach is an insulator, any electric field will generally travel around the stomach (and therefore through or by the pancreas). Another potential benefit is that laparoscopic surgery to the stomach is well known. While some effect of the field on the stomach may occur, optionally, the effect is small and/or counteracted by applying a field to the stomach to correct the effect.

Optionally, the pancreatic control signals are synchronized to the electrical activity of the stomach, for example to have a minimal effect on the stomach. Optionally, the delay and/or sequence length is optimized by experimentation, for example, to be 0, 1, 2, 4, 6 or other number of seconds, or intermediate or greater values. In particular, the pulse may be applied during a refractory or during a depolarization phase of the stomach (or other) smooth muscle. Alternatively or additionally, the delay and/or sequence length are varied so that no single effect on the stomach (if any) dominates. Optionally, the delay is calculated using a local sensing electrode (maybe the same as the stimulating electrode) at the application location. Alternatively or additionally, an expected or measured activation time at another part of the stomach is taken into account.

Depending on the tissue locations to which the electrodes are attached, various inter-electrode distances may be used, for example, 1 cm, 2 cm, 3 cm, 4 cm or smaller, intermediate or larger values. As can be appreciated, the larger the distance, in general, the larger the field strength at points not directly between the electrodes. This is useful, for example, when the pancreatic tissue to be electrified is not directly between the electrodes.

In some cases, the exact electrification level of the electrodes will depend on various factors, for example, distance between the electrodes, tissue types, tissue properties and electrode orientation. Optionally, a calibration stage is carried out in which a suitable field strength is found. In one example, current and/or voltage are varied in a staircase manner over a series of trials until a significant effect is determined, for example, each step can be carried out under a different glucose ingestion event. Optionally, the calibration is also used to determine that few or no undesirable effects are being caused by effect of the electric field on other tissue. The results of such calibration can determine, for example, which electrodes to stimulate, simulation strength, stimulation polarity, timing (e.g., delay and/or duration), triggers for stimulating or not stimulating (e.g., not when colon is full, detected using an impedance sensor), and or which of several possible sequences to use.

Optionally, an insulating backing is provided on the electrodes to assist in directing the field. For example, a backing may be provided between an electrode and the tissue to which it is attached, to prevent or reduce the effects of the field on the tissue. In an exemplary embodiment of the invention, the backing comprises a silicone pad of dimensions 20 mm×40 mm.

Figure 6C:
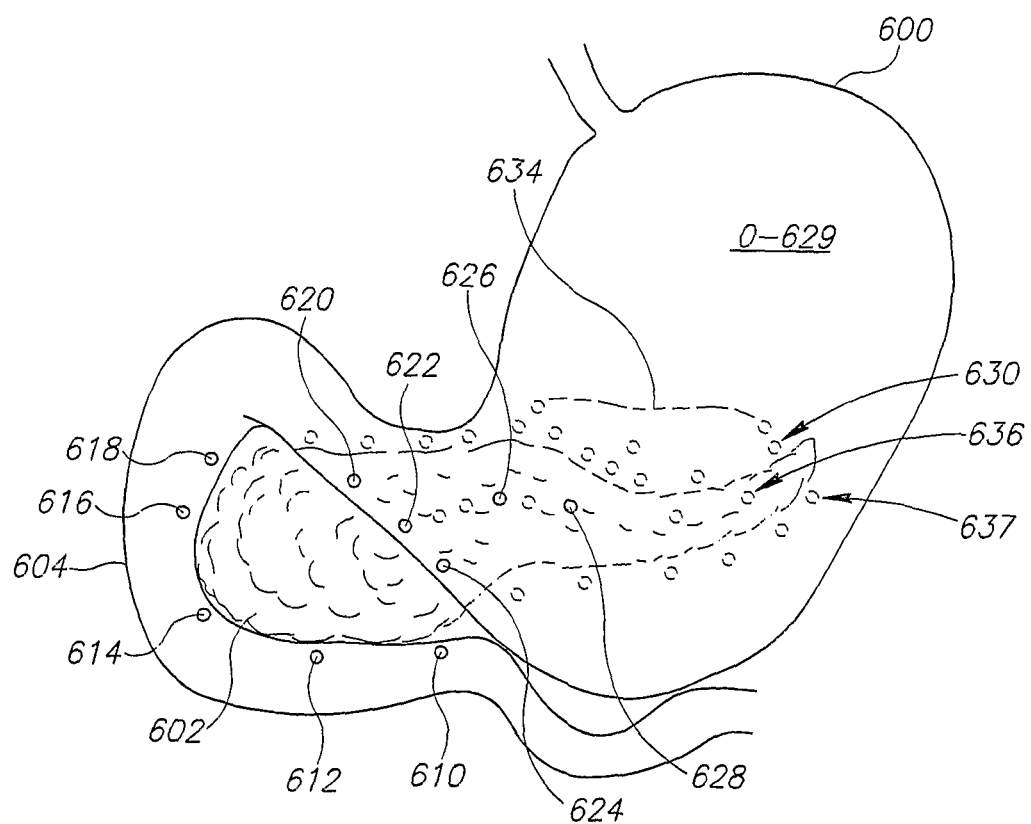
FIG. 6C is a schematic illustration of an abdominal cavity showing electrode placement on a stomach in proximity to a pancreas, in accordance with an exemplary embodiment of the invention.

FIG. 6C illustrates exemplary locations for electrodes on a stomach 600 and/or a duodenum 604, near a pancreas 602. A plurality of electrode locations 610-632 are shown and many other locations are possible as well. In addition to the organs shown, attachment can be to one or more of the following organs: abdominal muscles, the liver, other abdominal organs, other parts of the GI tract, such as the small intestines or the colon, for example the transverse colon, ligaments, blood vessels and/or fatty tissue. In general, the organs can be on any of the six cardinal sides of the pancreas.

In the figure, solid electrodes are above the organs and dashed electrodes are below the organ (e.g., the stomach). The exemplary electrode location shown are, electrodes 610-618 along the duodenum, electrodes 620-624 along the stomach opposite the duodenum, electrodes 626 and 628 near the center of the stomach, electrode 629 near the top of the stomach, two lines of electrodes 630 and 632 generally along the pancreas on the far side of the stomach, a line of electrodes 634 offset from electrodes 630 and a line of electrodes 636 between the pancreas and the stomach. Other electrode locations can be used as well, for example, generally any point on a surface of the organs near the pancreas or positioned so that there is a significant current through the pancreas. Optionally, the electrodes will be provided with an electrification sequence so that different organs and/or parts of organs are electrified at different stimulation sessions of the pancreas.

Various electrode configurations can be used, for example, two electrodes with opposite polarities, or one electrode and the casing of the device, or pairs of electrodes, with opposite polarities or groups of electrodes, where each group has a same polarity.

In addition, it should be noted that depending on the electrodes selected it is possibly to intentionally electrify only part of the pancreas or selectively electrify different parts.

Another issue to be noted is that the figure shows point electrodes. While point electrodes may be used, as well as mesh and area electrodes, in an exemplary embodiment of the invention, the electrodes are wire electrodes. Such wire electrodes may be curved or coiled. Optionally, however, the wires are substantially straight and have and orientation. The orientation may be, for example, parallel to, perpendicular to or oblique to the pancreas and/or each other (e.g., in pairs of electrodes).

When electrodes that are meant for stimulating a pancreas are attached to the stomach, the electrodes may be placed in the gastric muscle. Optionally, however, the electrodes are sutured to the muscle but remain on the outside of the stomach (or other organ). One potential advantage is utilizing the insulative properties of various organ covering membranes. Another potential advantage is reducing damage to the organ and/or danger of invagination. Optionally, a covering of the pancreas is removed or reduced, to assist in electric conduction to the pancreas.

One exemplary electrode configuration is two sets of electrodes on a same side of the pancreas. For example, electrodes 620 and 624 or 610 and 612 can apply between them a field which will also cover part of the pancreas. Another example is electrodes 634 paired with electrodes 630. In this last example, not only are the electrodes on a same side of the pancreas, but they are also oriented so a significant portion of the field will not flow through the pancreas as no part of the pancreas is directly between or slightly offset from being directly between the electrodes.

Another exemplary electrode configuration is on opposite sides of the pancreas. For example, electrodes from set 630 (or 636) paired with electrodes from sets 632. Optionally, a plurality of electrodes are chosen from each set, to allow selective electrification of different parts of the pancreas. Another example is one electrode from set 636 and one electrode of 610-618 and/or the transverse colon (not shown).

Another exemplary electrode configuration is electrodes spaced from the pancreas, for example, electrodes 626 and 628.

Another exemplary electrode configuration is electrodes whose field will travel around an organ, for example the stomach. The stomach is hollow, and thus generally a good insulator. One example is electrodes 636 (or 630-634) paired with electrode 626.

Another exemplary electrode configuration is as follows. Four electrodes are attached or placed at the top of the pancreas, with alternate electrodes are shorted together, for example the left most electrode being positive or negative. In an exemplary embodiment of the invention, the leftmost electrode is 2-3 cm from a head of the pancreas. The following three electrodes are 1-2 cm apart and the last electrode is 6-7 cm from a tail of the pancreas. In an exemplary embodiment of the invention, the electrodes are needle electrodes suitable for laparoscopic implantation. In various implementations, fewer or a greater number of such alternating electrodes may be used and various orders of electrodes (e.g., 2-1-2-1—the numbers indicating electrodes of the same polarities) may be provided as well. In some such orders, the number of different electrodes of different polarities is not equal. The distances between the electrodes need not be uniform. In particular, the electrodes need not lie on a straight line. Optionally, however, the electrodes are placed at a location easy to reach using a minimally invasive technique.

Calibration and Programming

Pancreatic controller 102 may be implanted not only, after a stable disease state is known, but also during an ongoing disease progression. Under these conditions and even in the steady state, cells that are to be controlled by controller 102 are expected to be diseased and/or over-stressed and may behave somewhat unpredictably. Thus, in an exemplary embodiment of the invention, optimizing the control of the pancreas may require calibrating the controller after it is implanted. However, it is noted that such calibration is not an essential feature of the invention and may even be superfluous, especially if a reasonable estimate of the pancreatic physiological state can be determined before implantation.

Figure 7:
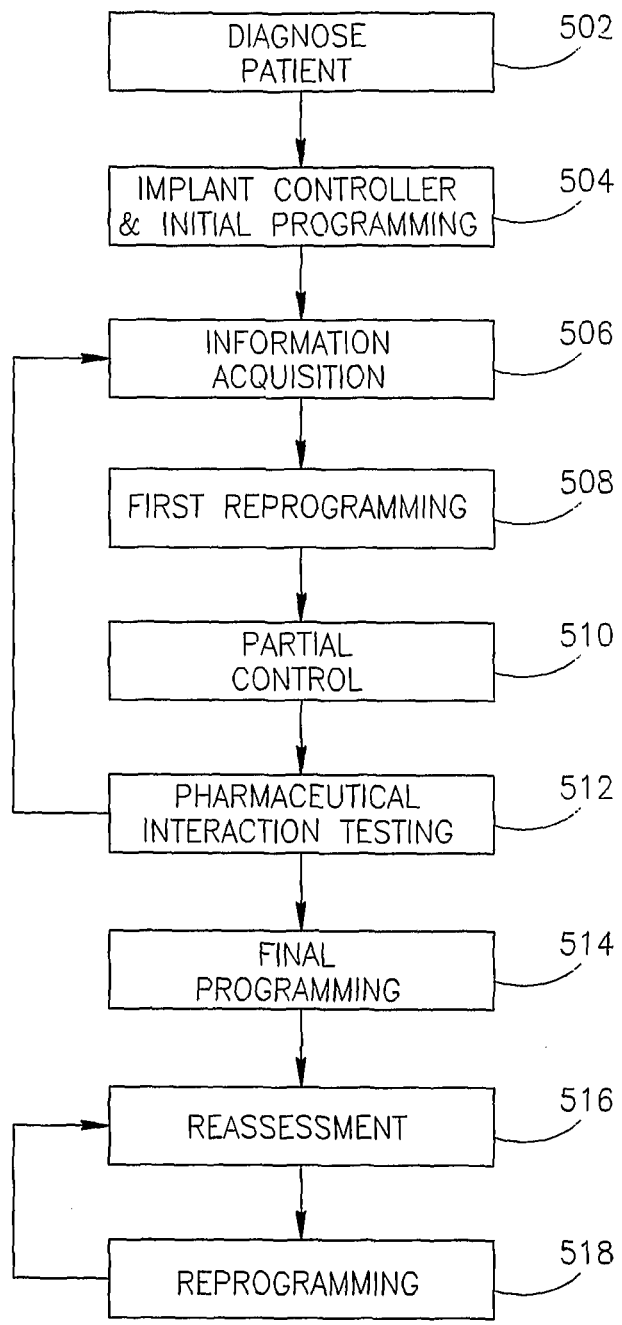
FIG. 7 is a flowchart of an exemplary method of controller implantation and programming, in accordance with an exemplary embodiment of the invention.

FIG. 7 is a flowchart of an exemplary method of controller implantation and programming, in accordance with an exemplary embodiment of the invention. Other methods may also be practiced.

Before implantation, a patient is optionally diagnosed (502) and an expected benefit of implantation is optionally determined. It is noted however, that controller 102 may also be used or diagnostic purposes, due to its ability to take measurements over extended periods of time and determining the response of the pancreas cells to different stimuli and situations.

A controller is then implanted, for example as described above, and an initial programming provided (504). The initial programming may be performed while the controller is outside the body. However, In an exemplary embodiment of the invention, the controller is capable of extensive programming when inside the body, for example as described below, to enable the controller to selectively apply one or more of the many different logic schemes and pulses, possibly differently to one or more of the controlled areas.

During an information acquisition step (506) the behavior of the pancreas is tracked, possibly without any active control of the pancreas. This information acquisition optionally continues all through the life of the controller. In an exemplary embodiment of the invention, the acquired information is periodically- and/or continuously-reported to a treating physician, for example using external unit 116. An exemplary report is the glucose levels in the body and the main events that affected the glucose level.

Alternatively to mere information gathering, the information acquisition also uses test control sequences to determine the pancreatic response to various pulse forms and sequences.

In an exemplary embodiment of the invention, the information acquisition step is used to determine physiological pathologies and especially to detect and feedback- and/or feed-forward-mechanisms that are impaired. Such mechanisms are optionally supplemented, replaced and/or overridden by controller 102.

Alternatively or additionally, the information acquisition is geared to detecting feed-back and feed-forward interactions in the pancreas, especially interactions between hormones, possibly dependent on glucose levels, hormone levels and/or stimulation history. This information may be used to provide parameters for a predetermined model of the pancreas. Alternatively, a new model may be generated, for example using a neural-network program.

Possibly, various protocols are tried on small control regions to determine their effect.

The information acquisition, and later the calibration and programming may be performed on a per-person basis or even on a per-islet or per pancreatic portion basis. Optionally, a base line programming is determined from other patients with similar disorders.

Optionally, various test sequences are timed to match patient activities such as eating, sleeping, exercising and insulin uptake. Also the programming of the controller may be adapted to a sleep schedule, meal taking schedule or other known daily, weekly or otherwise periodic activities.

Possibly, the acquisition is enhanced with testing of hormonal levels and/or other physiological parameters for which sensors may or may not be provided on the pancreatic controller. These measurements may be used to learn which glucose levels (or other physiological parameter) and/or level changes are caused by which hormonal level. Thus, normal and/or abnormal hormonal levels can be later determined without a dedicated sensor.

Possibly the additional sensors are off-line, e.g., laboratory blood testing. Alternatively or additionally, an ambulatory monitor is provided to the patient, into which the patient enters various information.

After a better picture of how the pancreas is acting is formed, a first reprogramming (508) may be performed. Such reprogramming may use any means known in the art such as magnetic fields and electromagnetic waves.

The reprogramming optionally implements partial control of the pancreas (510). Such partial control may be used to avoid overstressing the entire pancreas. Some of the controlled parts may be suppressed, for example using hyperpolarizing pulses as described above. It is noted however, that since the pancreatic damage does not usually cause immediate life threatening situations and because the pancreas is formed of a plurality of substantially independent portions, there is considerably more leeway in testing the effect of control sequences and even the long term effects of such sequences, that there is in other organs such as the heart.

In an optional step 512, the interaction of pharmaceutical or hormonal treatment with the controller may be determined. In this context is it noted that cardiac and nerve electrophysiological pharmaceuticals may be useful also for treatment of pancreatic disorders. Alternatively, pancreatic control may be desirable to offset negative side effects of such pharmaceuticals taken for non-metabolic disorders. Alternatively or additionally, the effect of pharmaceuticals on pancreatic cell behavior and/or feedback interactions, is determined.

Steps 508-512 may be repeated a plurality of times before settling down to a final programming 514. It is noted that even such final programming may be periodically re-assessed (516) and then modified (518), for example, as the pancreas and/or the rest of the patient improves or degrades, or to apply various long-term effect control sequences.

In an exemplary embodiment of the invention, a tissue viability testing of the controlled and or/uncontrolled parts of the pancreas is optionally performed periodically, for example to assess patient state to update the patient base line and to assess the efficiency of the therapy. Exemplary methods of viability testing include analyzing electrical activity, responses to changes in glucose level or insulin levels and/or responses to various types of electrical stimulation.

In an exemplary embodiment of the invention, the programming, measurements and/or prior attempted treatments (including possibly pharmaceutical treatments) are stored in a memory portion of controller 102. Alternatively or additionally, the programming may include special sequences that take into account taking of pharmaceuticals. In an exemplary embodiment of the invention, when a patient takes a pharmaceutical or insulin controller 102 is notified, for example by manual input into external unit 116 or automatically by the administration method. If the patient neglected to take the pharmaceutical, insulin, and/or glucose, a compensatory control sequence is provided, possibly irrespective of whether an alert is provided to the patient.

Experiment

In an exemplary experiment, a mesh unipolar electrode was placed under a pig pancreas and a needle electrode was inserted into the overlying abdominal wall as a ground. A pulsed current (5 Hz, 5 mA, 5 ms duration) was applied for five minutes and resulted in decrease in serum glucose from 89 to 74 mg/dl. Serum insulin increased from 3.8 to 5.37, microU/ml, measured using the ELISA method. Both glucose levels and insulin levels returned to the baseline after 30 minutes. in a different animal, the application for 5 minutes of a pulse of 3 Hz, 12 mA and 5 ms duration resulted in an insulin increase from 8.74 microU/ml to 10.85 microU/ml.

Figure 8A:
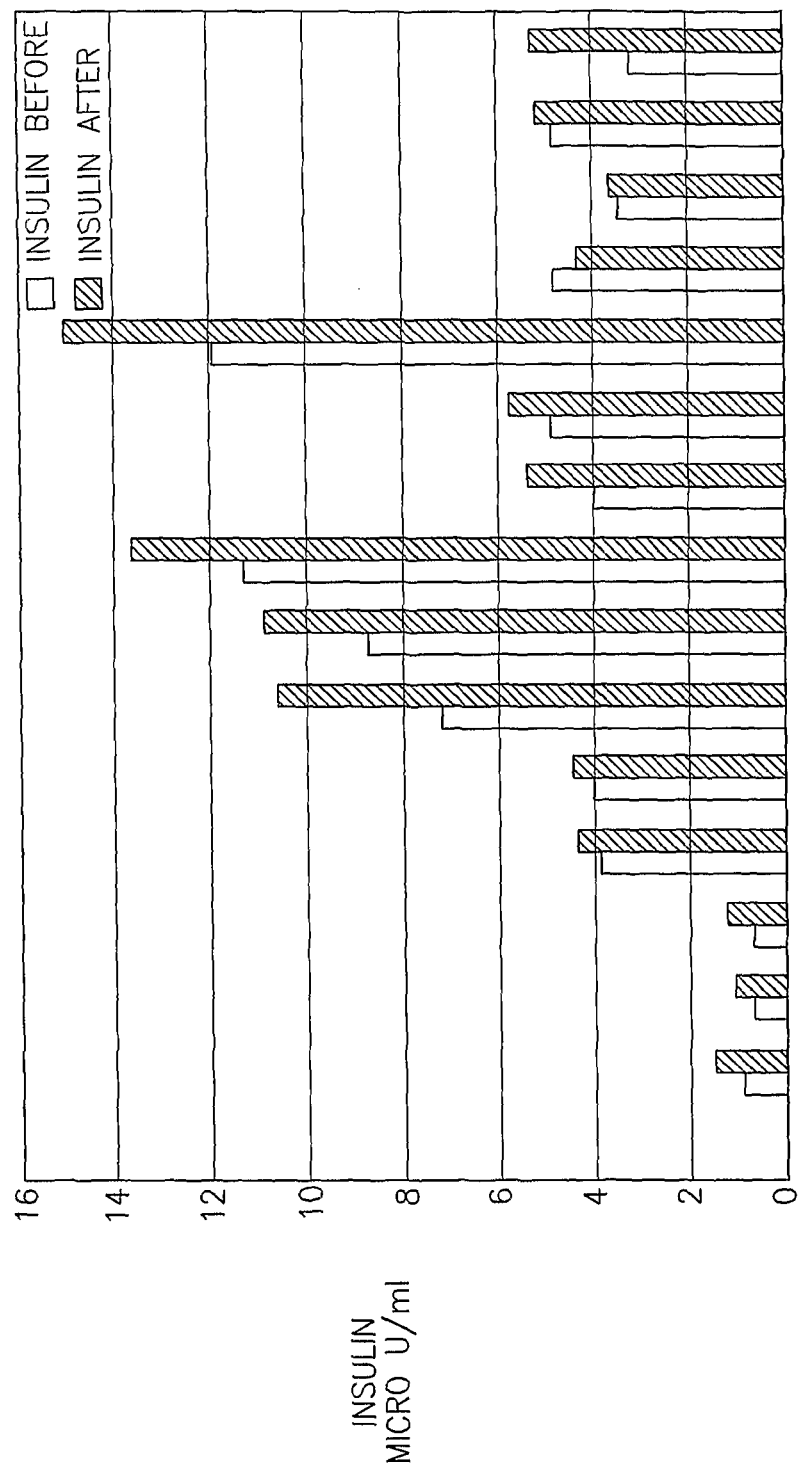
FIG. 8A is a chart showing the effect of electrical stimulation on insulin levels, in six animals.

FIG. 8A is a chart showing the effect of such electrical stimulation on insulin levels, in six animals. However it should be noted that, clinically, the effect on insulin and glucose levels is not very large, as they are near baseline and remain near baseline and the change in insulin levels will have a relatively small physiological effect.

Figure 8B:
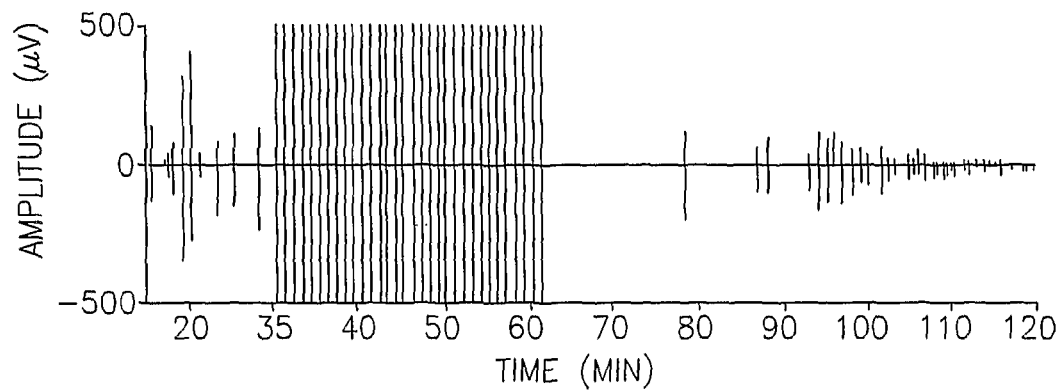
FIGS. 8B-8D are charts of an experiment in an in-situ pancreas, showing an increase in insulin secretion, in accordance with an exemplary embodiment of the invention.
Figure 8C:
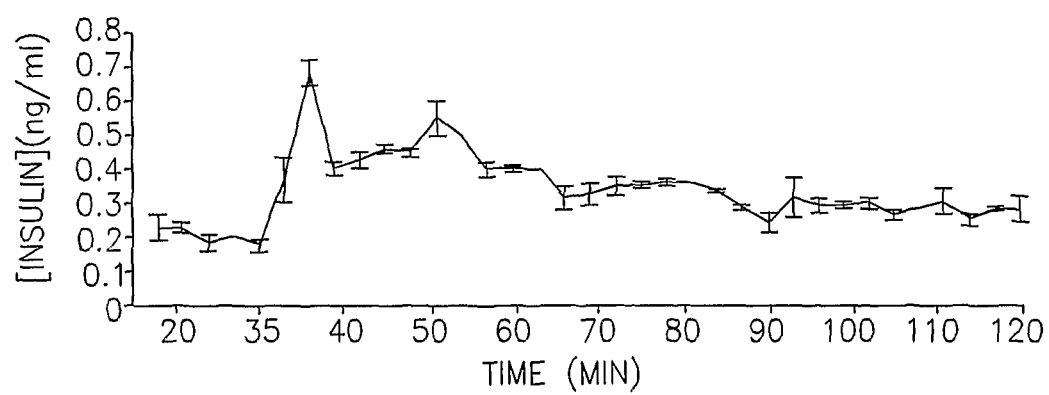
Figure 8D:
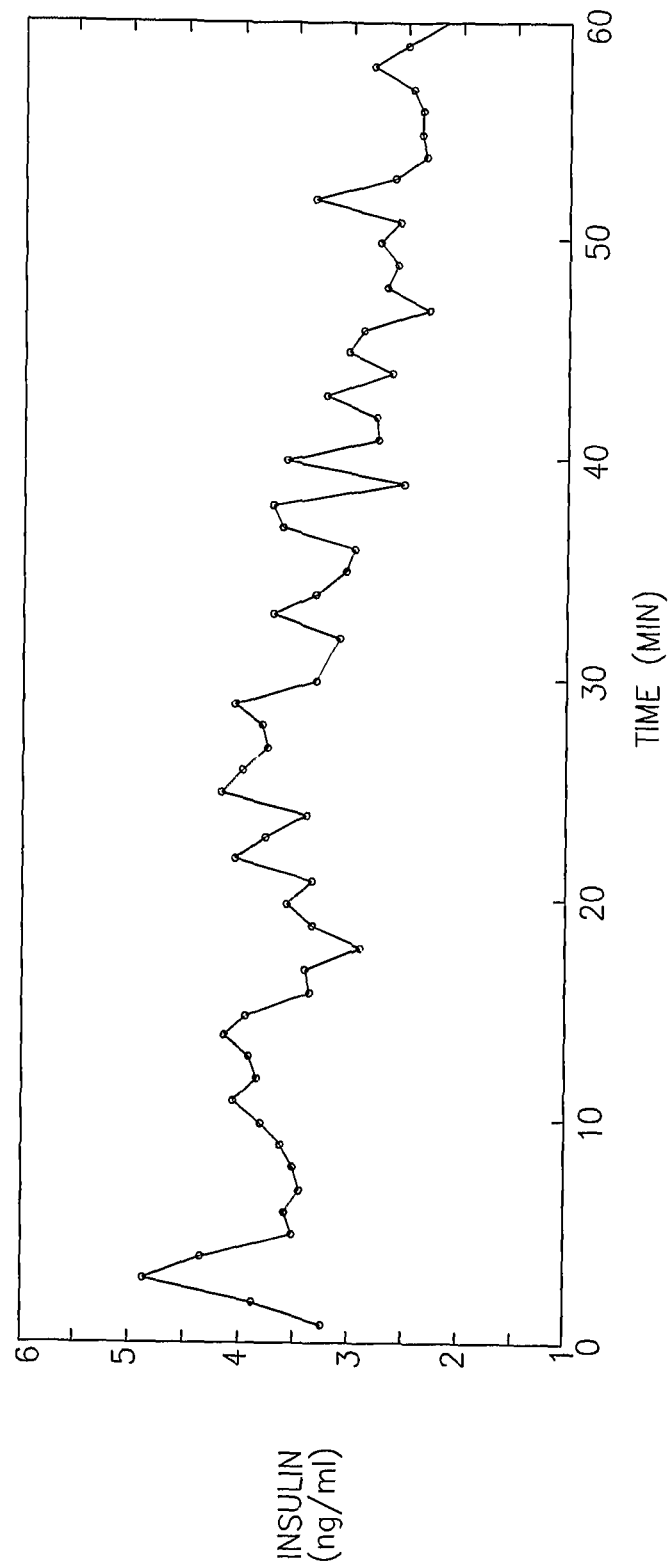

FIGS. 8B-8D are charts of an experiment in an in-situ pancreas, showing an increase in insulin secretion, in accordance with an exemplary embodiment of the invention. In this experiment, similar to the rat pancreas experiments described below, a pulse of bi-phasic, 5 Hz, 5 ms, was applied for one second of every minute. FIG. 8B shows the electrical activity measured. The area between 30 and 60 minutes is where the stimulation was applied. FIG. 8C shows a significant increase in insulin during the application of the signal, which indicates that in a practical system an increase, of, for example, more than 20%, 40%, 60%, 80%, 100%, 200%, or more can be achieved. FIG. 8D shows measurement during a control experiment with no stimulation.

Additional Experiments

Figure 9:
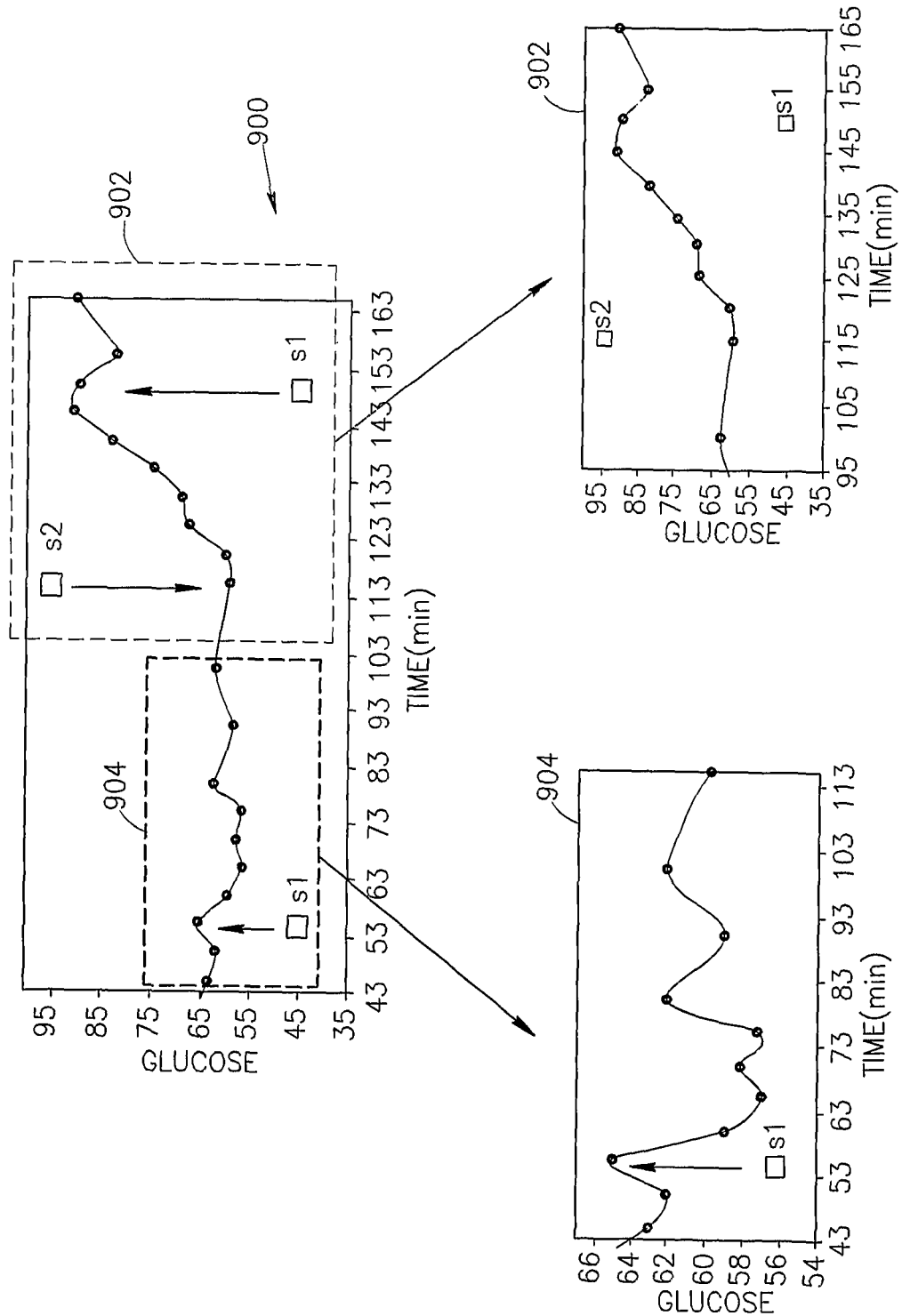
FIG. 9 is a graphic showing the effect of electrical stimulation on blood glucose levels, in an experiment in which glucose levels are increased faster than would be expected solely by inhibition of insulin secretion.
Figure 12A:
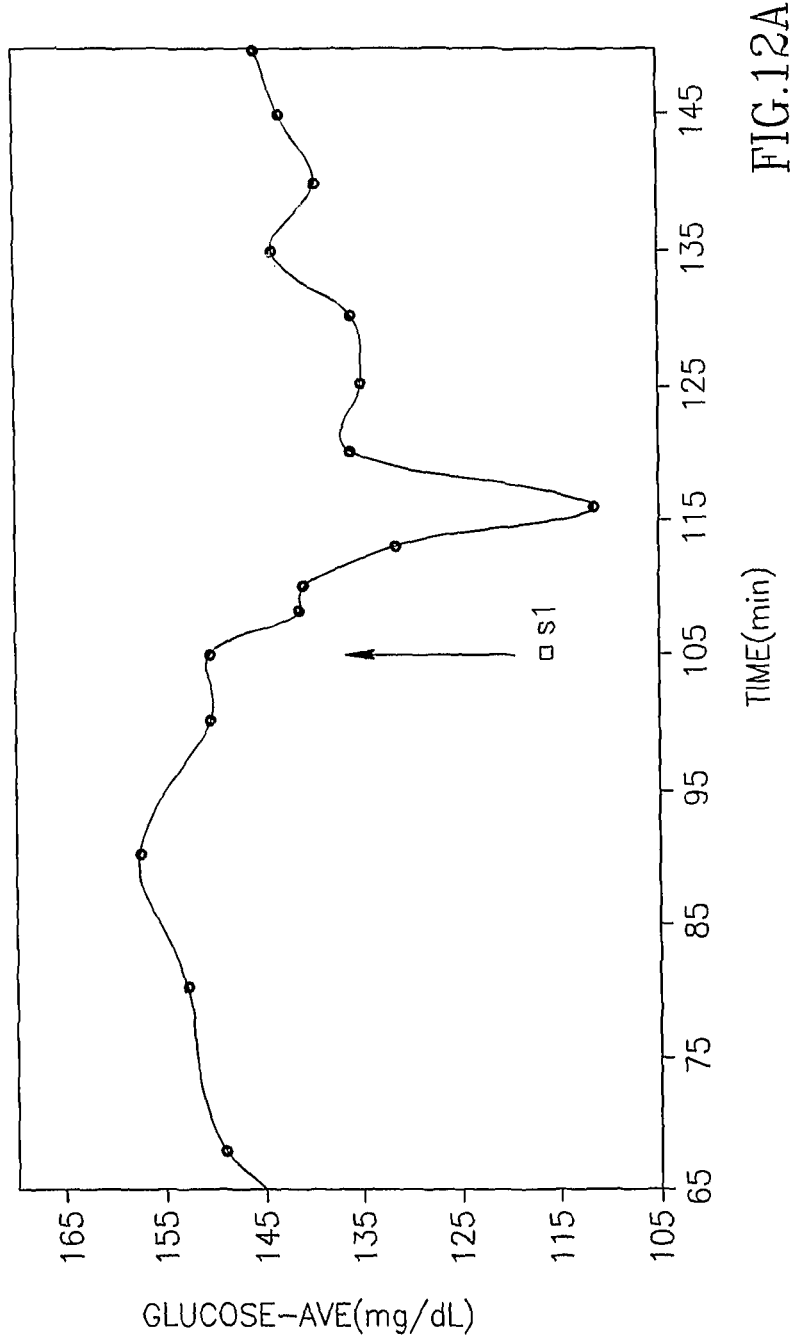
FIGS. 12A-12B are a chart and a pulse diagram, respectively, of an experiment showing reduction in glucose levels as a result of applying an electrical pulse in accordance with an exemplary embodiment of the invention.
Figure 12B:
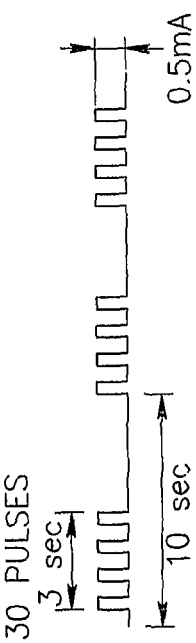

FIG. 9 is a chart showing the effect of electrical stimulation on blood glucose levels, in an experiment in which glucose levels are increased faster than would be expected solely by inhibition of insulin secretion.

In a sub-chart 904 of chart 900, glucose levels are reduced by the application of a stimulation pulse S1. In a sub-chart 902 of chart 900, glucose levels are increased by the application of a stimulation pulse S2 and then reduced by an application of pulse S1 again. It is hypothesized that merely reducing insulin secretion would not be sufficient to explain such a fast and large increase in glucose levels. Instead, the secretion of glucagon is causing a release of glucose from the liver, raising the blood glucose level.

Chart 900 is from an experiment on a rat which was anesthetized with pentobarbitone (40 mg/1 Kg). After fasting the rat was given a continuous infusion of 5% glucose at a rate of 2 cc/Hr. During the experiment, the rat was ventilated with oxygen. The sample shown on chart 900 are the results of an analysis by a glucometer "Glucotrend", by Rosche, of blood from the right jugular vein every 5 minutes. S1 and S2 have a similar form, except that S2 has a 2 mA amplitude and a 3.5 minute duration, while S1 has a 1 mA amplitude and a 5 minute duration. The pulse includes an initial spike followed by a 150 ms delay and a train of 7 50% duty cycle spikes spread over 400 ms. The entire pulse is repeated every 10 seconds. The initial spike is 50 ms long. Both electrodes were Iridium Oxide coated Titanium. The geometry of the electrodes was a coil, 8 mm long, 1.2 mm diameter, with a 100µ diameter 3 fillar wire. The coil was glued on a silicone pad (for insulation and prevention of mechanical damage. Two such electrodes were placed along the pancreas, one above and one below (when the rat is on its back).

FIGS. 10A-10B, 11A-11B, 12A-12B and 13A-13B are pairs of figures, each pair showing a chart and a pulse diagram, of additional experiments using a similar setup to that of FIG. 9.

In FIGS. 10, 12 and 13 both electrodes were above the pancreas and the signal was applied for 5 minutes.

In FIG. 11, both electrodes were under the pancreas and the signal was applied for 5 minutes.

Additional Experiments in a Perfused Rat Pancreas

A series of experiments were carried out on a perfused rat pancreas. The pancreas is actually disconnected from any control system (e.g., blood, nerves), but not disconnected from its ligaments and surrounding organs. In an anesthetized rat, all main blood vessels are tied off around the pancreas and a cannula is inserted to the descending aorta, the thoracic aorta is tied off last and the circulation of blood substitute (with glucose) is allowed through the celiac trunk to the liver, pancreas and duodenum. The perfusate is then collected from the portal vein for further examination. This does kill the rat. In general, the application rate of once a minute was chosen since it generally matches the natural burst rate of the pancreas. For example, some of the pulses applied has a waveform of bi-phasic, 5 Hz, phase duration 5 ms applied for 1 second every minute. In general, a range of different frequencies were tried out. In other creatures (e.g., humans) and/or various conditions, this rate may be different. The glucose levels were generally controlled to be about 10 mM.

Figure 14:
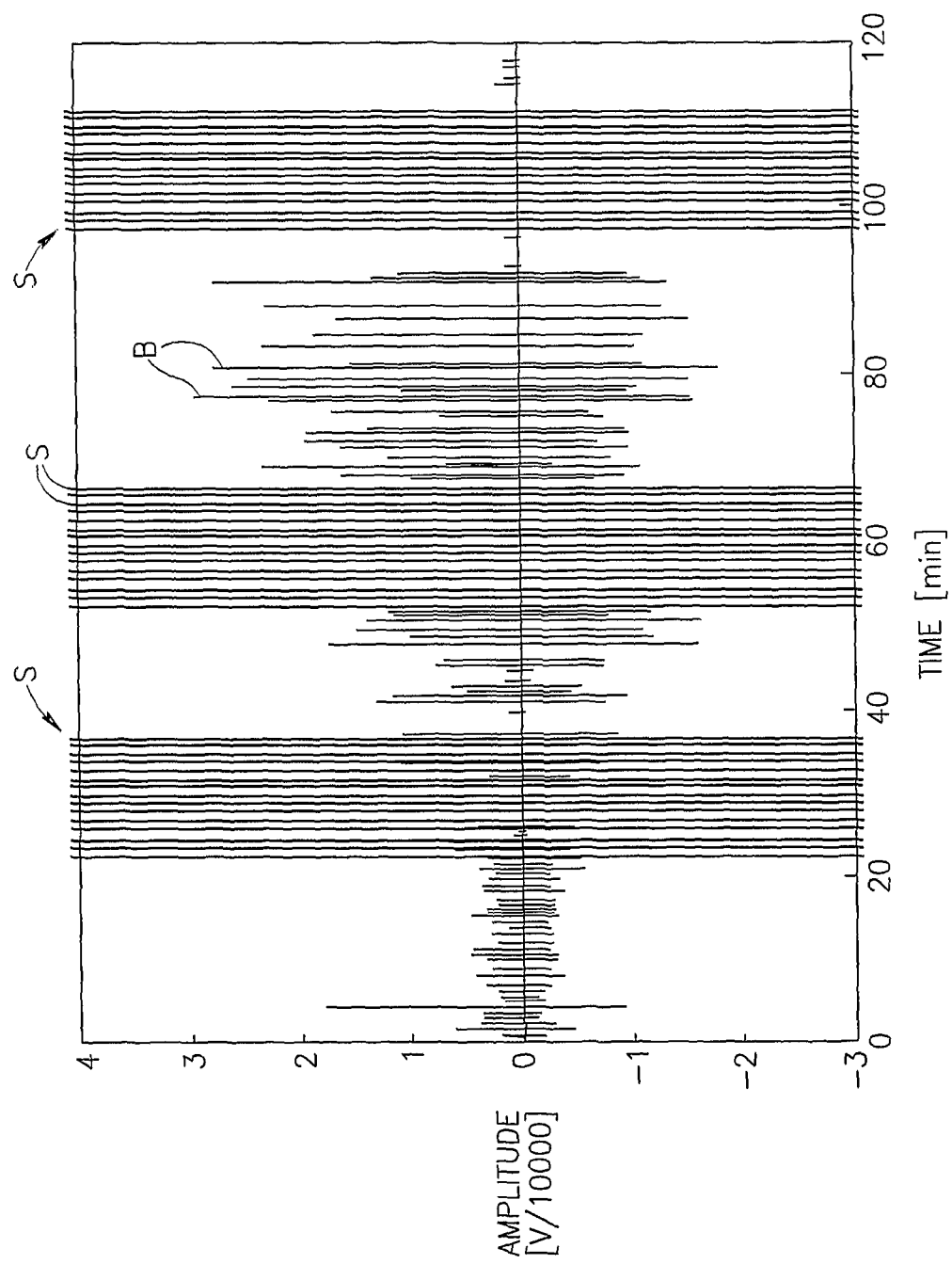
FIG. 14 is a chart showing an experiment in which applying stimulation pulses increased the amplitude of bursts but did not induce new bursts.

FIG. 14 is a chart showing an experiment in which applying stimulation pulses increased the amplitude of bursts but did not induce new bursts. Due to the electrical nature of the measurement, stimulation pulses appear as lines that span the entire vertical range of the chart. This is generally true in the other charts as well. For clarity, (some) bursts are measured with the letter "B", and stimulation pulses with the letter "S". In this experiment, performed in situ, in the rat, as described above, the pulse was a bi-phasic rectangular balanced pulse at 5 Hz, 10 ms pulse length, 10 mA maximum amplitude, 0.5 second application duration and was applied every minute. This pulse apparently did not induce significant new bursts when applied at a non-bursting time and increased the amplitude of bursts occurring and/or during after the pulse. Possibly a burst did occur during the pulse and is not detected due to measurement system limitations. In addition, the rate of the bursts appeared not to change, however, it is believed that using other parameters, burst rate can be controlled electrically, not only using direct pacing.

It should be noted that the charts showing electrical activity are schematic only and do not show all the fine details of the electrical signals measurements, due to resolution limitations of the drafting and presentation process.

Figure 18A:
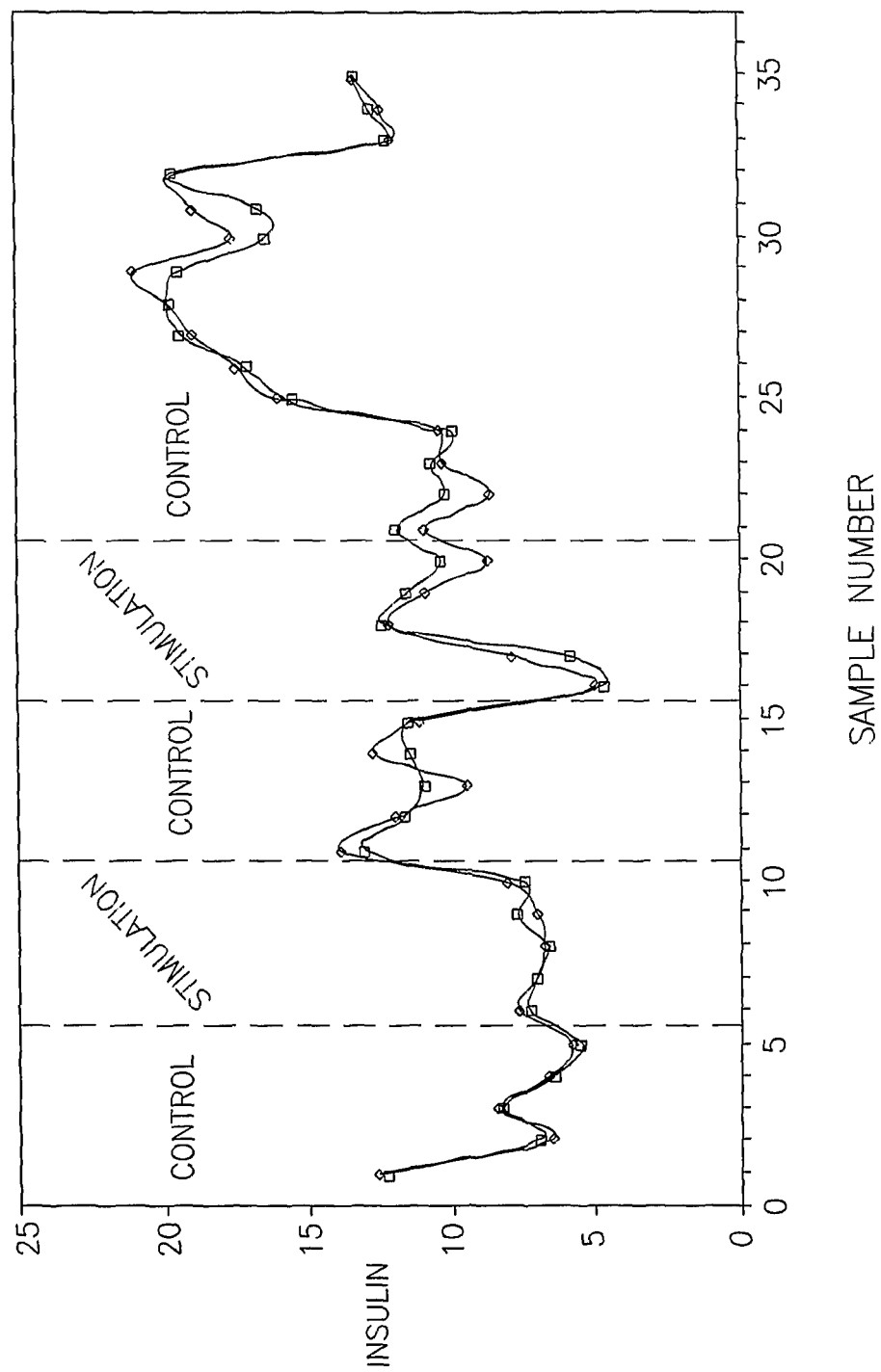
FIGS. 18A and 18B are charts showing changes in insulin level apparently caused by stimulation.
Figure 18B:
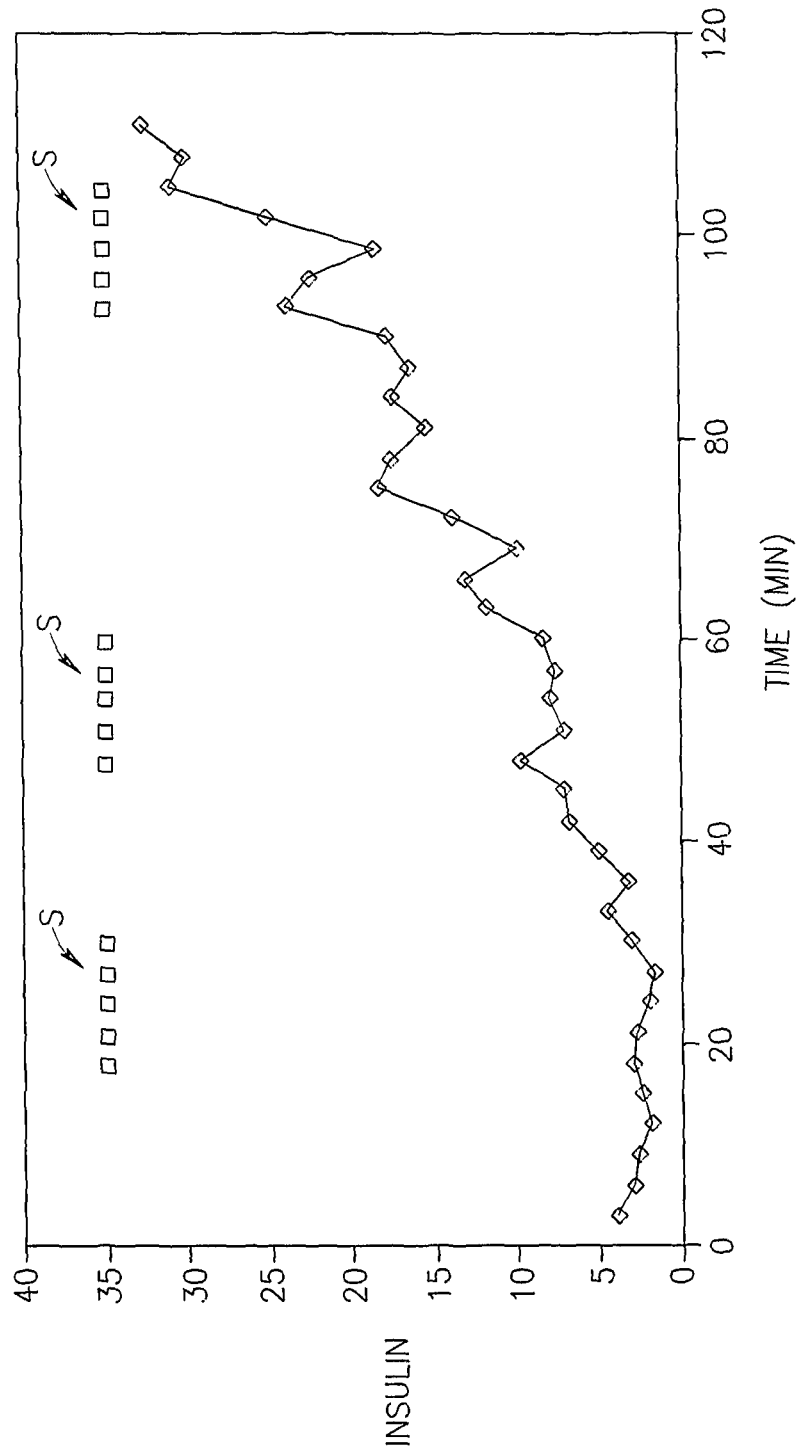

FIG. 18B, shows a measurement of insulin levels (shown in this and other charts in units of micro-units per milliliter). Stimulation apparently caused a corresponding increase in insulin level. However, in the first two stimulations, the level apparently did not increase immediately or during the stimulation, but only towards the end or after the end of the pulse. It is hypothesized, that a pulse may have two effects on beta cells, one of priming them for insulin secretion (e.g., promoting generation) and one of initiating or suppressing secretion. It is hypothesized (and as will be supported by other experimental results below) that longer pulses may have the effect of preventing insulin secretion, possibly by hyper-polarization of beta cells. Depending on the degree of hyper polarization and the amount of insulin generated in the cells and/or possibly on the environmental cues (e.g., glucose level and/or hormone level), a cell may be stimulated to secrete even during an application of the electric field, may be free to secrete after the field is removed, or may be prevented from secretion for a duration after the field is removed. If the stimulations are close enough together, the cell may be prevented from secretion until the stimulation series is completed or until its internal activities are strong enough (e.g., stimulated by internal insulin stores) to overcome the hyper-polarization. In this and other observed effects, it should be noted that while various mechanism have been hypothesized, the discovered effects may be used in some embodiments of the invention even without a correct understanding of the biochemical and electro-physiological processes behind them. Thus, pulses having lengths of between 1 and 40 ms may have significantly different physiological effects. This may suggest using pulses of lengths 0.5, 1, 2, 5, 10, 15, 20, 32 and 40 ms or pulses of shorter, intermediate or greater duration to achieve various effects.

An alternative interpretation is that the frequency affects the behavior of the beta cells. Thus, various frequencies, such as 2 Hz, 5 Hz, 10 Hz, 15 Hz, 20 Hz or smaller intermediate or larger frequencies may be used to achieve various effects.

An alternative, composite interpretation is that the combination of pulse duration (e.g., one or both of the length of each sub-pulse, measured in milliseconds in some examples and the length of each train, measured in whole seconds and fractions thereof in some examples) and frequency dictates a total about of stimulation, which total stimulation may determine the effect of the pulse, at least for some ranges of frequencies and amplitudes.

Figure 15A:
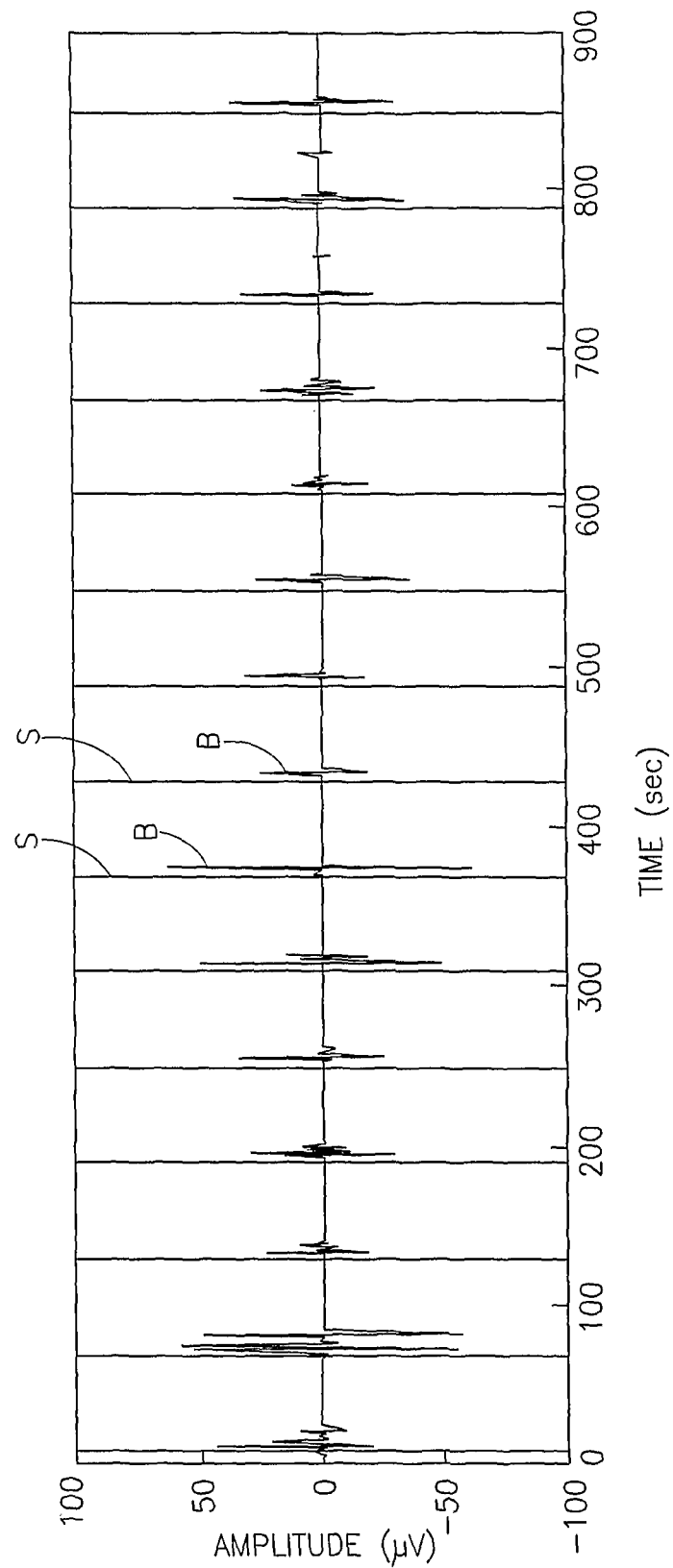
FIGS. 15A-15C are a chart and two enlargements thereof of an experiment showing that a stimulation pulse synchronizes burst activity, possibly without immediately generating a new burst.
Figure 15B:
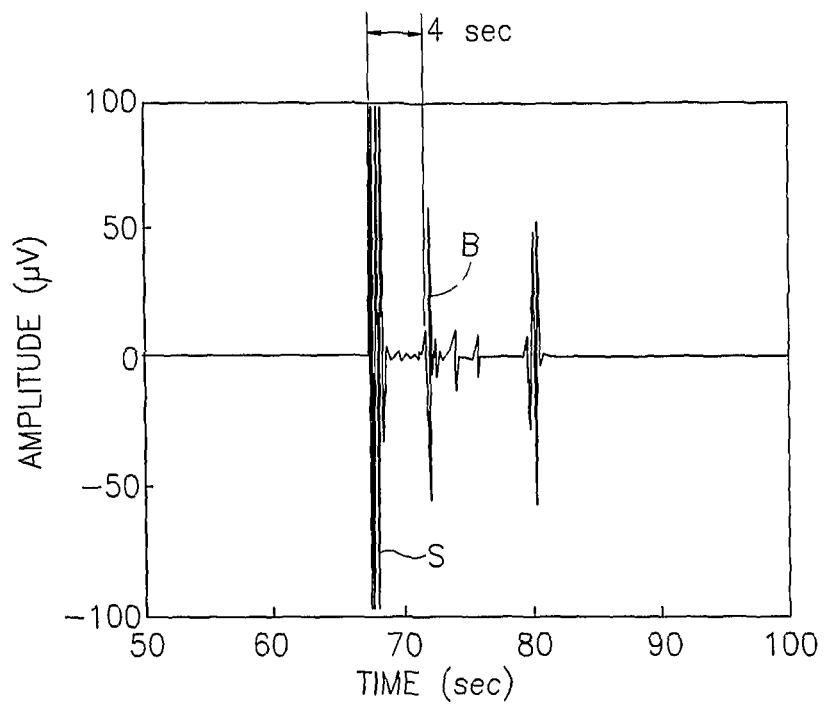
Figure 15C:
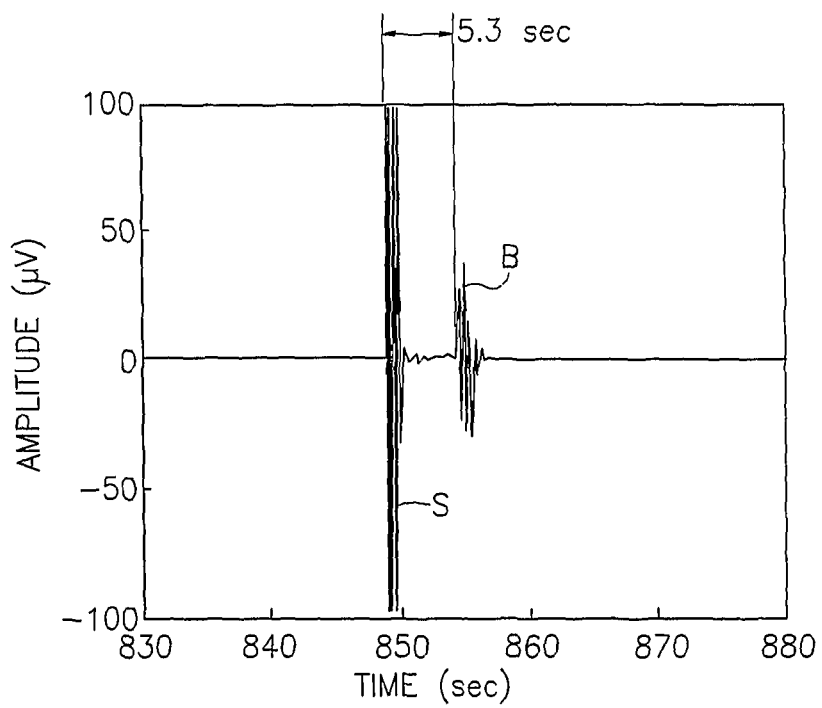

FIGS. 15A-15C are a chart and two enlargements thereof of an experiment showing that a stimulation pulse synchronizes burst activity, possibly without immediately generating a new burst. The experiment is in-situ, as above, with the stimulation parameters defining a bi-phasic rectangular balanced pulse at 10 mA, 40 ms at 20 Hz, applied for 500 ms. FIGS. 15B and 15C show enlargements of two stimulation pulses, showing that no immediate bursts were apparently generated (unless they are quite short and masked by the stimulation). Possibly if the stimulation rate were considerably slower, naturally occurring bursts would occur. In an exemplary embodiment of the invention, the burst rate is controlled (e.g., made higher or lower than natural) to some extent by applying this type of pulse.

Figure 16A:
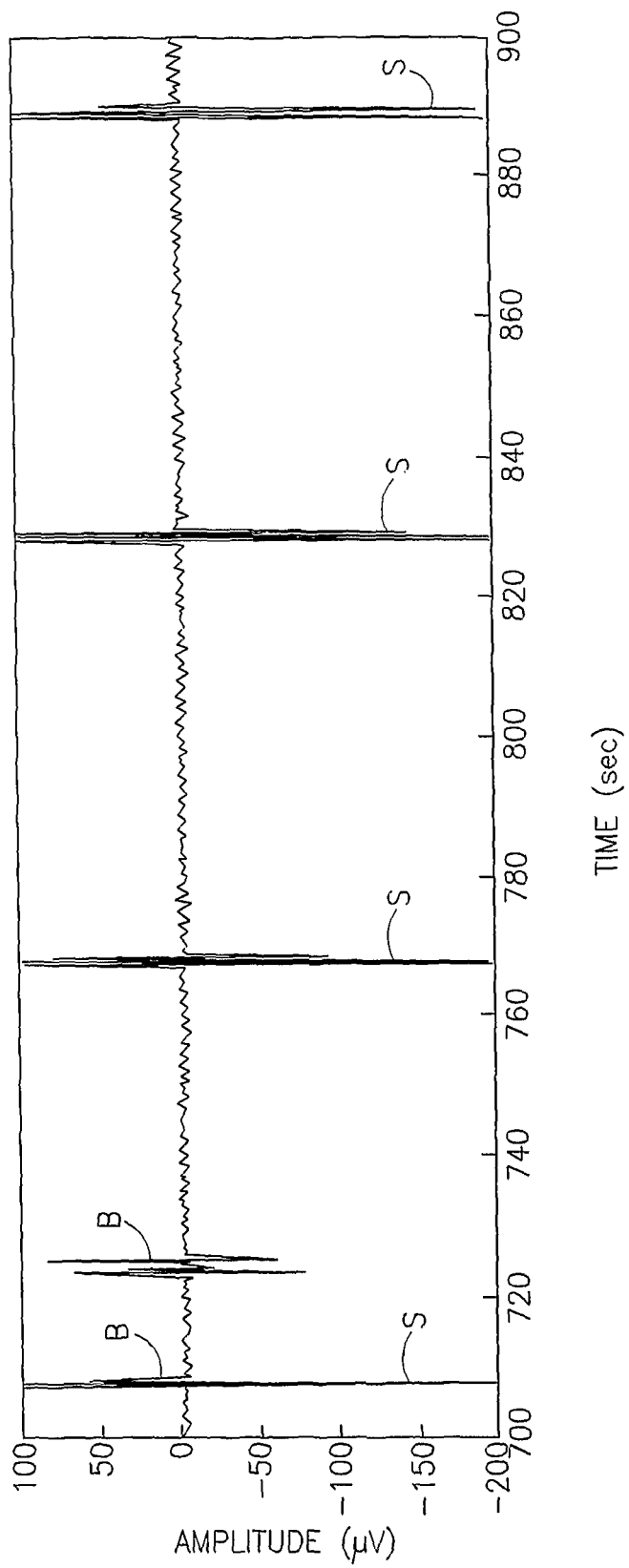
FIGS. 16A-16C are a chart and two enlargements thereof of an experiment showing new burst induction by a stimulation pulse.
Figure 16B:
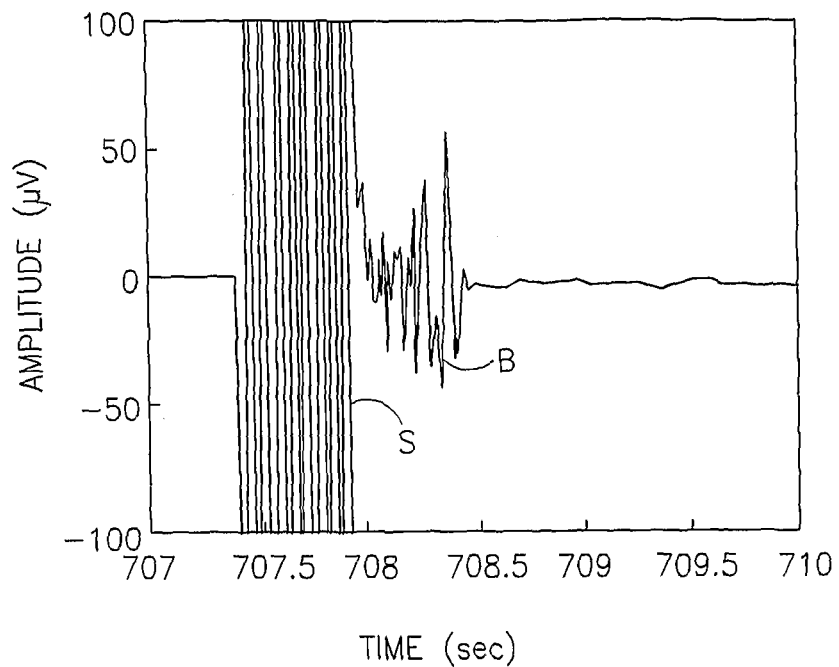
Figure 16C:
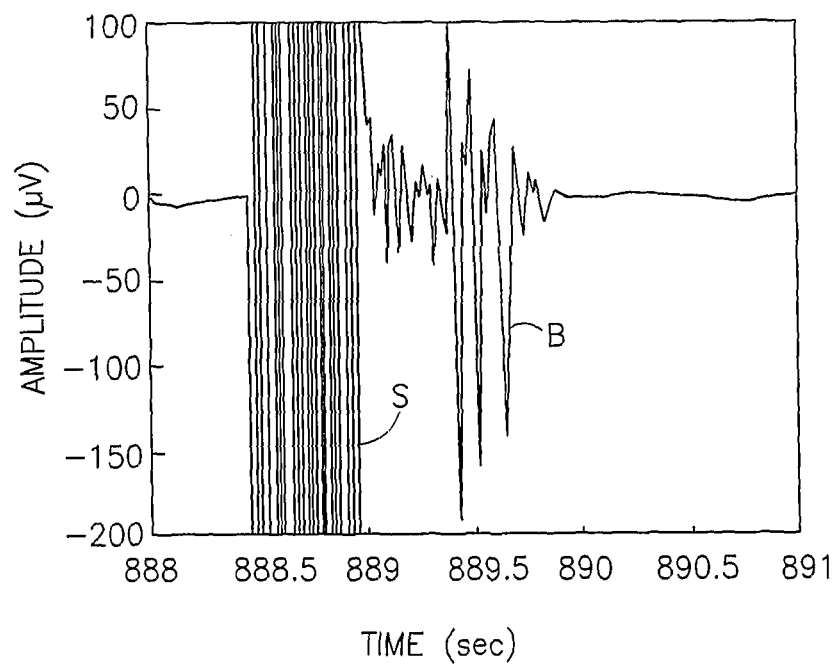

FIGS. 16A-16C are a chart and two enlargements thereof of an experiment showing new burst induction by a stimulation pulse. The effect of the new burst is substantially immediate. As noted above, it is hypothesized that the length of the stimulation pulse is what determines if there will be a delay before such a burst occurs and/or the extent of such a delay. One possible support for this is that no second burst after about 5 seconds is shown in FIG. 16, leading one to believe that this type of pulse stimulates the creation of a single burst, at a variable delay and/or can be used to delay the onset of a naturally occurring burst. In any case, once a burst occurs, natural mechanisms, such as re-polarization and exhaustion may prevent a next burst from occurring too soon.

Figure 17:
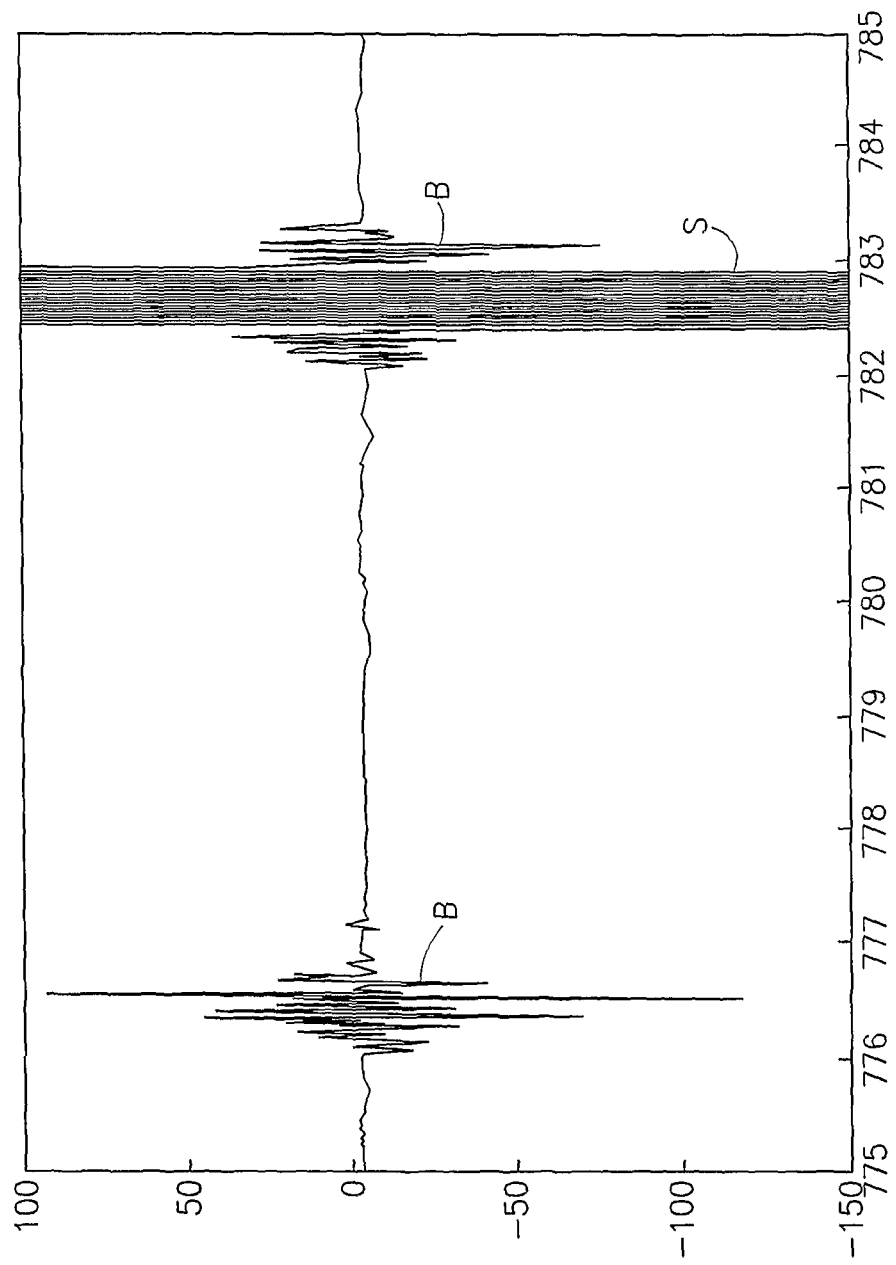
FIG. 17 is a chart of an experiment showing that a stimulation in the middle of a burst did not stop the burst.

FIG. 17 is a chart of an experiment showing that a stimulation in the middle of a burst did not stop the burst, in some embodiments of the invention. The burst on the left is shown for comparison, so that the effect of the pulse on the burst (e.g., on length) may be seen. The effect on the length and amplitude is not clear and may be negligible or may be significant for length and/or amplitude. As noted above, FIG. 14 shows an increase in amplitude as a result of such a stimulation. The pulse parameters are 10 mA, 2 ms, at 20 Hz, for 500 ms, applied every 1 minute.

FIGS. 18A and 18B are charts showing changes in insulin level apparently caused by stimulation. FIG. 18B was discussed above. FIG. 18A shows two duplicate sets of measurements, made on the same samples, for ensuring accuracy of the insulin measurement. As can be seen, insulin levels increase during or after stimulation relative to during stimulation. It is believed that the rightmost increase in insulin level may be a delayed effect of the stimulation which causes a generally increased activity of beta cells, as well possibly a momentary increase in output. Stimulation (using these pulse parameters) apparently causes enhancement in insulin values that may be delayed. Possibly, the stimulation period itself does not allow an increase, even though the stimulation effect is that of an increase. Samples are made three minutes apart. The pulse parameters were 10 mA, 10 ms, at 20 Hz, for 500 ms, repeated every 1 minute.

Figure 19:
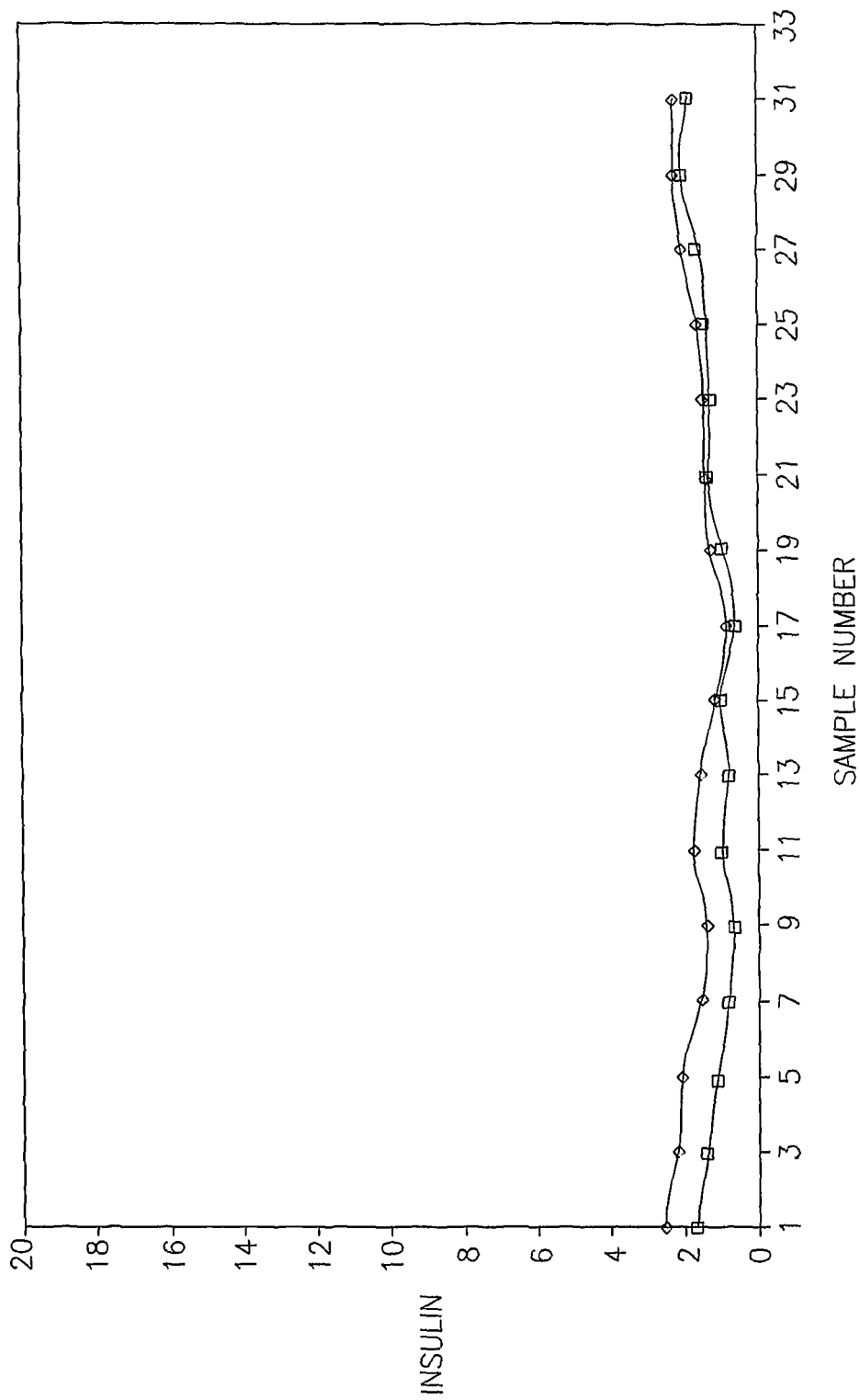
FIG. 19 is a chart showing relative constant glucose levels in a perfused rat pancreas without stimulation.

For reference, FIG. 19 is a chart showing baseline relatively constant insulin levels in a perfused rat pancreas, without stimulation.

Additional Experiments in Living Mini Pigs

Two mini-pigs (named Venus and Shifra) were utilized for these experiments. The pigs, of weight between 35 and 40 Kg had electrodes implanted into their pancreas. Either four or six electrodes were implanted, however, only four were utilized, with two electrodes implanted at each end of the pancreas and shorted together. The electrodes were wire electrodes separated 2 cm within the pair and inserted to a depth of 3-5 mm, this length being electrically conducting. The pigs were starved and then either fed pig feed or provided with sugar (sucrose) cubes to eat. The experiments were repeated for the same animal with and without stimulation, as will be described below. The pigs have remained alive and are apparently unharmed by the experimentation, which occurred over a period of several months.

Figure 20A:
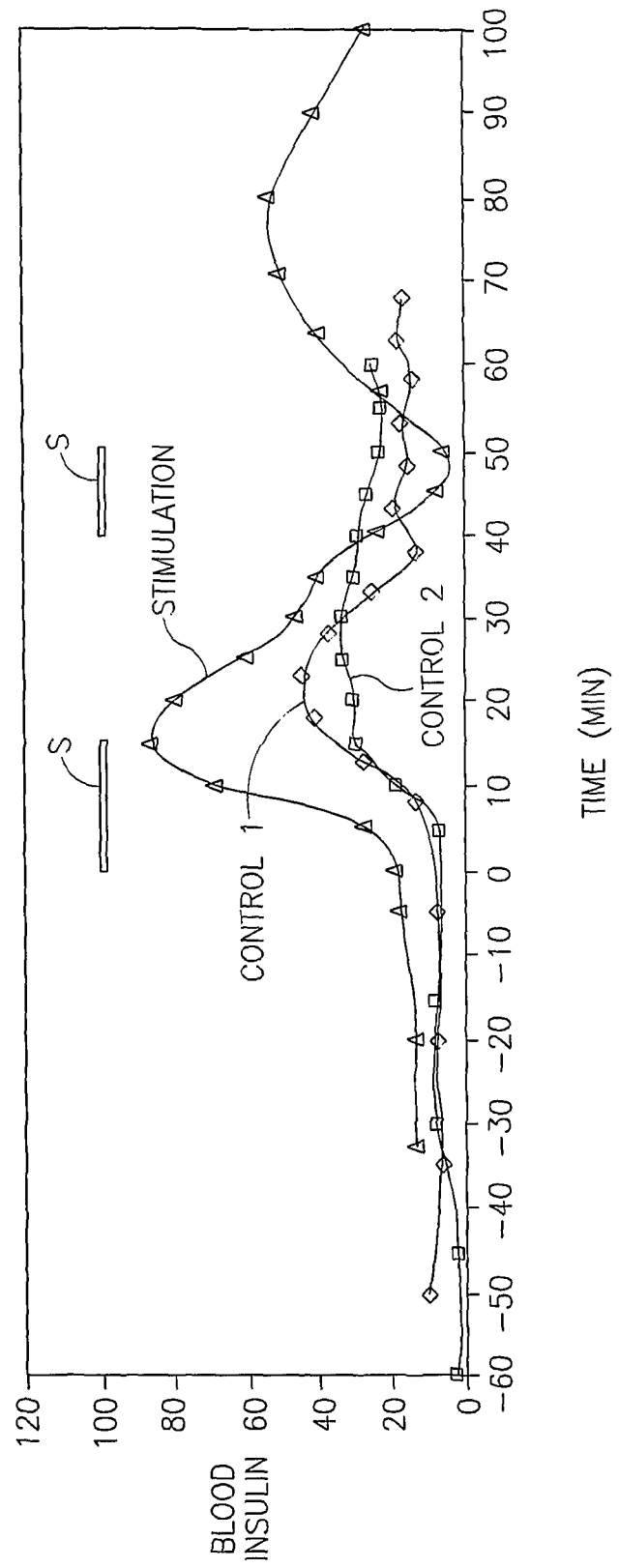
FIG. 20A is a chart showing changes in insulin levels with and without stimulation, in a live mini-pig given sugar cubes to eat.

FIG. 20A is a chart showing changes in insulin levels with and without stimulation, in a live mini-pig given sugar cubes (30 cubes of 2.5 grams sucrose each, eaten in a few minutes), after starvation. A follow up experiment did not show considerable different between feeding sucrose and feeding glucose, which, being a fluid is technically more difficult to feed to a pig. Two stimulation series were applied, one 15 minutes long and the second 10 minutes long. Time zero is the start of feeding. The pulse was 100 Hz, 10 ms, 1 second length, every minute, amplitude is 5 mA.

As shown, insulin increase in the stimulation experiment is faster and greater than without stimulation. Possibly this is an enhancement effect by which the insulin activity (response of the pancreas) is amplified by the stimulation.

Figure 20B:
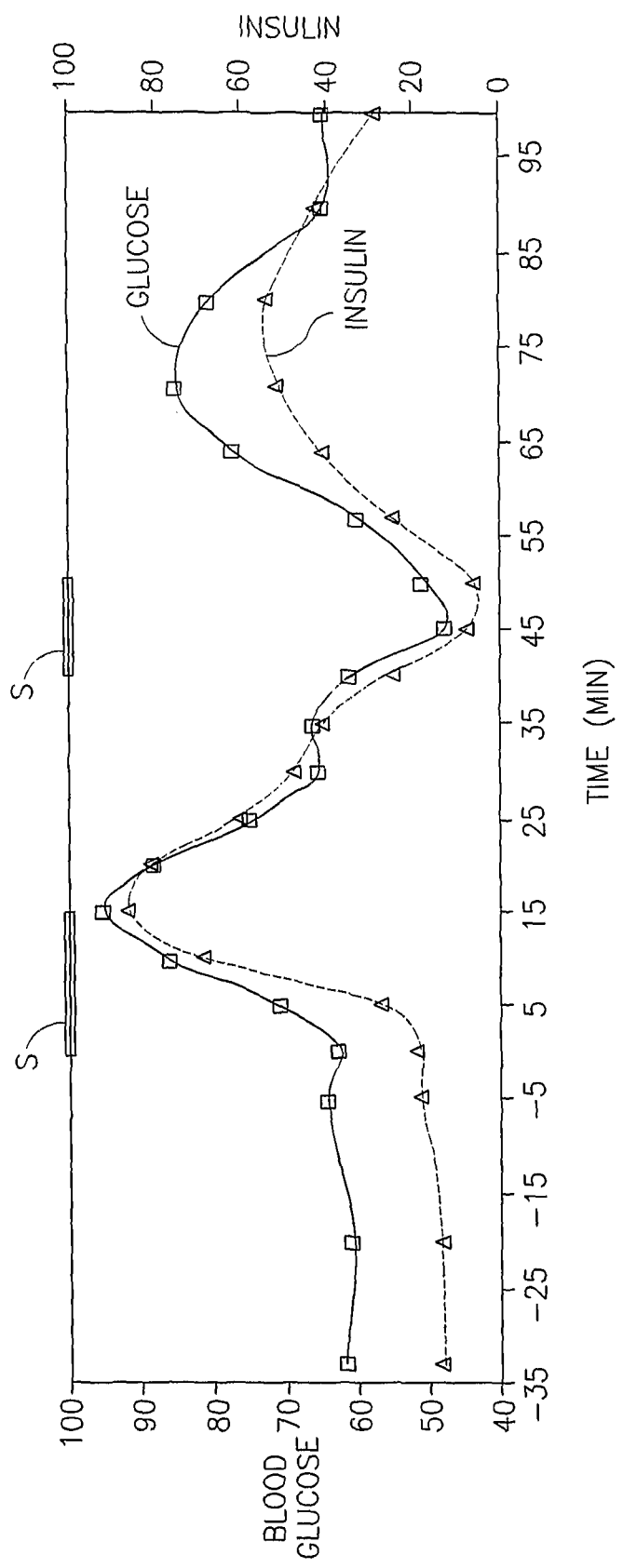
FIG. 20B is a chart corresponding to chart 20A, showing for the stimulation case the relationship between glucose level and insulin level.

FIG. 20B is a chart corresponding to chart 20A, showing for the stimulation case the relationship between glucose level and insulin level. As noted above, and in the discussion of FIG. 21A, there exist physiological mechanisms, such as glucagon secretion that increase glucose secretion if insulin level go high. In some embodiments of the invention, a smaller stimulation may be applied to reduce this glucose secretion.

Figure 20C:
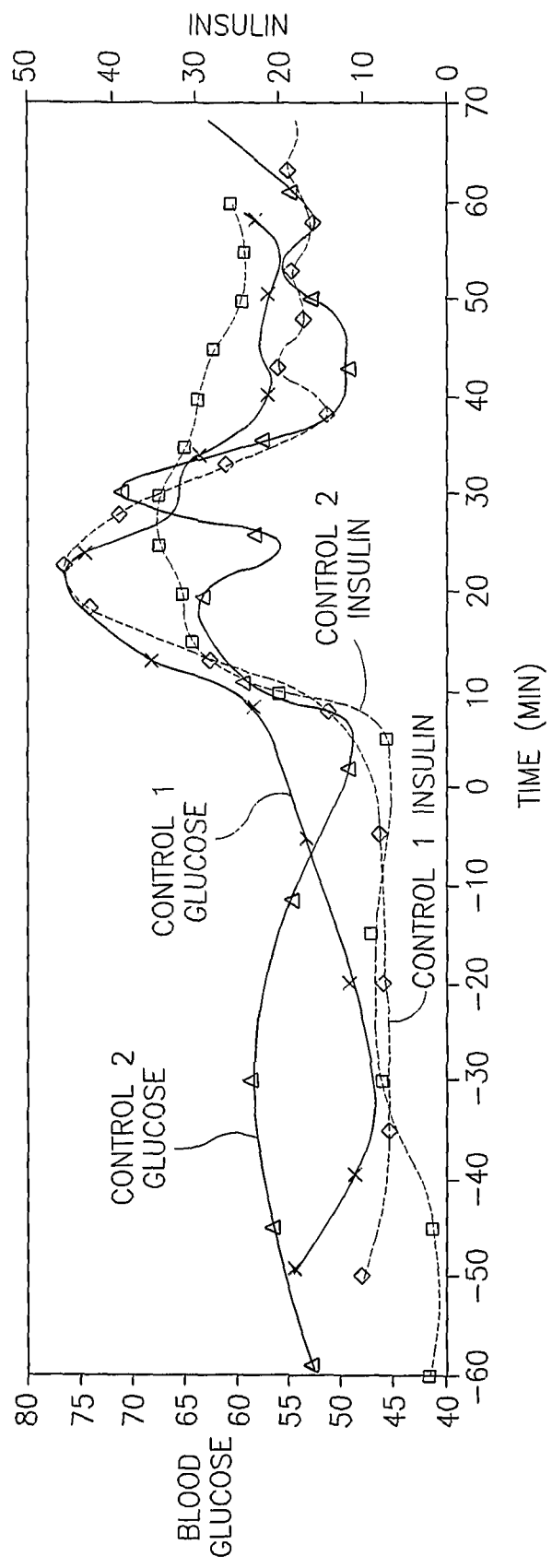
FIG. 20C is a chart corresponding to chart 20A, showing for the non-stimulation cases, the relationship between glucose and insulin level.

FIG. 20C is a chart corresponding to chart 20A, showing for the non-stimulation cases, the relationship between glucose and insulin level.

Figure 21A:
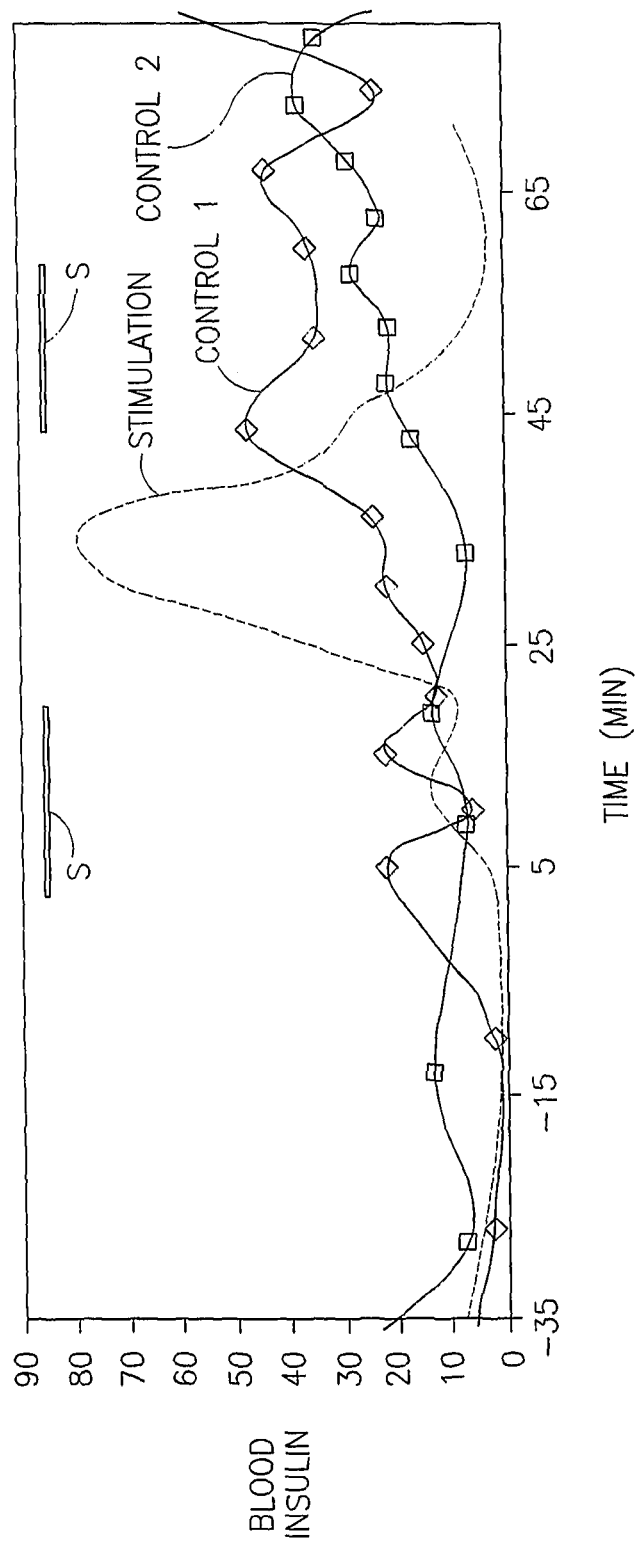
FIG. 21A is a chart showing changes in insulin levels with and without stimulation, in a live mini-pig given food.

FIG. 21A is a chart showing changes in insulin levels with and without stimulation, in a live mini-pig given food, about 700 grams, after starvation. It should be realized that provision of food is generally less controlled than provision of sugar. Two stimulation series were applied, one 15 minutes long and the second 10 minutes long. Time zero is the start of feeding. The pulse was 100 Hz, 10 ms, 1 second length, every minutes, amplitude is 5 mA. The effect on insulin levels is significant after the first stimulation, but not after the second, possibly due to exhaustion of pancreas or due to low glucose levels (shown in FIG. 20B). It is hypothesized that the pulse, as applied, does not arbitrarily cause the secretion of insulin, but amplifies or primes existing physiological mechanisms. Thus, stimulation when glucose levels are low does not cause necessarily increase insulin levels to high levels (which might be dangerous in this situation). This may be a direct property of the pulse or it may be caused by various physiological mechanisms. Another possible interpretation is that had observation been continued, the increase in insulin levels observed after the second stimulation would have continued. The relative delay and/or reduced rate of this increase may be due to one or more of the above described mechanisms.

Figure 21B:
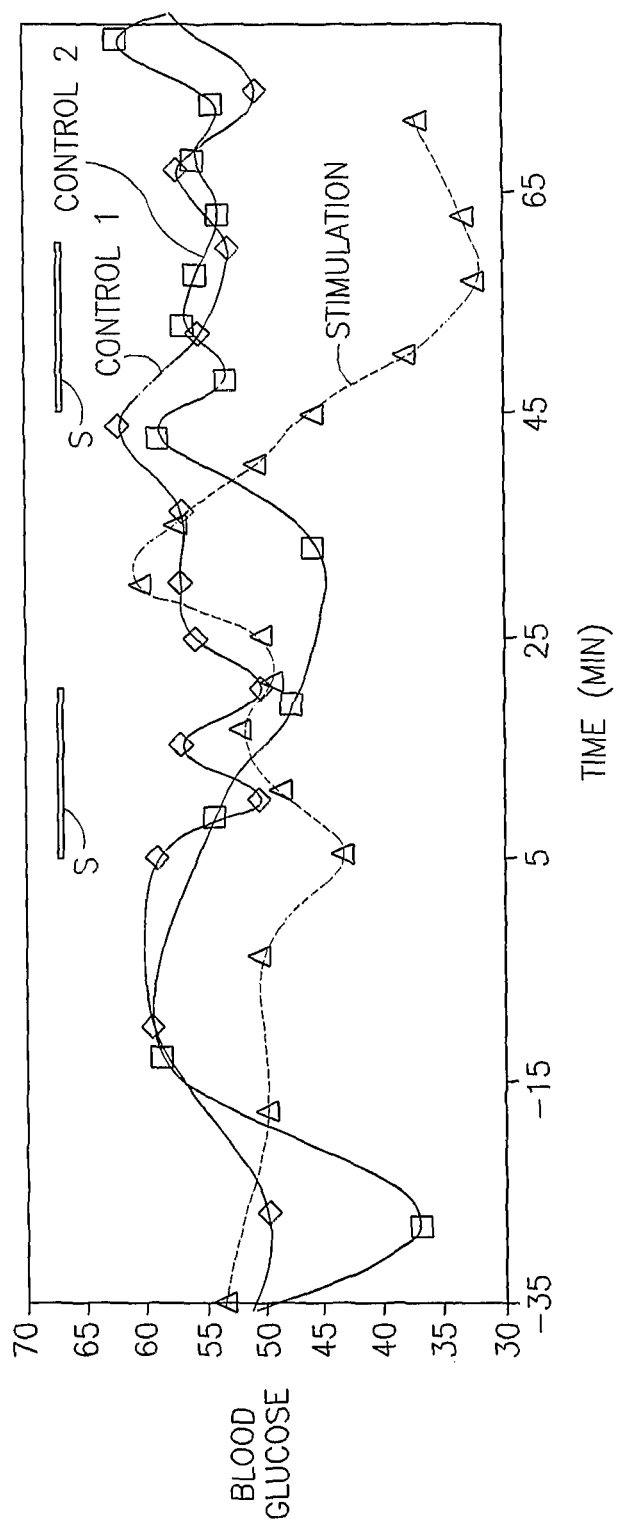
FIG. 21B is a chart corresponding to chart 21A, showing blood glucose levels.

FIG. 21B is a chart corresponding to chart 21A, showing blood glucose levels. While the blood glucose went up after the first stimulation, it went up by less than the control situations and peaked sooner. This suggests that the pulse may have directly or indirectly affected glucose levels. one possible mechanism is that insulin secretion causes glucagon secretion or that glucagon secretion was directly induced by the pulse. Possibly, these effect is more pronounced if the insulin is produced as a bolus, so that insulin levels build up considerably and/or fast in the pancreas and/or in the body.

The above experiments clearly show that application of electric fields can affect the behavior of the pancreas, for example increasing or decreasing insulin output with our without creating new bursts, and that different pulses have different behaviors.

Further Experiments in Living Mini Pigs

In the following experiments on living mini-pigs, the following protocol was used. A pair of electrodes were implanted in the pancreas of adult, female Sinclair mini-pigs. After being given two weeks to recover from surgery, two types of protocols were executed. In a control protocol 3 blood samples were taken while the pig was fasting. At time 0 a 75 g glucose load was administered orally. Blood samples were taken every 5 minutes for a total of about 100 minutes. Stimulation protocols were the same as the control protocols except that stimulation was applied immediately after the ingestion of the glucose. The pulse parameters were: biphasic waveform of 5 ms each phase applied every 200 ms (5 Hz). The amplitude is 6-10 mA. Stimulation duration was 15 minutes in this and the following experiments.

Figure 22A:
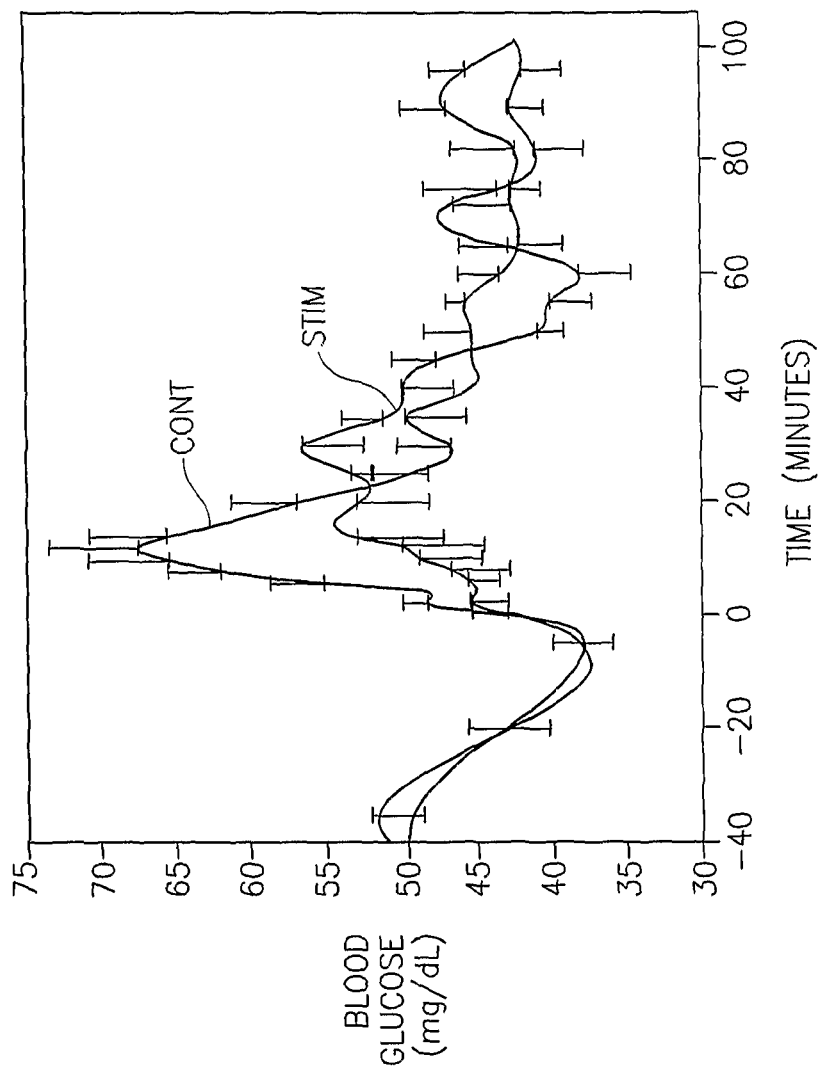
FIG. 22A is a chart showing a delay in glucose peaking and reduction in levels thereof under conditions of stimulation in a series of experiments in a first pig, in accordance with an exemplary embodiment of the invention.

FIG. 22A is a chart showing a delay in glucose peaking and reduction in levels thereof under conditions of stimulation in a series of experiments in a first pig, in accordance with an exemplary embodiment of the invention. Both control and stimulation values are averages of 9 days each. It should be noted that the glucose peak is both reduced and delayed 20 minutes and also spread out over time. Some of these experiments may be also be factored-in in the charts of FIGS. 35A and 35B.

Figure 22B:
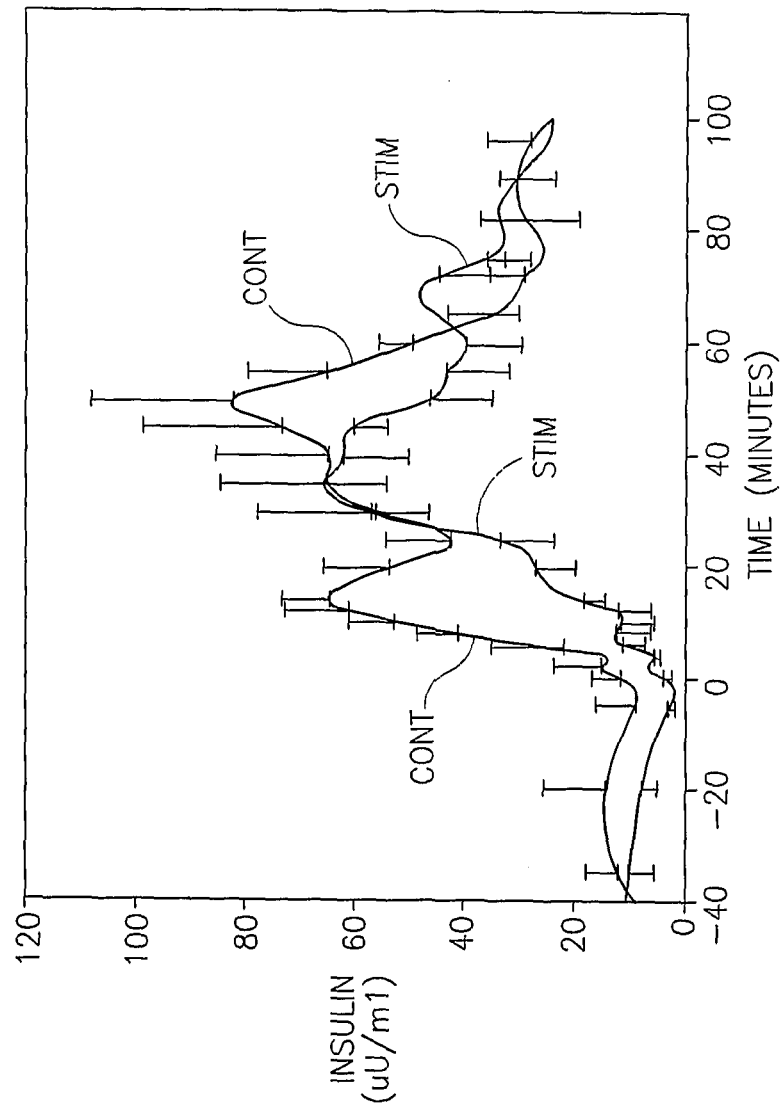
FIG. 22B is a chart showing a delay in insulin peaking and reduction in levels thereof in a series of experiments under conditions of stimulation in the first pig in accordance with an exemplary embodiment of the invention.

FIG. 22B is a chart showing a delay in insulin peaking and reduction in levels thereof in some of the experiments of FIG. 22A. These results are for 6 control days and 7 stimulation days. It should be noted that insulin levels are apparently reduced over nearly all the digestion time, as are total insulin levels and the size of the peak (but possibly the height of the peak is not substantially reduced). This suggests that a non-insulin factor is reducing glucose levels. Reduction of both glucose levels and insulin levels is expected to reduce the strain on the pancreas for some disease conditions, for example, by reducing disease-induced over stimulation of the pancreas. It should be noted that the delay and/or reduction in glucose peak may be sufficient to allow a patient to be free of the need for pharmaceutical or insulin intervention. Alternatively or additionally, by spreading out the peak, a patient may be able to take (only) slowly absorbed insulin rather than fast insulin, thus possibly simplifying the treatment protocol and/or preventing hypo-glycemic events associated with fast insulin. Further, by reducing such peaks, less damage is caused to the patient's body systems from excessive insulin and/or glucose levels. Alternatively or additionally, glucose monitoring may be performed less often, such as once a day or even less often, rather than several times a day. In an exemplary embodiment of the invention, a treatment protocol comprises reducing and/or delaying glucose peaks and concurrent slow acting treatment, such as a daily shot of "slow" insulin or suitable pharmaceuticals.

As can be seen, even after the stimulation pulse series stopped, glucose and insulin levels did not peak as much as in the control situation. This may be a direct effect of the stimulation or may be an indirect effect, for example, due to reduction in the glucose change rate. As shown below, in human experiments, longer stimulation times were applied. It should be appreciated that, as noted above, in some treatment protocols, it may be desirable to stop stimulation during the digestion of glucose, for example, to see the pancreatic response and/or to allow it to rest.

Figure 22C:
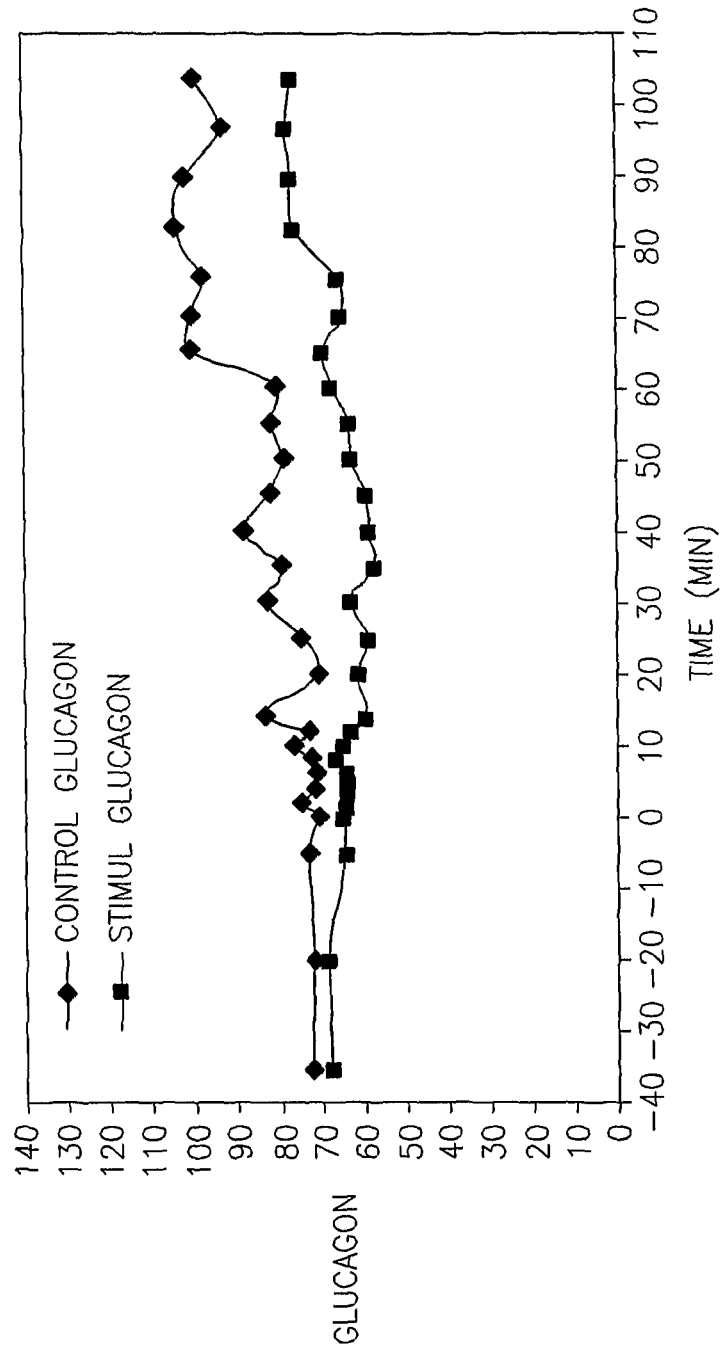
FIG. 22C is a chart showing glucagon reduction as a result of the application of a stimulation in accordance with an exemplary embodiment of the invention.
Figure 23:
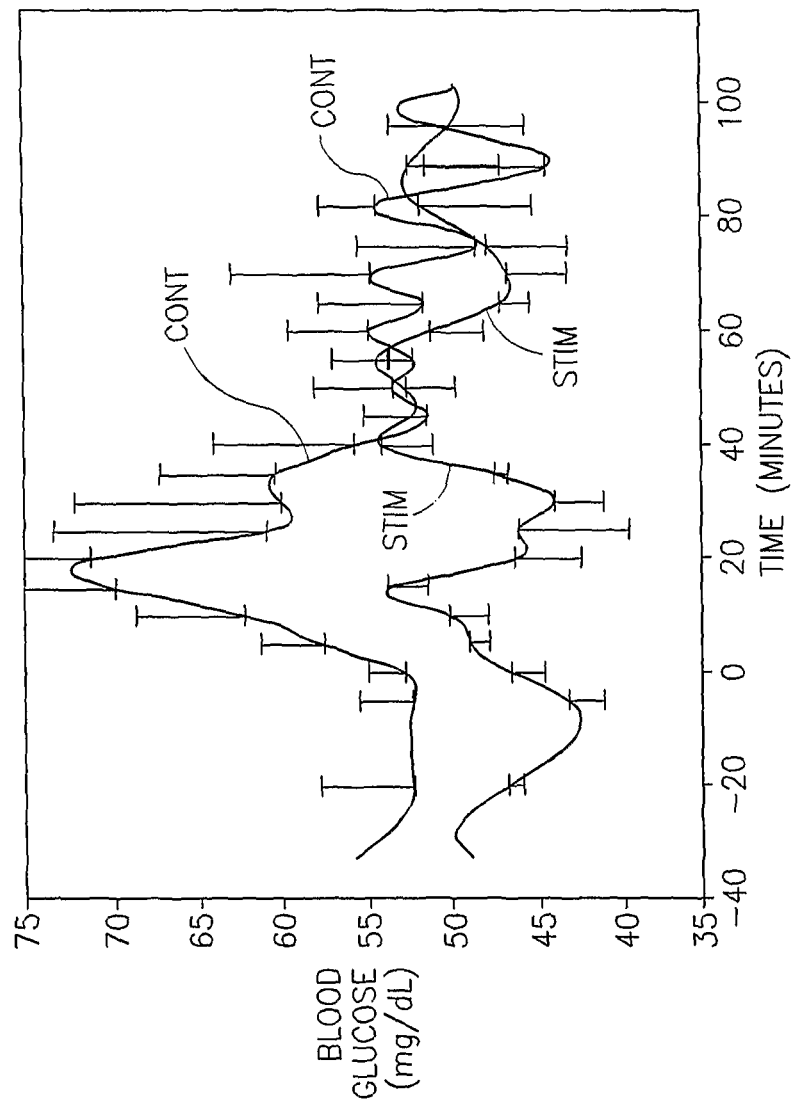
FIG. 23 is a chart showing a reduction in glucose levels under conditions of stimulation in a series of experiments in a second pig, in accordance with an exemplary embodiment of the invention.

FIG. 23 is a chart showing a reduction in glucose levels under the same conditions of stimulation of FIG. 22 in a series of experiments in a second pig, in accordance with an exemplary embodiment of the invention. The results are an average of 3 control days and 4 stimulation days.

Figure 24:
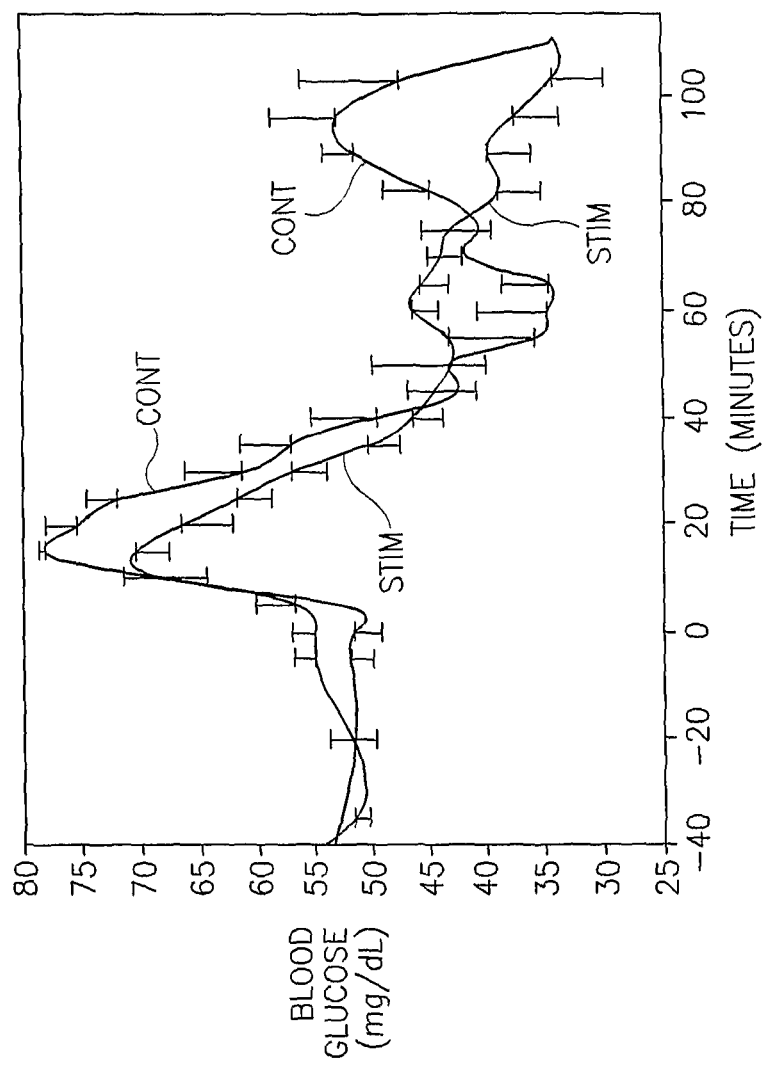
FIG. 24 is a chart showing a reduction in glucose levels under conditions of stimulation in a series of experiments in a third pig, in accordance with an exemplary embodiment of the invention.

FIG. 24 is a chart showing a reduction in glucose levels under the same conditions of stimulation as FIGS. 22 and 23, in a series of experiments in a third pig, in accordance with an exemplary embodiment of the invention. The results are an average of 5 control days and 12 stimulation days.

FIG. 22C is a chart showing glucagon reduction as a result of the application of a stimulation pulse series, in accordance with an exemplary embodiment of the invention. The stimulation results are an average of three studies and one control study is used, all selected from the experiments of FIG. 22, for which glucagon levels were measured. It should be noted that the glucagon reduction is mostly relative to that of a baseline, where normal behavior is that glucagon increases when insulin and glucose do. However, some absolute reduction in Glucagon is apparent but possibly not statistically meaningful. The reduction in glucagon secretion appears to continue for a considerable time after the stimulation is stopped. Reducing glucagon secretion prevents the liver from adding to the glucose levels. While this result may indicate direct control of glucagon levels using electrical stimulation, an alternative explanation is that increased somatostatin levels reduced both insulin and glucagon. Another possible explanation is that alpha cells, which secrete glucagon were desensitized. Another possible explanation is that the control of glucagon was indirect by the control of insulin (which itself, as noted, may be indirectly a result of the control of glucose levels via a non-insulin mechanism).

Figure 25:
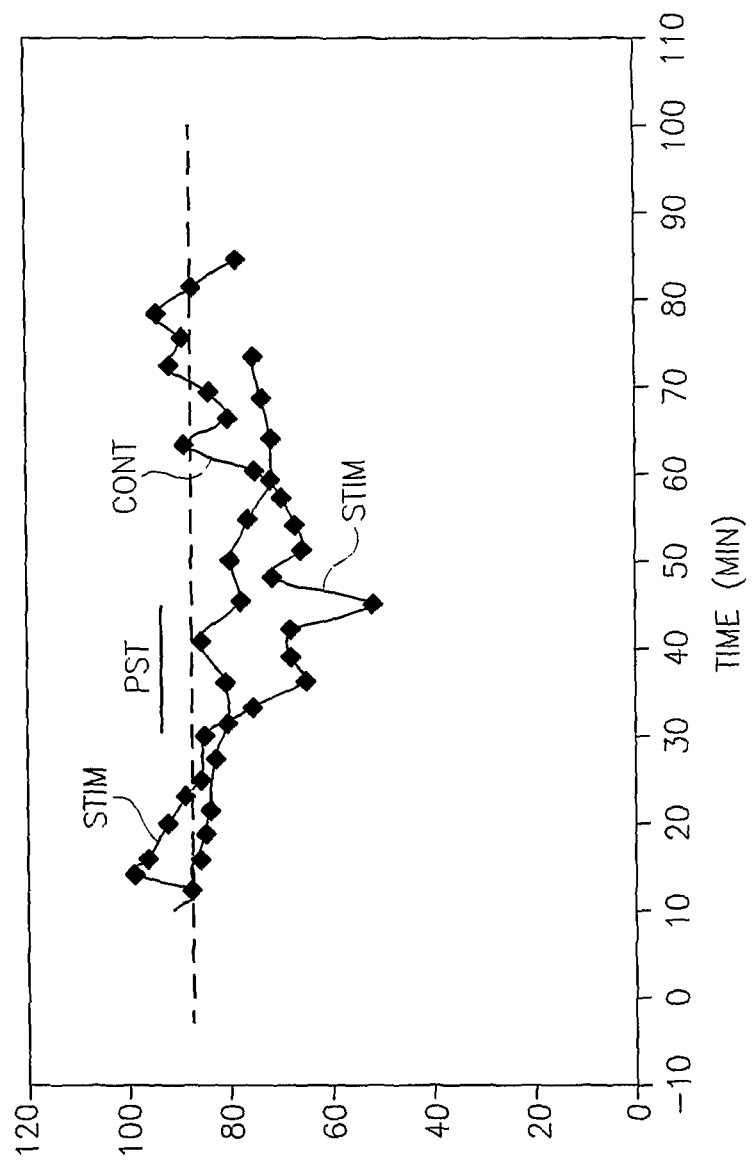
FIG. 25 is a chart illustrating that a glucose reduction stimulation in accordance with an exemplary embodiment of the invention, works under conditions of IV hyperglycemic clamping.

FIG. 25 is a chart illustrating that a glucose reduction stimulation in accordance with an exemplary embodiment of the invention, works under conditions of IV hyperglycemic clamping, for a single experiment. It should also be noted that the reduction in glucose levels was only to baseline levels and not below. In this experiment, a pig was clamped to high glucose levels using an IV of Dextrose, using an initial bolus of 50% Dextrose of about 20-25 cc and then a constant infusion of 70-90 ml/hour for the duration of the experiment, including the recovery of glucose values. The experiment was started after the glucose levels stabilized. The stimulation length is 15 minutes. As shown, the glucose level recovered after about 20 minutes.

Figure 26:
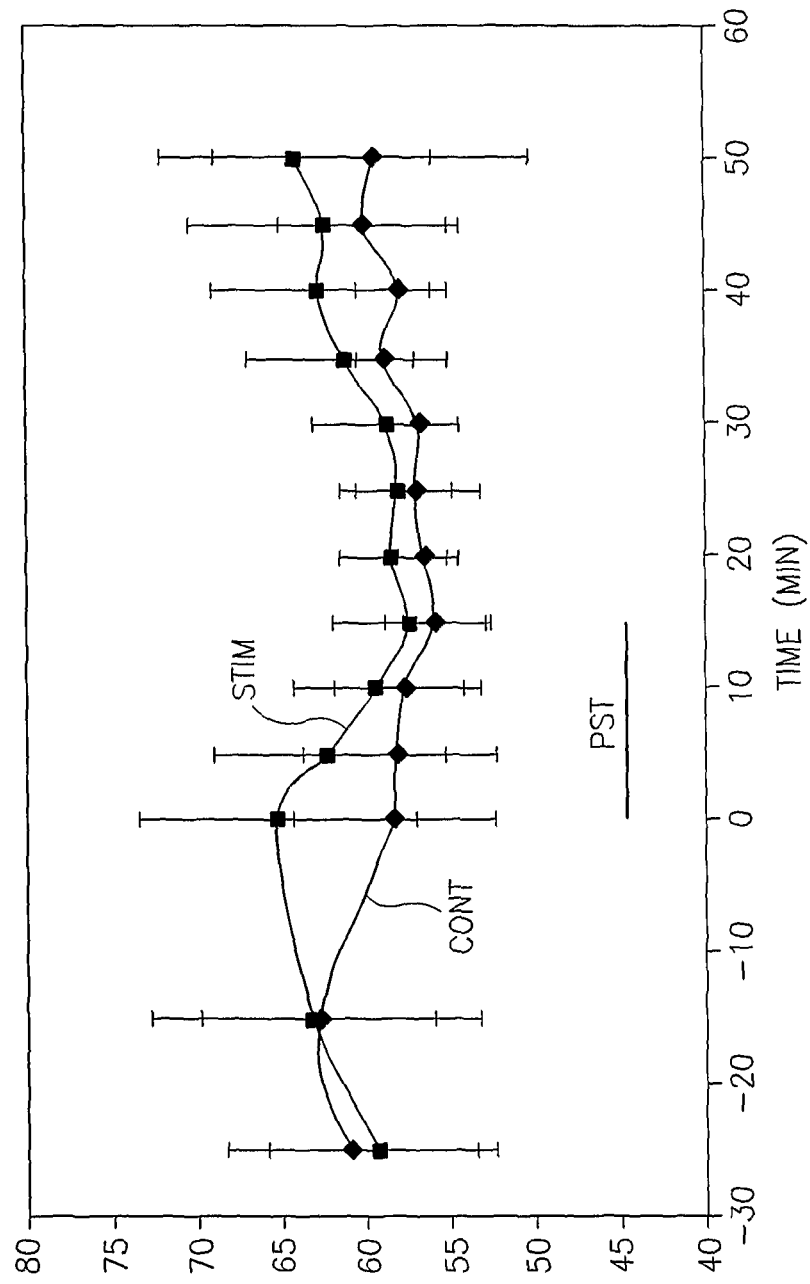
FIG. 26 is a chart showing a lack of dangerous effect of stimulation in accordance with an exemplary embodiment of the invention, on normal glucose levels.

FIG. 26 is a chart showing a lack of dangerous effect of stimulation in accordance with an exemplary embodiment of the invention, on normal glucose levels. An average of 2 control days and 4 stimulation days is shown. As noted above this may be used as a basis for design of open loop protocols in which a possible over stimulation is not considered as being dangerous (but possibly energy wasting).

In an additional experiment, two pigs were stimulated continuously for 24 hours a day for two weeks, using the 5 Hz, 5 ms, bi-phase, 5 mA pulse series and no adverse reactions or effects on pancreatic function or pancreatic histology were visible. In particular, no effects on exocrine functions could be seen by way of changes in feces.

Results from Experiments in a Human

A series of experiments was carried out on a human volunteer patient. The patient is a 45 year old female with a one year history of type II diabetes. The patient is of Indian extraction, 71 Kg in weight, 1/61 Meters in height and is treated with Gliclazide 80 mg and Metformin 500 mg twice a day. The patient was undergoing abdominal surgery for gall bladder removal. Prior to surgery, the Patient had a fasting insulin level of 11.1 microunits per ml, fasting C-peptide level of 2 ng/ml and HbA1C of 5.8%.

To remove the gall bladder, a midline laparotomy was performed. Then the lesser sack was opened through the gastro-colic omentum. The Stomach and intestines were retracted respectively allowing exposure of about 7×5 cm of the pancreas. Four commercial stainless steel temporary cardiac pacing wires manufactured by A&E medical corporation were inserted to the pancreatic tissue, one pair on one end and one pair on the other. Two pancreatic recording leads were also attached, one between the two electrodes on one side of the pancreas and closer to one electrode and the other recording lead between the two PST electrodes. The electrodes were channeled a 7 Fr JP abdominal drain harboring an electronic circuit and suture fixed to the pseudocapsule of the pancreas. The electrodes and the drain were routed and extracted through the left abdominal wall. A second, negative pressure, drain was placed near the pancreas and routed to the right abdominal wall. the electrode attaching procedure took 1.25 hours. Amylase values were 127.5 U/L the first day and ~30 U/L the next day, indicating a good recovery. GI motility came back on the first day and no fever was found over and after the experimental period. On the sixth day following surgery the electrodes were removed, uneventfully. Several series of stimulation and measurement were conducted over the few days after the surgery. There have been no reported side effects of any type following the electrode placement, stimulation and removal. Two types of protocols were conducted. A control protocol and a stimulation protocol. In the control protocol, 3 blood samples were taken while the patient was fasting. At time 0 a 75 gr glucose load was administered orally. Blood samples were collected for a three hour period following the glucose administration. One control experiment was conducted on the morning of the surgery, prior to lead implantation, another was conducted a day after the surgery. The stimulation protocol was similar to the control protocol except that electrical stimulation having the parameters of (5 Hz, 5 ms, bi-phasic 5 mA) was given with or after the glucose. The stimulation protocols were executed on the second and fourth day after surgery.

Figure 27:
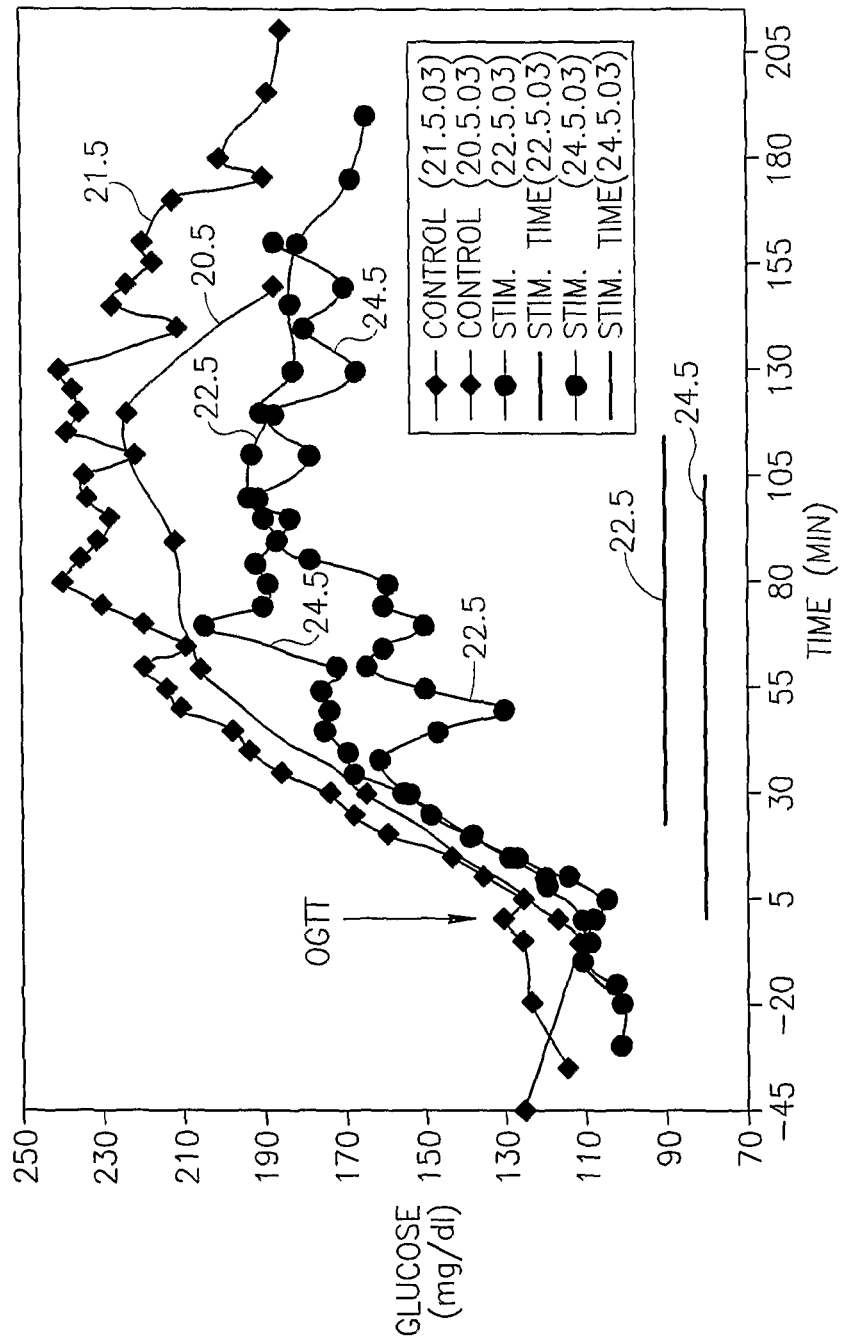
FIG. 27 is a chart showing the effect, in a human, on glucose levels, of a stimulation in accordance with an exemplary embodiment of the invention.

FIG. 27 is a chart showing the effect, in a human, on glucose levels, of a stimulation in accordance with an exemplary embodiment of the invention. As with the mini-pigs, the glucose peaks are reduced and/or delayed.

Figure 28:
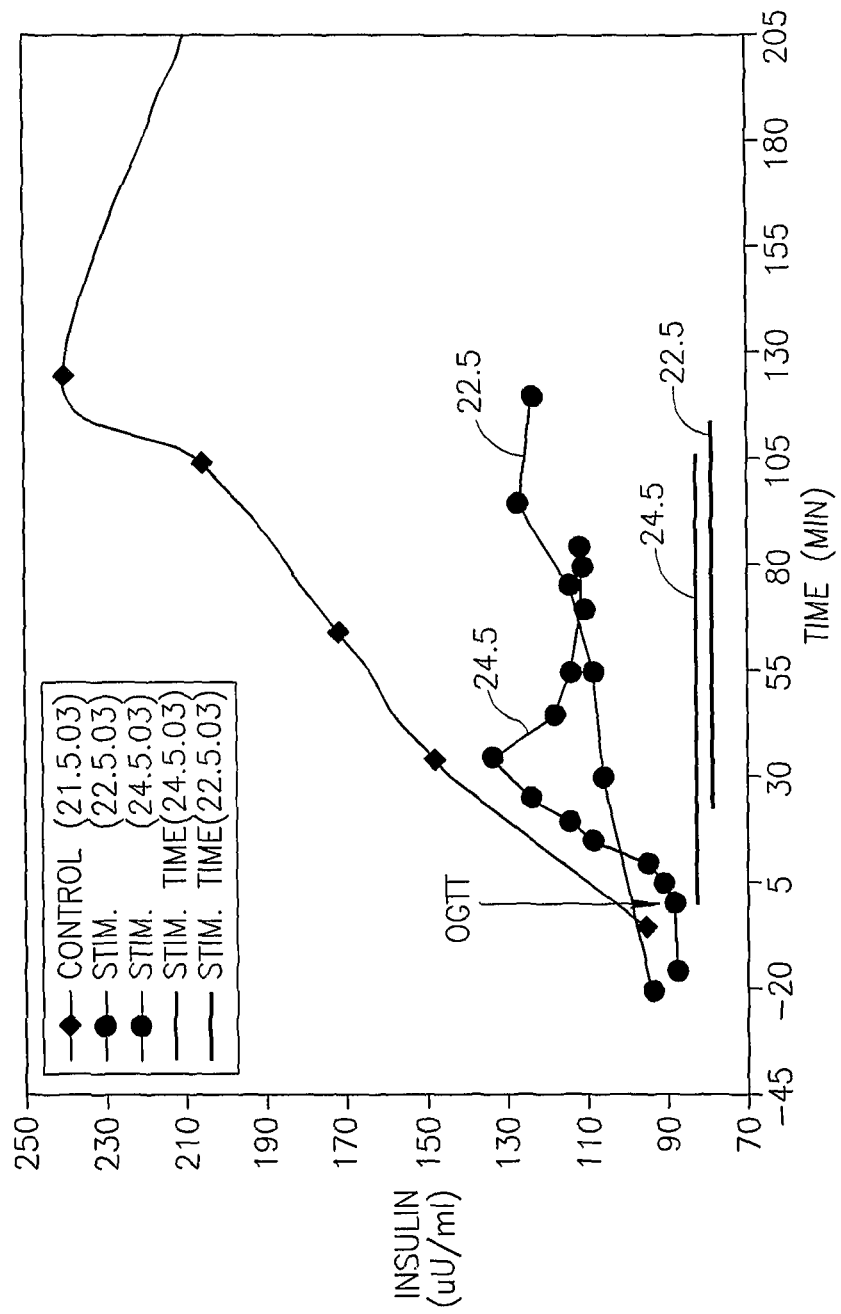
FIG. 28 is a chart showing the effect, in a human, on insulin levels, of a stimulation in accordance with an exemplary embodiment of the invention.

FIG. 28 is a chart showing the effect on insulin levels, of the experiments of FIG. 27. Insulin levels were not measured in the first control case, but measured in others, as shown. Insulin peaks values were clearly reduced and delayed as compared to the control situation.

Figure 29:
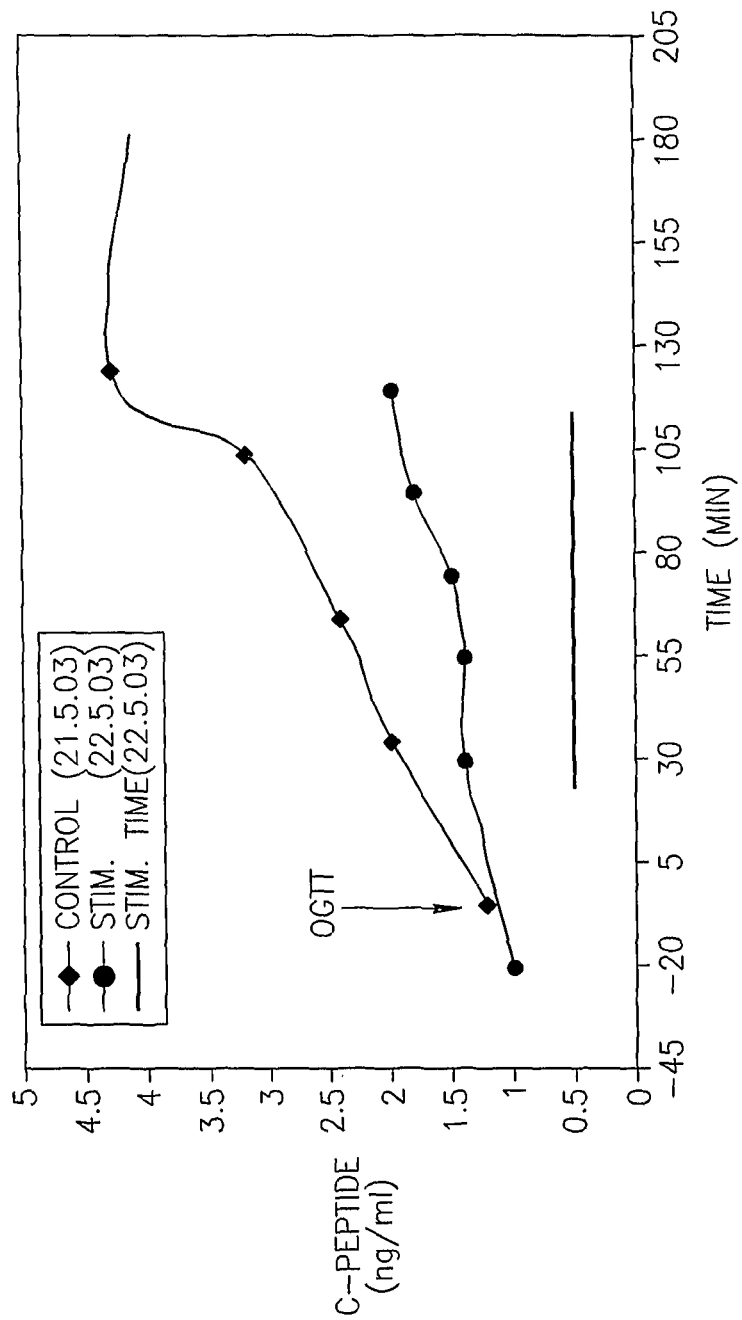
FIG. 29 is a chart showing the effect, in a human, on c-peptide levels, of a stimulation in accordance with an exemplary embodiment of the invention.

FIG. 29 is a chart showing the effect on c-peptide levels, of some of the experiments of FIG. 27. C-peptide values were reduced and the peak apparently delayed. These measurements were carried out only in one control protocol and one stimulation protocol. This measurement is used to validate the insulin measurements.

Figure 30A:
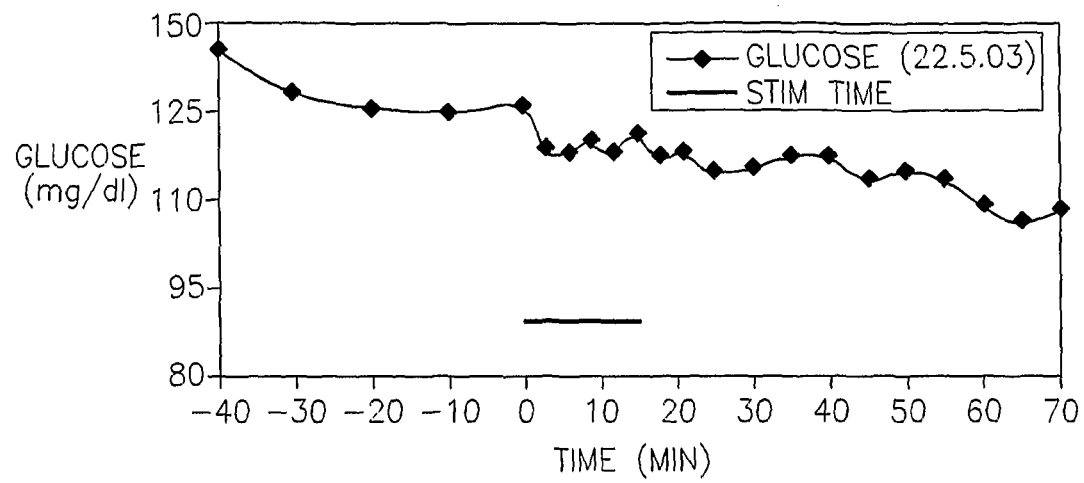
FIGS. 30A and 30B are charts showing a lack of dangerous effect of stimulation in accordance with an exemplary embodiment of the invention, on the glucose levels of a fasting human.
Figure 30B:
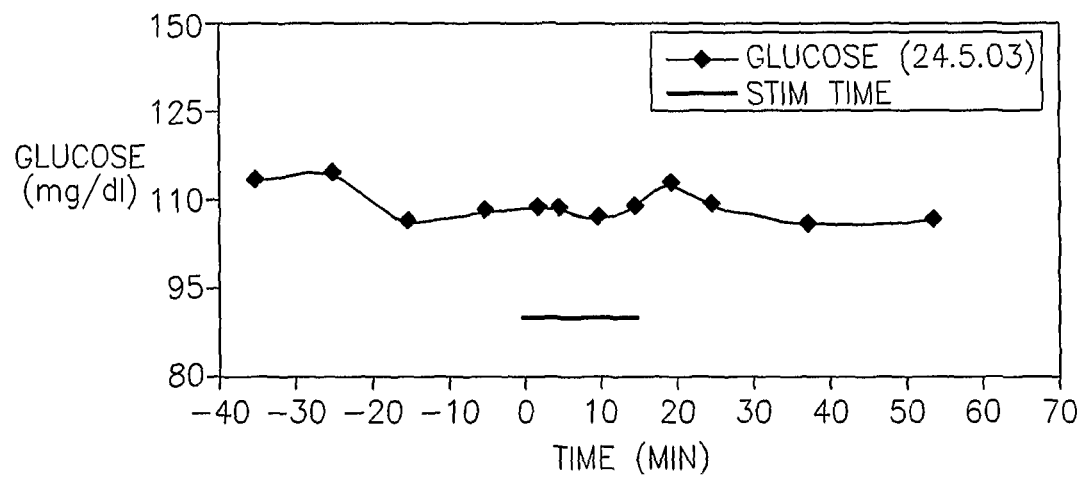

FIGS. 30A and 30B show the effect of electrical stimulation during fasting on glucose levels, on two different occasions during the five day convalescence period of FIG. 27. No substantial reduction in glucose levels is observed.

Figure 31A:
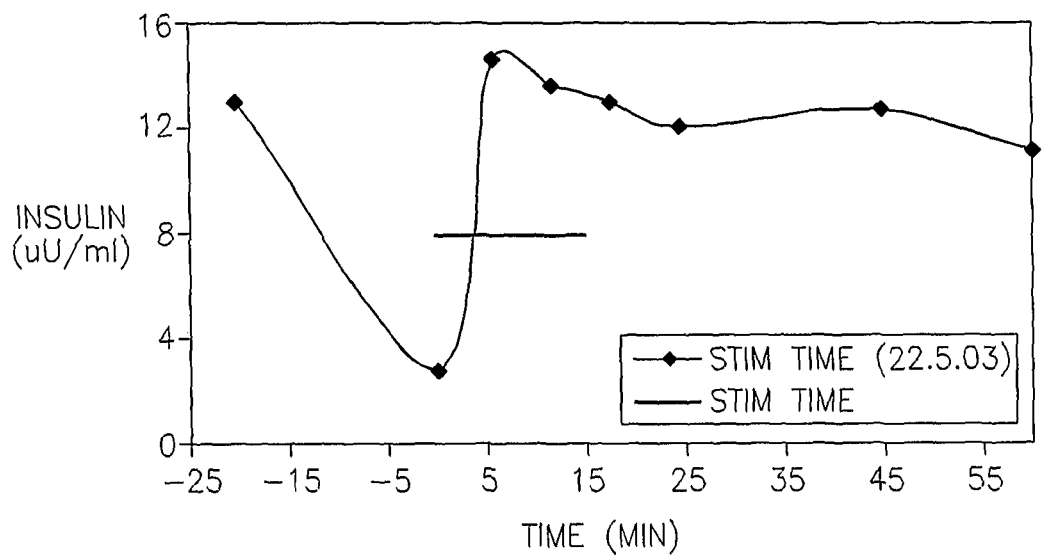
FIGS. 31A and 31B are charts showing a lack of dangerous effect of stimulation in accordance with an exemplary embodiment of the invention, on the insulin levels of a fasting human.
Figure 31B:
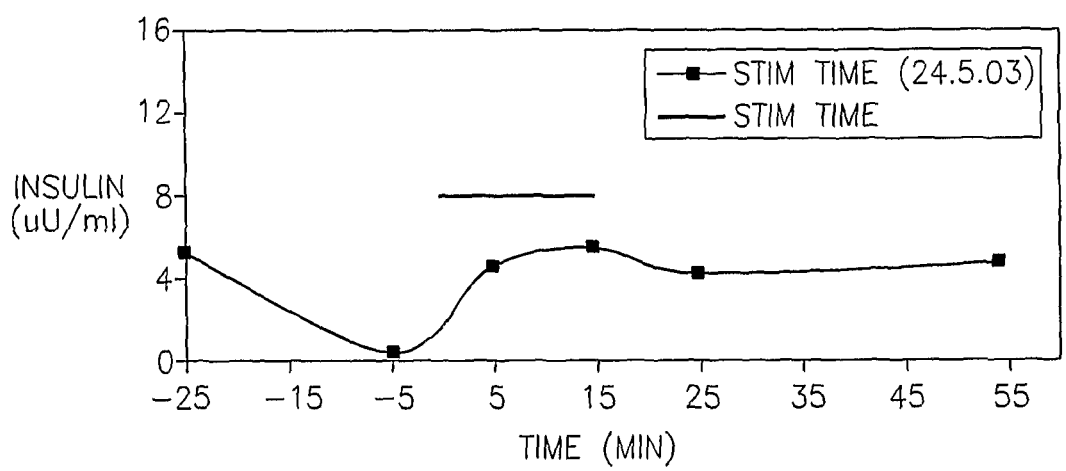

FIGS. 31A and 31B, which correspond to FIGS. 30A and 30B show the effect of electrical stimulation during fasting, on insulin levels. No substantial change in insulin level is observed, except possibly for a small increase in insulin level, which appears to be a return to baseline. The pre-stimulation dip may be caused by patient apprehension, in any case, if this dip is ignored, the insulin levels are seen to remain relatively constant before, during and after stimulation. Also, the insulin values remain low (e.g., under 20) at all times.

Insulin and Glucose Reduction in Animals

Figure 32A:
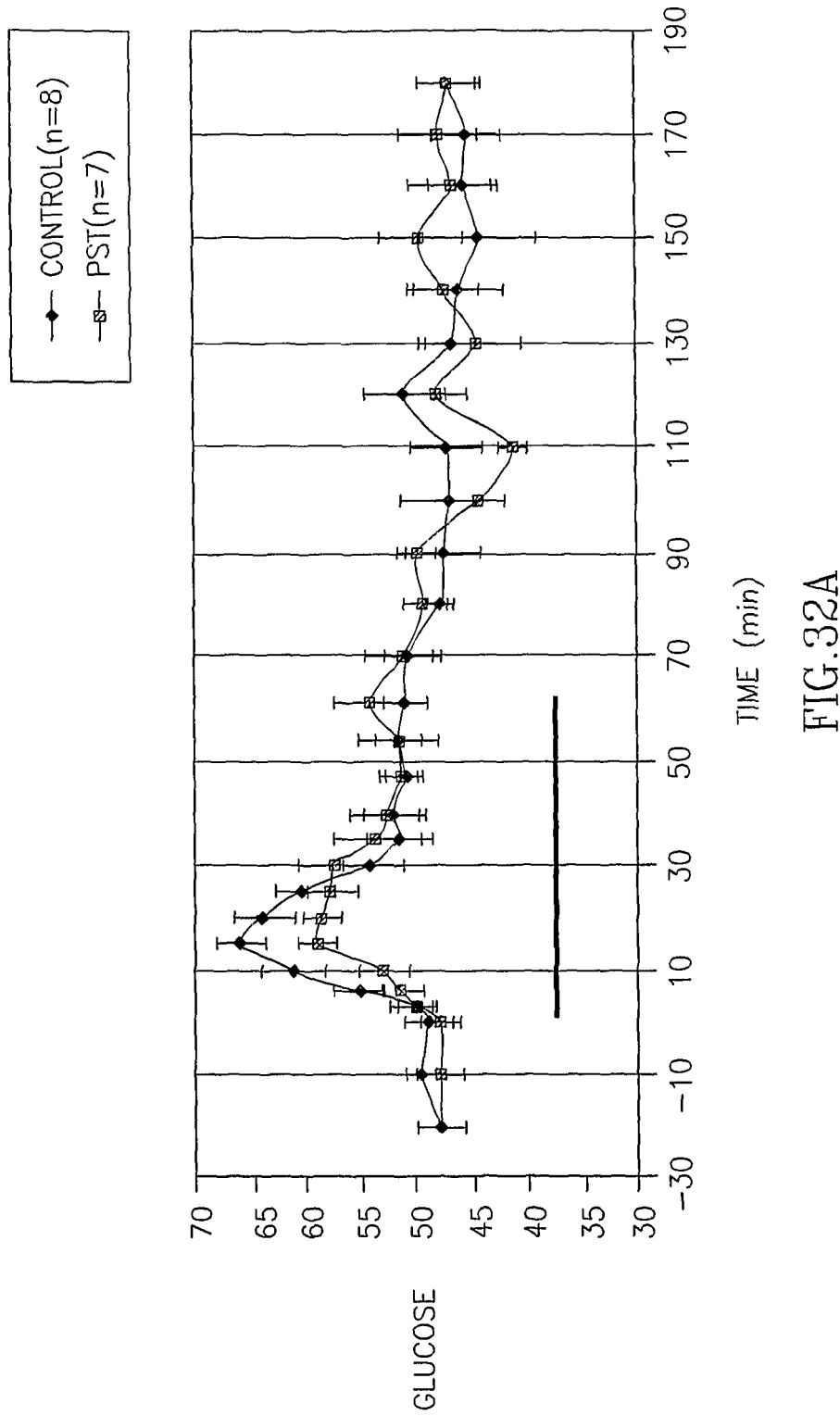
FIGS. 32A and 32B are charts showing glucose and insulin reduction in a pig, in accordance with an exemplary embodiment of the invention.
Figure 32B:
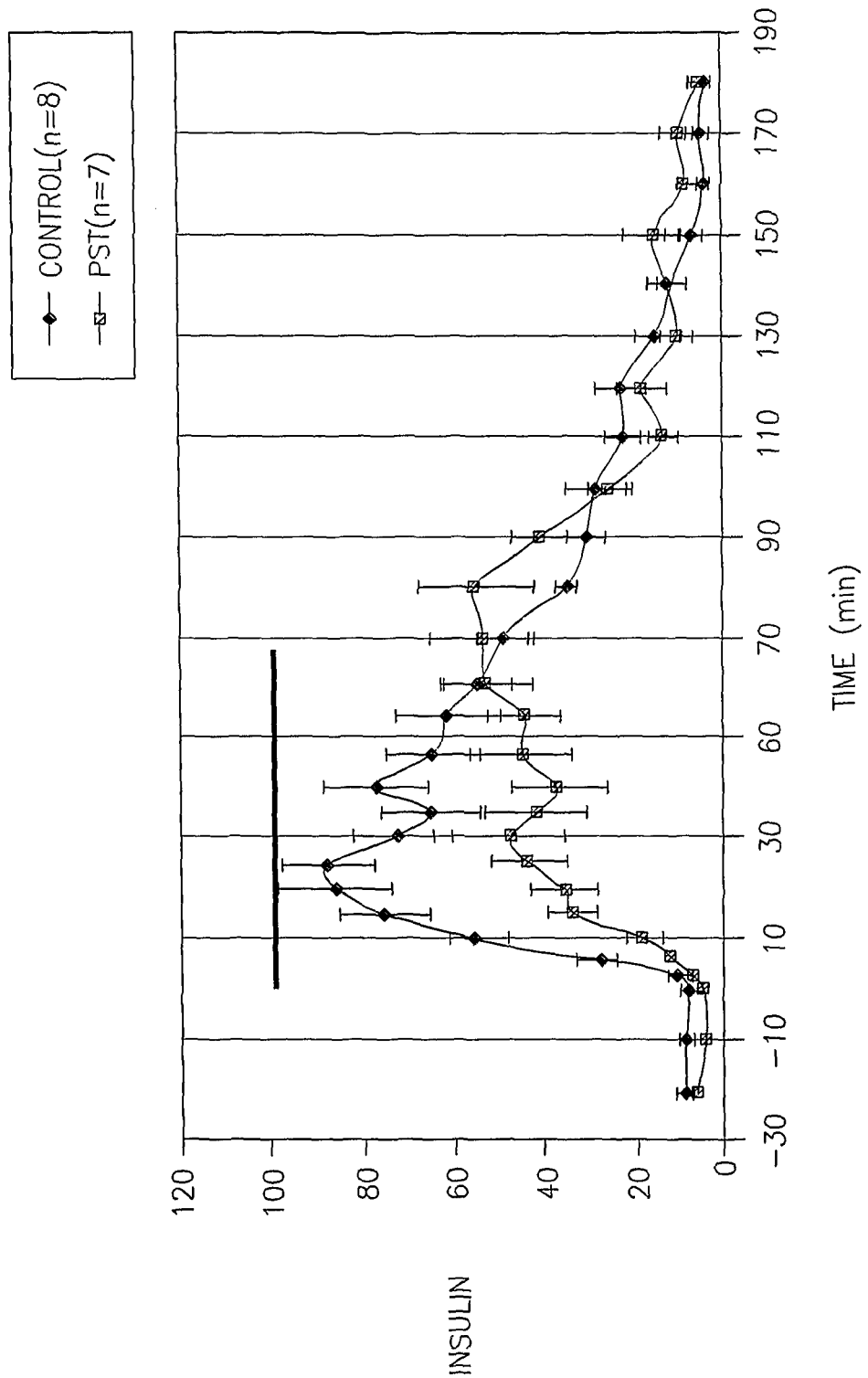
Figure 32C:
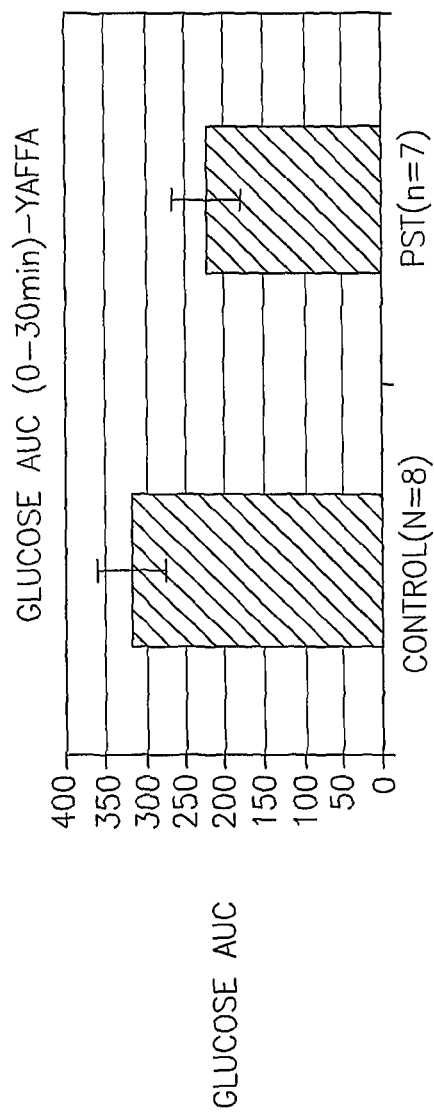
FIGS. 32C and 32D show accumulated levels of glucose and insulin in the pig of FIGS. 32A and 32B.
Figure 32D:
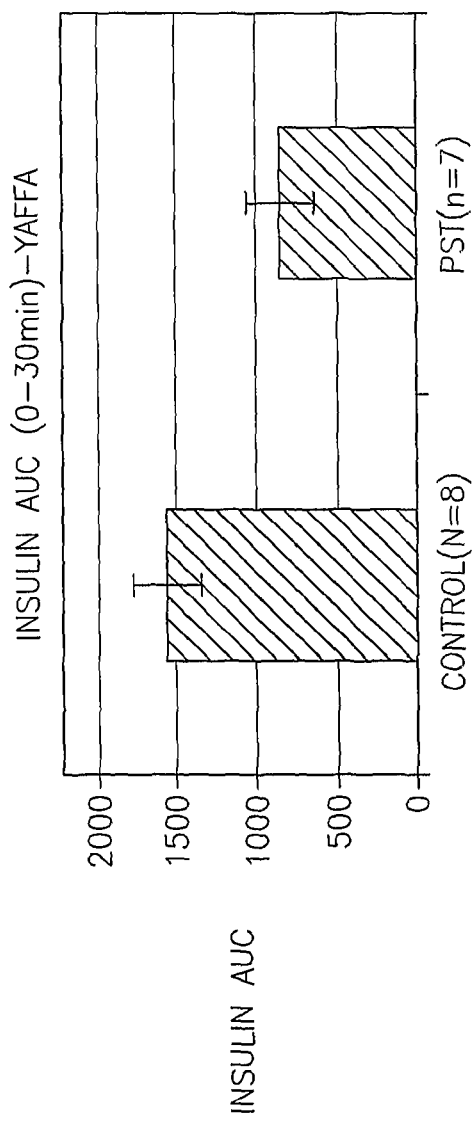
Figure 33A:
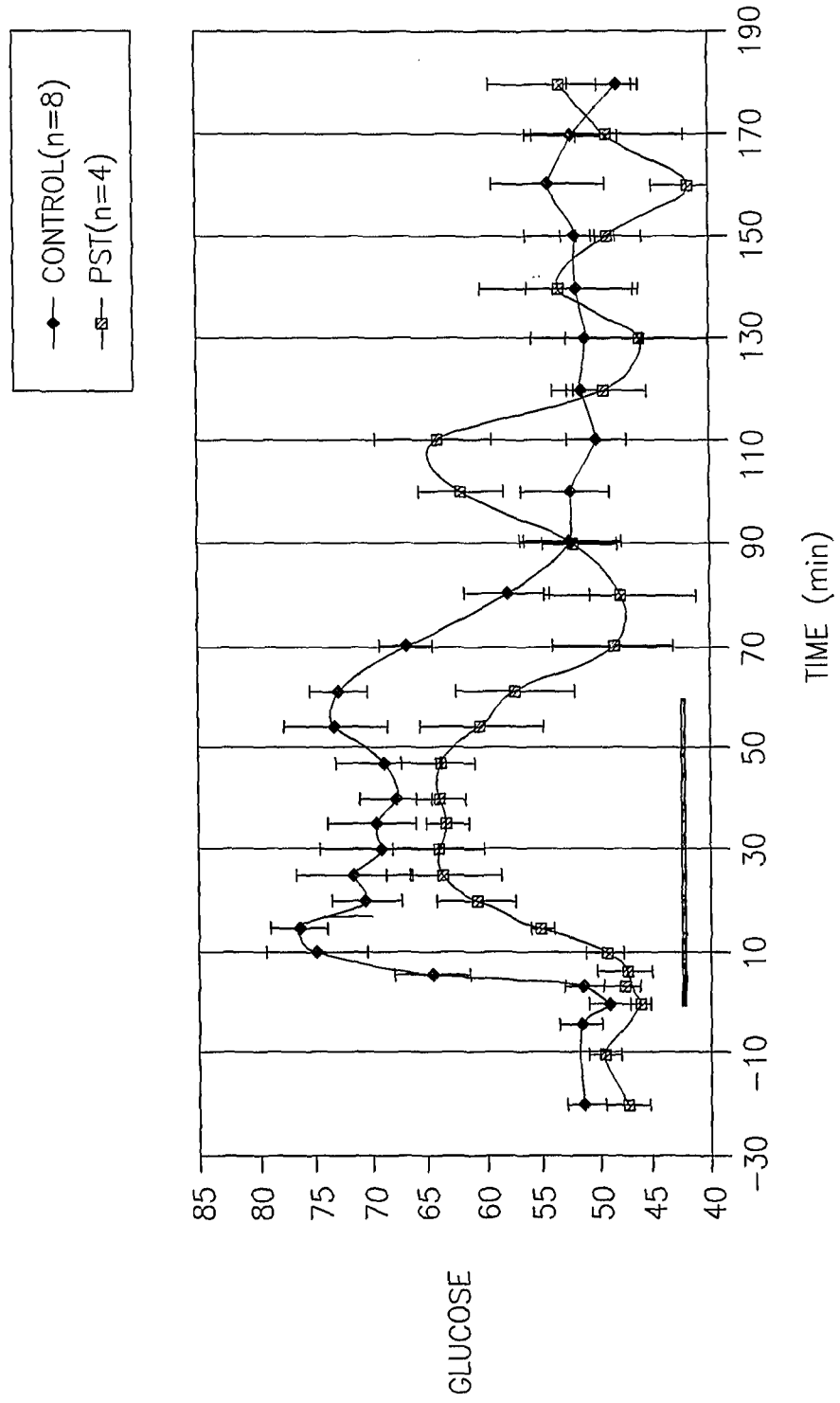
FIGS. 33A and 33B are charts showing glucose and insulin reduction in another pig, in accordance with an exemplary embodiment of the invention.
Figure 33B:
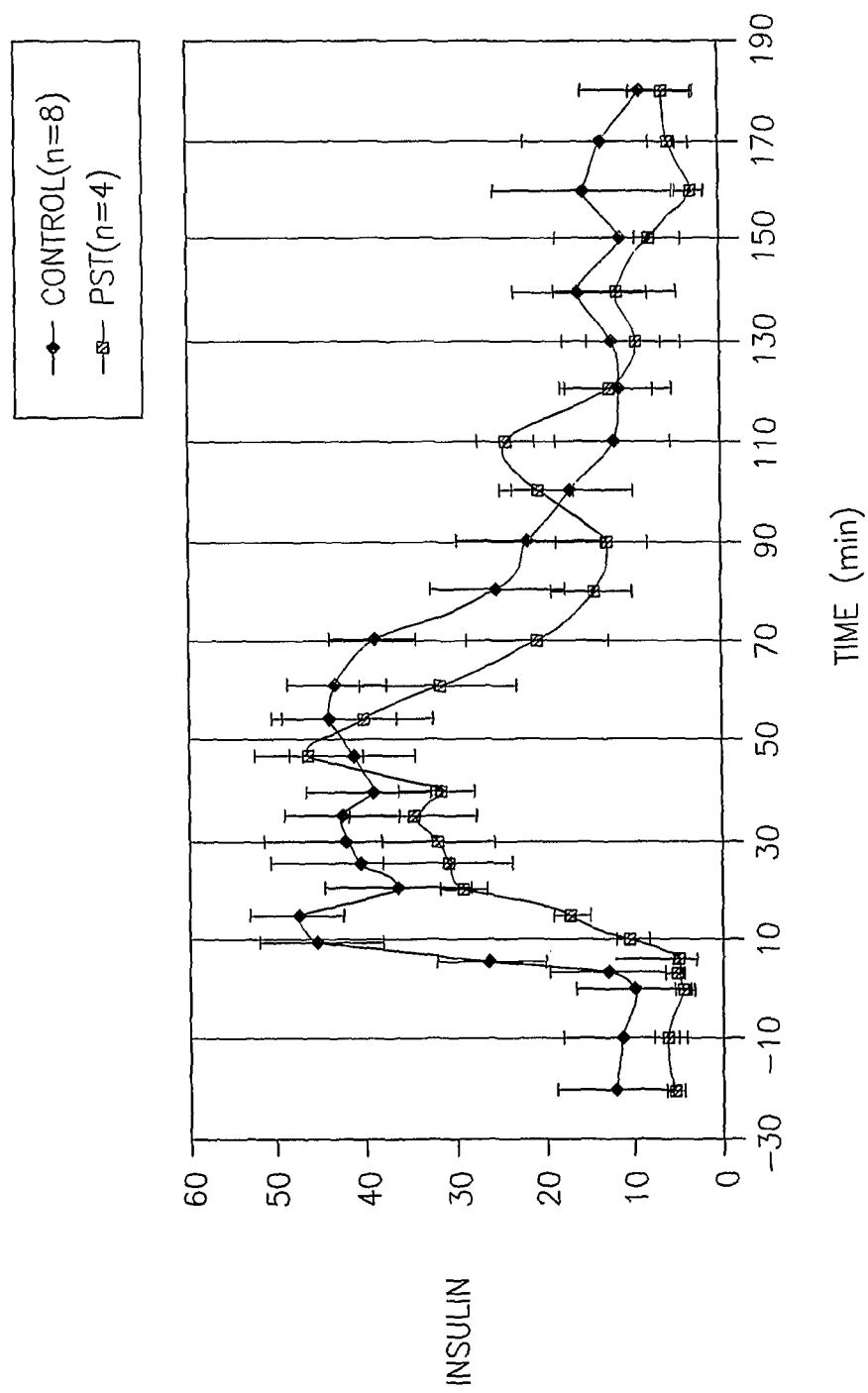
Figure 33C:
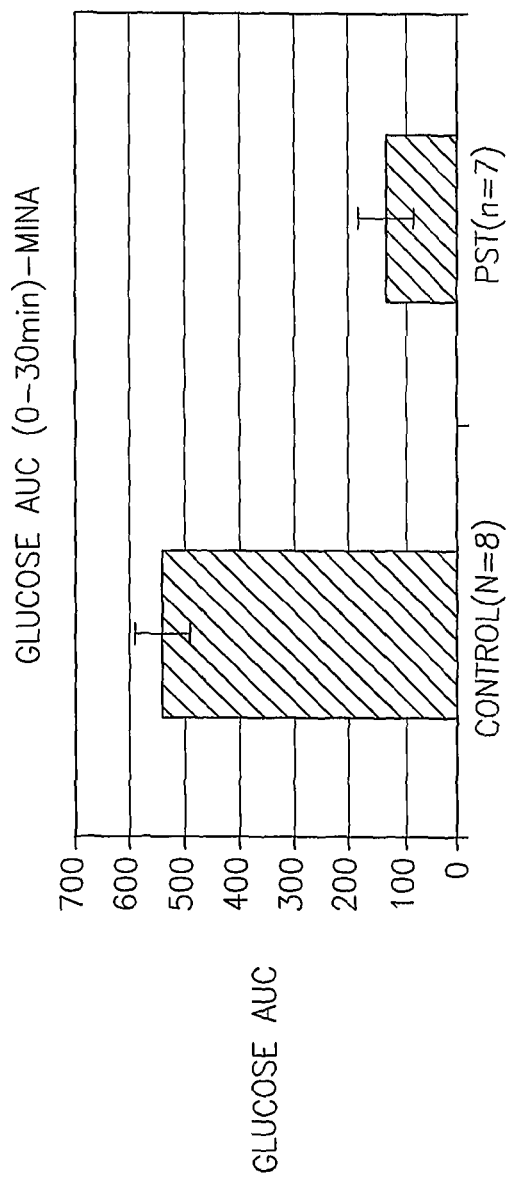
FIGS. 33C and 33D show accumulated levels of glucose and insulin in the pig of FIGS. 33A and 33B.
Figure 33D:
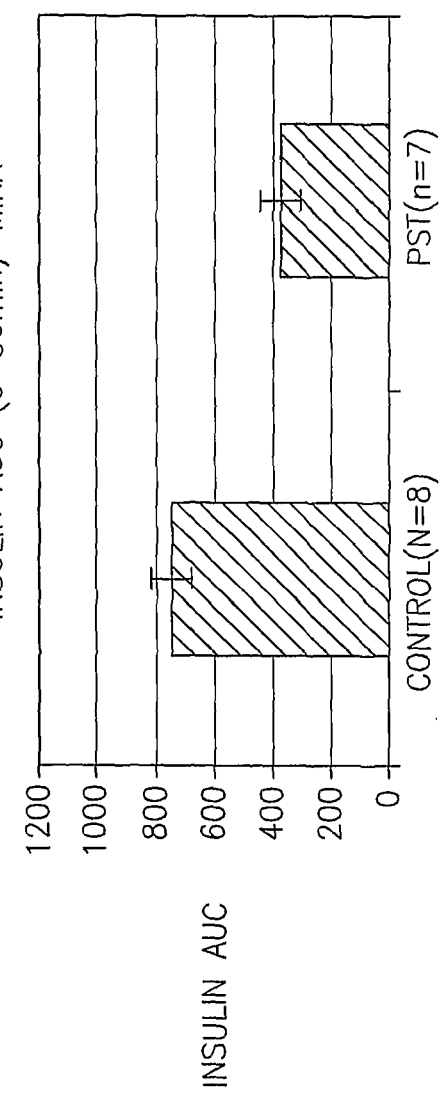

FIGS. 32A and 32B are charts showing glucose and insulin reduction in a pig, in accordance with an exemplary embodiment of the invention. FIGS. 32C and 32D show accumulated levels of glucose and insulin in the pig of FIGS. 32A and 32B.

A pig (i.e., of the type of FIG. 22*ff*) was fed an oral amount of glucose of 75 grams glucose mixed with 14 grams of fish gelatin and 1 cup of water. The feeding time is about 2-3 minutes, starting at time 0. The horizontal line in the figure shows the time of application of a pulse having the parameters, as used above, of a bi-phasic pulse having a positive 5 msec section immediately followed by a negative 5 msec, applied once every 200 msec (e.g., a delay of 190 msec between electrifications), and continued for 1 hour. Glucose was measured using an AccuCheck glucometer, using blood from a jugular vein that was extracted once every 5 or ten minutes for both glucose and insulin level determination. Insulin level was measured using a radio-immuno-assay. In general, the same experimental parameters were used for all the pigs, except where noted otherwise, for example, durations were varied. Except where noted otherwise, the stimulation device was implanted.

The following electrode was used: a stitched line electrode, having a length of, for example, 15-22 mm, was used. The following attachment procedure was used. A needle (curved for the pancreas) and carrying an 00 nylon thread was pushed through the tissue and through a small silicon pad. The electrode is pulled along the thread so that it lies mainly in the tissue. The silicon pad is clipped to the tissue using a standard surgical clip. The more proximal part of the electrode has mounted thereon a small silicon pad with holes for suturing to the tissue (only done in stomach). The electrode itself is a Platinum-Iridium electrode coated with Titanium Nitride, to increase its capacitance and thereby enable larger fields to be applied. Other electrodes may be used as well.

As can be seen in FIG. 32A, glucose level was reduced (and a peak somewhat delayed) in a stimulated case (7 repeats averaged) relative to a control peak (8 repeats averaged). As can be seen in FIG. 32B, the insulin peak was both reduced and delayed. The time integral of insulin levels and of glucose levels over the first 30 minutes is also reduced considerably, as shown in FIGS. 32C and 32D. The time integral is simply the area under the curve between the times noted (e.g., 0 and 60 minutes).

FIGS. 33A-33D show similar results for another pig, with 8 control and 4 stimulation experiments. In this case, an insulin peak is not reduced in height, but only in width.

Figure 34:
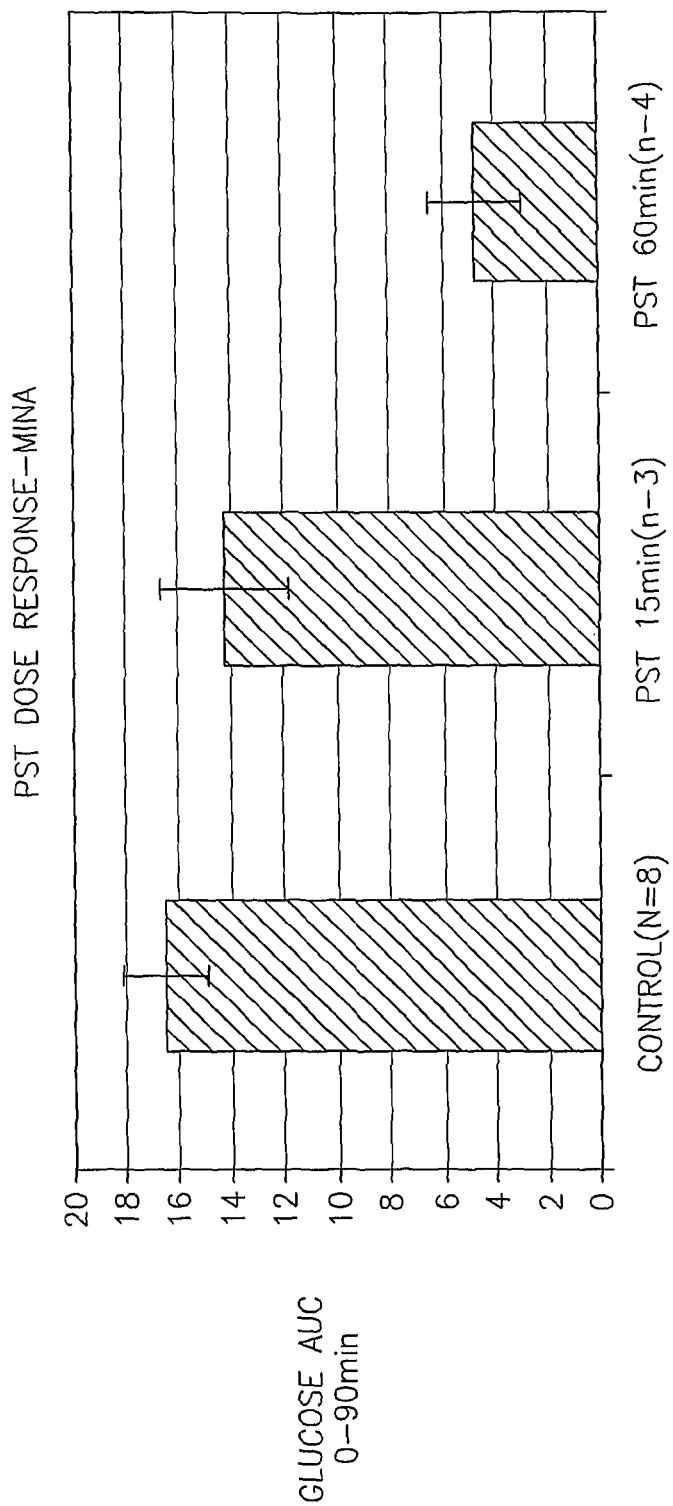
FIG. 34 shows accumulated levels of glucose under various field application conditions, in accordance with exemplary embodiments of the invention.

FIG. 34 shows accumulated levels of glucose under various field application conditions (control, 15 min signal and 60 minutes signal), in accordance with exemplary embodiments of the invention. In particular, the dose response is more significant for longer times.

Figure 35A:
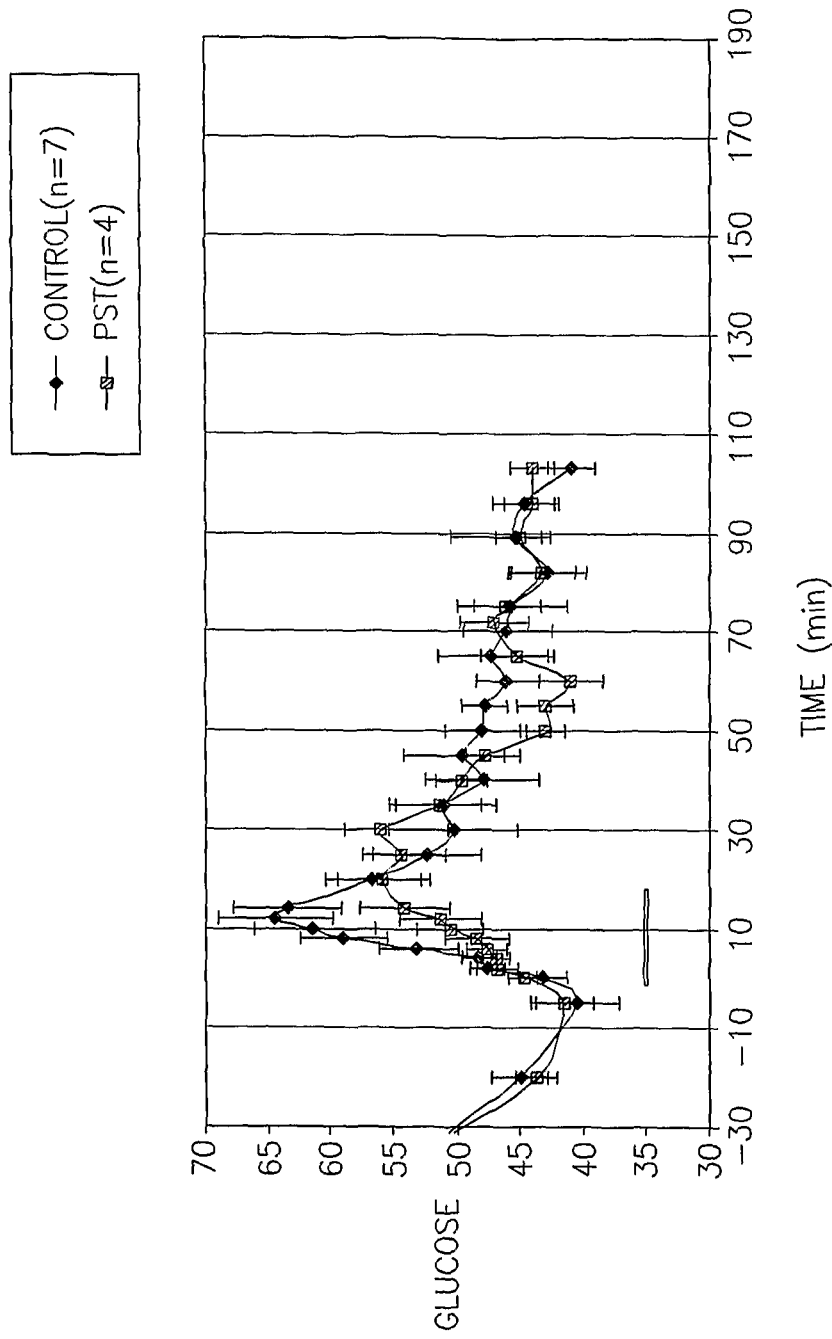
FIGS. 35A and 35B are charts showing glucose and insulin reduction in another pig, in accordance with an exemplary embodiment of the invention.
Figure 35B:
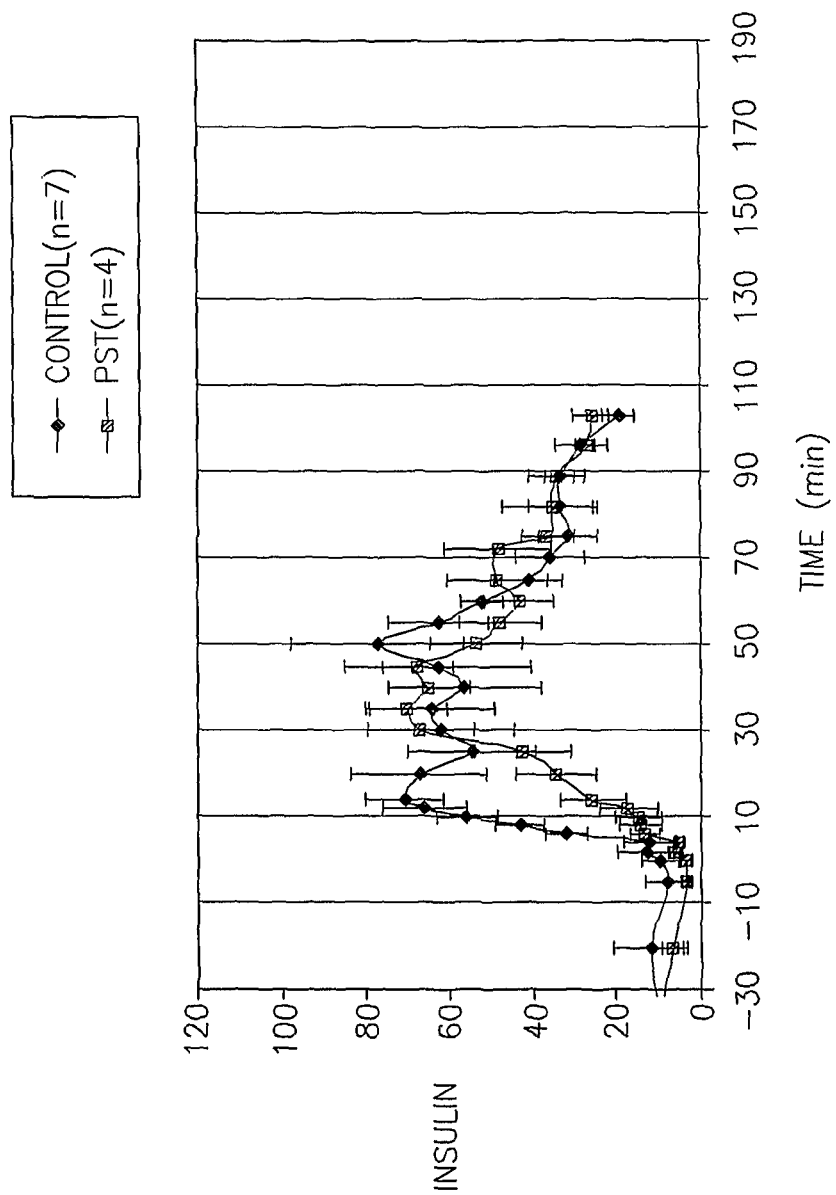
Figure 35C:
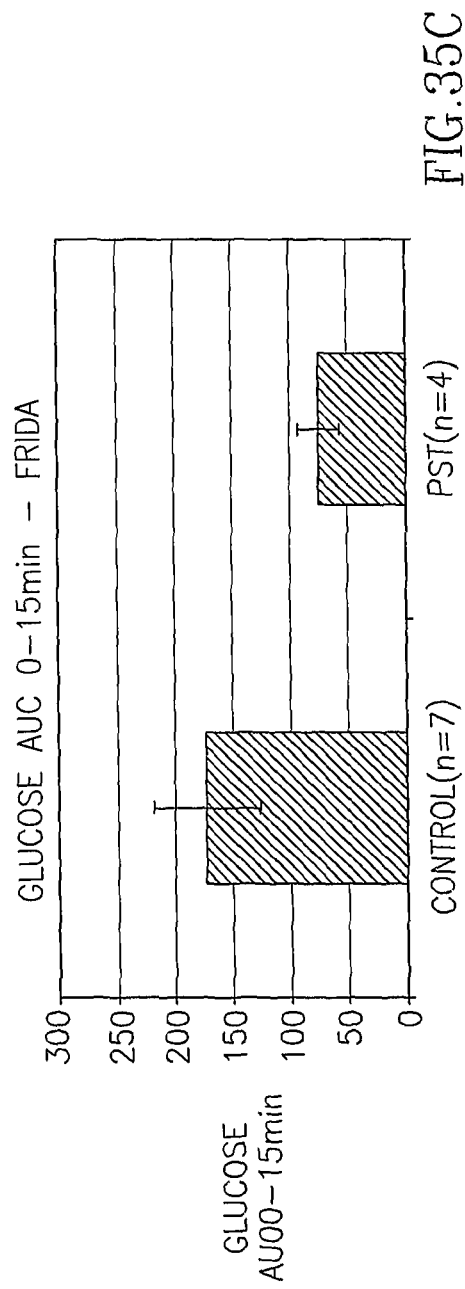
FIGS. 35C and 35D show accumulated levels of glucose and insulin in the pig of FIGS. 35A and 35B.
Figure 35D:
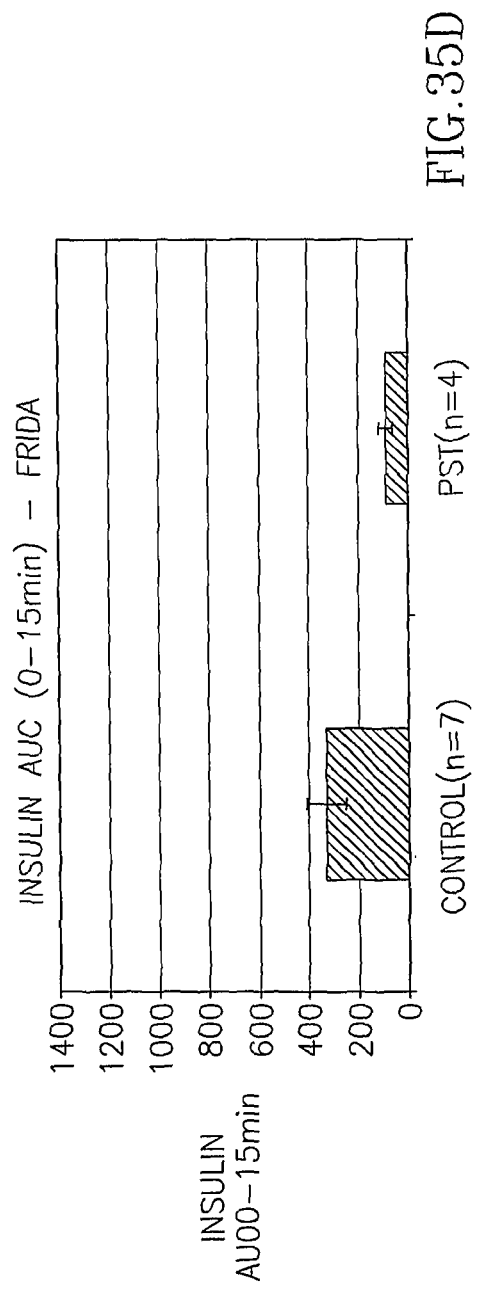

FIGS. 35A-35D are charts showing glucose and insulin reduction in another pig, in accordance with an exemplary embodiment of the invention, in which the device was external attached via temporary pacing electrodes (AEI) to the pancreas. The stimulus was applied for 15 minutes only. A delay in peak of insulin and glucose, as well as a reduction in the total amount can be seen. FIGS. 35C and 35D shows the accumulation over 15 minutes only. 7 control and 5 stimulus experiments were run. FIGS. 35A and 35B may include experimental results that were also used in FIGS. 22A and 22B.

Figure 36:
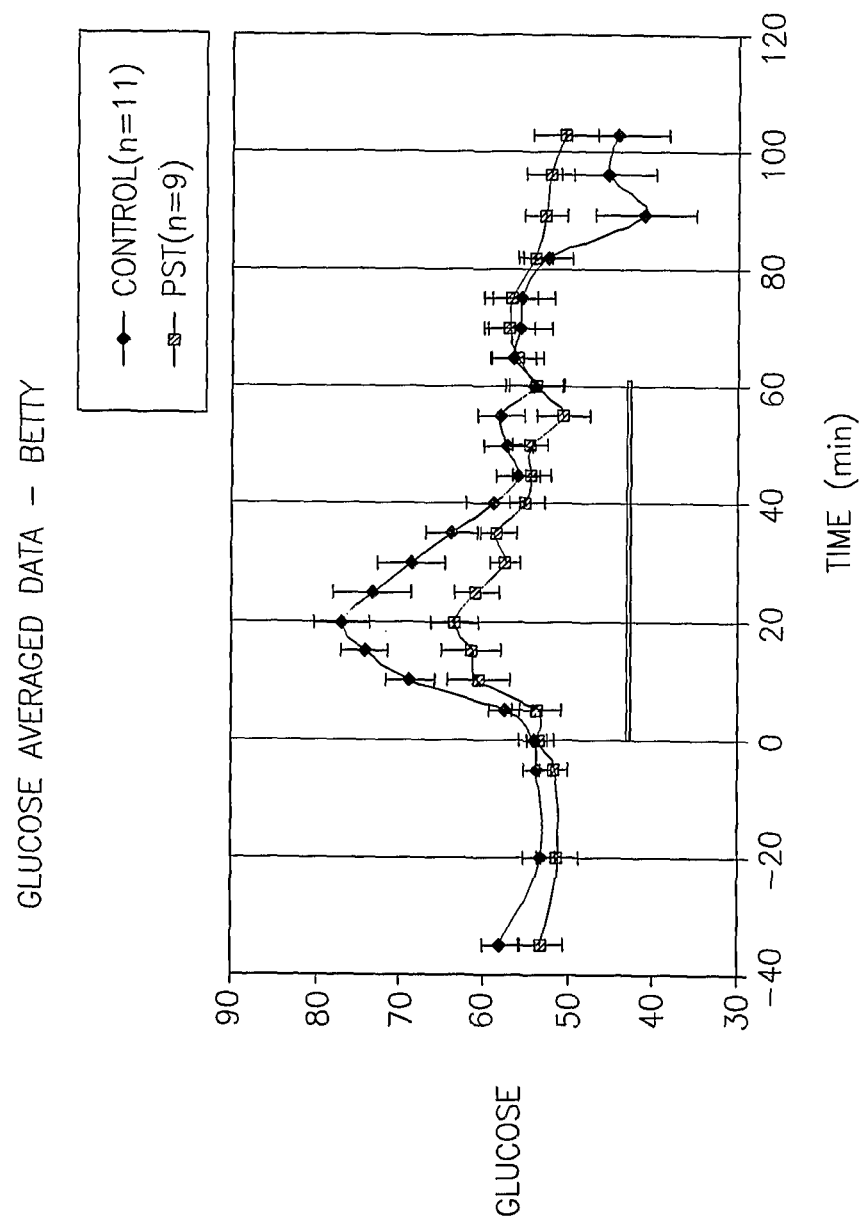
FIG. 36 shows glucose level reduction in another pig, in accordance with an exemplary embodiment of the invention.

FIG. 36 shows glucose level reduction in another pig, in accordance with an exemplary embodiment of the invention, in which a stimulus was applied for 15 minutes, using an external stimulator (and internal electrodes). A reduction in peak and total glucose levels are seen. In addition, the glucose response does not appear to be delayed. It is noted that in some disease situations, it is desirable to delay this glucose peak. In other disease situations it is desirable to maintain the timing of the response but reduce its amplitude. In some disease situations, merely truncating the response at a certain amplitude is a desirable effect. There were 11 control experiments and 9 stimulus experiments.

Figure 37A:
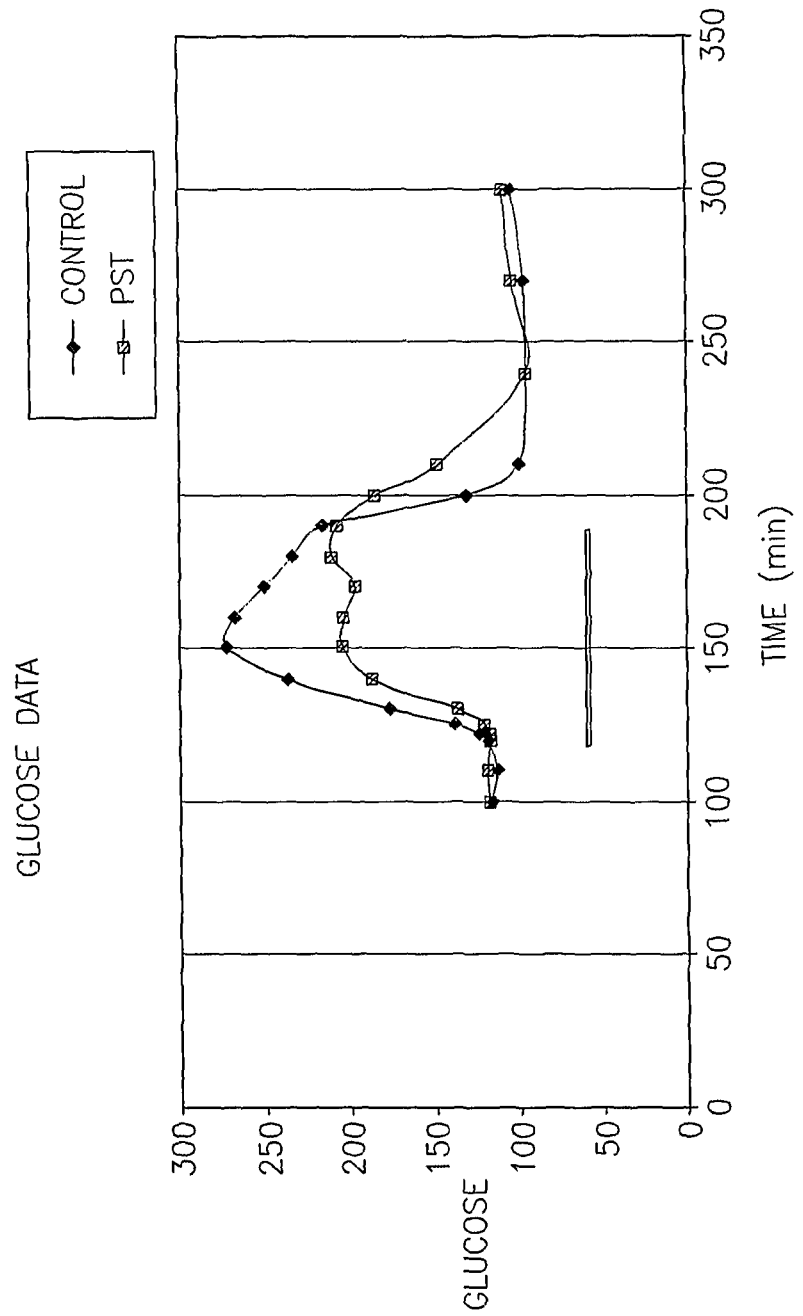
FIGS. 37A and 37B are charts showing glucose and insulin reduction in a dog, in accordance with an exemplary embodiment of the invention.
Figure 37B:
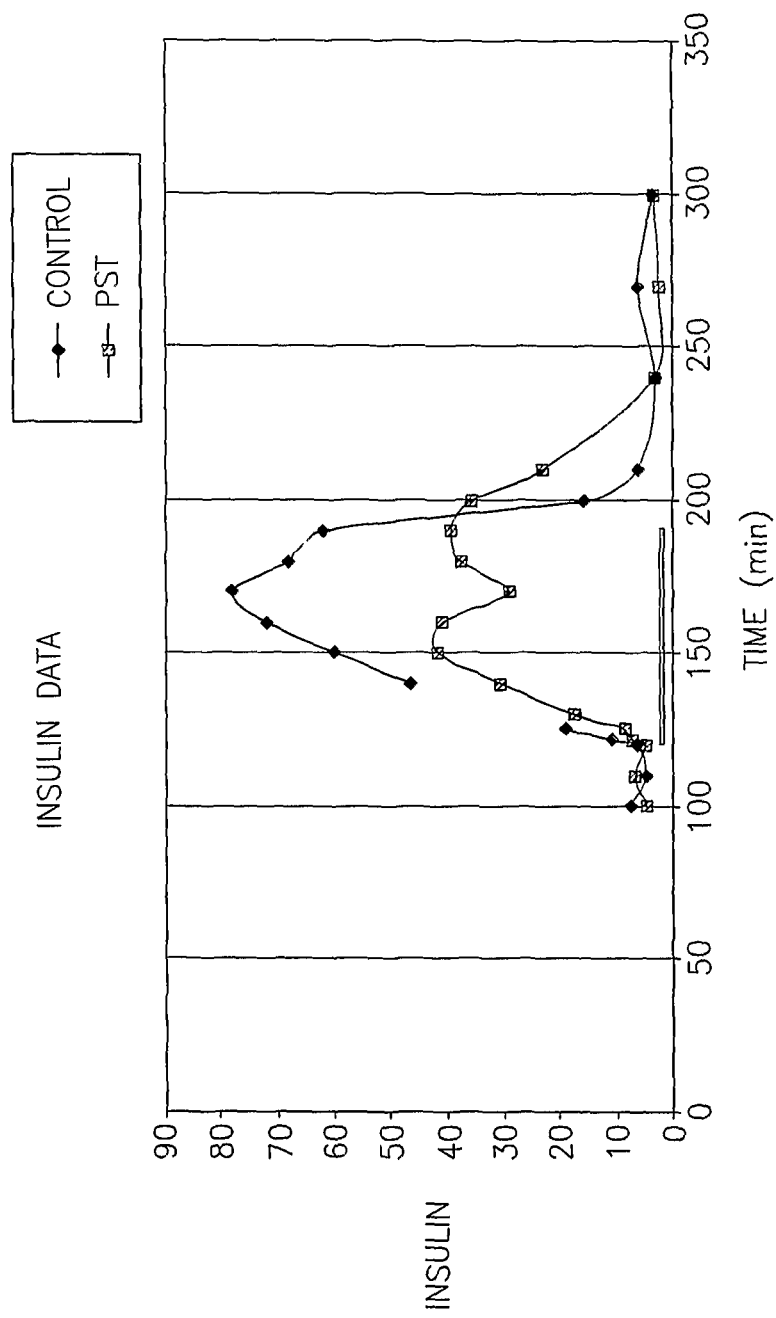

FIGS. 37A and 37B are charts showing glucose and insulin reduction in a dog, in accordance with an exemplary embodiment of the invention. A stimulus was applied for 60 minutes to a right lobe of a pancreas of a dog, one repetition. As can be seen, glucose peaks and insulin peaks were reduced but not significantly delayed. The pulse applied was the same as for the pigs. The glucose was injected via a tube into the stomach and was provided at 1.5 grams per Kg body weight.

While not statistically significant perhaps, the response of the dogs appears to be close to the response of the human with regard to truncating the peak(s) as compared to delaying and truncating. Possibly this varies between people and/or disease states.

Figure 38A:
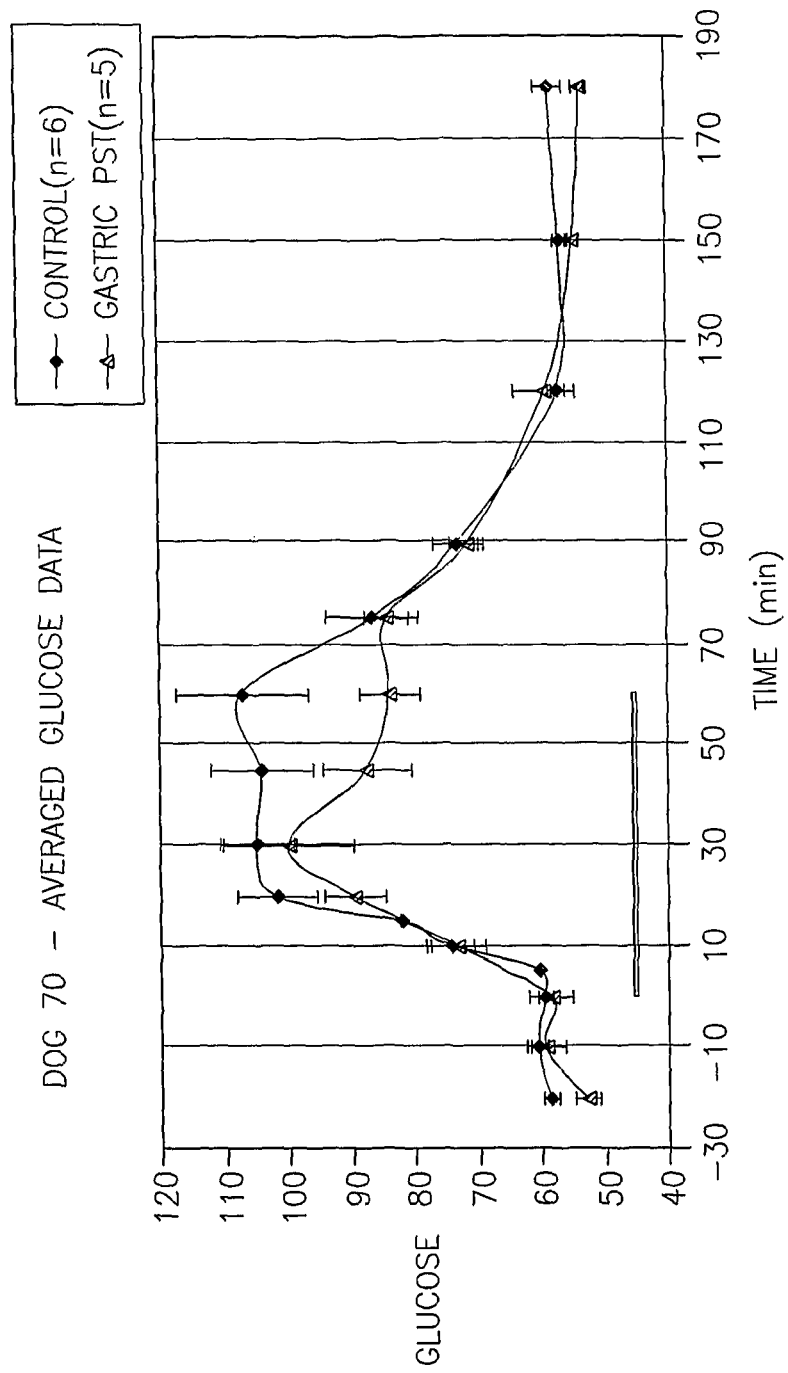
FIGS. 38A and 38B are charts showing glucose reduction in two dogs, where electrodes were placed on a stomach, in accordance with an exemplary embodiment of the invention.
Figure 38B:
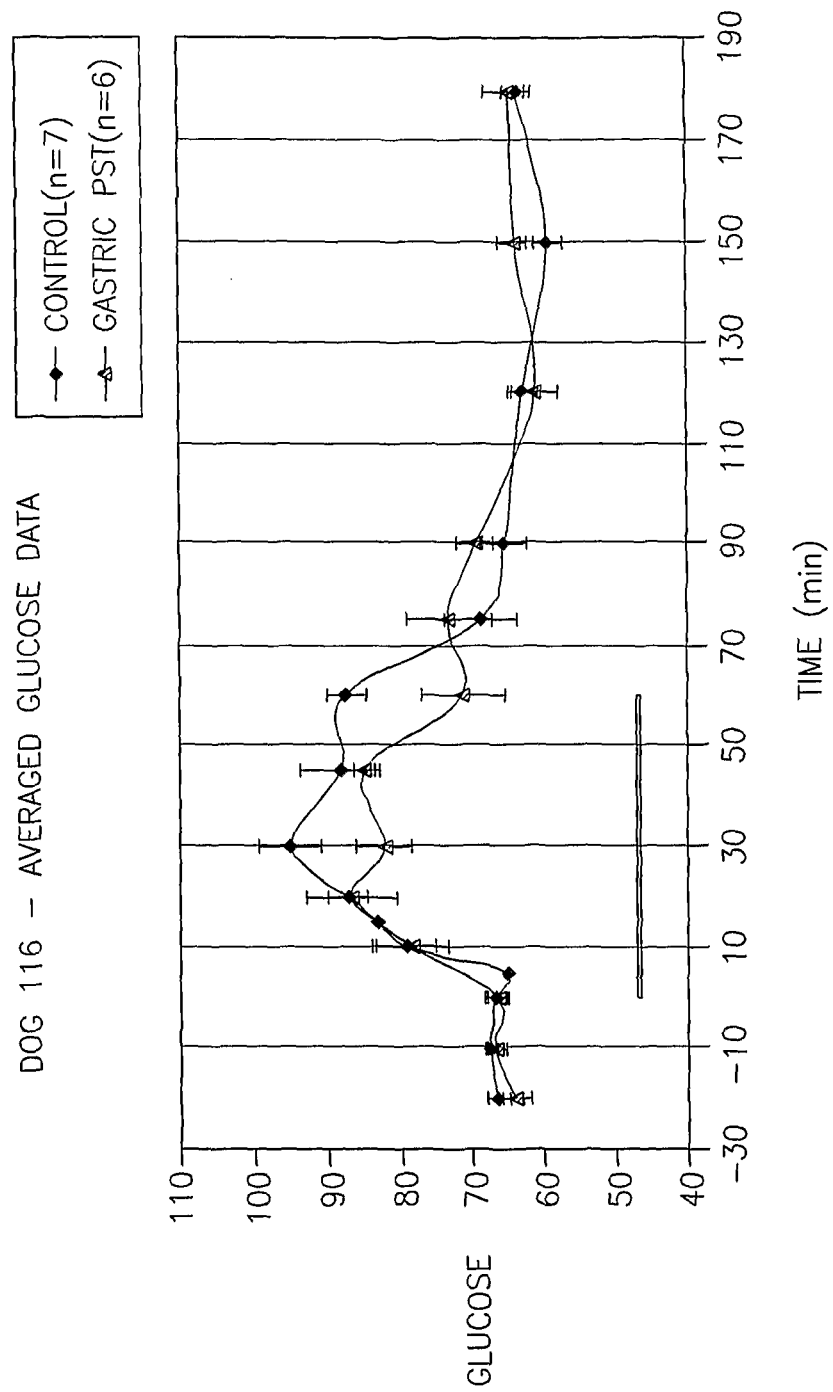

FIGS. 38A and 38B are charts showing glucose reduction in two dogs, where electrodes were placed on a stomach, in accordance with an exemplary embodiment of the invention, there were 6 control repetitions and 5 stimulus repetitions, for the first dog and 7 and 6, for the second dog. Glucose peaks are shown to be reduced, possibly providing an effect of a truncated peak, rather than a delayed and/or narrowed peak. In FIG. 38A, the field was applied to both posterior and anterior walls of the stomach, simultaneously, with two electrodes at each side. In FIG. 38B, a signal was applied only to the anterior wall. The field was the same sequence as used for the pigs and was synchronized to a sensing of electrical field in the antrum. At each "local sense event" (e.g., ~10 seconds) a 4 second sequence of stimulation was applied.

Figure 38C:
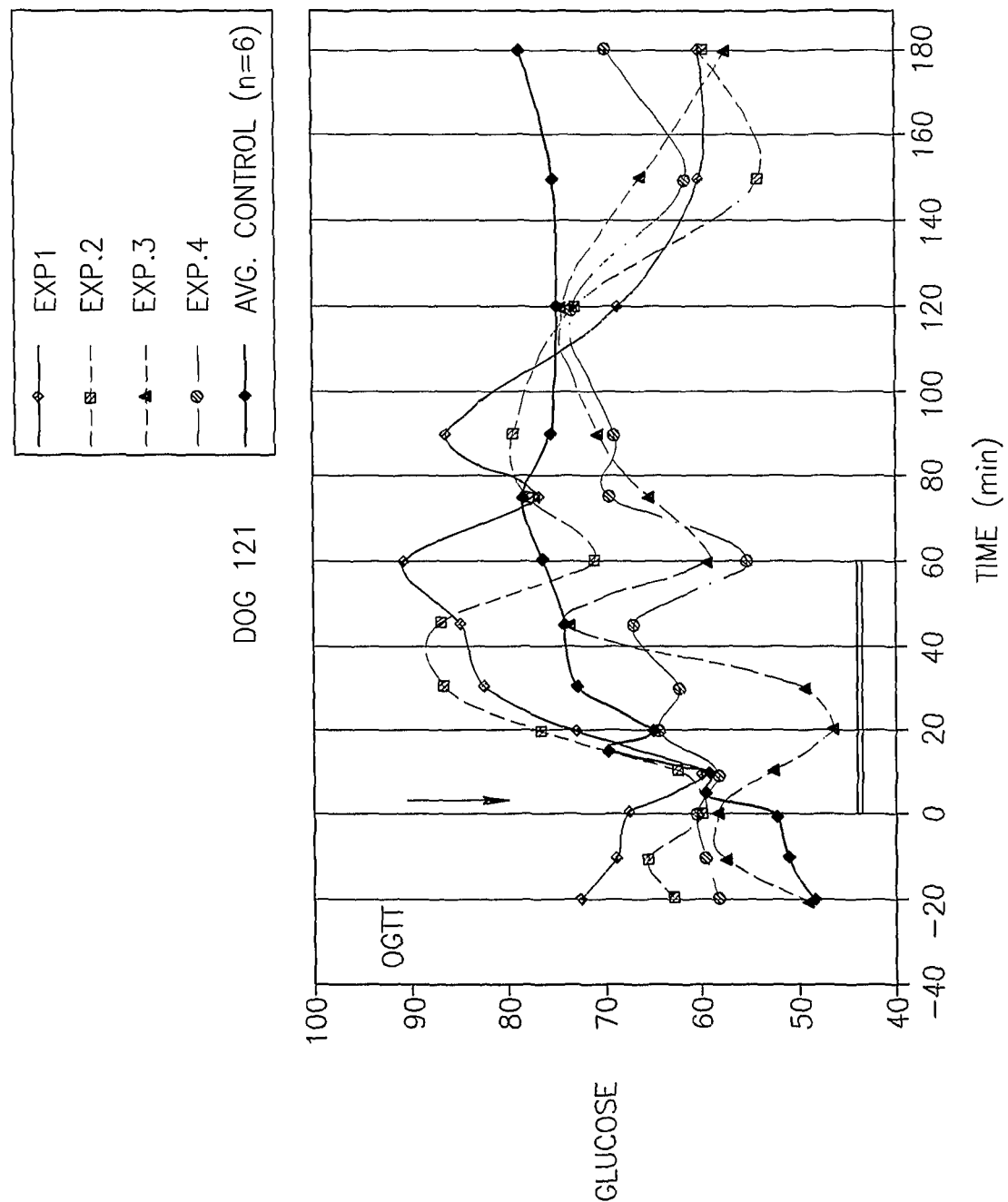
FIG. 38C is a chart showing varying effect of experiments with intermittent and experiments with continuous signal application to a dog, in accordance with exemplary embodiment of the invention.

FIG. 38C shows a series of four experiments in dogs, in which a signal, as used in pigs, was applied only to the posterior side of the stomach. Six control experiments were carried out and four stimulation experiments. The stimulation experiments are divided into two pairs. A first pair, in which glucose reduction is greater and a second pair in which glucose reduction is less pronounced. In the experiments with more pronounced glucose reduction, the stimulation signal was applied every other sensed "local event". In the experiments with a less pronounced reduction, the signal was applied every "local event". It is hypothesized that less frequent excitation may allow recovery of whatever mechanism is operating, thereby allowing a greater effect to be achieved without an associated adaptation. In particular embodiments of the invention, the application may be less frequent, for example at a ratio of 1:5, 1:10 or less, or more frequent, for example at a ratio of 1:1.5 or more. Alternatively or additionally, the duration may be shorter than 4 seconds, for example, be 1 second or 2 seconds, or be longer, for example, 6 or 10. Other intermediate numbers are possible as well.

Figure 38D:
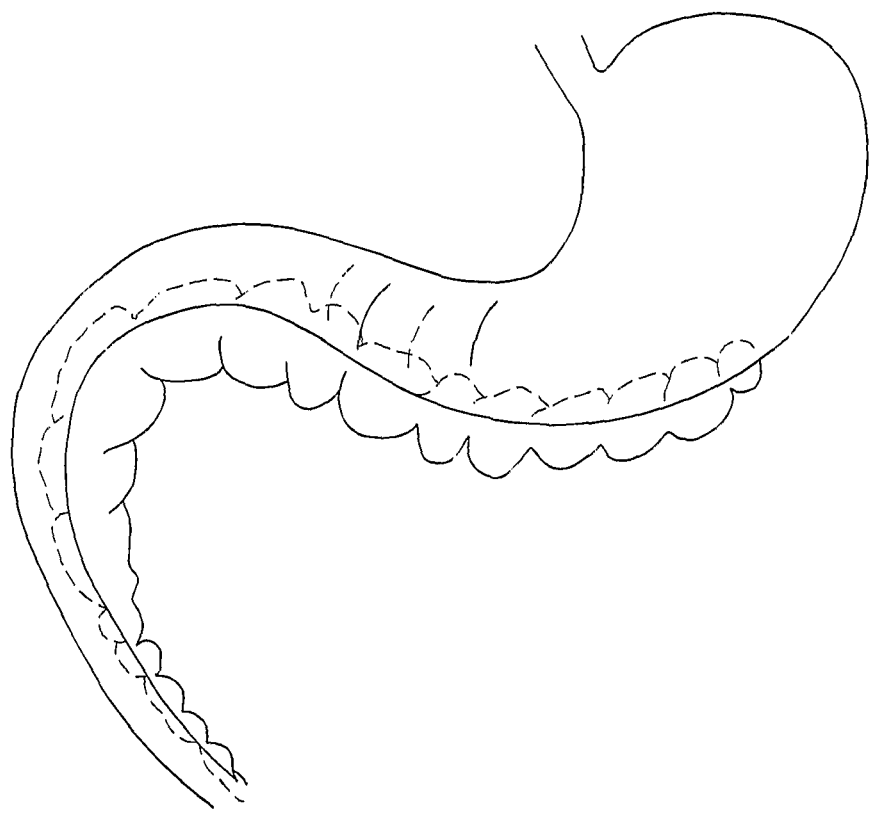
FIG. 38D is a schematic showing of the relative locations of a right lobe of a pancreas and a stomach in a dog.

For reference, FIG. 38D shows a line diagram of the pancreas (right lobe) and stomach of a dog.

Figure 39A:
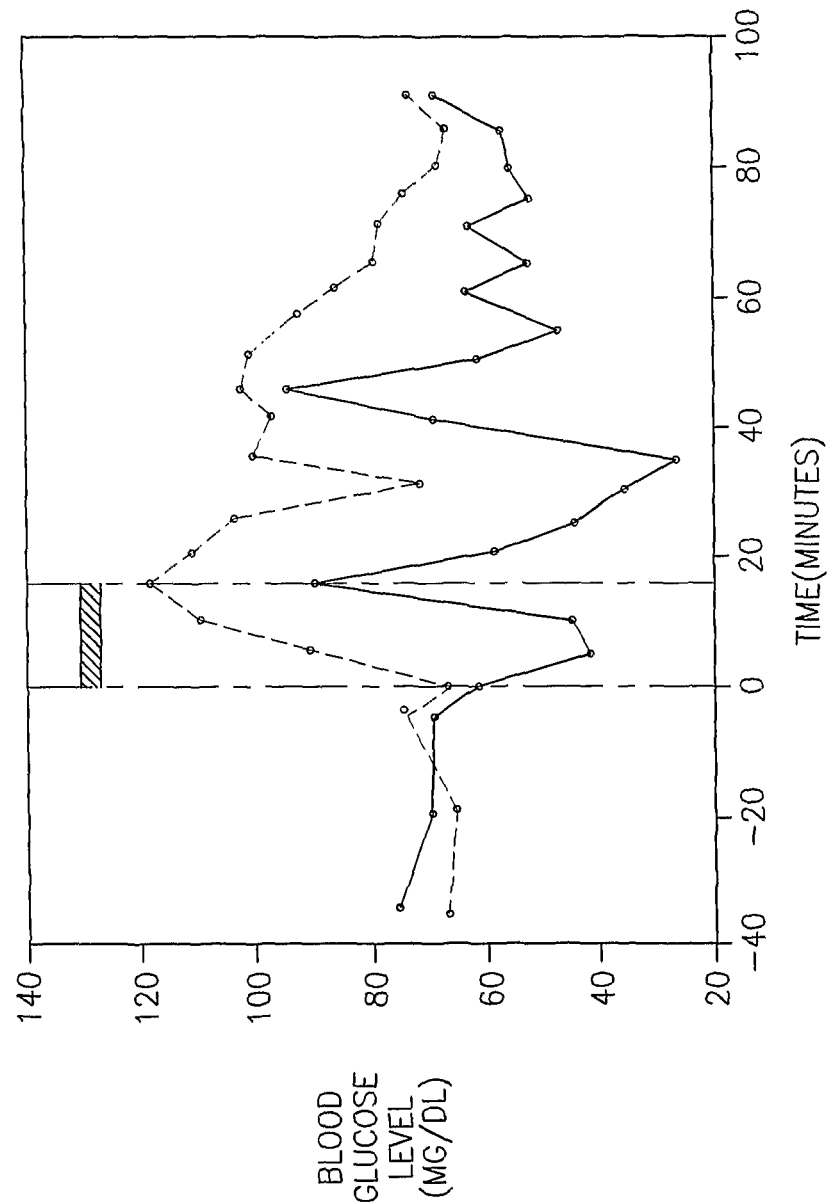
FIGS. 39A and 39B are charts showing glucose reduction in two dogs, where electrodes were placed on a stomach, in accordance with an exemplary embodiment of the invention.
Figure 39B:
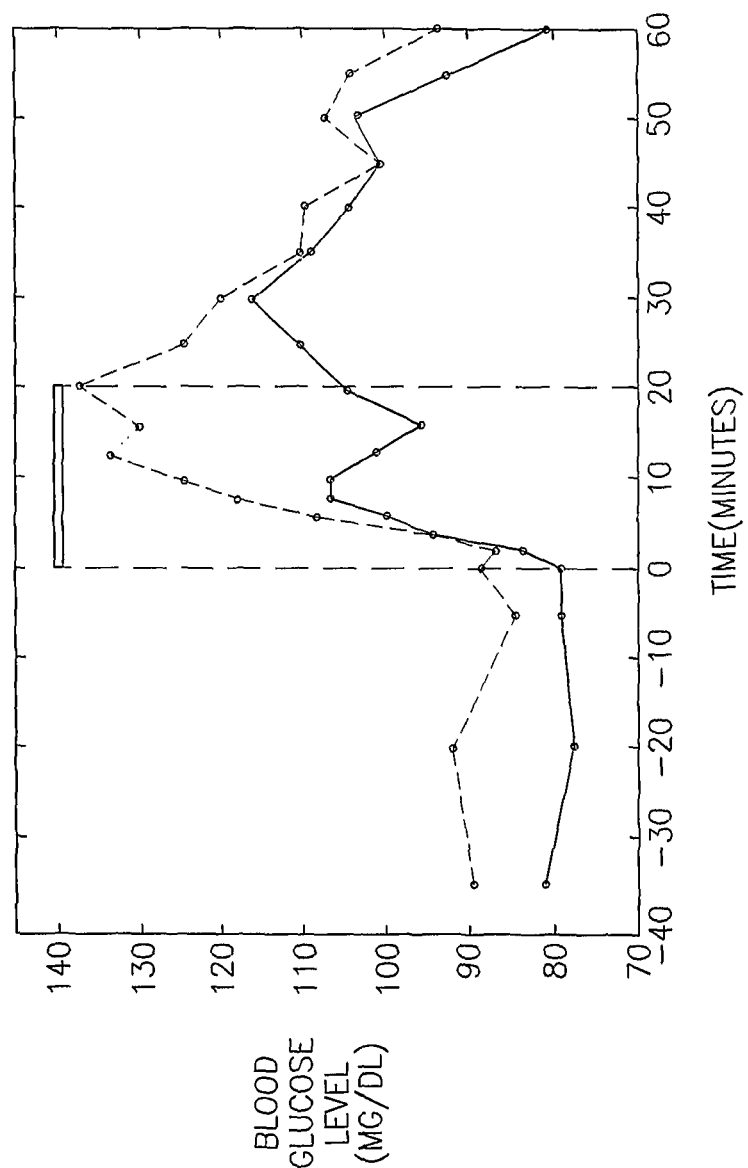

FIGS. 39A and 39B are charts showing glucose reduction in two dogs, where electrodes were placed on a stomach, in accordance with an exemplary embodiment of the invention. This was described in U.S. provisional application 60/488,964, filed Jul. 21, 2003, the disclosure of which is incorporated herein by reference.

Reference is made to FIG. 39A, which is a graph showing measurements of blood glucose levels taken during experiments performed in accordance with an embodiment of the present invention. A single dog was anesthetized, and 2 electrodes were implanted on an external anterior wall of the antrum of the dog, between about 2 cm and about 3 cm from the pylorus. The electrodes were driven to apply an electrical signal with a square waveform having 100 biphasic pulses, each phase of each pulse having an amplitude of 8 mA and a duration of 6 ms. The waveform was applied following detection of the onset of each slow wave of the stomach of the dog (about 4 to 5 times per minute). While this is a different pulse sequence from others used in experiments herein, it should be noted that there is some similarity between the sequences, thereby possibly explaining the effect.

Measurements were taken on two separate days, at about the same time on each day, following twelve-1 hour fasting, while the dog was conscious. An electrical signal was applied on one of these days, and the other day served as a control. On each of the days, glucose consumption, by injection into the mouth, began at time 0 and continued for about two minutes. The electrical signal was applied beginning at time 0 and continuing for about 15 minutes. Measurements were taken using the same glucose meter on both days, and validation of each measurement was performed using two different sets of measurement kits.

A dashed line and a solid line show the measurements taken on the control day and the signal application day, respectively. As can be seen, application of the electrical signal resulted in a substantial reduction in blood glucose level at all points during the measurement period.

Reference is made to FIG. 39B, which is a graph showing measurements of blood glucose levels taken during experiments performed in accordance with an embodiment of the present invention. A second dog, different from the dog described with reference to FIG. 39A, was anesthetized, and 2 electrodes were implanted on an external anterior wall of the antrum of the dog. The electrodes were implanted between about 2 cm and about 3 cm from the pylorus. An electrical signal like that described with reference to FIG. 39A was applied, and the same 5 experimental protocol was followed. In the experiment whose results are shown in FIG. 39B, however, the electrical signal was applied for approximately 20 minutes.

A dashed line and a solid line show the measurements taken on the control day and the signal 10 application day, respectively. As can be seen, application of the electrical signal resulted in a substantial reduction in blood glucose level during the measurement period.

Discussion

The above results indicate that control of glucose levels in a person may be possible, at least in part, without significantly increasing insulin levels and even decreasing such levels. While a physiological model is not necessary for applying these results, various pulse application logics may be formulated in conjunction with certain models. It should be noted, in addition, that each such model may explain only part of the effect with the complete effect being the result of a combination of different physiological pathways and effects.

One possible explanation for the effects of the insulin and glucose reducing pulses is that one or more non-insulin hormones are released, for example, GLP1 or other GI hormones, known or unknown, and that these hormones affect glucose uptake or glucose secretion. Possibly, such hormones act directly on the body cells or on the hypothalamus. These hormones may increase insulin effectiveness or sensitivity in various peripheral cells or the brain. Alternatively or additionally, the secretion of glucagon or a different hormone that affects glucose secretion is reduced.

In addition to direct electrical stimulation of the cells involved in hormone secretion in the pancreas, other possibilities exist. Possibly, the electrical stimulation changed blood flow patterns in the pancreas, as described above, to have its effect. Another explanation is that the electrical stimulation affected adipose tissue levels in the pancreas itself. Another possible explanation is that the electrical stimulation affects neural pathways in the pancreas and/or the liver. Possibly such neural pathways control Glucagon secretion or activate non-insulin dependent glucose transporters in cells of remote tissue. For example, it is known that implanted islets have incorrect Glucagon secretion. This is possibly due to missing nervous connections. The nerves that are stimulated may be, for example, nerves that cause secretion and/or prevent secretion. Alternatively or additionally, the nerves may be, for example, nerves that that sense pancreatic, glucemic and/or hormonal activities. Alternatively or additionally, the gap junctions of nerves and/or other excitable pancreatic tissue may be affected. It should be noted that for some nervous tissue type effects, the percentage of pancreas simulated may be less important due to propagation of the effect of the stimulation by the propagation of nervous signals in the pancreas and/or outside of the pancreas.

One possible explanation involving nerves is that the electrical field affects nerves in or near the pancreas either directly or indirectly. Possibly, these nerves release materials that affect the muscles, brain or other organs. Possibly, the nerves directly affect the brain which then causes the release of such materials. Alternatively or additionally, the nerves affect other tissues to release such materials, possibly via ganglionic connections. Following is a partial list of signaling chemicals whose secretion may be affected (e.g., increased and/or decreased) by the effects of the stimulation: Nitric oxide, ATP, Adenosine, Dopamine, Norepinephrine, Acetylcholine, Serotonin (5-HT), GABA, Glutamate, Aspartate, Glycine, Histamine, Angiotensins Bombesin, Bradykinin Calcitonin, Calcitonin Gene-Related Peptide Carnosine, Cholecystokinin Corticotropin, Corticotropin-Releasing Hormone Delta Sleep-Inducing Peptide, FMRFamide Galanin, Gastric Inhibitory Polypeptide Gastrin-Releasing Peptide, Gastrins Glucagon, Gonadorelin MSH, DISH Release-Inhibiting Hormone MSH-Releasing Hormone, Motilin Neuropeptide Y, Neurophysins Neurotensin, Opioid Peptides-endorphins Pancreatic Polypeptide, Peptide PHI Pituitary Hormone Release Inhibiting Hormones, Pituitary Hormone-Releasing Hormones Prolactin Release-Inhibiting Hormone, Prolactin-Releasing Hormone Protirelin, Secretin Somatomedins, Somatostatin Somatotropin-Releasing Hormone, Tachykinins Vasoactive Intestinal Peptide, Vasopressins, orexin, insulin and/or substance P, and/or any other known or unknown signaling chemical.

Another possible explanation is that the electrical stimulation affected other organs in the abdominal cavity, such as the liver, the stomach or possibly fat cells in the Omentum and caused them to change their activity and/or secret hormones. In any case, placing the electrodes on the pancreas, at either end, has this desired effect, both in pigs and in humans.

It should be noted that a practical device may include one or more sensors, for use in laboratory or operative settings, which sensors indicate if a pulse is having one of the above-described effects (e.g., on glucagon, on glucose secretion, on glucose uptake and/or on nervous tissue) and assist thereby with programming and/or control of pancreatic controller 102.

Exemplary Applications

The above pancreatic controller 102 may be used after a diabetic state is identified. Optionally however, the controller is used to better diagnose an evolving disease state and/or to prevent a final diabetic state from ever occurring, for example by supporting the pancreas. Thus, a temporary device embodiment is optionally provided additionally to permanently implanted device.

In another application, strict control of body insulin output and blood glucose levels is used not only to prevent obese patient from developing diabetes by overworking of the pancreas, but also (simultaneously or alternatively) for reducing body weight. Such a scheme may require strict prevention of elevated glucose levels in blood, to avoid damage to the body. However, it is expected that by reducing insulin production at "normal" glucose levels, feelings of hunger may be suppressed, as well as reducing the increase in mass of adipose tissue.

In an exemplary embodiment of the invention, controller 102 is a stand alone device. However, a dual organ controller may be useful in some disease states. In one example, it is noted that many patients with pancreatic disorders also have cardiac problems. Thus, a combined cardiac/pancreatic controller may be provided, possibly sharing one or more of a casing, programming means, power supply and control circuitry. In another example, a controller for the uterus and a pancreatic controller may be combined to protect against pregnancy related diabetes and improper uterine contractions.

Another exemplary dual organ controller is used for both the stomach and the pancreas. Such a controller is useful for obese persons, to suppress stomach contractions and prevent feelings of hunger. At the same time, insulin level may be controlled to prevent hunger, or, in diabetic patients, to prevent hyper- or hypoglycemia. In addition, as noted above, delay of gastric emptying may also be used to delay glucose absorption, leading to a delay and/or reduction in insulin peaking. Such delay may be used in addition to or instead of direct pancreatic stimulation, in some embodiments of the invention.

In an exemplary embodiment of the invention, the same electrodes are used for electrification of the pancreas and of the stomach, thus providing both obesity control and glucose control with a same set of electrodes. It is noted, that reducing eating may also reduce glucose load. Such multi-use electrodes may be placed, for example, on the pancreas, on the stomach or between the pancreas and the stomach. Placing electrodes on the abdominal wall and/or stomach and/or other internal organs may be useful also for non-pancreatic stimulation, for example, if the organ to be stimulated is relatively sensitive to electrode attachment and/or relatively hard to reach by a desired surgery method.

Reference is now made to FIGS. 40-43, which are graphs showing the results of experiments carried out in accordance with some embodiments of the present invention. In each of three Sinclair minipigs, four pairs of electrodes were implanted in a longitudinal orientation with respect to the axis of the stomach. This longitudinal orientation is described hereinbelow with reference to FIG. 49A. In each experiment, after at least 16 hours of overnight fasting, the minipig was given an oral load of 75 g glucose. Blood samples were taken before and after the administration of the glucose load, for a total period of 140 minutes. Glucose and insulin were measured from these samples. (In some experiments, glucose or insulin was not measured.)

For each minipig, some experiments were performed using a 60-minute signal application period, beginning at the time of administration of the glucose load. The signal application period included the application of a series of biphasic pacing pulses, each followed by an ETC signal. Signal parameters are described hereinbelow with reference to FIG. 50. Other experiments were performed in a control mode, in which no signal was applied to the stomach. The control and signal application periods were designated in a random order.

Figure 40A:
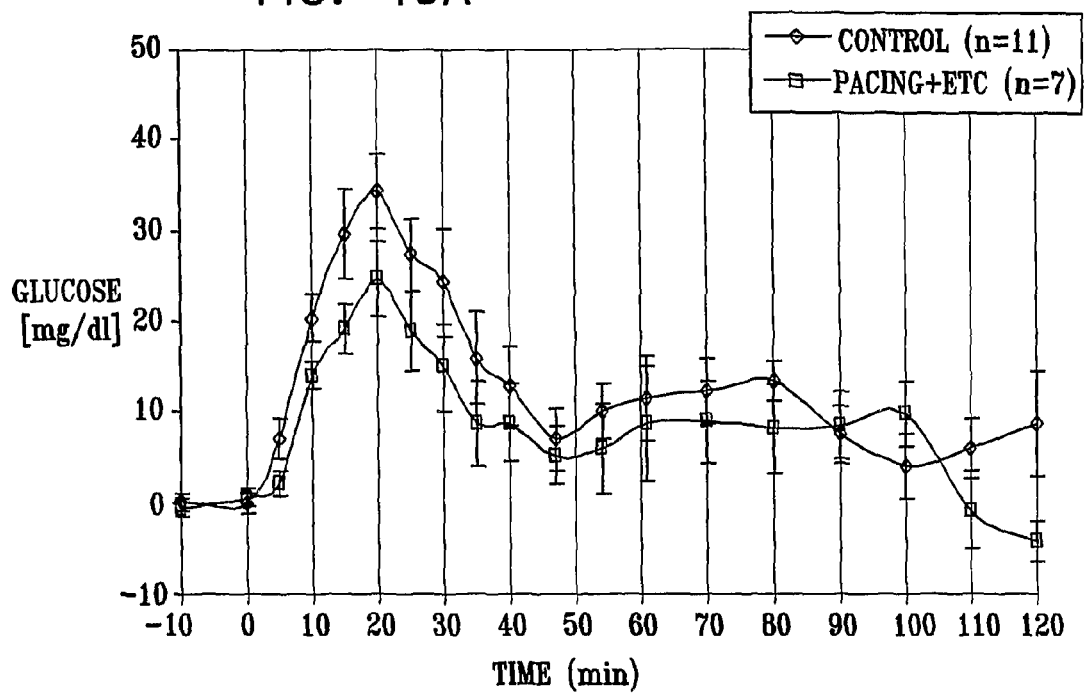
FIGS. 40-48 are charts showing experimental results, derived in accordance with exemplary embodiments of the present invention.
Figure 40B:
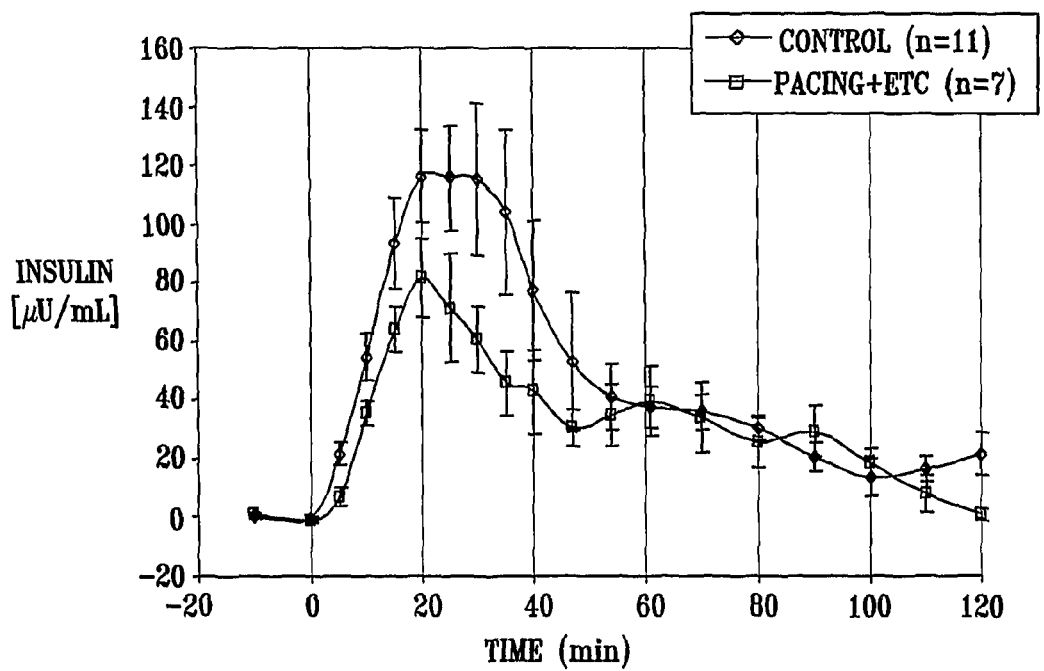
Figure 41A:
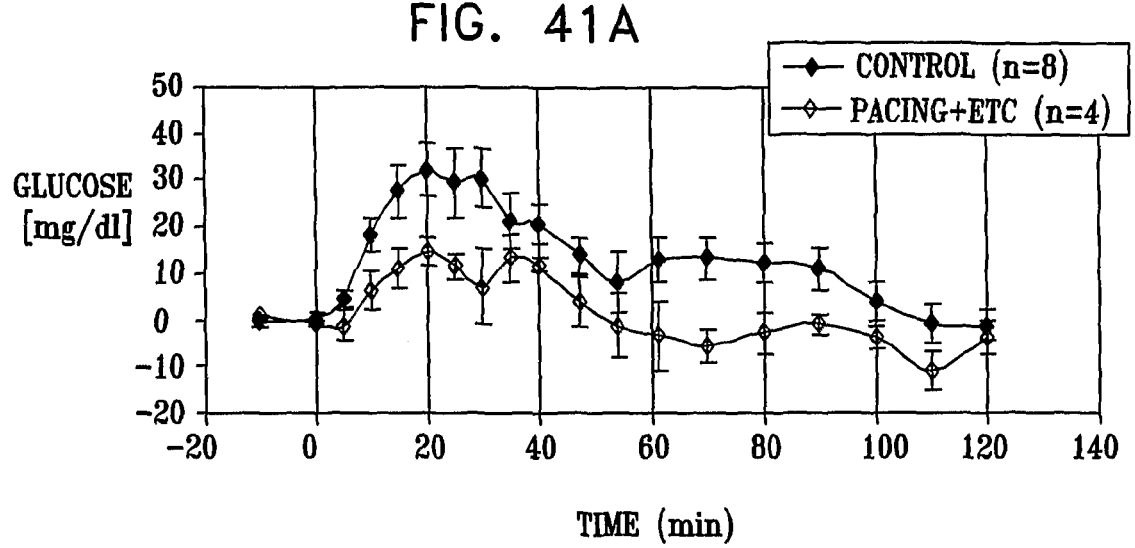
Figure 41B:
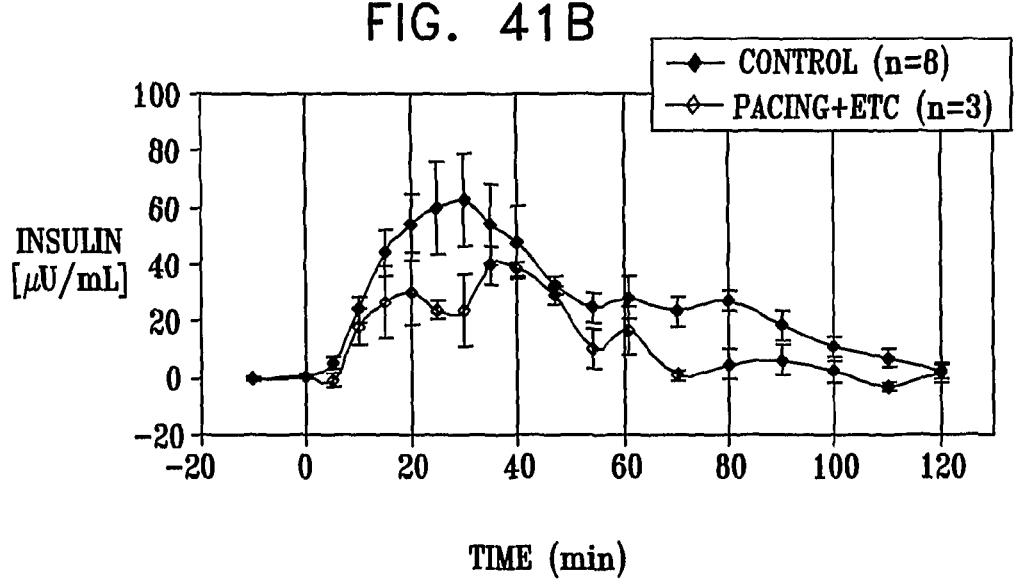
Figure 42A:
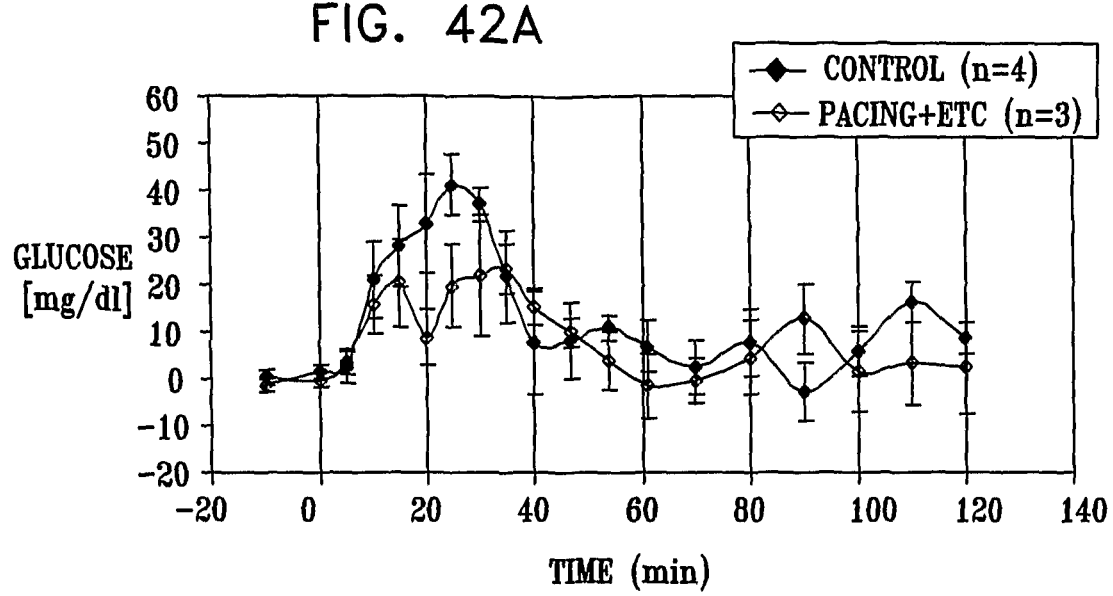
Figure 42B:
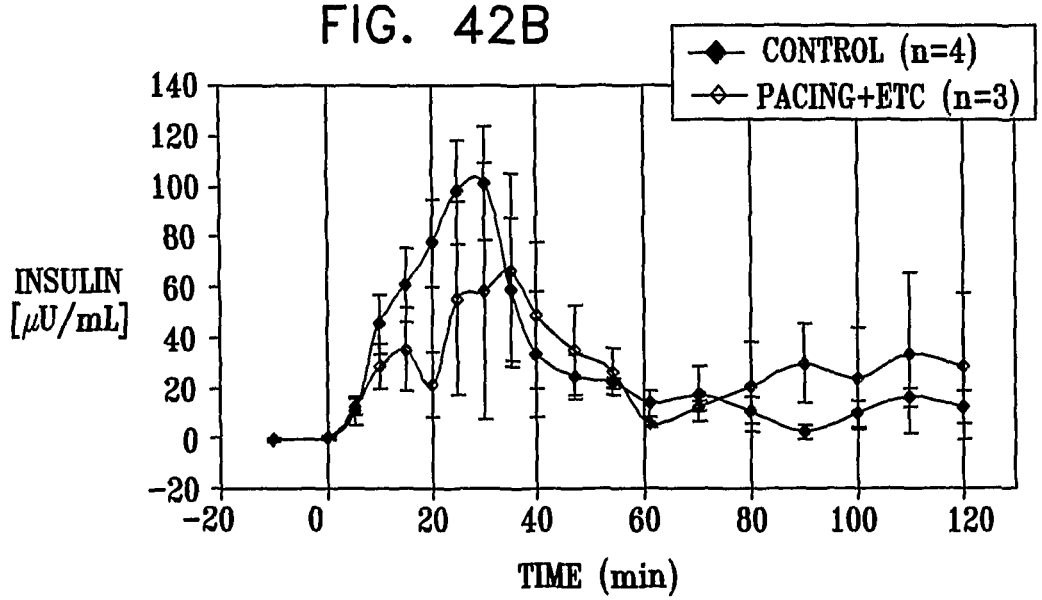

FIGS. 40A and 40B show experimental results obtained with the first minipig, derived using gastric electrodes positioned in a longitudinal orientation with respect to the axis of the stomach. Eleven control experiments were performed, and seven signal application experiments were performed. Both glucose and insulin are seen to be substantially reduced in the signal application periods, compared to the control period. Similar results are seen in FIGS. 41A and 41B (for the second minipig) and FIGS. 42A and 42B (for the third minipig).

Figure 43:
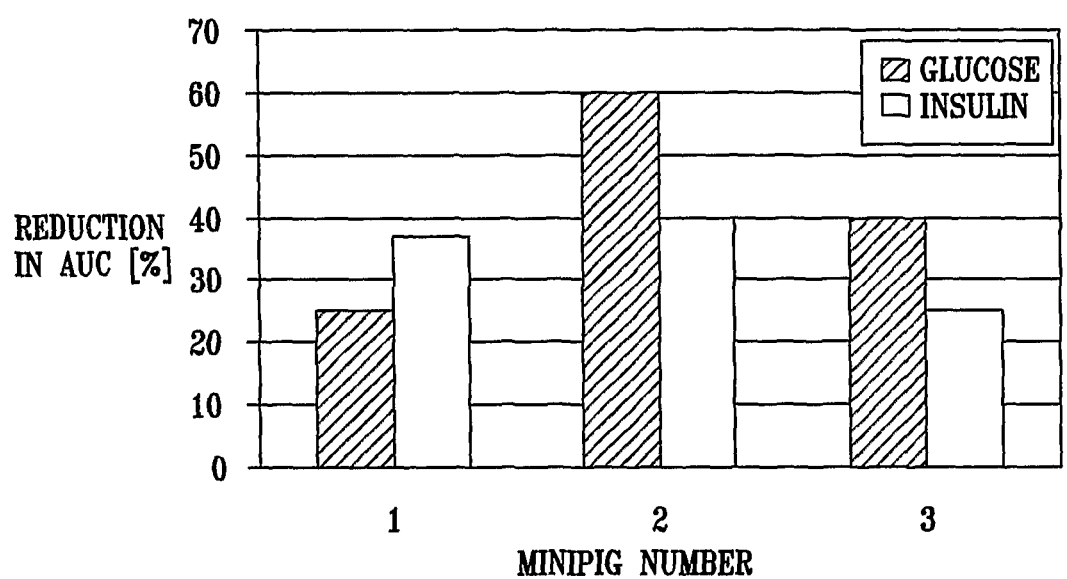

FIG. 43 shows a graph summarizing the results of the experiments shown in FIGS. 40-42. The area under the curve (AUC) for both glucose and insulin in all three minipigs was substantially reduced during the 60 minute signal application period. In particular, glucose AUC reduction ranged from 25% to 60%, and insulin AUC reduction ranged from 25% to 40%.

Reference is now made to FIGS. 44-46, which are graphs showing the results of experiments carried out in accordance with some embodiments of the present invention. In each of three Sinclair minipigs (different from the minipigs described hereinabove), four pairs of electrodes were implanted in a perpendicular orientation with respect to the axis of the stomach. This perpendicular orientation is described hereinbelow with reference to FIG. 49B. It is noted that the implantation sites of the electrodes in the perpendicular orientation were generally the same as the implantation sites of the electrodes in the longitudinal orientation, only the orientation differed. The experimental protocol was otherwise generally similar to that described hereinabove with reference to FIGS. 40-43.

Figure 44A:
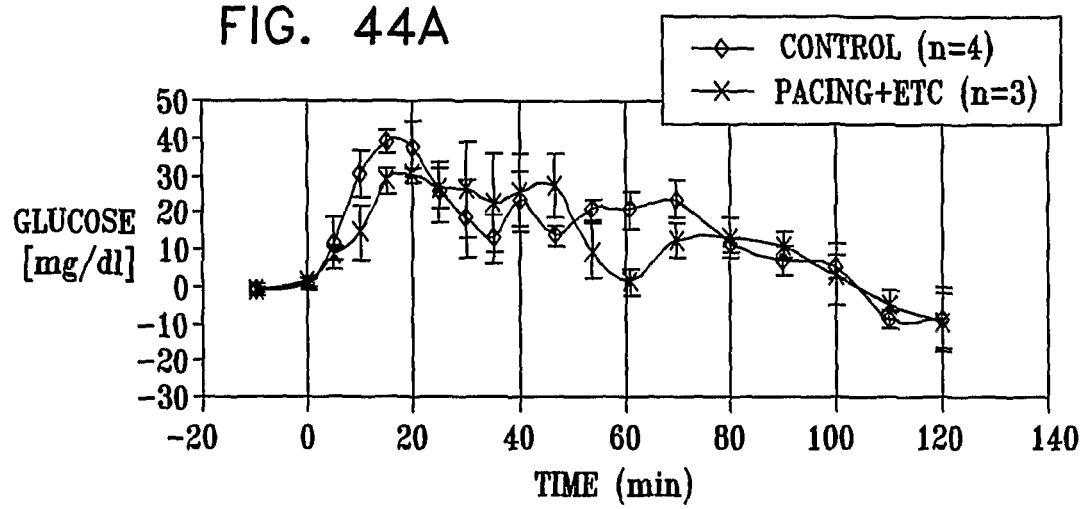
Figure 44B:
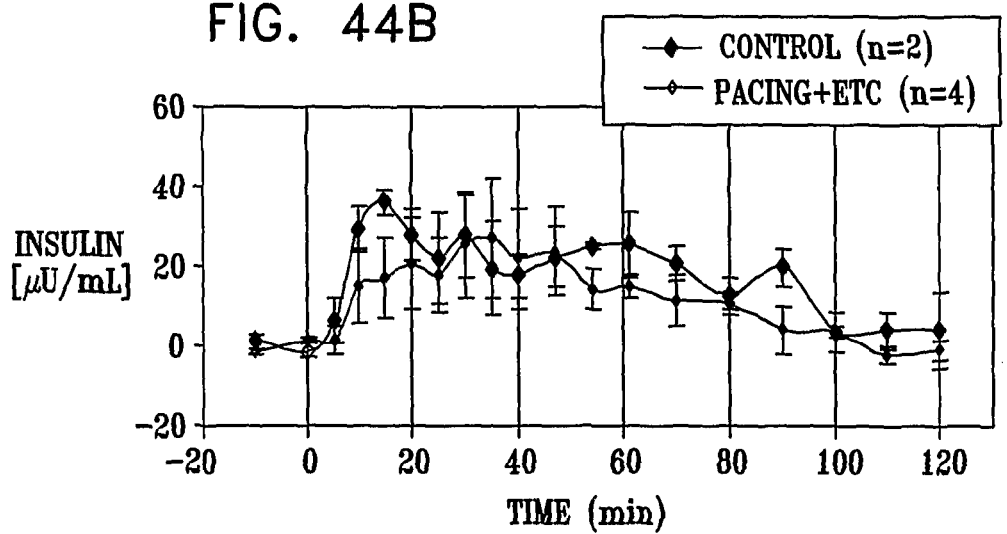
Figure 45A:
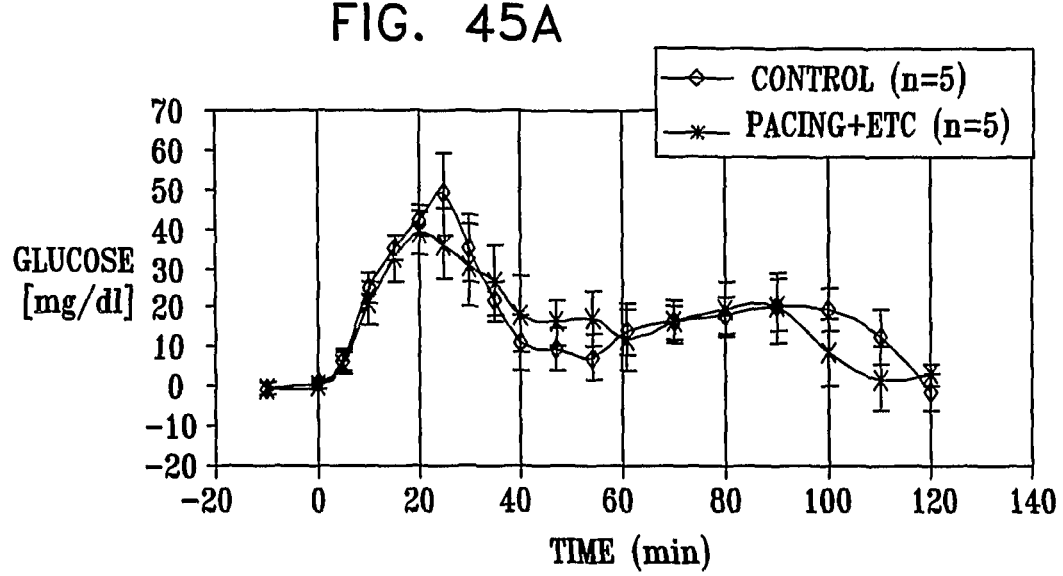
Figure 45B:
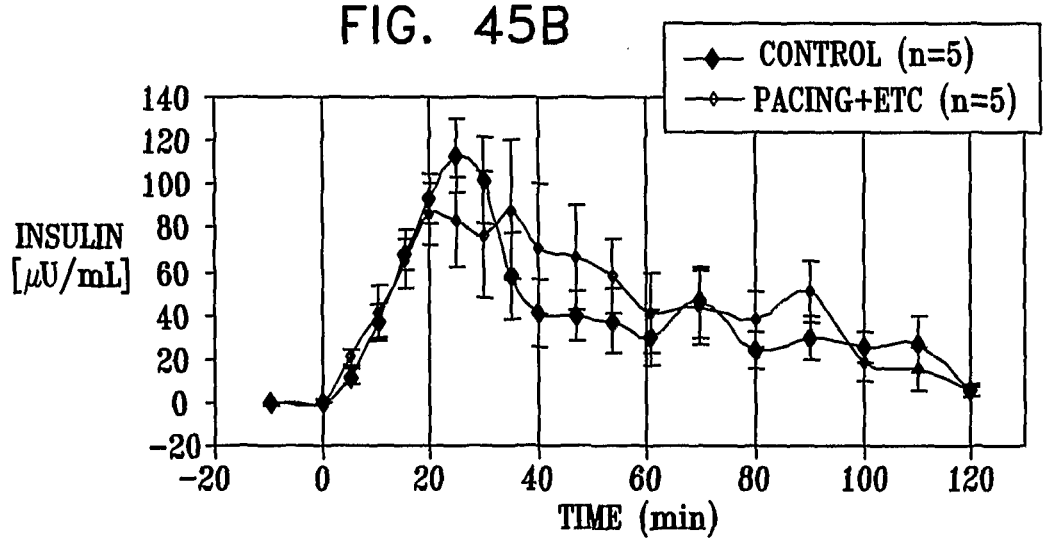
Figure 46A:
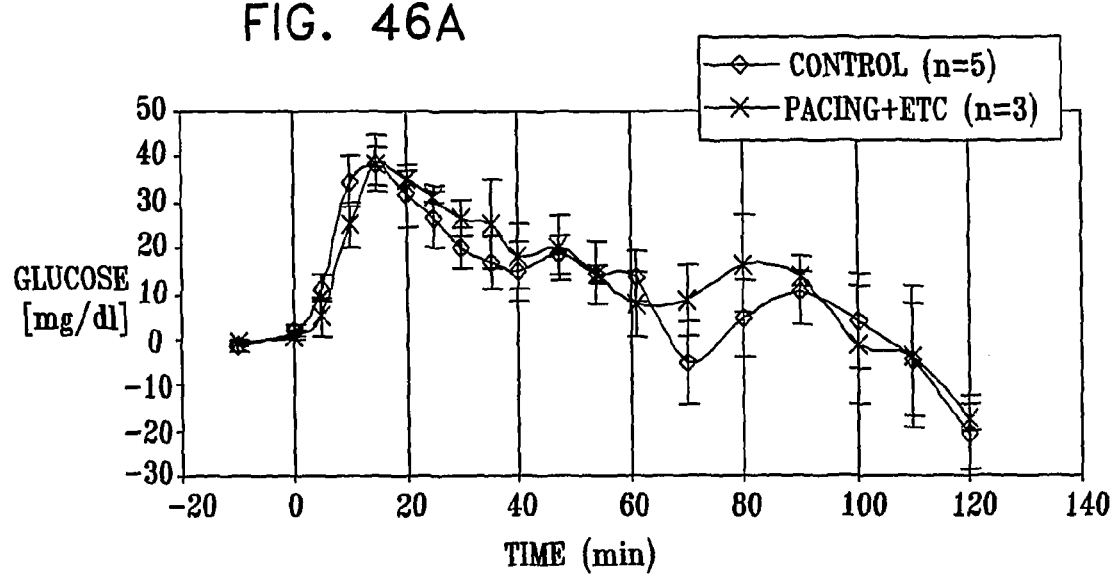
Figure 46B:
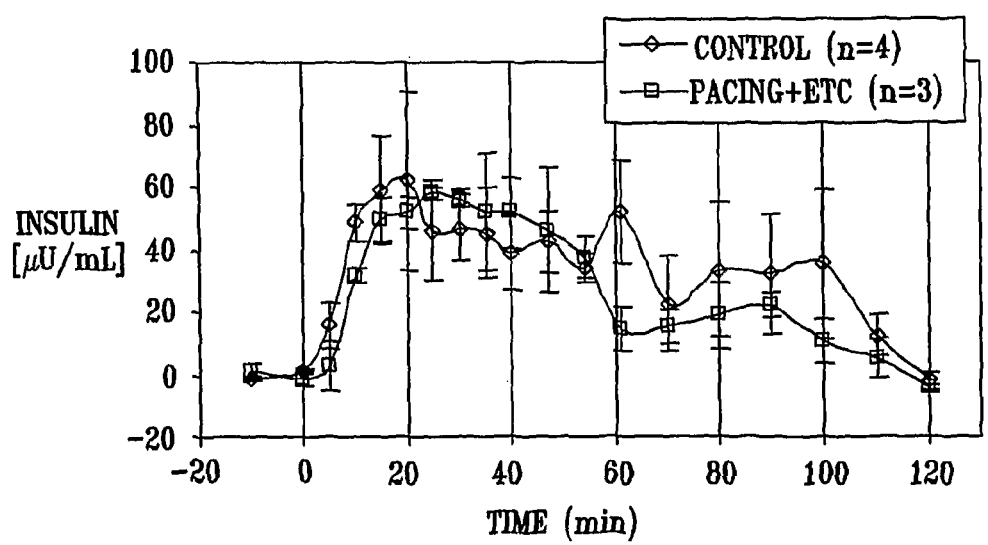

FIGS. 44A and 44B show experimental results obtained with the first minipig in which gastric electrodes were sutured in a perpendicular orientation with respect to the axis of the stomach. Peak glucose and peak insulin levels are seen to be reduced in the signal application periods, compared to the control period. Similar results are seen in FIGS. 45A and 45B, although not in FIGS. 46A and 46B. In general, the reductions in glucose and the reductions in insulin are seen to be less pronounced in the perpendicular-orientation minipigs compared to the longitudinal-orientation minipigs.

Reference is now made to FIGS. 47 and 48, which are graphs showing the results of experiments carried out in accordance with some embodiments of the present invention. In each of two Sinclair minipigs (different from the minipigs described hereinabove), four pairs of electrodes were implanted in a "mixed" orientation with respect to the axis of the stomach. This mixed orientation includes two pairs of electrodes having a longitudinal orientation, and two pairs of electrodes having a perpendicular orientation. Further details of the mixed orientation are described hereinbelow with reference to FIG. 49C. It is noted that the implantation sites of the electrodes in the mixed orientation were generally the same as the implantation sites of the electrodes in the longitudinal and perpendicular orientations; only the orientation differed. The experimental protocol was otherwise generally similar to that described hereinabove with reference to FIGS. 40-43.

Figure 47A:
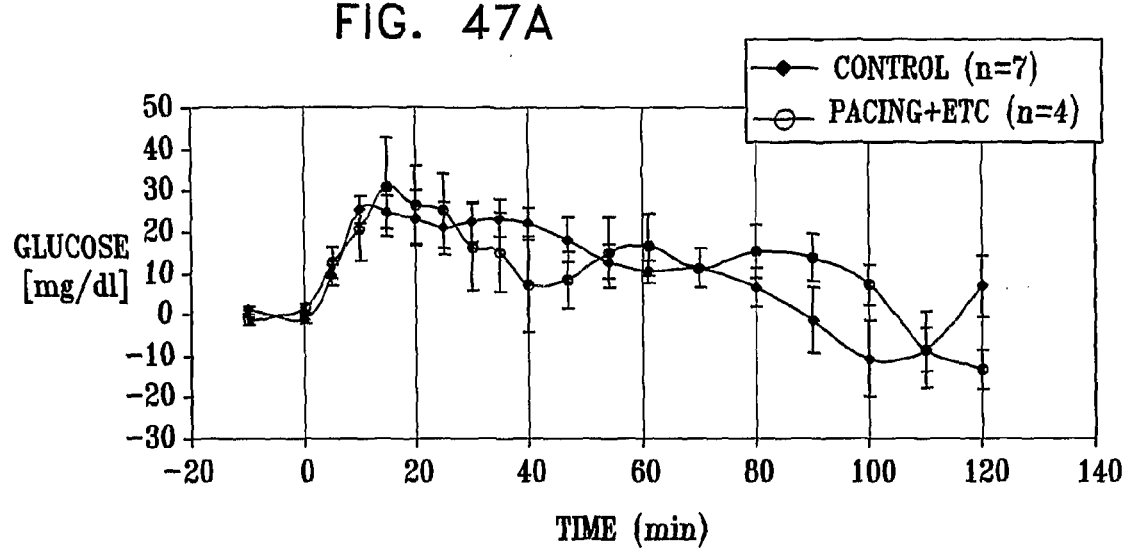
Figure 47B:
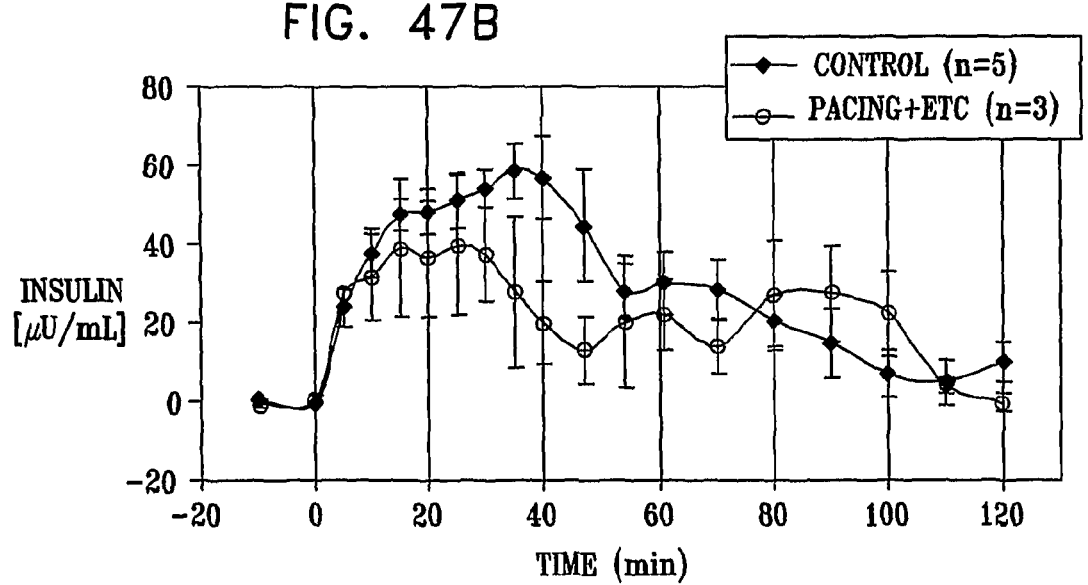

FIGS. 47A and 47B show experimental results obtained with the first minipig in which gastric electrodes were sutured in a mixed orientation with respect to the axis of the stomach. No substantial reduction in glucose levels is seen in the signal application experiments compared to the control experiments (FIG. 47A). It is worthy of note that insulin levels were substantially lower in the signal application experiments, compared to the control experiments (FIG. 47B), without producing an increase in blood glucose levels.

Figure 48A:
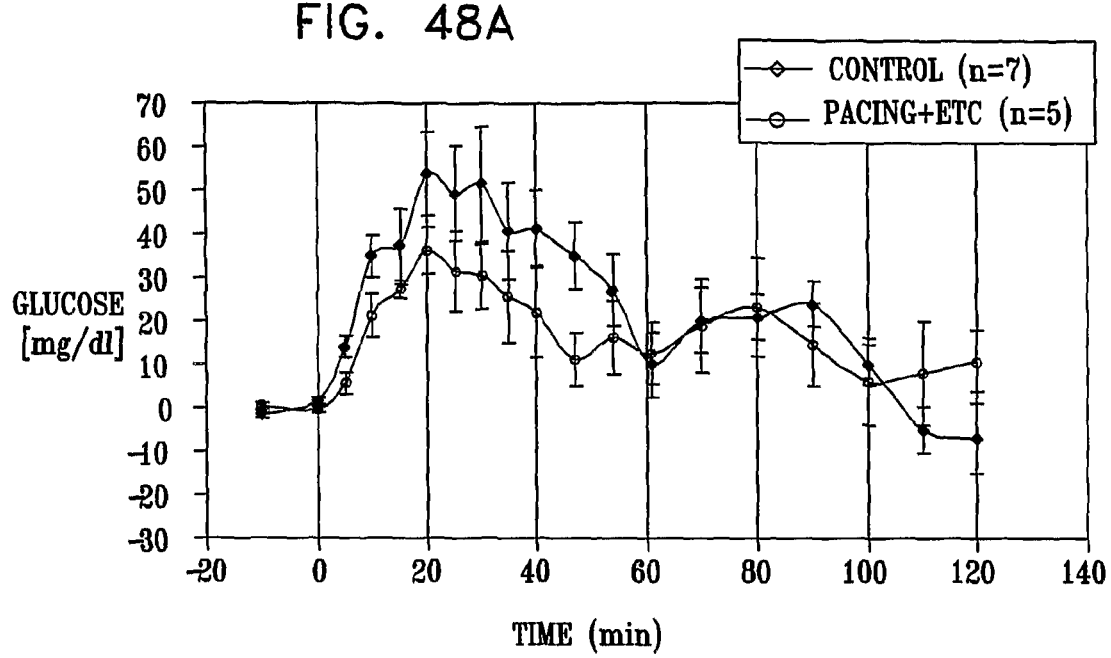
Figure 48B:
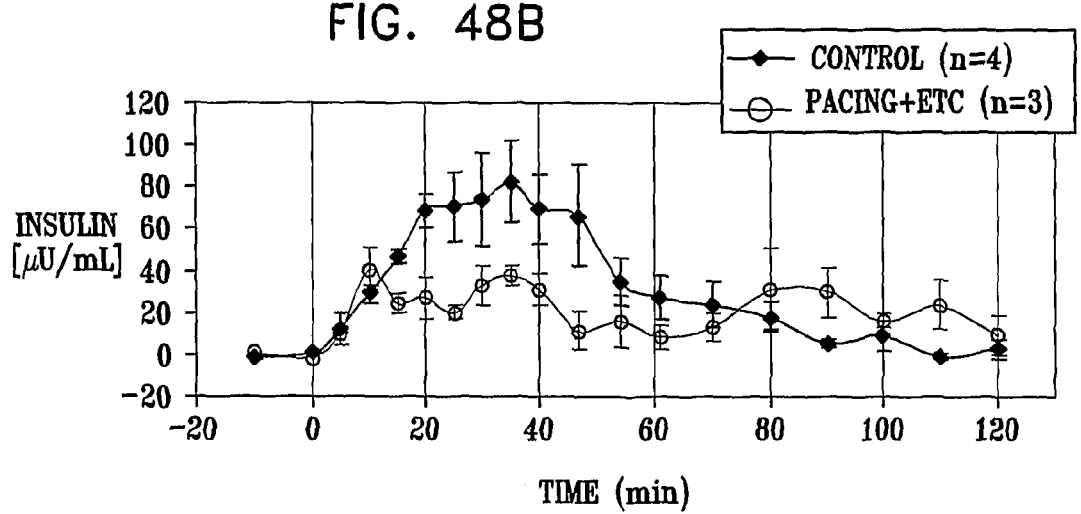

FIGS. 48A and 48B show experimental results obtained with the second minipig, derived using gastric electrodes positioned in a mixed orientation with respect to the axis of the stomach. A significant reduction in glucose levels (FIG. 48A) and insulin levels (FIG. 48B) is observed. It is noted that the control glucose levels for this minipig are considerably higher than normal minipig glucose levels, and that in this circumstance, a particularly strong effect of the signal application on glucose and insulin is observed.

Figure 49A:
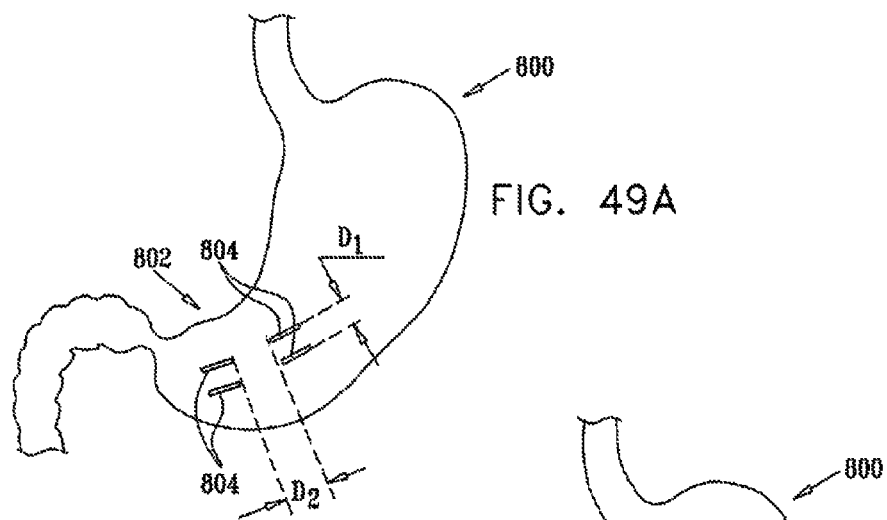
FIGS. 49A, 49B, and 49C are schematic illustrations of implantation protocols, in accordance with respective embodiments of the present invention.

FIG. 49A is a schematic illustration of an anterior antrum 802 of a stomach 800, having implanted thereon two pairs of longitudinally-oriented electrodes 804, in accordance with an embodiment of the present invention. (Two additional pairs of electrodes 804, not shown, are at corresponding locations on the posterior antrum.) In the context of the present patent application and in the claims, this orientation of electrodes on the stomach is referred to as a "longitudinal orientation with respect to the curved long axis of the stomach." One of the pairs is sutured to the distal antrum, and the other pair is sutured to the proximal antrum, adjacent to the body of the stomach. A distance D2 of between about 1 and about 5 cm typically separates the pairs of electrodes. In the longitudinal-orientation minipig experiments described hereinabove with reference to FIGS. 40-43, D2 was between about 2 and about 3 cm. A distance D1 of between about 1 and about 3 cm typically separates individual electrodes 804 in each pair of electrodes. In the longitudinal-orientation minipig experiments described hereinabove, D1 was about 2 cm.

Figure 49B:
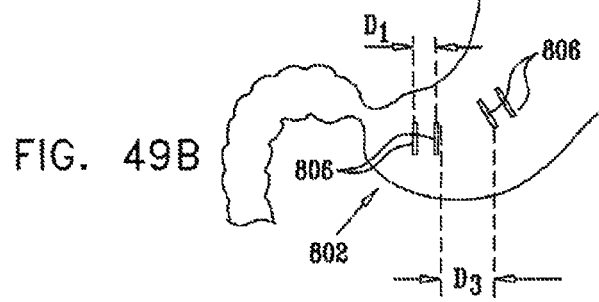

FIG. 49B is a schematic illustration of anterior antrum 802, showing two pairs of perpendicularly-oriented electrodes 806, in accordance with an embodiment of the present invention. (Two additional pairs of electrodes 806, not shown, are at corresponding locations on the posterior antrum.) In the context of the present patent application and in the claims, this orientation of electrodes on the stomach is referred to as a "perpendicular orientation with respect to the curved long axis of the stomach." A distance D3 of between about 1 and about 7 cm typically separates the pairs of electrodes in the perpendicular orientation. In the perpendicular-orientation minipig experiments described hereinabove, D3 was about 5 cm. D1 in these experiments was about 2 cm.

It is noted that although "perpendicular" and "longitudinal" orientations are described herein with respect to some embodiments, the scope of the present invention includes a complete range of angles therebetween, e.g., 0-30 degrees from the curved long axis of the stomach, 30-60 degrees from the curved long axis of the stomach, and 60-90 degrees from the curved long axis of the stomach. For some applications, the angle is selected during the implantation procedure of the electrodes, e.g., responsive to real-time monitoring of glucose or insulin levels when the electrode pairs are placed at different angles with respect to each other or with respect to the curved long axis of the stomach.

Figure 49C:
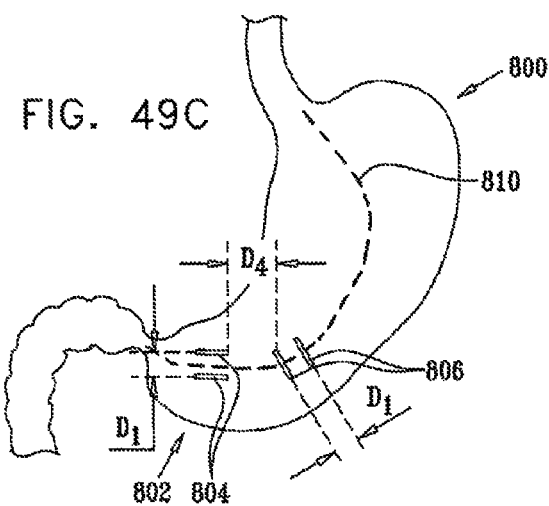

FIG. 49C is a schematic illustration of anterior antrum 802, showing one pair of longitudinally-oriented electrodes 804 and one pair of perpendicularly-oriented electrodes 806, in accordance with an embodiment of the present invention. (An additional pair of electrodes 804 and an additional pair of electrodes 806, not shown, are at corresponding locations on the posterior antrum.) In the context of the present patent application and in the claims, an orientation of electrodes on the stomach combining at least one longitudinal electrode and at least one perpendicular electrode is referred to as a "mixed orientation with respect to the curved long axis 810 of the stomach." A distance D4 of between about 1 cm and about 5 cm typically separates the pairs. In the experiments described hereinabove with respect to the mixed orientation, D3 was about 3 cm.

Reference is now made to FIGS. 49A, 49B, and 49C. It is noted that in the longitudinal orientation configuration (FIG. 49A), electrode pairs were closer to each other than when they were sutured to the antrum in the perpendicular orientation (FIG. 49B) or in the mixed orientation (FIG. 49C). Therefore, it may be that an explanation for some or all of the differences observed between the results described hereinabove with reference to FIGS. 40-43 and those described hereinabove with reference to FIGS. 44-48 may be due to the distance between the electrode pairs. Therefore, whereas in some embodiments of the present invention, electrodes are sutured to the stomach in the longitudinal orientation, the perpendicular orientation, or the mixed orientation (e.g., in order to derive results like those described hereinabove), in other embodiments of the present invention, the distance between adjacent pairs of electrodes is regulated (e.g., in order to derive results like those described hereinabove), and the orientation is not necessarily regulated. For example, two adjacent pairs of antral electrodes may be separated by between about 1 and about 4 cm (e.g., 2-3 cm), and may be placed in any orientation described hereinabove, or in a different orientation.

In some embodiments of the invention, the orientations of the electrodes are defined as a spatial relationship between a vector of the electrodes and a vector of the pancreas or the stomach. In an exemplary embodiment of the invention, the vector of the electrodes is defined as a vector interconnecting the centers of the electrodes. The vector of the stomach can be, for example, a tangent to the main axis of the stomach near the electrodes and optionally along the surface of the stomach (e.g., a tangent to the stomach or a cylindrical approximation thereof). The vector of the pancreas can be, for example, its main axis, or an axis of a lobe thereof. In some embodiments of the invention, different axes and/or vectors are defined for different parts of the organ affected by the electric field. Electrodes for providing such different vector effects on a same organ may be provided.

Optionally, the electrodes are positioned to have a known angle between the vectors of the electrode and an organ vector. One or more of a spatial angle and an angle relative to the vertical (or other axis) of the body may be considered. In an exemplary embodiment of the invention, the angle is selected to be, for example 0, 20, 40, 60, 80, 90 degrees, or intermediate angles. Angles greater than 0 or smaller than 90 may be provided, as changes in polarity.

Optionally, the electrodes are positioned so that the electrode vector has a certain projection on the organ vector. Optionally, the projection size depends not only on the angle, but also on the amplitude of the field.

In an exemplary embodiment of the invention, a desired electrode location is defined as a relative angle or projection which can then be achieved using various positions, spacings and/or locations of the electrodes. The exact position may depend, for example, on organ position and shape and/or on a desired or undesired effect on nearby organs. Such effects may also be characterized by the vector angles.

In some embodiments of the invention (for example if there are nearby organs which affect the spatial form of the electric field), the vector may be defined taking into account the field shape closer to the target organ.

Optionally, the electrodes are rotated during implantation, so that a desired vector effect is measured at the target tissue.

For some applications, a vector is selected in order to reduce a possible side effect of signal application, e.g., conscious sensation of the signal application, nausea, GI arrhythmia, or local tissue irritation.

Alternatively or additionally, different electrodes are selectively activated to provide different effective vectors. For example, to avoid adaptation to the signal application, or local irritation in response to prolonged use of a single vector, electrodes may be activated to define one vector on one day, and to define another vector on the next day. (Alternatively, a different schedule is used.)

In an exemplary embodiment of the invention, the following electrode is used for the stomach electrodes: stitch electrodes having inner and outer silicone rubber sheathing, multifilar MIP35N®/Silver DFT, helical coil, coaxial conductors and area of 25 mm2 titanium nitride coated, platinum-iridium electrode portions. The electrodes are, for example, 5, 10, 15, 20 or 30 mm long.

In an exemplary embodiment of the invention, a straight, tapered point stainless steel suture needle is affixed to the end of each stitch electrode. In an exemplary embodiment of the invention, a suture pad, for example of silicone, is provided adjacent the electrode. This pad is, for example, 3-7 mm in diameter and includes one or more apertures for thread. Optionally, the cathodic (−) conductor is indicated by a black dot in the suture pad. Leads can be used in two lengths, for example, 60 and 52 centimeters. In an exemplary embodiment of the invention, the leads bifurcate into individual, monopolar leads at about the mid-point (e.g., 32.5 or 24.5 centimeters from the proximal ends, respectively) and may be used, for example, to attach to a different body organ such as the duodenum, and to provide strain relief. The lead connectors are optionally IS-1-BI type.

In an exemplary embodiment of the invention, when attached, lead retention force is greater than 10 N.

In the pancreas, electrodes with a greater flexibility are optionally used, to prevent damage to the pancreas.

Figure 50:
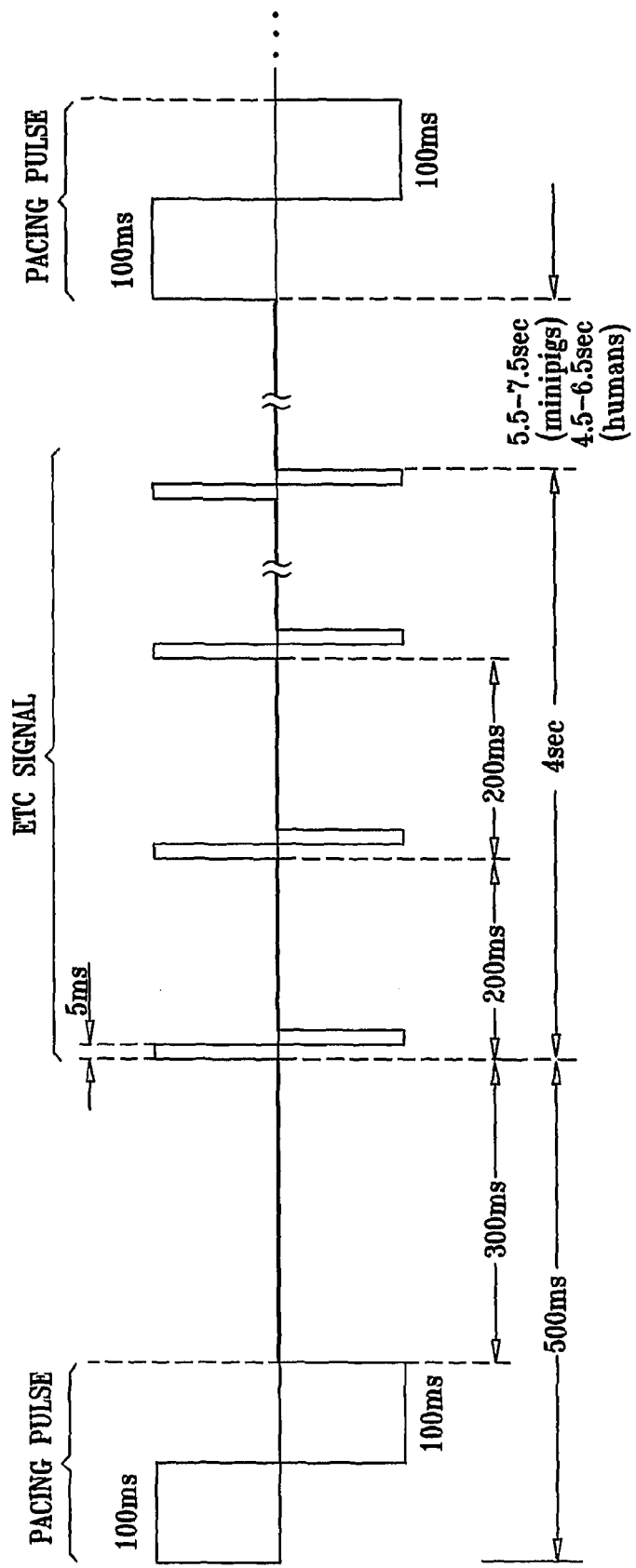
FIG. 50 is a schematic illustration of a signal application protocol, in accordance with an embodiment of the present invention.

FIG. 50 is a graph showing the signal application protocol used in the minipig experiments described hereinabove with reference to FIGS. 40-48, in accordance with an embodiment of the present invention. A biphasic pacing pulse was applied, each phase being 4 mA, and 100 ms in duration. After 300 ms, a 4-second ETC signal vas applied, comprising a train of biphasic pulses, each phase being 4 mA, and 5 ms in duration. The biphasic pulses in the ETC signal were applied at 5 Hz, i.e., with a 200 ms delay between the onset of each successive pulse. Following the ETC signal, no signal was applied for a waiting period lasting between 5.5 and 7.5 seconds. The duration of the waiting period varied between experiments, and had the following values for the experiments shown in the following figures—FIGS. 40 and 42-46: 7.5 seconds; FIGS. 41, 47, and 48: 5.5 seconds. Thus, the duration of an entire cycle from one biphasic pacing pulse to the next biphasic pacing pulse ranged from 10-12 seconds. (In other experiments not described herein, the waiting period was set as low as 1.5 seconds, and produced reductions in both glucose and insulin. In yet other experiments not described herein, the waiting period was set greater than 7.5 seconds, and produced reductions in both glucose and insulin.)

It is noted that the scope of the present invention includes applying pacing pulses without the ETC signal, as well as applying the ETC signal without applying pacing pulses. It is noted that the ETC signal and the pacing pulses may have different effects on the tissue which they affect (e.g., stomach, liver, pancreas tissue), and that these different effects may combine synergistically to produce the results described herein. Nevertheless, the effect of the ETC signal in the absence of pacing pulses, or of the pacing pulses in the absence of the ETC signal, may still have value in the treatment of some patients or some pathologies (e.g., diabetes or obesity), and the scope of the present invention includes such protocols. The effects of such protocols are hypothesized to include protection of affected tissue and/or improvement of the timing behavior of the affected tissue.

In the minipig experiments described hereinabove, all four pairs of antral electrodes were activated simultaneously to apply their respective pacing and ETC signals. Other experiments performed (results not shown) included activating (a) only the two posterior antral electrode pairs, (b) only the two anterior antral electrode pairs, (c) only the distal antral electrode pairs (anterior and posterior), and (d) only the proximal antral electrode pairs (anterior and posterior). Reductions in glucose and/or insulin were obtained in a number of these experiments, and the scope of the present invention includes such electrode activation protocols.

Figure 51A:
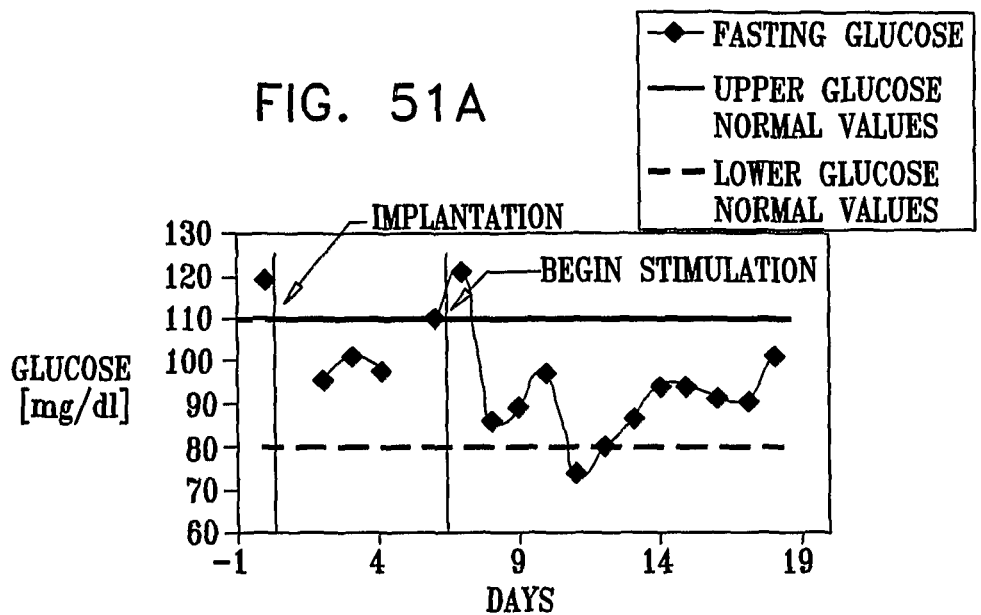
FIGS. 51 and 52 are charts showing experimental results, derived in accordance with an exemplary embodiment of the present invention.
Figure 51B:
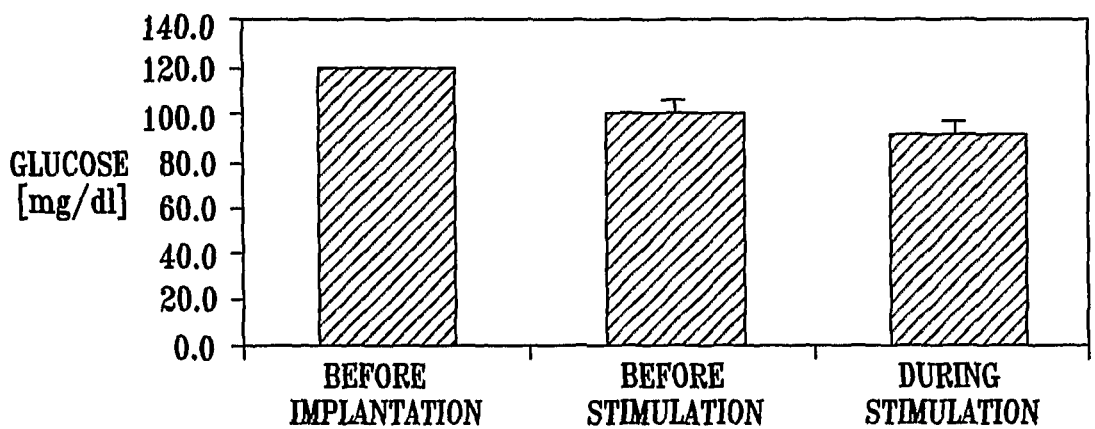

Reference is now made to FIGS. 51A and 51B, which are graphs showing experimental results from a first human patient, from an experiment performed in accordance with an embodiment of the present invention. The patient had type II diabetes for a prolonged period, prior to initiation of this experiment. Electrodes were implanted on the patient's stomach in the same configuration as that shown in and described with reference to FIG. 49A. Distances D1 and D2 were about 2 cm and about 2-3 cm, respectively.

A biphasic pacing pulse and ETC signal were applied to the antrum of the patient's stomach, simultaneously from all four pairs of electrodes. The pacing pulse and ETC signal were configured as described hereinabove with reference to FIG. 50, except that the waiting period separating the end of the ETC signal from the onset of the next biphasic pacing pulse lasted for between 4.5 and 6.5 seconds. Thus, the duration of an entire cycle from one biphasic pacing pulse to the next biphasic pacing pulse ranged from 9-11 seconds. The inventors have noted an overall tendency towards an enhanced acute glucose and insulin response as the duration of the cycle is reduced. However, longer cycle lengths also reduce glucose and/or insulin levels.

The experimental protocol included two-hour signal application periods including alternating pacing pulses and ETC signals. Each signal application period commenced at the time of administration of an OGTT. This protocol lasted for about ten days, and is referred to herein as the "acute" phase. During the acute phase, a total of three signal application periods occurred, on three different days. During a second, "chronic" phase of the experiment, the 2-hour signal application periods occurred three times a day, beginning at the onset of meals. (It is noted that the scope of the present invention includes providing signal application periods unsynchronized to meals, not responsive to a blood glucose measurement obtained within the last several hours or the last day, and/or less frequently than once a day, e.g., once every 2-5 days.)

Prior to the onset of this experiment, the patient was on a regular medication regimen that included sulfonylurea and metformin. With these medications, the patient's fasting glucose levels were generally at the borderline of the normal and high ranges (typically 100-120 mg/dl), prior to the beginning of this experiment. Following several days of signal application as described hereinabove, the patient's fasting blood glucose levels dropped to a low value of 70 mg/dl. In light of this change, the patient's physician elected to discontinue the administration of sulfonylurea. Notably, in the presence of ongoing daily signal application, and in the absence of the sulfonylurea, the patient's fasting blood glucose levels remained in the normal range.

Other measured changes in this patient at hospital discharge compared to pre-implantation are shown in the following table:

|  | Baseline | Discharge | Change |
| --- | --- | --- | --- |
| Fasting blood glucose (mg/dl) | 119 | 101 | −15% |
| Post-prandial blood glucose (mg/dl) | 177 | 155 | −12% |
| Fasting blood insulin (uU/ml) | 19.5 | 15.6 | −20% |
| Post-prandial blood insulin (uU/ml) | 198.6 | 60.6 | −69% |
| HbA1c | 7.1 | 6.6 | −7% |

Figure 52A:
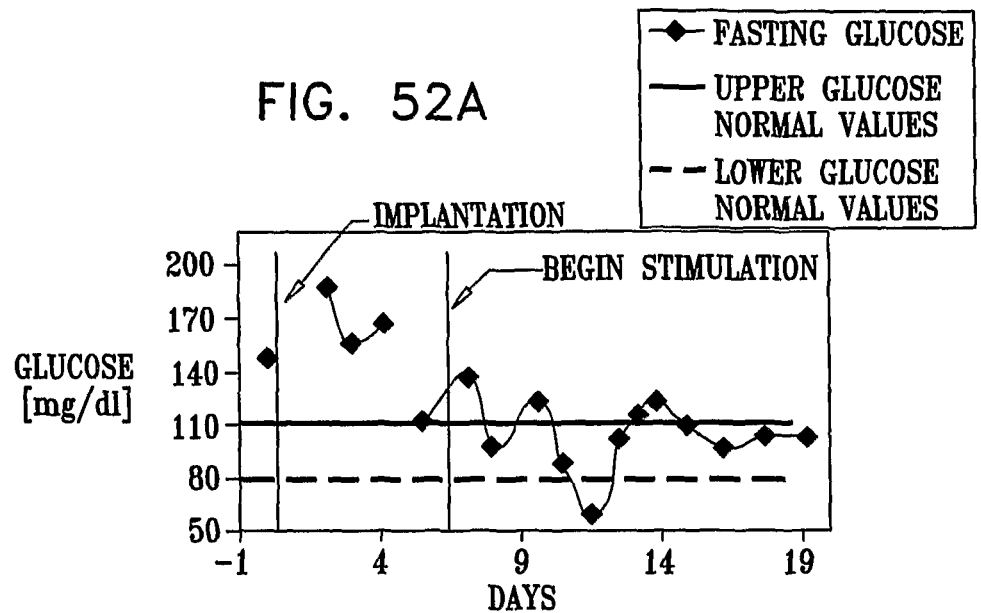
Figure 52B:
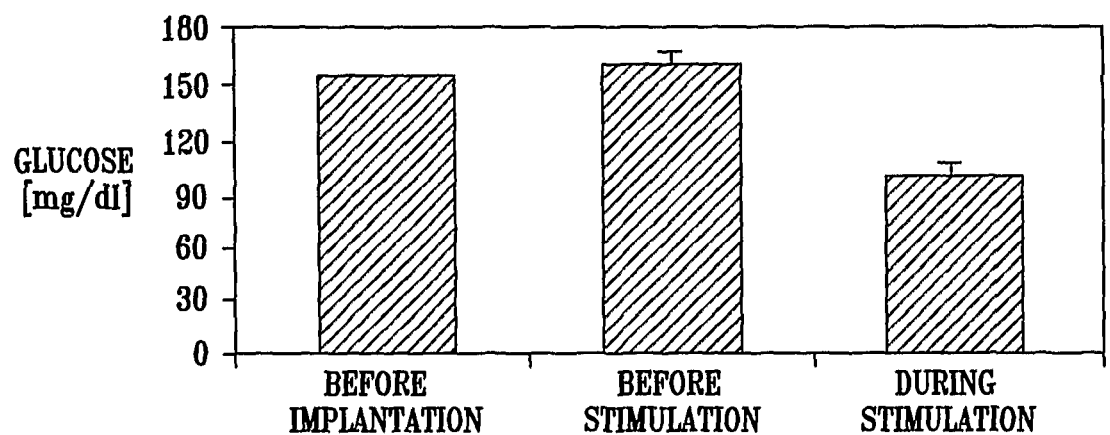
Figure 53:
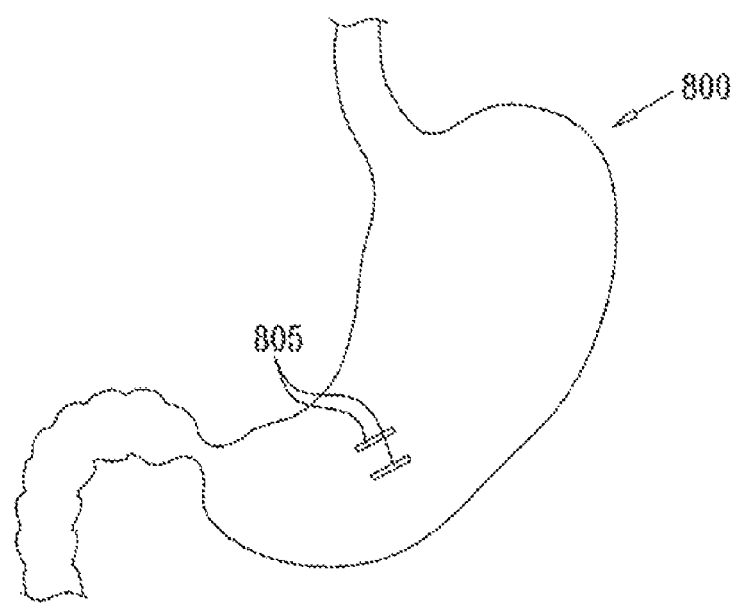
FIG. 53 is a schematic illustration of a plurality of electrodes 805 implanted on a stomach 800, in accordance with an embodiment of the present invention.

Reference is now made to FIGS. 52A and 52B, which are graphs showing experimental results from a second human patient, from an experiment performed in accordance with an embodiment of the present invention. This patient had type II diabetes for a prolonged period, prior to initiation of this experiment. Electrodes were implanted on the patient's stomach in the same manner as that described with respect to the first patient. Signal application protocols were generally the same as those described with respect to the first patient.

Prior to the onset of this experiment, the second patient was also on a regular medication regimen that included sulfonylurea and metformin. Even with these medications, the patient's fasting glucose levels were generally above the normal range, prior to the beginning of this experiment. Following several days of signal application as described hereinabove, the patient's fasting blood glucose levels dropped substantially, to a low value of 63 mg/dl. In light of this change, the patient's physician elected to discontinue the administration of sulfonylurea. Notably, in the presence of ongoing daily signal application, and in the absence of the sulfonylurea, the patient's fasting blood glucose levels remained in the normal range.

Other measured changes in this patient at hospital discharge compared to pre-implantation are shown in the following table:

|  | Baseline | Discharge | Change |
| --- | --- | --- | --- |
| Fasting blood glucose (mg/dl) | 147 | 104 | −29% |
| Post-prandial blood glucose (mg/dl) | 193 | 164 | −15% |
| Fasting blood insulin (uU/ml) | 7.9 | 4.8 | −39% |
| Post-prandial blood insulin (uU/ml) | 30.4 | 14.3 | −53% |
| HbA1c | 7.5 | 7.2 | −4% |

In summary, compared to the corresponding values prior to the signal application periods, both patients displayed a reduction in glucose and insulin levels, a reduction in HbA1c, and a reduction in the pharmaceutical regimen deemed appropriate for managing their diabetes.

Although other mechanisms may be responsible for some of the minipig and/or human results described hereinabove, some embodiments of the present invention provide one or both of the following mechanisms:

Mechanism 1: The application of the pacing pulses and/or ETC signal through electrodes attached to the stomach affects tissue of the stomach (e.g., muscle tissue, or, indirectly, nervous tissue), and thereby leads to the observed results. In an embodiment, signals are chemically or neurally transmitted from the stomach, to the pancreas, liver, ganglia, brain, or another structure, leading to a reduction in blood glucose and insulin. Various pathways are described hereinabove.

Mechanism 2: The application of the pacing pulses and/or ETC signal through electrodes attached to the stomach affects tissue outside of the stomach, e.g., the pancreas, liver, or another structure outside of the stomach. In an embodiment, although a first portion of the current driven through the electrodes enters the stomach directly, a second portion of the current does not enter the stomach. In this embodiment, this second portion of the current affects the functioning of the pancreas, liver, or other structure, thereby leading to a reduction in blood glucose and insulin.

As shown herein, a change in electrode orientation can vary the effect of an applied electric field. In accordance with some embodiments of the present invention, one or more of the following mechanisms is provided, and may, for example, be used in designing electrode placements and/or sequences.

Mechanism 1: The affected tissue has an orientation sensitivity, for example, favoring a state in which the field voltage varies along a column of cells or along fibers or perpendicular to tissue layers. As the field orientation varies from the tissue orientation, the effect is reduced. Different orientations elicit different behaviors, and, in some applications, overlapping of two behaviors occurs for certain orientation angles.

Mechanism 2: The current flow and/or density depends on the orientation.

Mechanism 3: The amount of relevant tissue within the field depends on the orientation (e.g., for anatomic/geometric reasons).

Mechanism 4: For certain desired effects, a plurality of tissues should act in concert (e.g., some active, some inactive and/or some modulated). At certain orientations, the correct tissues and/or tissue types are acted upon in a manner which generates a desired effect.

In an embodiment, a device comprising a control unit and a plurality of electrode pairs implanted on a patient's antrum is configured to treat both obesity and diabetes of the patient. For some applications, the same electrodes apply the same signal (e.g., the biphasic pacing pulse and ETC signal described hereinabove), which in the short term improves diabetes-related blood measurements, and over the longer term leads to a reduction of the patient's weight.

Alternatively or additionally, the same electrodes apply a signal configured to treat diabetes (e.g., the biphasic pacing pulse and ETC signal described hereinabove), and, at a different time, apply a signal configured to treat obesity (e.g., by inducing satiety). For some applications, the signal configured to treat obesity includes a signal known in the art for application to the stomach in order to treat obesity. For example, some such signals are described in U.S. Pat. Nos. 6,600,953, 5,690,691, and 5,423,872, which are incorporated herein by reference. For some applications, the signal configured to treat obesity includes a biphasic pacing pulse and an ETC signal, as described hereinabove with reference to FIG. 50. However, instead of utilizing a 5 Hz ETC signal (as described), the ETC signal is applied at between about 10 Hz and about 100 Hz, e.g., between about 50 Hz and about 90 Hz. In an embodiment, the ETC signal applied for obesity control is about 80 Hz. For some applications, the duration of each phase in the biphasic ETC pulses is between about 4 and about 9 ms, e.g., about 6 ms. The total duration of the train of ETC pulses applied for obesity control is typically 1.2 seconds, but may also be shorter or longer than 1.2 seconds. Such a signal treats obesity, it is believed, by inducing satiety at an earlier time than satiety would otherwise occur. The sensation of satiety may be related to a reduction of a rate of slow waves in the antrum, which reduction is induced by the applied signal. Alternatively or additionally, the sensation of satiety may be related to shape changes in the stomach, which are induced by the applied signal.

In an embodiment, the ETC signal applied for obesity and/or diabetes control is not applied following a biphasic pulse (as described hereinabove), but is instead applied following a sensed naturally-occurring depolarization, e.g., a slow wave in the antrum. For example, the ETC signal may be applied 10-500 ms (e.g., 300 ms) following the sensed depolarization.

In some embodiments, the electrodes that are used for treating diabetes and treating obesity are applied to the stomach in a longitudinal orientation, in a perpendicular orientation, or in a mixed orientation, with respect to the curved long axis 810 of the stomach.

Alternatively, electrodes that are used for treating diabetes are applied in one orientation (e.g., longitudinal), and electrodes that are used for treating obesity are applied in a different orientation (e.g., perpendicular). For some applications, a pair of diabetes-treating electrodes and a pair of obesity-treating electrodes are applied to the stomach over a common site, e.g., in a tic-tac-toe board configuration, where the angle between the pairs may be 90 degrees, or less than 90 degrees (e.g., 0-30 degrees, 30-60 degrees, or 60-89 degrees). Alternatively, the pair of diabetes-treating electrodes and the pair of obesity-treating electrodes are lined up next to each other, or end to end. In an embodiment, a patch is provided, which serves as a mount for a pair of diabetes-treating electrodes and a pair of obesity-treating electrodes.

In an exemplary embodiment of the invention, an electrode design is provided which allows for providing electric fields of various orientations. Optionally, the orientations are changed during implantation and/or during use, for example to determine an optimal activation sequence or when a change in orientation is desired to achieved a different effect.

One example of such an electrode design is a net electrode, for example a 5×5 net, where the nodes or segments (depending on the design of the electrode) are each individually addressable. By using selective shorting together of individual nodes (or segments), various shaped and/or oriented electrodes may be created. In particular, curved electrodes can be created. In general, a higher resolution of orientation angle can be achieved for higher resolution nets.

In one example, such a next electrode includes 25 wires that are connected to a controller.

In an alternative net electrode design, transistors or other switches at the next electrode or nearby are used to select (by addressing) which segments are connected to which input lines (e.g., power lines from a controller).

In an embodiment of the present invention, two electrodes in an electrode pair are not parallel with each other, but instead are separated by an angle of 1-45 degrees, 45-90 degrees, or 90-180 degrees.

For some applications, the obesity-treating electrodes are activated in response to detection of eating by a patient, in order to induce an early sensation of satiety. In this case, the obesity-treating electrodes are typically (but not necessarily) activated for a relatively-short time, e.g., for half an hour, or for 10-20 minutes. Subsequently thereto, the diabetes-treating electrodes are activated, typically for a longer time (e.g., about 30 minutes to several hours). Alternatively, the diabetes-treating electrodes are activated during activation of the obesity-treating electrodes. Still further alternatively, the diabetes-treating electrodes are activated for a short time (e.g., 1-10 minutes) prior to the activation of the obesity-treating electrodes, and then, typically, following the activation of the obesity-treating electrodes.

In an embodiment, the diabetes-treating electrodes are activated independently of any detection of eating. For example, the diabetes-treating electrodes may be activated once or twice every day, or once or twice every week. In accordance with an embodiment of the present invention, the obesity-treating electrodes and/or the diabetes-treating electrodes are activated in response to a manually-entered signal from the patient. In accordance with an embodiment of the present invention, the obesity-treating electrodes and/or the diabetes-treating electrodes are activated in response to an indication that the stomach is at a low level of activity (e.g., because the patient has not eaten for a long time). For some applications, activation of the diabetes-treating electrodes while the stomach is at a low level of activity minimizes any interfering effect of the signal application on digestion, which might occur in some patients if the signal were applied when the stomach is at a high level of activity. In an embodiment, if a patient is identified as someone who reacts to signal application by the obesity-treating electrodes by (a) increasing an already high blood glucose level, (b) decreasing an already low blood glucose level, or (c) otherwise undesirably modulating glucose levels, then the obesity-treating electrodes are typically only activated in response to an indication of a moderate or otherwise suitable blood glucose level (e.g., as determined by an implanted or external sensor).

In general, some embodiments of the present invention provide sensing or determining an indication of glucose or insulin levels, and driving or withholding driving the obesity-treating electrodes responsive thereto. Alternatively or additionally, some embodiments of the present invention provide sensing or determining an indication of glucose or insulin levels, and driving or withholding driving the diabetes-treating electrodes responsive thereto. In particular, although some embodiments and experimental results described herein relate to driving the diabetes-treating electrodes when the blood glucose level is high, or about to be high, the scope of the present invention includes a mode in which the diabetes-treating electrodes are activated responsive to an indication of a moderate (i.e., not high) blood glucose level. This mode typically provides chronic control of blood glucose levels, rather than an acute reduction of blood glucose levels.

For some applications, the diabetes-treating electrodes and/or the obesity-treating electrodes are applied to the antrum (e.g., as shown in FIG. 49A, 49B, or 49C). For other applications, the diabetes-treating electrodes and/or the obesity-treating electrodes are applied to the body of the stomach, some on the posterior portion of the stomach and some on the anterior portion of the stomach, or else exclusively on either the anterior or the posterior portion of the stomach. For some applications, the diabetes-treating electrodes and/or the obesity-treating electrodes are implanted on other sites described herein, e.g., the abdominal wall or the duodenum.

It is to be understood that for some applications, the obesity-treating electrodes and diabetes-treating electrodes described hereinabove are the same electrodes being activated in different modes.

It is further to be understood that whereas some embodiments of the present invention are described hereinabove with respect to fixing electrodes to a particular tissue (e.g., the stomach), the scope of the present invention includes implanting the electrodes near the tissue (e.g., within 1, 2, or 4 cm of the tissue).

It will be appreciated that the above described methods of controlling a pancreas, stomach, duodenum, colon, gastrointestinal tract, or other tissue, may be varied in many ways, including changing (a) the order of steps, (b) which steps are performed more often and which less often, (c) the arrangement of electrodes, (d) the type and order of pulses applied and/or (e) the particular sequences and logic schemes used. Further, the location of various elements may be switched, without exceeding the sprit of the disclosure (for example, the location of the power source). In addition, a multiplicity of various features, both of method and of devices have been described. It should be appreciated that different features may be combined in different ways. In particular, not all the features shown above in a particular embodiment are necessary in every similar exemplary embodiment of the invention. Further, combinations of the above features are also considered to be within the scope of some exemplary embodiments of the invention. In addition, some of the features of the invention described herein may be adapted for use with prior art devices, in accordance with other exemplary embodiments of the invention. Further, various means for carrying out the above described functions are included in the scope of the invention, for example, electrifying means, pulse generating means and/or sensing means. The particular geometric forms used to illustrate the invention should not be considered limiting the invention in its broadest aspect to only those forms. (For example, where a ball electrode is shown, in other embodiments an ellipsoid electrode may be used.) Although some limitations are described only as method or apparatus limitations, the scope of the invention also includes apparatus programmed and/or designed to carry out the methods, for example using firmware or software programming, and methods for electrifying the apparatus to have the apparatus's desired function.

Also within the scope of the invention are surgical kits which include sets of medical devices suitable for implanting a controller and such a controller. Section headers in this application are provided only to assist in navigating the application and should not be construed as necessarily limiting the contents described in a certain section, to that section. Measurements are provided to serve only as exemplary measurements for particular cases, the exact measurements applied will vary depending on the application. When used in the following claims, the terms "comprises," "comprising," "includes," "including," or the like means "including but not limited to." Additionally, in the context of the present patent application and in the claims, it is to be understood that a subset of a set may include one member of the set, some members of the set, or all of the members of the set.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
a plurality of electrodes, configured to be fixed to a stomach of a patient; and
a control unit, configured to:
   drive, even in an absence of a detection of eating by the patient, the plurality of electrodes to apply to the stomach a first signal, and configure the first signal to reduce a blood glucose level of the patient, and
   drive, responsive to a detection of eating by the patient, the plurality of electrodes to apply to the stomach a second signal, different from the first signal, and configure the second signal to treat obesity of the patient,
wherein the plurality of electrodes driven to apply the first signal is identical with the plurality of electrodes driven to apply the second signal.

2. The apparatus according to claim 1, wherein the control unit is configured to configure the first signal to comprise an ETC signal.

3. The apparatus according to claim 1, wherein the control unit is configured to configure the second signal to comprise an ETC signal.

4. The apparatus according to claim 1, wherein the control unit is configured to drive the plurality of electrodes to apply the first and the second signals at different times.

5. The apparatus according to claim 1, wherein the plurality of electrodes are configured to be fixed to an antrum of the stomach.

6. The apparatus according to claim 5, wherein the plurality of electrodes comprises at least two pairs of electrodes, configured to be fixed to the antrum.

7. The apparatus according to claim 6, wherein the plurality of electrodes comprises at least four pairs of electrodes, configured to be fixed to the antrum.

8. The apparatus according to claim 6, wherein one of the pairs is configured to be fixed to a posterior portion of the antrum, and wherein another one of the pairs is configured to be fixed to an anterior portion of the antrum.

9. The apparatus according to claim 6, wherein the at least two pairs of electrodes are configured to be fixed to the antrum in a longitudinal orientation with respect to a curved long axis of the stomach.

10. The apparatus according to claim 6, wherein the at least two pairs of electrodes are configured to be fixed to the antrum in a perpendicular orientation with respect to a curved long axis of the stomach.

11. The apparatus according to claim 6, wherein the at least two pairs of electrodes are configured to be fixed to the antrum in a mixed orientation with respect to a curved long axis of the stomach.

12. The apparatus according to claim 6, wherein the at least two pairs of electrodes comprise a first pair and a second pair of electrodes, configured to be fixed to the antrum at different respective orientations with respect to a curved long axis of the stomach.

13. Apparatus, comprising:
a set of electrodes, configured to be implanted at an implantation site in a patient selected from the group consisting of: a stomach of the patient, and an intestinal site of the patient; and
a control unit, configured to:
   drive a first subset of the set of electrodes to apply a first signal to the site, and configure the first signal to reduce a blood glucose level of the patient, and to have a first frequency component, and
   drive a second subset of the set of electrodes to apply to the site a second signal, different from the first signal, and configure the second signal to treat obesity of the patient, and to have a second frequency component different from the first frequency component.

14. The apparatus according to claim 13, wherein the control unit is configured to drive the second subset to apply the second signal having the second frequency component without driving the second subset to apply a pacing pulse to the implantation site prior to applying the second signal.

15. The apparatus according to claim 13, wherein the control unit is configured to configure the first signal having the first frequency component to be non-excitatory.

16. The apparatus according to claim 13, wherein the control unit is configured to configure the second signal having the second frequency component to be non-excitatory.

17. The apparatus according to claim 13, wherein the control unit is configured to drive the first subset to alternate application to the implantation site of (a) a pacing pulse and (b) the first signal having the first frequency component.

18. The apparatus according to claim 17, wherein the control unit is configured to initiate applying the first signal having the first frequency component within 500 ms following the pacing pulse.

19. The apparatus according to claim 13, wherein the first subset and the second subset comprise at least one electrode in common.

20. The apparatus according to claim 13, wherein the first subset and the second subset are identical.

21. The apparatus according to claim 13, wherein the first subset and the second subset have no electrodes in common.

22. The apparatus according to claim 13, wherein the control unit is configured to drive the first and the second subsets of electrodes at different times.

23. The apparatus according to claim 13, wherein the first frequency component is smaller than the second frequency component.

24. The apparatus according to claim 23, wherein the first frequency component is less than 10 Hz, and wherein the second frequency component is greater than 10 Hz.

25. The apparatus according to claim 24, wherein the second frequency component is between 60 Hz and 100 Hz.

26. The apparatus according to claim 24, wherein the first frequency component is less than half of the second frequency component.

27. The apparatus according to claim 26, wherein the first frequency component is less than one fifth of the second frequency component.

28. A method, comprising: fixing at least two pairs of electrodes to a stomach site of a patient, in a longitudinal orientation with respect to a curved long axis of the stomach; and driving the electrodes to apply a first signal configured to treat diabetes and a second signal configured to treat obesity.

29. The method according claim 28, wherein driving the electrodes comprises driving the electrodes even in the absence of a detection of eating by the patient.

30. The method according to claim 28, wherein driving the electrodes comprises driving the electrodes responsive to a detection of eating by the patient.

31. The method according to claim 28, wherein fixing the at least two pairs of electrodes comprises fixing the at least two pairs of electrodes to an antrum of the stomach of the patient.

32. The method according to claim 31, wherein fixing the at least two pairs of electrodes comprises fixing at least four pairs of electrodes to the antrum.

33. The method according to claim 31, wherein fixing the at least two pairs of electrodes comprises fixing one of the pairs to a posterior portion of the antrum and fixing another one of the pairs to an anterior portion of the antrum.

34. The method according to claim 28, wherein driving the electrodes to apply the signal comprises driving the electrodes to apply an ETC signal having a frequency component.

35. The method according to claim 34, wherein driving the electrodes to apply the ETC signal comprises driving the electrodes to apply the ETC signal without driving the electrodes to apply a pacing pulse to the implantation site prior to applying the ETC signal.

36. The method according to claim 34, comprising driving the electrodes to alternate application to the stomach site of (a) a pacing pulse and (b) the ETC signal.

37. The method according to claim 36, comprising initiating applying the ETC signal within 500 ms following the pacing pulse.

38. The method according to claim 34, wherein driving the electrodes comprises setting the frequency component to be less than 10 Hz.

39. The method according to claim 34, wherein driving the electrodes comprises setting the frequency component to be greater than 10 Hz.

40. A method, comprising:
fixing at least two pairs of electrodes to a stomach site of a patient, in a perpendicular orientation with respect to a curved long axis of the stomach; and
driving the electrodes to apply a first signal configured to treat diabetes and a second signal configured to treat obesity.

41. The method according to claim 40, wherein driving the electrodes comprises driving the electrodes even in the absence of a detection of eating by the patient.

42. The method according to claim 40, wherein driving the electrodes comprises driving the electrodes responsive to a detection of eating by the patient.

43. The method according to claim 40, wherein fixing the at least two pairs of electrodes comprises fixing the at least two pairs of electrodes to an antrum of the stomach of the patient.

44. The method according to claim 43, wherein fixing the at least two pairs of electrodes comprises fixing at least four pairs of electrodes to the antrum.

45. The method according to claim 43, wherein fixing the at least two pairs of electrodes comprises fixing one of the pairs to a posterior portion of the antrum and fixing another one of the pairs to an anterior portion of the antrum.

46. The method according to claim 40, wherein driving the electrodes to apply the signal comprises driving the electrodes to apply an ETC signal having a frequency component.

47. The method according to claim 46, wherein driving the electrodes to apply the ETC signal comprises driving the electrodes to apply the ETC signal without driving the electrodes to apply a pacing pulse to the stomach site prior to applying the ETC signal.

48. The method according to claim 46, comprising driving the electrodes to alternate application to the stomach site of (a) a pacing pulse and (b) the ETC signal.

49. The method according to claim 48, comprising initiating applying the ETC signal within 500 ms following the pacing pulse.

50. The method according to claim 46, wherein driving the electrodes comprises setting the frequency component to be less than 10 Hz.

51. The method according to claim 46, wherein driving the electrodes comprises setting the frequency component to be greater than 10 Hz.

52. A method, comprising:
fixing at least two pairs of electrodes to a stomach site of a patient, in a mixed orientation with respect to a curved long axis of the stomach; and
driving the electrodes to apply a first signal configured to treat diabetes and a second signal configured to treat obesity.

53. The method according to claim 52, wherein driving the electrodes comprises driving the electrodes even in the absence of a detection of eating by the patient.

54. The method according to claim 52, wherein driving the electrodes comprises driving the electrodes responsive to a detection of eating by the patient.

55. The method according to claim 52, wherein fixing the at least two pairs of electrodes comprises fixing the at least two pairs of electrodes to an antrum of the stomach of the patient.

56. The method according to claim 55, wherein fixing the at least two pairs of electrodes comprises fixing at least four pairs of electrodes to the antrum.

57. The method according to claim 55, wherein fixing the at least two pairs of electrodes comprises fixing one of the pairs to a posterior portion of the antrum and fixing another one of the pairs to an anterior portion of the antrum.

58. The method according to claim 52, wherein driving the electrodes to apply the signal comprises driving the electrodes to apply an ETC signal having a frequency component.

59. The method according to claim 58, wherein driving the electrodes to apply the ETC signal comprises driving the electrodes to apply the ETC signal without driving the electrodes to apply a pacing pulse to the stomach site prior to applying the ETC signal.

60. The method according to claim 58, comprising driving the electrodes to alternate application to the stomach site of (a) a pacing pulse and (b) the ETC signal.

61. The method according to claim 60, comprising initiating applying the ETC signal within 500 ms following the pacing pulse.

62. The method according to claim 58, wherein driving the electrodes comprises setting the frequency component to be less than 10 Hz.

63. The method according to claim 58, wherein driving the electrodes comprises setting the frequency component to be greater than 10 Hz.

* * * * *

UNITED STATES PATENT AND TRADEMARK OFFICE
CERTIFICATE OF CORRECTION

PATENT NO. : 8,666,495 B2
APPLICATION NO. : 10/599015
DATED : March 4, 2014
INVENTOR(S) : Harel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1693 days.

Signed and Sealed this

Twenty-ninth Day of September, 2015

Michelle K. Lee
*Director of the United States Patent and Trademark Office*